US009115363B2

(12) United States Patent
Benghezal et al.

(10) Patent No.: US 9,115,363 B2
(45) Date of Patent: Aug. 25, 2015

(54) **GENE EXPRESSION AND ERADICATION SYSTEM IN *HELICOBACTER PYLORI***

(75) Inventors: Mohammed Benghezal, Scarborough (AU); Aleksandra Weronika Debowski, Greenwood (AU); Miriam Sehnal, Doubleview (AU); Yakhya Dieye, Kuala Lumper (MY); Se-Hoon Park, Kangbuk-gu (KR); Barry Marshall, Subiaco (AU)

(73) Assignee: Ondek Pty Ltd, New South Wales (AU)

( * ) Notice: Subject to any disclaimer, the term of this patent is extended or adjusted under 35 U.S.C. 154(b) by 93 days.

(21) Appl. No.: 14/003,786

(22) PCT Filed: Mar. 9, 2012

(86) PCT No.: PCT/AU2012/000245
§ 371 (c)(1),
(2), (4) Date: Nov. 25, 2013

(87) PCT Pub. No.: WO2012/119203
PCT Pub. Date: Sep. 13, 2012

(65) Prior Publication Data
US 2014/0072595 A1     Mar. 13, 2014

(30) Foreign Application Priority Data

Mar. 9, 2011   (AU) ................................. 2011900849
Apr. 29, 2011  (AU) ................................. 2011901589

(51) Int. Cl.
*C12N 15/74*  (2006.01)
*A61K 35/00*  (2006.01)

(52) U.S. Cl.
CPC ............. *C12N 15/74* (2013.01); *A61K 2035/11* (2013.01)

(58) Field of Classification Search
CPC . A61K 2039/5256; A61K 38/00; A61K 31/65
USPC .......... 435/320.1, 375, 455, 471, 252.3, 69.1
See application file for complete search history.

(56) References Cited

U.S. PATENT DOCUMENTS 5,989,832 A * 11/1999 Trias et al. ..................... 435/7.2
6,060,241 A *  5/2000 Corthesy-Theulaz ....... 435/6.15
(Continued)

FOREIGN PATENT DOCUMENTS

CN   200780049696.5    12/2009
EP        1690942    *  8/2006 ............. C12N 15/71
(Continued)

OTHER PUBLICATIONS

Censini, Stefano et al, PNAS, vol. 93(25), Dec. 10, 1996, pp. 14648-14653, cag a Pathogenicity Island of *Helicobacter pylori* Encodes type I Specific and Disease associated virulence factors.*
(Continued)

*Primary Examiner* — Albert Navarro
*Assistant Examiner* — Ginny Portner
(74) *Attorney, Agent, or Firm* — Pepper Hamilton LLP

(57) ABSTRACT

The present invention relates to a gene expression and eradication system for *Helicobacter pylori* (*H. pylori*). In particular, the present invention relates to a genetic construct comprising, in the 5'-3' direction: (a) a promoter sequence and (b) a DNA sequence of interest, wherein the promoter sequence comprises a polynucleotide sequence capable of regulating expression of the DNA sequence of interest in *Helicobacter pylori* and wherein said promoter sequence is modified to comprise a tetracycline (tet) operator sequence.

13 Claims, 34 Drawing Sheets

(56) References Cited

U.S. PATENT DOCUMENTS

| | | | |
|---|---|---|---|
| 6,096,521 A * | 8/2000 | Haas et al. | 435/70.1 |
| 6,271,017 B1 * | 8/2001 | Labigne et al. | 435/252.3 |
| 6,828,140 B2 * | 12/2004 | Gardner et al. | 435/252.3 |
| 7,973,600 B2 * | 7/2011 | Yu | 330/124 R |
| 8,080,647 B2 * | 12/2011 | Gordon-Kamm et al. | 536/23.7 |
| 8,715,929 B2 * | 5/2014 | Benghezal et al. | 435/6.1 |
| 2002/0168681 A1 * | 11/2002 | Yocum et al. | 435/7.1 |
| 2003/0186281 A1 * | 10/2003 | Hillen | 435/6 |
| 2004/0029129 A1 * | 2/2004 | Wang et al. | 435/6 |
| 2004/0052799 A1 * | 3/2004 | Smith et al. | 424/184.1 |
| 2004/0181036 A1 * | 9/2004 | Green et al. | 530/350 |
| 2005/0123511 A1 * | 6/2005 | McCreavy et al. | 424/93.2 |
| 2011/0218118 A1 * | 9/2011 | Watt et al. | 506/10 |
| 2012/0225454 A1 * | 9/2012 | Benghezal et al. | 435/69.3 |

FOREIGN PATENT DOCUMENTS

| | | |
|---|---|---|
| WO | 02/07763 | 1/2002 |
| WO | 2006/084695 | 8/2006 |
| WO | 2008/055316 | 5/2008 |
| WO | 2010/139018 | 12/2010 |

OTHER PUBLICATIONS

Bockelmann, Uta et al, Applied and Environmental Microbiology, vol. 75(1), pp. 154-163, Jan. 2009, Quantitative PCR Monitoring of Antibiotic Resistance Genes and Bacterial Pathogens in Three European Artifical Groundwater Recharge Systems.*

Ribeiro, Marcelo L. et al, FEMS Immunology and Medical Microbiology, vol. 40, pp. 57-61, 2004, Detection and high level tetracycline resistance in clinical isolates of *Helicobacter pylori* using PCR-RFLP.*

McClain, Mark S. et al, Journal of Microbiological Methods, vol. 95, 2013, pp. 336-341, Control of gene expression in *Helicobacter pylori* using the Tet repressor.*

Niehus, Eike e tal, Microbiology, 2002, vol. 148, pp. 3827-3837, Growth Phase-dependent and differential transcriptional control of flagellar genes in *Helicobacter pylori*.*

Wu, B et al, FEBS Letters, vol. 519, 2002, pp. 87-92, Bifunctional phosphomannose isomerase/GDP-D-mannose pyrophosphorylase is the point of control for GDP-d-mannsoe biosynthesis in *Helicobacter pylori*.*

Boneca, Ivo G. et al, Applied and Environmental Microbiology, Apr. 2008, pp. 2095-2102, vol. 74(7), Development of Inducibile Systems to Engineer Conditional mutants of Essential Genes of *Helicobaceter pylori*.*

Carpenter, Beth M. et al, Applied and Environmental Microbiology, Dec. 2007, vol. 73(23), pp. 7506-7514, Expanding the Helicobactger pylori Genetic Toobox:Modification of an Endogenous Plasmid for use as a Transcriptional Reporter and Complementation Vector.*

Ribeiro, Marcelo L et al, FEMS Immunology and Medical Microbiology, vol. 40, 2004, pp. 57-61, Detection of high-level tetracycline resistance in clinical isolates of *Helicobacter pylori* using PCR-RFLP.*

Gorrell, Rebecca J. et al, FEMS IMmunology and Medical Microbiology, vol. 44, 2005, pp. 213-219, Restriction of DNA encoding selectable markers decreases the transformation efficiency of *Helicobacter pylori*.*

Belli, Gemma et al, Nucleic Acids Research, 1998, vol. 26, No. 4, An activator/repressor dual system allows tight tetracycline-regulated gene expression in budding yeast.*

Bertram, Ralph et al, Microbial Biotechnology Review, 2008, vol. 1(1), pp. 2-16, The application of Tet repressor in prokaryotic gene regulation and expression.*

Quan et al., "Construction of a tetR-integrated Salmonella enterica serovar typhi CVD908 strain that tightly controls expression of the major merozoite surface protein of *Plasmodium falciparum* for application in human vaccine production", Infection and Immunity, 2002, 70(4):2029-38.

Hilderbrandt et al., "*Helicobacter pylori* lipopolysaccharide modification, Lewis antigen expression, and gastric colonization are cholesterol-dependent", BMC Microbiology, 2009, 9:258.

Wu et al., "Bifuctional phosphomannose isomerase/GDP-D-mannose pyrophosphorylase is the point of control for GDP-D-mannose biosynthesis in *Helicobacter pylori*", FEBS Letters, 2002, 519:87-92.

Schoep et al., "Surface properties of *Helicobacter pylori* urease complex are essential for persistence", PLoS One, 2010, 5(11):e15042.

Thibonnier et al. "Trans-Translation in *Helicobacter pylori*: Essentiality of Ribosome Rescue and Requirement of Protein Tagging for Stress Resistance and Competence", PLoS One, 2008, 3(11):e3810.

Guo et al. "*Helicobacter pylori* mutagenesis by mariner in vitro transposition", FEMS Immunology and Medical Microbiology, 2001, 30(2):87-93.

Boneca et al. "Development of Inducible Systems to Engineer Conditional Mutants of Essential Genes of *Helicobacter pylori*", Applied and Environmental Microbiology, 2008, 74(7):2095-2102.

* cited by examiner

Mutants have growth inhibition in the presence of Mannose in vitro

| OD$_{600}$ | 1 | 2 | 3 | 4 | 5 | 6 | 7 | 8 | x47RC (mdaB) |
|---|---|---|---|---|---|---|---|---|---|
| Normal | 1.237 | 1.177 | 1.153 | 1.156 | 1.030 | 1.147 | 1.060 | 0.967 | 1.327 |
| Man.0.5% | 0.019 | 0.019 | 0.042 | 0.045 | 0.047 | 0.062 | 0.026 | 0.046 | 1.261 |

FIGURE 20

```
          RBS            Start
          TAGGAGAATAACATATG      4uPtetO5
          TAGGAGAATAACATCTG      5uPtetO5
          TAGGAGAATAACATTTG      6uPtetO5
          TAGCAGAATAACATATG      1uPtetO5
          TAGCAGAATAACATCTG      2uPtetO5
          TAGCAGAATAACATTTG      3uPtetO5
```

GENE EXPRESSION AND ERADICATION SYSTEM IN HELICOBACTER PYLORI

CROSS-REFERENCE TO RELATED APPLICATIONS

This application claims priority to and is a United States National Stage filing under 35 USC §371 of International PCT Application Serial No. PCT/AU2012/000245, filed Mar. 9, 2012, which claims priority to Australian Application Nos. 201190849, filed Mar. 9, 2011, and 2011901589, filed Apr. 29, 2011, each of which is incorporated herein by reference in its entirety.

FIELD

The present invention relates to a gene expression and eradication system for Helicobacter pylori (H. pylori). In particular, the present invention relates to Tet inducible gene expression system in H. pylori, wherein a transformed H. pylori can be used for controllable expression of a gene in vitro and/or in vivo. The present invention further relates to a method of controlling the colonization ability of H. pylori, especially genetically modified H. pylori, by modifying or deleting the ability of H. pylori to utilize certain sugars.

BACKGROUND

More than half of the world's population is chronically infected with the gastric pathogen H. pylori. Infection is usually acquired in early childhood and lasts for a lifetime with the majority of infected individuals remaining asymptomatic. H. pylori infection is the main cause of peptic ulcer disease (Kuipers et al. 1995), and is a significant risk factor for the development of gastric adenocarcinoma (Wilson & Crabtree 2007; Amieva & El-Omar 2008; Wroblewski et al. 2010). Furthermore, treatment of H. pylori is becoming increasingly difficult with the emergence of antibiotic resistance (Zullo et al. 2007; Graham & Shiotani 2008) and consequently alternatives to antibiotic treatment need to be identified. Elucidating the mechanisms of H. pylori persistence may lead to the discovery of novel drug targets and the development of alternative eradication therapies.

Genetics, including insertion mutagenesis, gene replacement and gene over-expression, has contributed tremendously to deciphering bacterial biological phenomena through the study of recombinant and mutant strains' phenotypes. This approach has been extensively used to characterize several H. pylori virulence factors, such as urease, CagA, VacA and flagella (Algood & Cover, 2006). Though initially useful, there is growing opinion in the field of bacterial genetics that the use of knockout mutants limits the study to complete a loss of function as this approach does not allow for investigating whether a specific gene or set of genes encoding virulence determinants is necessary to maintain the infection state once it has been established or whether these virulence determinants are necessary for the entire infection cycle (Gandotra et al. 2007; Liu et al. 2008). Moreover, severe phenotypes affecting bacterial growth are subjected to compensatory adaptation either at the physiological or genetic level or both. Therefore, a genetic tool, based on an inducible expression of the target gene, is better suited to constructing conditional knockouts for physiological and phenotypic studies. Of note, genetic studies based on the use of conditional knockouts enable the investigators to test for the temporal requirement of the target gene expression and their corresponding products, distinguish their role during the different steps of an infection, such as colonisation and maintenance of the infection. This approach is of particular importance for H. pylori infection which is a persistent and lifelong infection.

Recently a plasmid based inducible system based on the $LacI^q$ system in E. coli has been developed to study essential genes in H. pylori (Boneca et al. 2008). Unfortunately, the $LacI^q$ system does not repress gene expression efficiently and it requires large amounts of the inducer molecule to induce gene expression which makes it unfeasible to use as a tool to study the infection process in an animal model. Moreover, the DNA restriction barrier and DNA modification of H. pylori strains differ and prevent a systematic use of plasmids in this bacterium.

Thus, there remains a need for a genetic tool, based on an inducible expression of a target gene, in H. pylori that functions in vitro and in vivo. Moreover, there is a continuing need to develop eradication methods for H. pylori, especially the eradication of genetically modified H. pylori that can be used as a biological delivery vehicle for peptides and the like.

SUMMARY

Inventors have developed a tetracycline-based inducible gene expression system for H. pylori. The conditional knockout strategy used allows the turning on or turning off, of a single target gene at various time points during the course of an infection.

Accordingly, in a first aspect the present invention provides a genetic construct comprising, in the 5'-3' direction: (a) a promoter sequence and (b) a DNA sequence of interest, wherein the promoter sequence comprises a polynucleotide sequence capable of regulating expression of the DNA sequence of interest in Helicobacter pylori and wherein said promoter sequence is modified to comprise a tetracycline (tet) operator sequence.

In some embodiments, the DNA sequence of interest encodes at least one heterologous antigen, or a functional fragment thereof. In some embodiments, the heterologous antigen, or a functional fragment thereof is from a pathogenic microorganism, preferably a pathogenic microorganism selected from the group consisting of a virus, a bacterium, a protozoan and a fungus.

In some embodiments, the heterologous antigen is selected from the group consisting of a human immunodeficiency virus (HIV) antigen, an HTLV antigen, an SIV antigen, an RSV antigen, a PIV antigen, an HSV antigen, a CMV antigen, an Epstein-Barr virus antigen, a Varicella-Zoster virus antigen, a mumps virus antigen, a measles virus antigen, an influenza virus antigen, a poliovirus antigen, a rhinovirus antigen, a hepatitis A virus antigen, a hepatitis B virus antigen, a hepatitis C virus antigen, a Norwalk virus antigen, a togavirus antigen, an alphavirus antigen, a rubella virus antigen, a rabies virus antigen, a Marburg virus antigen, an Ebola virus antigen, a papilloma virus antigen, a polyoma virus antigen, a metapneumovirus antigen, a coronavirus antigen, a Vibrio cholerae antigen, a Plasmodium falciparum antigen, a Plasmodium vivax antigen, a Plasmodium ovate antigen, a Plasmodium malariae antigen, a Plasmodium knowlesi antigen, a Streptococcus pneumoniae antigen, Streptococcus pyogenes antigen, a Helicobacter pylori antigen, a Streptococcus agalactiae antigen, a Neisseria meningitidis antigen, a Neisseria gonorrhoeae antigen, a Corynebacterium diphtheriae antigen, a Clostridium tetani antigen, a Bordetella pertussis antigen, a Haemophilus antigen, a Chlamydia antigen and an Escherichia coli antigen.

In some embodiments, the construct of the invention further comprises (c) a gene termination sequence.

In a second aspect the present invention provides a genetic construct comprising, in the 5'-3' direction: (a) a promoter sequence and (b) a urease operon, wherein the promoter sequence comprises a polynucleotide sequence capable of regulating expression of the urease operon in *Helicobacter pylori* and wherein said promoter sequence is modified to comprise a tetracycline (tet) operator sequence.

In some embodiments, the urease operon is isolated from a *H. pylori* strain. Preferably, the urease operon comprises subunits A and B.

Preferably, the genetic construct is a plasmid vector. In some embodiments, the plasmid vector is capable of inserting the genetic construct of the present invention into the chromosome of *H. pylori*. Preferably, the insertion of the genetic construct into the chromosome is by homologues recombination.

In some embodiments, the promoter before modification to include the tet operator sequence is exogenous or comprises exogenous nucleic acids not normally or naturally found in and/or produced by *H. pylori*. Preferably, the promoter is endogenous or comprises endogenous nucleic acids normally found in and/or produced by *H. pylori* in nature. More preferably, the promoter is a promoter for urease, particularly urease subunit A of *H. pylori*. In some embodiments the promoter is selected from the group consisting of amiE promoter, core urease promoter, revtetR promoter and flaA promoter.

Once obtained the promoter is modified to introduce a tetracycline (tet) operator sequence.

In a third aspect, the present invention provides an isolated, genetically modified *H. pylori* comprising a genetic construct comprising, in the 5'-3' direction: (a) a promoter sequence and (b) a DNA sequence of interest, wherein the promoter sequence comprises a polynucleotide sequence capable of regulating expression of the DNA sequence of interest in *H. pylori* and wherein said promoter sequence is modified to comprise a tetracycline (tet) operator sequence.

In a fourth aspect, the present invention provides an isolated, genetically modified *H. pylori* comprising a genetic construct comprising, in the 5'-3' direction: (a) a promoter sequence; (b) a urease operon; and (c) a gene termination sequence, wherein the promoter sequence comprises a polynucleotide sequence capable of regulating expression of the urease operon in *Helicobacter pylori* and wherein said promoter sequence is modified to comprise a tetracycline (tet) operator sequence.

In a fifth aspect, the present invention provides a method of genetically modifying a *Helicobacter pylori* comprising:
(i) providing a genetic construct comprising, in the 5'-3' direction: (a) a promoter sequence and (b) a DNA sequence of interest, wherein the promoter sequence comprises a polynucleotide sequence capable of regulating expression of the DNA sequence of interest in *Helicobacter pylori* and wherein said promoter sequence is modified to comprise a tetracycline (tet) operator sequence; and
(ii) transforming said *Helicobacter pylori* to produce said genetically modified *Helicobacter pylori*.

In a sixth aspect, the present invention provides an immunogenic composition comprising a genetically modified *Helicobacter pylori* according to the third and fourth aspects, and a pharmaceutically acceptable carrier.

In some embodiments, the immunogenic composition further comprises an adjuvant.

In a seventh aspect the present invention provides a method for protecting a mammal against infection with a pathogenic microorganism comprising the step of administering an immunologically effective amount of an immunogenic composition according to the sixth aspect.

In an eighth aspect the present invention provides a method of controlling the ability of *H. pylori* to colonize the mucosa of a mammal said method comprising the step of metabolically controlling the Lewis antigen of the lipopolysaccharide (LPS) by modifying or deleting the phosphomannose isomerise in said *H. pylori*, wherein the addition of mannose to the diet of said mammal is required to maintain the colonization of the mucosa by the *H. pylori*.

Preferably, the loss of the Lewis antigen results in an improved function of dendritic cells in said mammal.

In some embodiments of the present invention, the *H. pylori* is specifically selected as a useful biological vehicle to deliver agents to the mucosa of a mammal. Preferably, *H. pylori* strains include those deposited at the American Type Culture Collection (ATCC) as ATCC Accession Nos: 43504; 43504D-5; 43526; 43579; 43629; 49396; 49503; 51110; 49503; 51111; 51407; 51652; 51653; 51932; and 53727. Also see, for example, U.S. Pat. No. 5,459,041 incorporated herein by reference. Other preferred strains of *Helicobacter pylori* include strains deposited at the National Measurement Institute under Accession Nos. V09/009,101; V09/009,102; V09/009,103; V10/014,059; V10/014,060 and V09/009,104.

Non-limiting examples of a mammal included in the present invention are a primate, a canine, an equine, a bovine, a porcine, an ovine and a rodent.

The various delivery forms of the compositions are readily prepared for use in the practice of the present invention given the specific types and ratios of specific *H. pylori*, plasmid vectors and other delivery mechanisms described herein, and those formulation techniques known to those in the formulary arts, such as are described in Remington's Pharmaceutical Sciences, 20$^{th}$ edition, Mack Publishing Company, which text is specifically incorporated herein by reference.

BRIEF DESCRIPTION OF FIGURES

FIG. 20 shows cell growth in presence or absence of mannose for 8 clones harboring the mannose shunt.

BRIEF DESCRIPTION OF SEQUENCES

Figure 1:
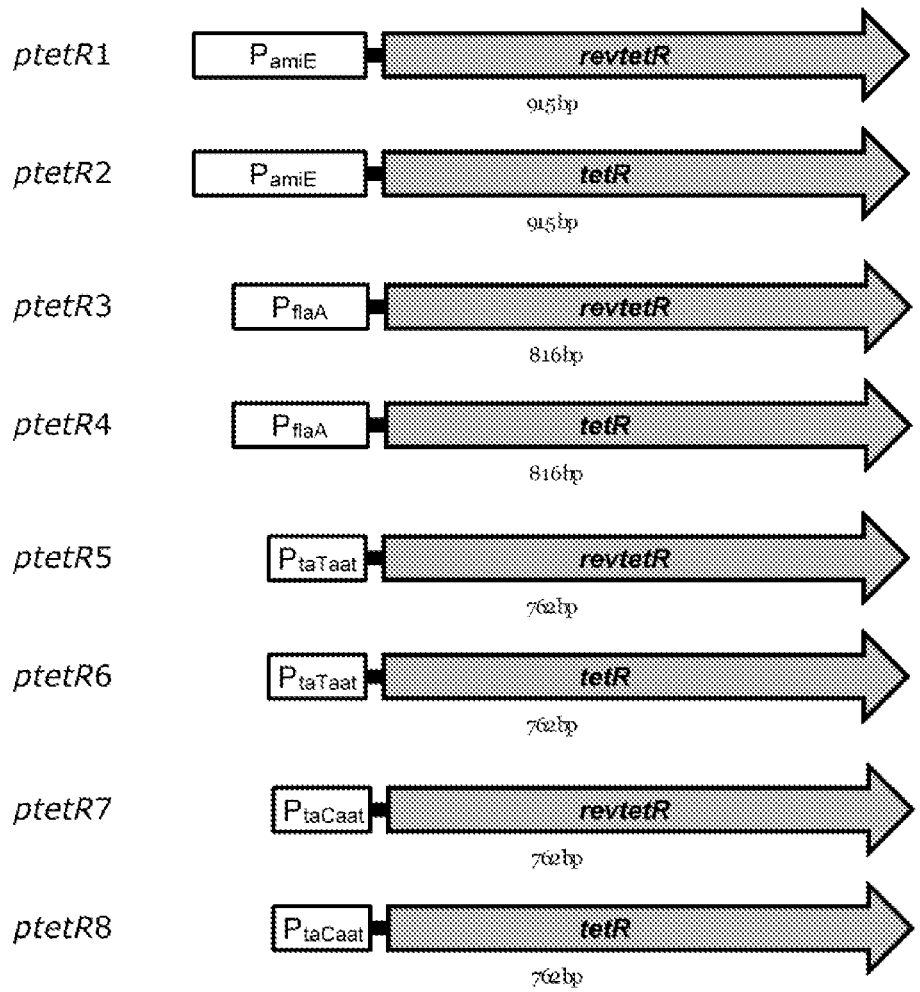
FIG. 1 shows a schematic diagram of ptetR constructs driving expression of TetRs in *H. pylori*.

The following nucleic acid and amino acid sequences are referenced throughout the description of the present invention:

SEQ ID NO:1 pMdaB—derivative of pBlu-SK-alt, contain regions of homology to HP0630 and HP0631, contains multiple cloning site.
SEQ ID NO:2 pMdaB-RCAT—derivative of pMdaB, rpsL-CAT.
SEQ ID NO:3 pMdaB-ptetR1—derivative of pMdaB, PamiE-revtetR.
SEQ ID NO:4 pMdaB-ptetR2—derivative of pMdaB, PamiE-tetR.
SEQ ID NO:5 pMdaB-ptetR3—derivative of pMdaB, PflaA-revtetR.
SEQ ID NO:6 pMdaB-ptetR4—derivative of pMdaB, PflaA-tetR.
SEQ ID NO:7 pMdaB-ptetR5—derivative of pMdaB, PtaTaat-revtetR.
SEQ ID NO:8 pMdaB-ptetR6—derivative of pMdaB, PtaTaat-tetR.
SEQ ID NO:9 pMdaB-ptetR7—derivative of pMdaB, PtaCaat-revtetR.
SEQ ID NO:10 pBlu_uPtetO1-GFP—derivative of pBlu-BI, uPtetO1-GFP.
SEQ ID NO:11 pBlu_uPtetO2-GFP—derivative of pBlu-BI, uPtetO2-GFP.

SEQ ID NO:12 pBlu_uPtetO3-GFP—derivative of pBlu-BI, uPtetO3-GFP.
SEQ ID NO:13 pTrpA—derivative of pBlu-SK-alt, contain regions of homology to HP 1277, contains multiple cloning site.
SEQ ID NO:14 pTrpA-RCAT—derivative of pTrpA, rpsL-CAT.
SEQ ID NO:15 pGltDH—derivative of pBlu-SK-alt, contain regions of homology to HP0379 and HP0380, contains multiple cloning site.
SEQ ID NO:16 pGltDH-RCAT—derivative of pGltDH, rpsL-CAT.
SEQ ID NO:17 pHdapB—derivative of pHSG576, contains regions of homology to HP0509 and HP0511, contains multiple cloning site.
SEQ ID NO:18 pHdapB-RCAT—derivative of pHdapB, rpsL-CAT.
SEQ ID NO:19 urePtetOI—urease promoter harboring two insertions of the tetracycline operator, before −35 and between −35 and −10 positions respectively.
SEQ ID NO:20 urePtetOII—urease promoter harboring one insertion of the tetracycline operator, between −35 and −10 positions.
SEQ ID NO:21 urePtetOIII urease promoter harboring three insertions of the tetracycline operator, before −35, between −35 and −10 and after −10 positions respectively.
SEQ ID NO:22 urePtetOIV—urease promoter harboring two insertions of the tetracycline operator, between −35 and −10 and after −10 positions respectively.
SEQ ID NO:23 urePtetOV—urease promoter harboring one insertion of the tetracycline operator, after −10 position.
SEQ ID NO:24 tet1 ptetR construction.
SEQ ID NO:25 tet2 ptetR construction.
SEQ ID NO:26 tet3 ptetR construction.
SEQ ID NO:27 tet4 ptetR construction.
SEQ ID NO:28 tet5 ptetR construction.
SEQ ID NO:29 tet6 ptetR construction.
SEQ ID NO:30 tet7 ptetR construction.
SEQ ID NO:31 tet8 ptetR construction.
SEQ ID NO:32 tet9 ptetR construction.
SEQ ID NO:33 tet10 ptetR construction.
SEQ ID NO:34 tet11 ptetR construction.
SEQ ID NO:35 tet12 ptetR construction.
SEQ ID NO:36 tet13 ptetR construction.
SEQ ID NO:37 tet14 ptetR construction.
SEQ ID NO:38 mbtet Forward primer for cloning ptetR into pBlu_mdaB.
SEQ ID NO:39 mbtet Reverse primer for cloning ptetR into pBlu_mdaB.
SEQ ID NO:40 ureArcat1 for inactivation of ureA with repsL-CAT.
SEQ ID NO:41 ureArcat2 for inactivation of ureA with repsL-CAT.
SEQ ID NO:42 ureArcat3 for inactivation of ureA with repsL-CAT.
SEQ ID NO:43 ureArcat4 for inactivation of ureA with repsL-CAT.
SEQ ID NO:44 ureArcat5 for inactivation of ureA with repsL-CAT.
SEQ ID NO:45 ureArcat6 for inactivation of ureA with repsL-CAT.
SEQ ID NO:46 ureArcat7 for inactivation of ureA with repsL-CAT.
SEQ ID NO:47 ureArcat8 for inactivation of ureA with repsL-CAT.
SEQ ID NO:48 ureAtetO1 for reconstruction of ureA promoter.
SEQ ID NO:49 ureAtetO2 for reconstruction of ureA promoter.
SEQ ID NO:50 ureAtetO3 for reconstruction of ureA promoter.
SEQ ID NO:51 ureAtetO4 for reconstruction of ureA promoter.
SEQ ID NO:52 ureAtetO5 for reconstruction of ureA promoter.
SEQ ID NO:53 ureAtetO6 for reconstruction of ureA promoter.
SEQ ID NO:54 ureAtetO7 for reconstruction of ureA promoter.
SEQ ID NO:55 ureAtetO8 for reconstruction of ureA promoter.
SEQ ID NO:56 urePseq primer for sequence ureAB promoter.
SEQ ID NO:57 tetOGFP1 for construction of uPtetO-GFP.
SEQ ID NO:58 tetOGFP2 for construction of uPtetO-GFP.
SEQ ID NO:59 tetOGFP3 for construction of uPtetO-GFP.
SEQ ID NO:60 tetOGFP4 for construction of uPtetO-GFP.
SEQ ID NO:61 tetOGFP5 for construction of uPtetO-GFP.
SEQ ID NO:62 tetOGFP6 for construction of uPtetO-GFP.
SEQ ID NO:63 MdaB1 is a pMdaB cloning vector.
SEQ ID NO:64 MdaB2 is a pMdaB cloning vector.
SEQ ID NO:65 MdaB3 is a pMdaB cloning vector.
SEQ ID NO:66 MdaB4 is a pMdaB cloning vector.
SEQ ID NO:67 GltDH1 is a pGltDH cloning vector.
SEQ ID NO:68 GltDH2 is a pGltDH cloning vector.
SEQ ID NO:69 GltDH3 is a pGltDH cloning vector.
SEQ ID NO:70 GltDH4 is a pGltDH cloning vector.
SEQ ID NO:71 TrpA1—a pTrpA cloning vector.
SEQ ID NO:72 TrpA2—a pTrpA cloning vector.
SEQ ID NO:73 TrpA3—a pTrpA cloning vector.
SEQ ID NO:74 TrpA4—a pTrpA cloning vector.
SEQ ID NO:75 DapB1—a pHdapB cloning vector.
SEQ ID NO:76 DapB2—a pHdapB cloning vector.
SEQ ID NO:77 DapB3—a pHdapB cloning vector.
SEQ ID NO:78 DapB4—a pHdapB cloning vector.
SEQ ID NO:79 DapB5—a pHdapB cloning vector.
SEQ ID NO:80 DapB6—a pHdapB cloning vector.
SEQ ID NO:81 MS_NdeI-Cre—forward primer for construction of pTrpA-uPtetO2-Cre.
SEQ ID NO:82 MS_Cre-SalI—reverse primer for construction of pTrpA-uPtetO2-Cre.
SEQ ID NO:83 MS_ureBseq—forward primer for Lox cassette.
SEQ ID NO:84 MS_ureIseq—reverse primer for Lox cassette.
SEQ ID NO:85 MS_NdeI-FliC—forward primer for construction of pMA-IEC-Ts-FliCsyn.
SEQ ID NO:86 MS_FliC-SalI—reverse primer for construction of pMA-IEC-Ts-FliCsyn.
SEQ ID NO:87 Cre *H. pylori* codon optimized.
SEQ ID NO:88 Lox6671 cassette.
SEQ ID NO:89 tetRs *H. pylori* codon optimized.
SEQ ID NO:90 1uPtetO5.
SEQ ID NO:91 2uPtetO5.
SEQ ID NO:92 3uPtetO5.
SEQ ID NO:93 4uPtetO5.
SEQ ID NO:94 5uPtetO5.
SEQ ID NO:95 6uPtetO5.
SEQ ID NO:96 pTrpA-as4uPtetO5-Cre.
SEQ ID NO:97 IEC-LLO.
SEQ ID NO:98 fliCsyn *H. pylori* codon optimized.
SEQ ID NO:99 IEC-Ts-fliCsyn.
SEQ ID NO:100 pHel2-IEC-Ts-FliCsyn.

DEFINITION OF TERMS

As used herein, certain terms may have the following defined meanings. As used in the specification and claims, the singular forms "a", "an" and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All strains of *H. pylori* are included in the scope of the present application as long as they have a functional urease gene. Particularly preferred strains of *H. pylori* include strains deposited at the American Type Culture Collection (ATCC) as ATCC Accession Nos: 43504; 43504D-5; 43526; 43579; 43629; 49396; 49503; 51110; 49503; 51111; 51407; 51652; 51653; 51932; and 53727. Also see, for example, U.S. Pat. No. 5,459,041 incorporated herein by reference. Other preferred strains of *Helicobacter pylori* include strains deposited at the National Measurement Institute under Accession Nos. V09/009,101; V09/009,102; V09/009,103; V10/014, 059; V10/014,060 and V09/009,104.

As used herein the term "isolated" is meant to describe a *H. pylori* cell, a polynucleotide or a polypeptide that is in an environment different from that in which the *H. pylori* cell, polynucleotide or polypeptide naturally occurs. An isolated genetically modified *H. pylori* cell may be present in a mixed population of *H. pylori* cells.

A "genetically modified" *H. pylori* refers to a *H. pylori* bacterium that differs in its pheno- and/or genotype from that of the corresponding wild type *H. pylori*. More specifically, a genetically modified *H. pylori* of the present invention is one that has been transformed with a genetic construct of the present invention. Methods for the genetic modification of bacteria in general including *H. pylori* are well-known in the art; cf. for example Sambrook, J. and Russell, D. W. (2001), "Molecular Cloning—A Laboratory Manual", Cold Spring Harbor Laboratory Press, New York, $3^{rd}$ Edition.

The term "urease" or "urease operon" refers to the genes encoding urease of *H. pylori* that have been described and sequenced (see, for example, Labigne et al., (1991), *J. Bacteriol.*, 173: 1920-1931). Of the seven genes involved in urease expression and secretion, only two genes encode the two structural subunits urease A and B of the urease enzyme. These two polypeptides form a polypeptide complex (operon) having urease activity.

Urease activity can be determined a number of ways. For example, it is known that urease converts urea into ammonium carbonate, which then decomposes into ammonia and carbon dioxide. Consequently, in the past, one test for detecting the presence of *H. pylori* included the steps of contacting a sample of gastric material with a composition containing urea and an indicator, namely a pH indicator that changes colour when there is a rise in pH. If urease is present within the gastric material it breaks down the urea, which results in the formation of ammonia after further decomposition and causes the pH indicator to change colour. *H. pylori* urease activity can also be detected by orally administering urea to a subject with subsequent monitoring of the exhaled dioxide and ammonia. Various test for urease activity are described in U.S. Pat. No. 4,748,113 and US Pat. Applic. No. 20030082664, which are incorporated herein by reference.

The term "functional fragment" when used herein, refers to any fragment of the polynucleotide, polypeptide or the like (i.e. a molecule which is reduced in size or truncated compared with the naturally occurring form) that still has the ability to function in the same fashion as the naturally occurring molecule.

The term "nucleic acid" used herein refers to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Percent identity (homology)" of two amino acid sequences or of two nucleic acids is determined using the algorithm of Karlin and Altschul, 1990, *Proc. Natl. Acad. Sci. USA*, 87:2264-2268, 1990, modified as in Karlin & Altschul (*Proc. Natl. Acad. Sci. USA* 90:5873-5877, 1993). Such an algorithm is incorporated into the NBLAST and XBLAST programs of Altschul et al. (*J. Mol. Biol.* 215:403-410, 1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide (eg., SEQ ID NO: 2). To obtain gapped alignments for comparison purposes, Gapped BLAST is utilised as described in Altschul et al. (*Nucleic Acids Res.* 25:3389-3402, 1997). When utilising BLAST and Gapped BLAST programs, the default parameters of the respective programs (eg., XBLAST and NBLAST) are used. These maybe found on the World Wide Web at the URL "ncbi.nim.nih.gov."

As used herein, the term "exogenous nucleic acid" refers to a nucleic acid that is not normally or naturally found in and/or produced by *H. pylori* in nature. As used herein, the term "endogenous nucleic acid" refers to a nucleic acid that is normally found in and/or produced by *H. pylori* in nature. An "endogenous nucleic acid" is also referred to as a "native nucleic acid" or a nucleic acid that is "native" to *H. pylori*.

The term "heterologous nucleic acid," as used herein, refers to a nucleic acid wherein at least one of the following is true: (a) the nucleic acid is foreign ("exogenous") to (i.e., not naturally found in) *H. pylori*; (b) the nucleic acid comprises a nucleotide sequence that is naturally found in (e.g., is "endogenous to") *H. pylori* (e.g., the nucleic acid comprises a nucleotide sequence that is endogenous to *H. pylori*) but is either produced in an unnatural (e.g., greater than expected or greater than naturally found) amount in the cell, or differs in sequence from the endogenous nucleotide sequence such that the same encoded protein (having the same or substantially the same amino acid sequence) as found endogenously is produced in an unnatural (e.g., greater than expected or greater than naturally found) amount in the cell; (c) the nucleic acid comprises two or more nucleotide sequences or segments that are not found in the same relationship to each other in nature, e.g., the nucleic acid is recombinant.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms.

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a *H. pylori* cell.

The terms "tet", "tet repressor" or "TetR" are used herein interchangeably and refer to the tet repressor inducible system.

The term "transformation" is used interchangeably herein with "genetic modification" and refers to a permanent or transient genetic change induced in a *H. pylori* cell following introduction of new nucleic acid. Genetic change ("modification") can be accomplished either by incorporation of the new DNA into the genome of the *H. pylori* cell, or by transient or stable maintenance of the new DNA as an episomal element such as a plasmid or expression vector, which may contain one or more selectable markers to aid in their maintenance in the recombinant *H. pylori* cell. Suitable methods of genetic modification include transfection, conjugation, protoplast fusion, electroporation, particle gun technology, calcium phosphate precipitation, direct microinjection, and the like. A general discussion of these methods can be found in Ausubel et al., Short Protocols in Molecular Biology, $3^{rd}$ ed., Wiley & Sons, 1995.

"Transforming nucleic acid sequence" as used herein means a plasmid vector, or other expression cassette containing a nucleic acid sequence encoding a genetic construct of the present invention. In some embodiments of the present invention the nucleic acid sequence can encode one or more antigens. "Transforming nucleic acid sequence" can also be used to mean a "transgene" in accordance with certain embodiments of the present invention. In another embodiment of the present invention the transforming nucleic acid sequence includes nucleic acid sequence encoding for a promoter and/or other regulatory elements.

A "genetic construct" is a nucleic acid sequence comprised of at least two elements (a) a promoter sequence and (b) a DNA sequence of interest, preferably an operon encoding urease subunits A and B. In some embodiments, the genetic construct also comprises (c) a gene termination sequence.

"Operably linked" refers to a juxtaposition wherein the components so described are in a relationship permitting them to function in their intended manner. For instance, a promoter is operably linked to a coding sequence if the promoter effects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

The term "promoter", when used with reference to the genetic construct of the present invention refers to a polynucleotide sequence capable of regulating expression of a DNA sequence of interest or urease operon in *H. pylori* in vitro and in vivo. More specifically, the promoter sequence has been modified to comprise a tetracycline (tet) operator sequence as defined herein. In some embodiments, the promoter is endogenous to *H. pylori*. In some embodiments the promoter is selected from the group consisting of amiE promoter, core urease promoter, revtetR promoter and flaA promoter.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A "vaccine composition", "vaccine", "immunogenic composition", and similar terms refer to a composition comprising a strain of live, genetically modified *H. pylori* that expresses a genetic construct of the present invention, such that when administered to a mammal, the *H. pylori* will establish a chronic infection and elicit an immune response in the mammal against the *H. pylori* per se or the expressed product of the DNA of interest as defined herein, For example, if the DNA of interest codes for an antigen then the immune response in the mammal will be against the antigen(s) expressed in the *H. pylori* and, thereby, provide at least partial protective immunity against the antigen. Such protective immunity may be evidenced by any of a variety of observable or detectable conditions, including but not limited to, diminution of one or more disease symptoms, shorter duration of illness, diminution of tissue damage, regeneration of healthy tissue, clearance of pathogenic microorganisms from the mammal, and increased sense of well being by the mammal. Although highly desired, it is understood by persons skilled in the art that no vaccine is expected to induce complete protection from a disease in every individual that is administered the vaccine or that protective immunity is expected to last throughout the lifetime of an individual without periodic "booster" administrations of a vaccine composition. It is also understood that a live vaccine comprising a genetically modified *H. pylori* described herein may be, at the discretion of a healthcare professional, administered to an individual who has not presented symptoms of disease, but is considered to be at risk of infection or is known to already have been exposed to a disease, e.g., by proximity or contact with infected mammals or contaminated air, liquids, or surfaces.

A "therapeutically effective amount" of a genetically modified *H. pylori* of the present invention as described herein is understood to comprise an amount effective to elicit the desired response but insufficient to cause a toxic reaction. A desired response, for example, may constitute the formation of a sufficient and/or acceptable detectable antibody titer level in a blood sample. The dosage and duration of treatment of the preparation to be administered to a mammal will be determined by the health professional attending the mammalian subject in need of treatment, and will consider the age, sex and weight of the subject, and the specific *H. pylori* and nucleic acid molecule being expressed.

The terms "oral", "enteral", "enterally", "orally", "non-parenteral", "non-parenterally", and the like, refer to administration of a genetically modified *H. pylori* of the present invention to a mammal by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein to the lower intestinal tract of the alimentary canal.

The term "inducing immune tolerance to an antigen," comprises mucosal delivery of a product of the DNA of interest eg antigen, by an isolated, genetically modified *H. pylori* secreting said product for the preparation of a medicament, medical food or nutraceutical for mucosal delivery.

A "heterologous" antigen is one not native to *H. pylori*, i.e., not expressed by *H. pylori* in nature or prior to introduction into *H. pylori*.

"Detectable immune response" as used herein is either an antibody (humoral) or cytotoxic (cellular) response formed in a mammal in response to an antigen that can be measured using routine laboratory methods including, but not limited to enzyme-linked immunosorbant assays (ELISA), radio-immune assays (RIA), Enzyme-linked ImmunoSPOT (ELISPOT), immunofluorescent assays (IFA), complement fixation assays (CF), Western Blot (WB) or an equivalent thereto.

"Colonizing the mucosa" as used herein refers to the ability of the *Helicobacter* strains of the present invention to establish an infection, preferably a chronic infection, in or on the lining of mammalian tissue including, but not limited to buccal mucosa, esophageal mucosa, gastric mucosa, nasal mucosa, bronchial mucosa and uterine mucosa. Preferably, the mucosa is the gastric mucosa.

"Chronic infection" as used herein means an infection that has a long duration of the order of weeks or months in contrast to "acute infection" or "transient infection" which last a short duration of the order of several days.

DESCRIPTION OF THE PREFERRED EMBODIMENTS

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional techniques of pharmacology, molecular biology (including recombinant techniques), cell biology, biochemistry, and immunology, which are within the skill of the art. Such techniques are well known to the skilled worker, and are explained fully in the literature. See, eg., Coligan et al. "Current protocols in Protein Science" (1999) Volume I and II (John Wiley & Sons Inc.); Sambrook et al., (Molecular Cloning: A Laboratory Manual, $2^{nd}$ & $3^{rd}$ Editions, Cold Spring Harbor Laboratory press (1989) (2001); and Bailey, J. E. and Ollis, D. F., Biochemical Engineering Fundamentals, McGraw-Hill Book Company, NY, 1986; "Oligonucleotide Synthesis" (M. J. Gait, ed., 1984); "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodicals) "Polymerase Chain Reaction" (Mullis et al., eds., 1994); and "Current Protocols in Immunology" (J. E. Coligan et al., eds., 1991).

In the broadest aspect, the present invention provides a genetic construct comprising, in the 5'-3' direction: (a) a promoter sequence and (b) a DNA sequence of interest, wherein the promoter sequence comprises a polynucleotide sequence capable of regulating expression of the DNA sequence of interest in *Helicobacter pylori* and wherein said promoter sequence is modified to comprise a tetracycline (tet) operator sequence.

As described elsewhere, the preferable promoter is a promoter from *H. pylori*, which is capable of regulating the expression of a gene "downstream" from the promoter. Particularly preferred promoters are those associated with the urease operon, especially UreA. Methods of isolating the promoter are well known in the art, but briefly genomic DNA obtained from an isolate of *H. pylori* is inserted into a suitable shuttle vector, e.g., a shuttle plasmid with selectable markers, e.g., antibiotic markers by standard techniques. Broadly, a suitable shuttle vector will include one, two, three or more of the following features, a cloning site, a *H. pylori* origin of replication, an *E. coli* origin of replication, and an antibiotic resistance gene and/or selectable marker. Art-known vectors suitable for this purpose, or readily adaptable for this purpose include, for example, the recombinant shuttle plasmid pHR106 described by Roberts et al. (*Appl Env Mircobiol.*, 54: 268-270 (1988)); the PJIR 750 and PJIR 751 plasmids described by Bannam et al. (*Plasmid*, 29:233-235 (1993)); the promoterless PPSV promoter selection vector of Matsushita et al. (Plasmid, 31, 317-319 (1994)), the shuttle plasmids pJIR1456 and pJIR1457, described by Lyras et al. (*Plasmid*, 39, 160-164 (1988)); and the pAK201 shuttle vector described by Kim et al. (*Appl Environ Microbiol.*, 55, 360-365 (1989)), the contents of which are incorporated herein by reference in their entireties. Removal of the *H. pylori* origin of replication converts the shuttle vector into a suicide vector.

The promoter is then altered or modified to introduce the coding sequence for a tetracycline (tet) operator sequence. The alterations to the promoter can be made using methods known in the art such as oligonucleotide-mediated (site-directed) mutagenesis and PCR mutagenesis. Site-directed mutagenesis (Carter et al., (1986), *Nucl. Acids Res.*, 13:4331; Zoller et al., (1987), *Nucl. Acids Res.*, 10:6487), cassette mutagenesis (Wells et al., (1985), *Gene*, 34:315), restriction selection mutagenesis (Wells et al., (1986), *Philos. Trans. R. Soc. London SerA*, 317:415) or other known techniques can be performed on cloned DNA to produce an urease variant DNA.

Once the coding sequence for a tetracycline (tet) operator sequence has been introduced the basic genetic construct of the present invention is produced. Then nucleic acid transfer protocols are used including transformation/transfection, electroporation, liposome mediated nucleic acid transfer, N-[1-(2,3-Dioloyloxy)propyl]-N,N,N-trimethylammonium methylsulfate meditated transformation, and others to introduce the genetic construct in to selected *H. pylori*. One skilled in the art will be readily able to select the appropriate tools and methods for the selection of *H. pylori* that have been successfully transformed according to the knowledge in the art and design choice.

In one embodiment of the present invention, the genetically modified *H. pylori* is modified such that the *H. pylori* requires mannose and/or galactose supplementation in the mammalian hosts diet in order to maintain the infection by the *H. pylori*. As stated elsewhere, one purpose of the present invention is to produce genetically modified *H. pylori* that can safely be used as a biological delivery vehicle for the expression of foreign peptides eg antigens. In order for this to be achieved a *H. pylori* strain is required that can establish an infection of the mucosa of a mammal long enough that the peptide is expressed. Once the genetically modified *H. pylori* has expressed the foreign agent it is preferably removed. One way of removing the genetically modified *H. pylori* is the use of tet system described herein. Another method is the use of a sugar shunt. *Helicobacter* genome analysis shows that mannose is made from glucose only. It is known that *H. pylori* LPS is decorated with Lewis antigens (fucose and galactose) that are essential for colonisation and immune-modulation through the DC sign receptor of dendritic cells. Thus, metabolic control of the Lewis antigen of the LPS can provide control of *H. pylori* colonisation/eradication and immune-modulation, respectively. In one embodiment, the phosphomannose isomerase (HP0043) of *H. pylori* is deleted to produce a genetically modified *H. pylori* that requires mannose supplementation to maintain colonization.

The invention will now be further described by reference only to the following non-limiting examples. It should be understood, however, that the examples following are illustrative, and should not be taken in any way as a restriction on the generality of the invention described herein.

Example 1

Construction of *H. pylori* Strains Expressing TetR and revTetR

Figure 2:
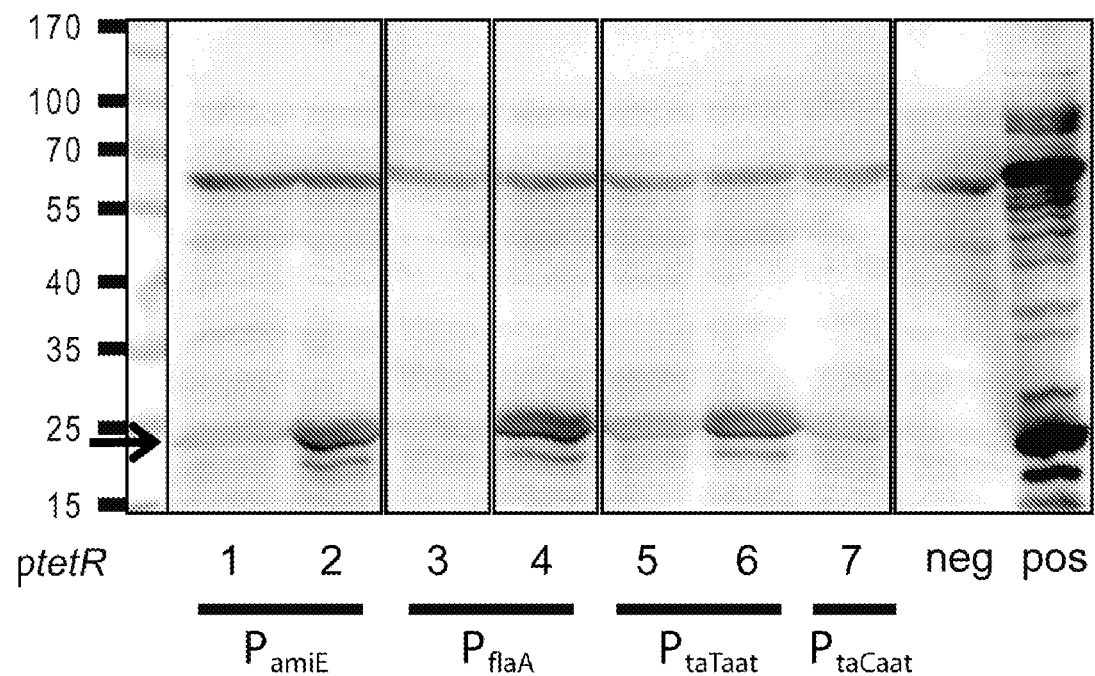
FIG. 2 shows a Westernblot analysis of expression of TetRs by *H. pylori* X47 strains mdab::ptetR 1-7. *E. coli* strain transformed with pMdaB-ptetR6 served as a positive control (pos). X47 recipient strain mdab::rpsL-CAT served as a negative control (neg). TetRs were detected using polyclonal rabbit anti TetR antibody at 1:2000 dilution. The TetR protein band is indicated by black arrow.
Figure 10:
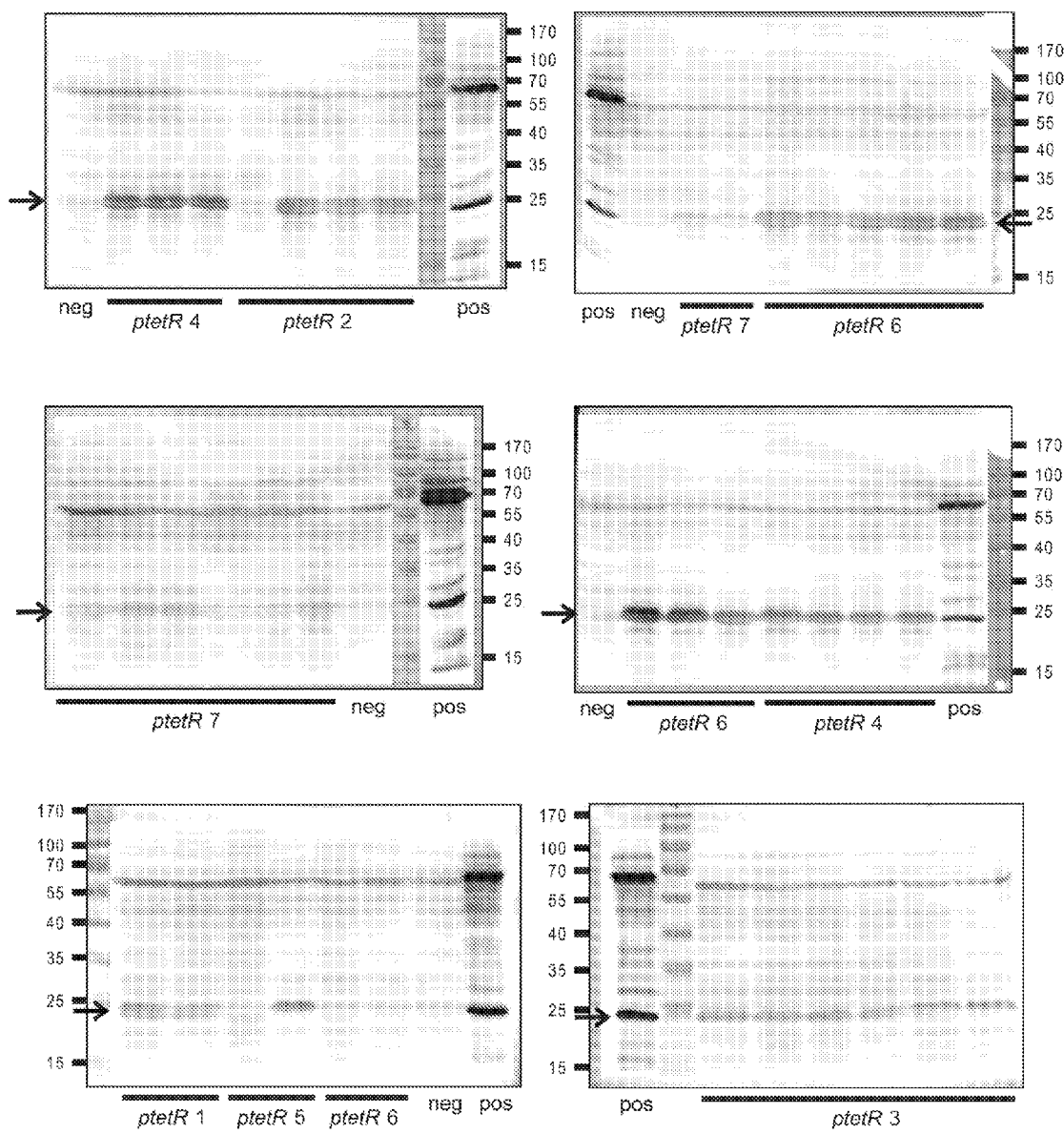
FIG. 10 shows Westernblot analysis of expression of TetRs by *H. pylori* X47 strains mdab::ptetR1-7. *E. coli* strain transformed with pMdaB-ptetR6 served as a positive control (pos). X47 recipient strain mdab::rpsL-CAT served as a negative control (neg). The TetR proteins band is indicated by black arrow.
Figure 11:
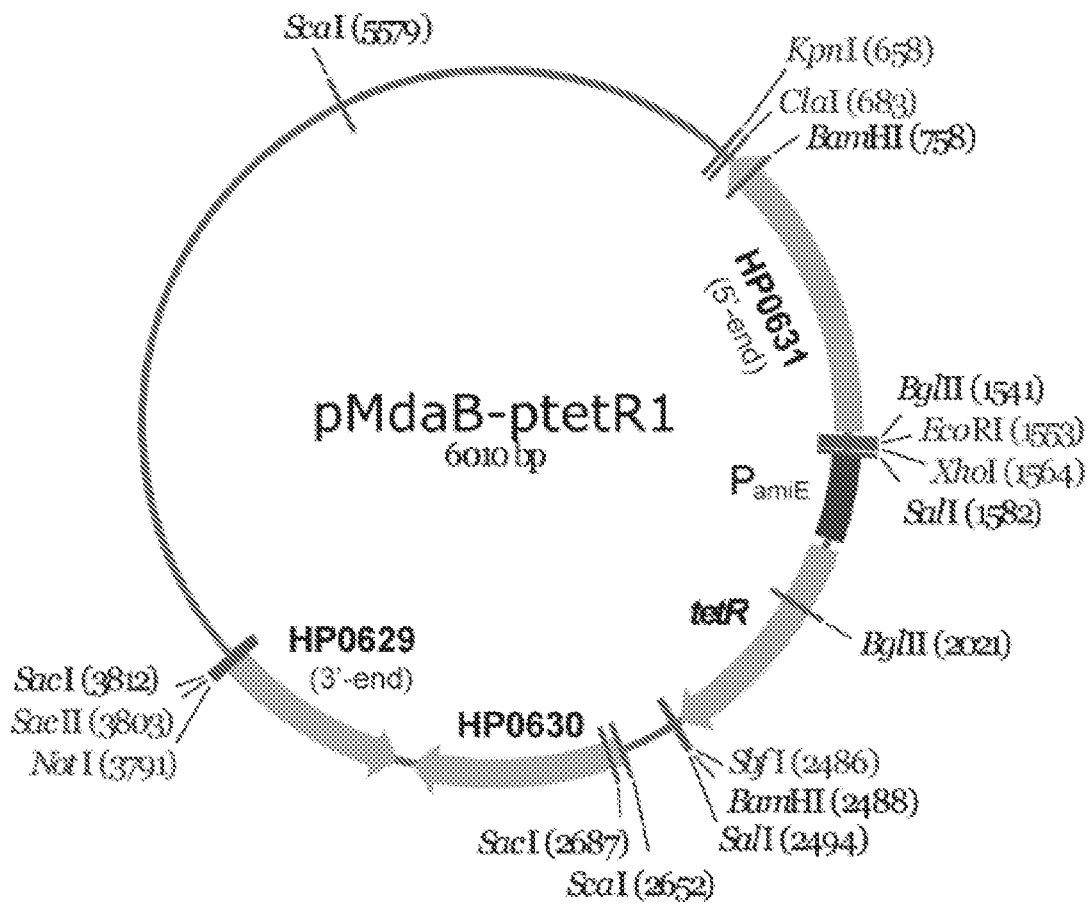
FIG. 11 shows vector map of pMdaB-ptetR, used for targeted integration into the *H. pylori* genome at the mdaB locus.

In order to express the tetracycline repressors, four different *H. pylori* promoters were selected, the amiE, flaA and both the wild-type and mutated core promoter of the urease operon (Davies et al. 2002). Sequences encoding tetR and revtetR were fused to each *H. pylori* promoter by multiple fusions PCR to generate a panel of promoter-tetR (ptetR1-8) constructs (FIG. 1). These constructs were cloned into the pMdaB plasmid generating plasmids pMdaB-ptetR1-8 (FIG. 11). Natural transformation of the recipient strain *H. pylori* X47 (X47 mdaB::rpsL-CAT) with these plasmids allowed for insertion of ptetR(1-7) promoters into the chromosome at the mdaB locus by homologous recombination. Expression of TetR and revTetR in these X47 mdaB::ptetR strains was analyzed by immunobloting. The expression of TetRs in the X47 mdaB::ptetR strains is significantly lower compared to the *E. coli* positive control (pos) (FIG. 2 and FIG. 10). The signal intensity of the TetR expressing strains is greater than the equivalent revTetR expressing strains.

Example 2

Construction of *H. pylori* Tetracycline Responsive Promoters

Figure 3:
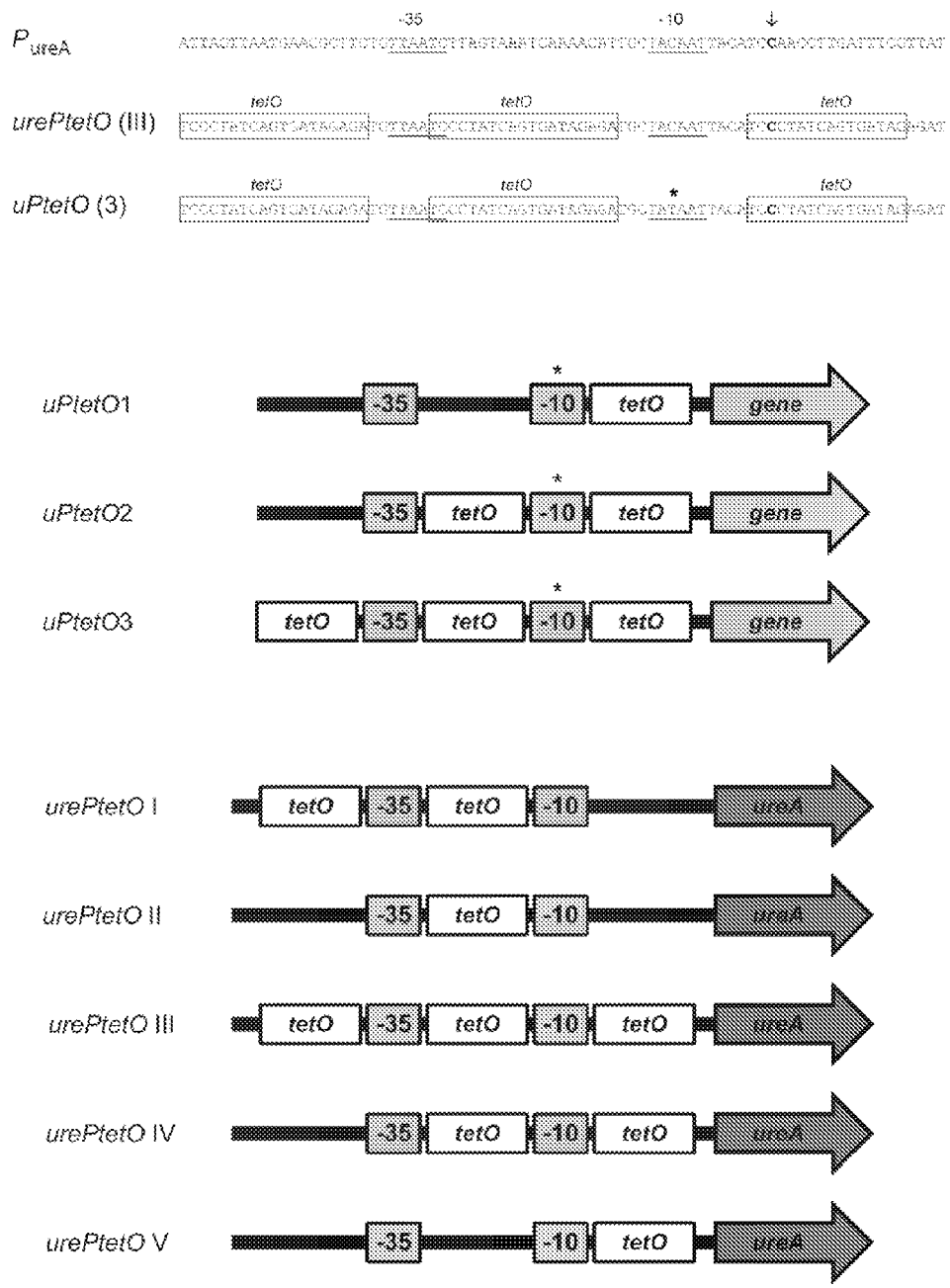
FIG. 3 shows tetracycline responsive promoters. (A) Nucleotide sequence of wild-type ureA promoter, $P_{ureA}$, (SEQ ID NO:109) and tetracycline responsive promoters urePtetOIII (SEQ ID NO: 101) and uPtetO(3) (SEQ ID NO: 102). −10 and −35 promoter sequences are underlined. Tet operator sequences are indicated by boxes. Arrow indicates transcriptional start point and star indicates the C to T mutation in the −10 box found in the uPtetO constructs. (B) Representative diagram of the uPtetO constructs. White tetO boxes indicate where the wild type $P_{ureA}$ promoter sequence has been replaced with tetO sequences (C) Representative diagram of the urePtetO constructs.

To generate a tetracycline responsive promoter, one or more tet operator (tetO) sequences were introduced into the ureA promoter sequence while trying to minimize disruption of key promoter elements. Three main sites were identified for tetO introduction, upstream of the −35 box, between the −35 and −10 box and just downstream of the transcriptional start point (FIG. 3A). Two sets of tet responsive promoters were designed. The first set of tet responsive promoters, uPtetO(1-3), was designed to drive and regulate expression of the target gene at any region in the *H. pylori* chromosome. They consist of the core ureA promoter containing a C to T mutation in the −10 box and one or more tetO sites (FIG. 3B). The second set of tet responsive promoters, urePtetO(I-V), was designed to regulate expression of ureA and ureB (urease operon) at their native locus. Several promoter constructs containing up to three tetO sites in different locations were designed and constructed using PCR methodology (FIG. 3C) and used to generate X47 *H. pylori* strains harbouring one or more tetO sites in the ureA promoter, named urePtetO.

Figure 4:
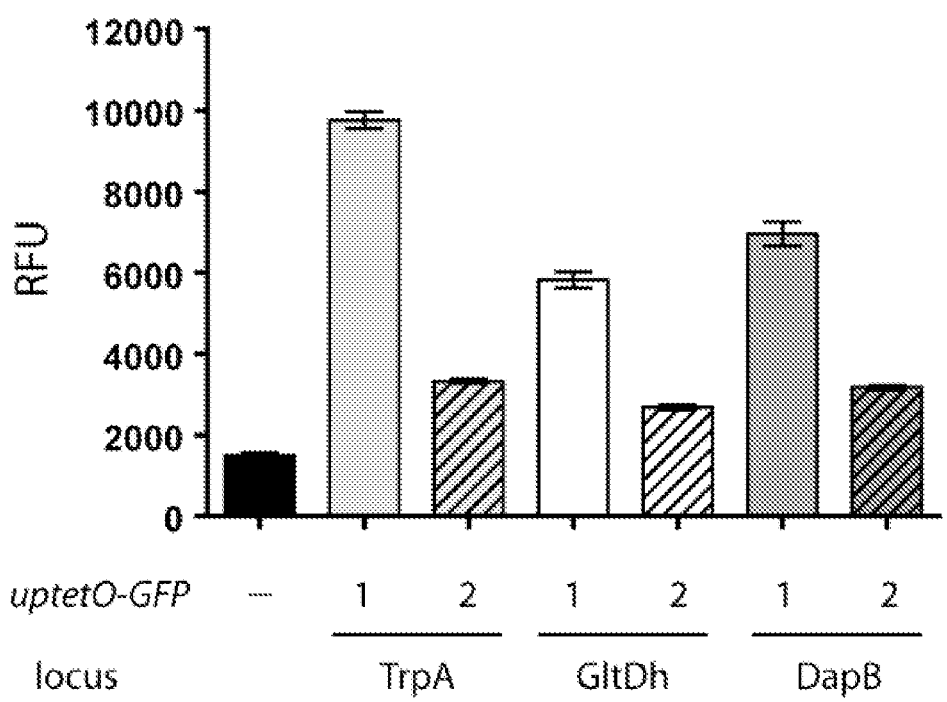
FIG. 4 shows GFP expression driven by uPtetO in *H. pylori*. Bacteria were transformed as indicated and grown in BHI to log phase ($OD_{600}$=0.5) and GFP activities were determined 24 hours later. The fluorescence intensity was normalized to the cell density and expressed in relative fluorescence units. Data are averages and error bars represent standard deviations. GFP activities of uptetO1 (open bars) and uptetO2 (hatch bars) strains that do not express TetR compared to wild-type auto fluorescence.
Figure 5:
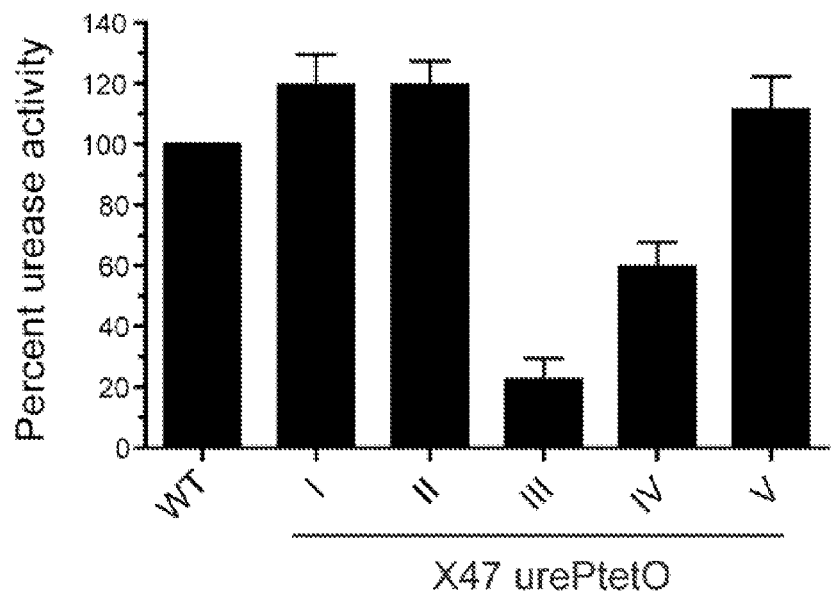
FIG. 5 shows urease expression by urePtetO in *H. pylori*. (A) Urease activity of X47 urePtetO strains. Urease activity is expressed as a percentage of wild-type parent (WT) urease activity. The urePtetO construct is specified under the bars. (B) Two week colonization of C57BL/6J mice by X47 strains with modified ureA promoter. Modifications to the ureA promoter did not prevent colonization. Colonization studies were done without prior adaptation of X47 urePtetO strains to mice.
Figure 5:
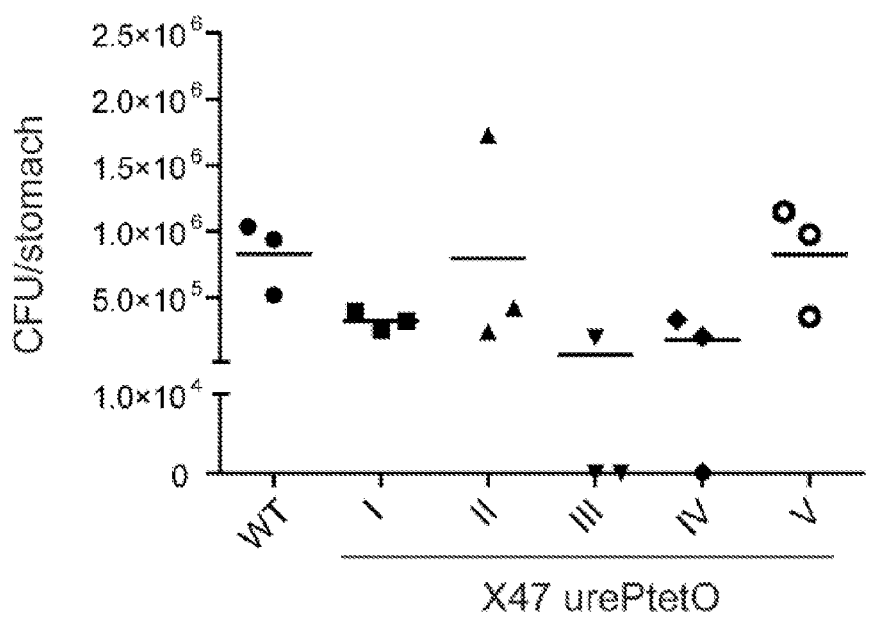

The strength of the uPtetO promoters in the absence of the tet repressor was evaluated at three different recipient loci using a reporter gene, gfp(mut2) (Cormack et al. 1996). GFP activity was greater in X47 strains harbouring uPtetO1 compared to strains with uPtetO2 and quantification of GFP activity showed that strength of uPtetO1 and uPtetO2 was also dependent on the recipient locus as GFP activity was greater in strains expressing GFP from the trpA locus as compared to the gltDH and dapB loci (FIG. 4). The urease activity of the urePtetO(I-V) strains was evaluated using urease activity assay and compared to the wild-type parent strain (FIG. 5). The urease activity in strains harbouring urePtetOI, II and V was similar to the wild-type parent strain, while urease activity was 75% lower in strains with urePtetOIII and 40% lower in strains with urePtetOIV. In order to rule out the occurrence of secondary mutations, arising during the genetic engineering of X47 urePtetO strains, that would affect colonization and to assess what level of urease expression is required for colonization, the recombinant strains were evaluated for their ability to colonize C57BL/6J mice (FIG. 5). The gastric colonization load was evaluated a week after oral challenge. All strains were successfully re-isolated from mice stomachs. The infection rate and load was reduced in strains urePtetOIV and urePtetOIII. Finally, the ureA promoter region was sequenced in the clones re-isolated from infected mouse stomachs and urePtetO sequences were found to be stable after passage through mice (data not shown).

Example 3

Regulation of uPtetO with ATc in *H. pylori*

GFP was used as a reporter to measure the induction and repression potential of uPtetO1 and uPtetO2 promoters. X47 mdaB::ptetR recipient strains were transformed with uPtetO-GFP constructs to generate a panel of strains expressing both GFP and TetR5 (Table 1).

TABLE 1

X47 Strains With Tetracycline Responsive GFP Expression

| Strain promoter | expression state | Tetracycline − | Tetracycline + |
|---|---|---|---|
| mdaB:: ptetR1; gltDH:: uPtetO1-GFP | amiE | ON | OFF |
| mdaB:: ptetR1; gltDH:: uPtetO2-GFP | amiE | ON | OFF |
| mdaB:: ptetR1; trpA:: uPtetO1-GFP | amiE | ON | OFF |
| mdaB:: ptetR1; trpA:: uPtetO2-GFP | amiE | ON | OFF |
| mdaB:: ptetR1; dapB:: uPtetO1-GFP | amiE | ON | OFF |
| mdaB:: ptetR1; dapB:: uPtetO2-GFP | amiE | ON | OFF |
| mdaB:: ptetR2; gltDH:: uPtetO1-GFP | amiE | OFF | ON |
| mdaB:: ptetR2; gltDH:: uPtetO2-GFP | amiE | OFF | ON |
| mdaB:: ptetR2; trpA:: uPtetO1-GFP | amiE | OFF | ON |
| mdaB:: ptetR2; trpA:: uPtetO2-GFP | amiE | OFF | ON |
| mdaB:: ptetR2; dapB:: uPtetO1-GFP | amiE | OFF | ON |
| mdaB:: ptetR2; dapB:: uPtetO2-GFP | amiE | OFF | ON |
| mdaB:: ptetR3; gltDH:: uPtetO1-GFP | flaA | ON | OFF |
| mdaB:: ptetR3; gltDH:: uPtetO2-GFP | flaA | ON | OFF |
| mdaB:: ptetR3; trpA:: uPtetO1-GFP | flaA | ON | OFF |
| mdaB:: ptetR3; trpA:: uPtetO2-GFP | flaA | ON | OFF |
| mdaB:: ptetR3; dapB:: uPtetO1-GFP | flaA | ON | OFF |
| mdaB:: ptetR3; dapB:: uPtetO2-GFP | flaA | ON | OFF |
| mdaB:: ptetR4; gltDH:: uPtetO1-GFP | flaA | OFF | ON |
| mdaB:: ptetR4; gltDH:: uPtetO2-GFP | flaA | OFF | ON |
| mdaB:: ptetR4; trpA:: uPtetO1-GFP | flaA | OFF | ON |
| mdaB:: ptetR4; trpA:: uPtetO2-GFP | flaA | OFF | ON |
| mdaB:: ptetR4; dapB:: uPtetO1-GFP | flaA | OFF | ON |
| mdaB:: ptetR4; dapB:: uPtetO2-GFP | flaA | OFF | ON |
| mdaB:: ptetR5; gltDH:: uPtetO1-GFP | taTaat | ON | OFF |
| mdaB:: ptetR5; gltDH:: uPtetO2-GFP | taTaat | ON | OFF |
| mdaB:: ptetR5; trpA:: uPtetO1-GFP | taTaat | ON | OFF |
| mdaB:: ptetR5; trpA:: uPtetO2-GFP | taTaat | ON | OFF |
| mdaB:: ptetR5; dapB:: uPtetO1-GFP | taTaat | ON | OFF |
| mdaB:: ptetR5; dapB:: uPtetO2-GFP | taTaat | ON | OFF |
| mdaB:: ptetR6; gltDH:: uPtetO1-GFP | taTaat | OFF | ON |
| mdaB:: ptetR6; gltDH:: uPtetO2-GFP | taTaat | OFF | ON |
| mdaB:: ptetR6; trpA:: uPtetO1-GFP | taTaat | OFF | ON |
| mdaB:: ptetR6; trpA:: uPtetO2-GFP | taTaat | OFF | ON |

Figure 6:
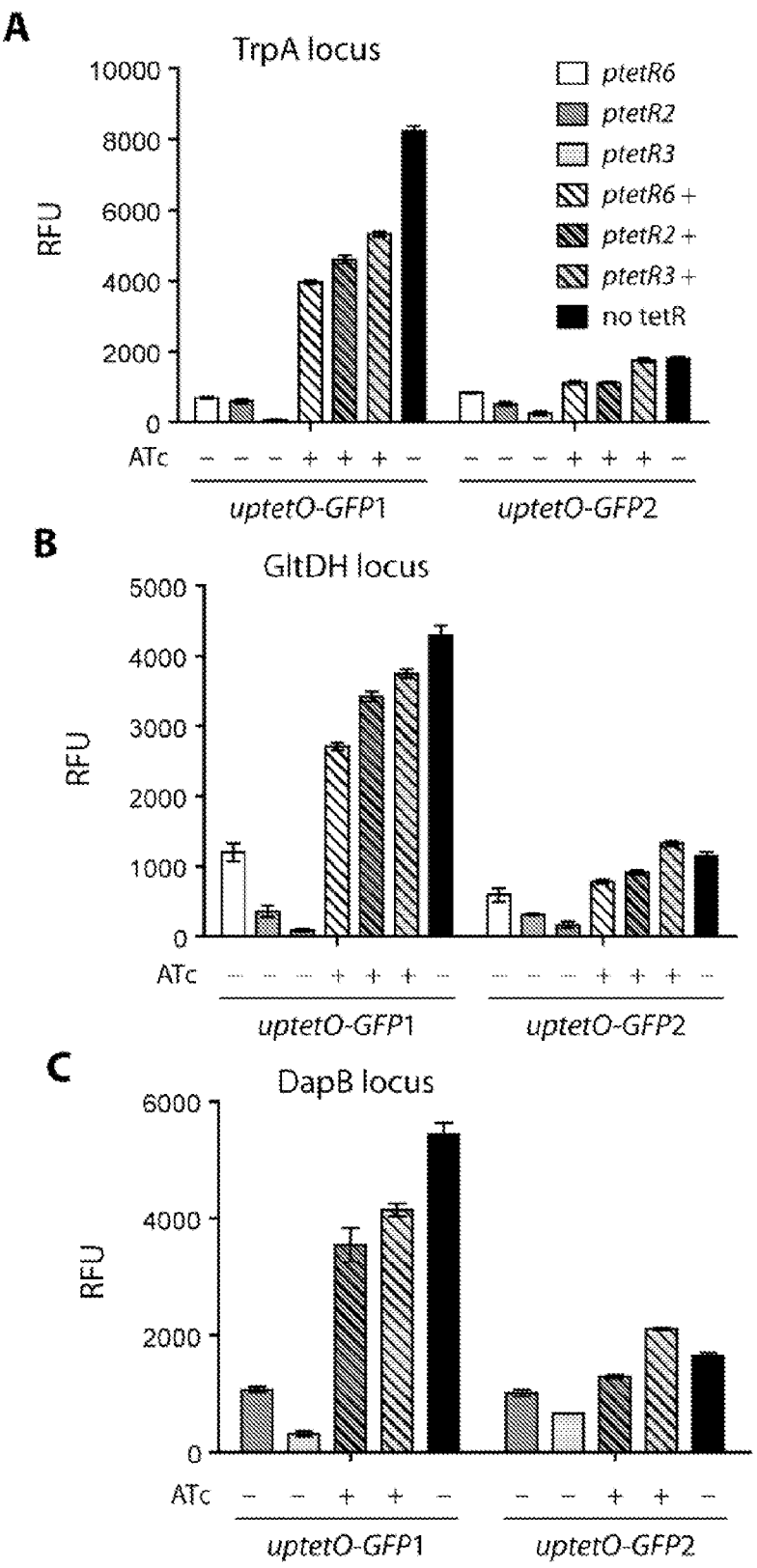
FIG. 6 shows Tet regulation of GFP expression in *H. pylori*. Comparison of GFP induction in strains with different ptetR constructs. Bacteria were transformed as indicated and grown in BHI to log phase ($OD_{600}$=0.5) before 100 ng/mL ATc was added (hatch bars). GFP activities were determined twenty four hours later. Vectors uptetO GFP1 and uptetO-GFP2 have been transformed into either the (A) TrpA, (B) GltDH, or (C) DapB locus. Three independently generated clones were used to measure GFP activities for each construct. All fluorescence measurements were carried out in triplicate. The fluorescence intensity was normalized to the cell density and expressed in relative fluorescence units. Data are averages and error bars represent standard deviations.

Anhydrotetracycline (ATc), a derivative of tetracycline with a very high binding affinity for both TetR and revTetR and low toxicity and antibiotic activity (Gossen & Bujard 1993; Kamionka et al. 2004), was used as an inducer to measure the induction and repression of uPtetO1 and uPtetO2. Based on the observed fluorescence intensities, addition of 50 ng/mL ATc to blood agar plates resulted in induction or repression of GFP expression in strains expressing TetR or revTetR respectively. Addition of 100 ng/mL ATc to TetR expressing strains grown in BHI media resulted in 4-9 fold induction of GFP expression for ptetR2 uPtetO1, 13-80 fold for ptetR4 uPtetO1 and 2-5 fold ptetR6 uPtetO1 at all three recipient loci. GFP induction was much lower for uPtetO2 strains, 1.5-3 fold for ptetR2, 3-8 fold for ptetR4 and 3-8 fold for ptetR6 (FIG. 6). However GFP activity in TetR expressing strains did not reach the levels observed in the absence of TetR, this was most noticeable when uPtetO1-GFP was located at the TrpA locus (FIG. 6A).

Example 4

Induction of Upteto by Atc in *H. pylori* is Dose- and Time-Dependent

Figure 7:
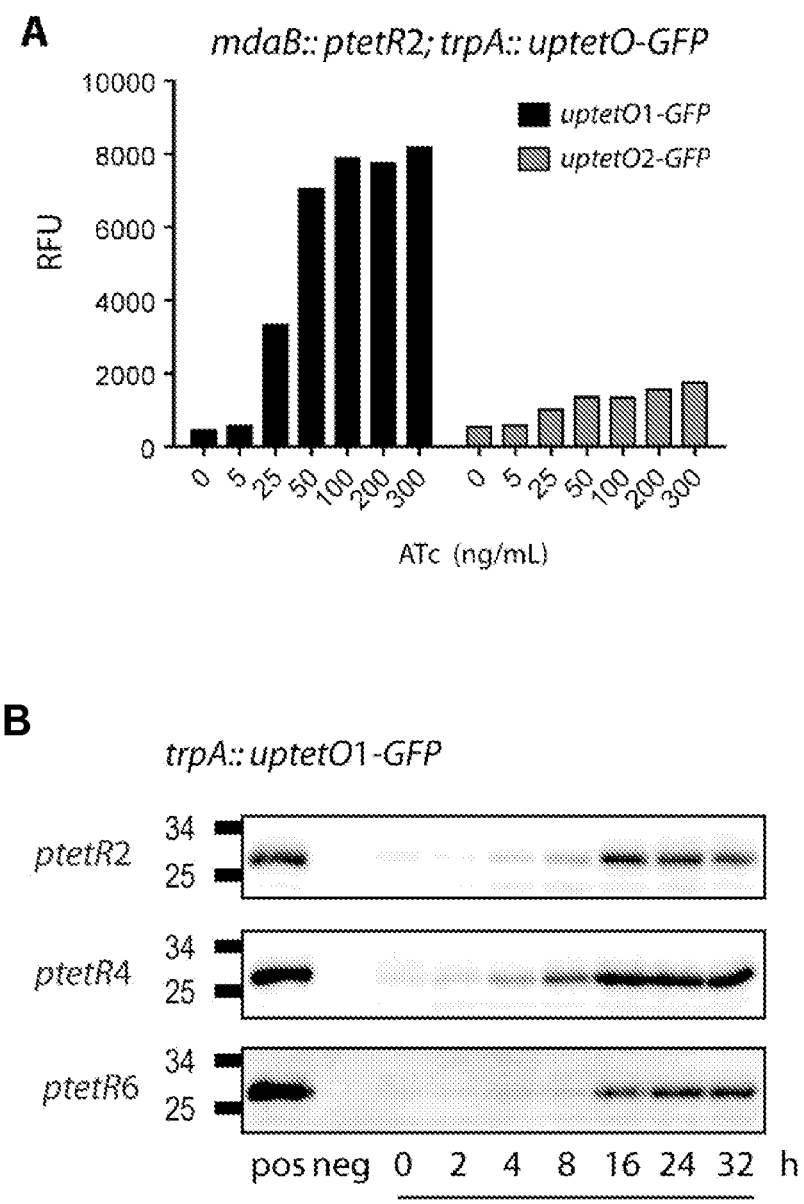
FIG. 7 shows the determination of the optimal inducer concentration, growth inhibition by ATc and kinetics of induction. (A) Inducer concentration. *H. pylori* were transformed as indicated and grown in BHI to log phase ($OD_{600}$=0.5) and increasing amounts of ATc were added. GFP fluorescence activities were determined twenty four hours later. (B) Time course of TetR-controlled GFP expression. Lysates from *H. pylori* (18 mg protein) expressing GFP with the uptetO1 promoter were separated on a 10% SDS-PAGE gel. Lane 1, constitutively expressed GFP by X47 lacking TetR (pos); lane 2, parent wild-type X47 (neg); lane 3, repressed GFP (+tetR); lanes 4-9, time course of induction of TetR-controlled GFP by 100 ng/ml ATc.

Further characterization of the tet inducible expression system in *H. pylori* was done by increasing inducer concentrations and by evaluating reporter gene expression at several different time points. Bacteria were grown in the presence of different concentrations of ATc. Quantification of GFP activities demonstrated that concentrations of 100 ng/mL ATc gave maximal GFP activities (FIG. 7A).

Induction with 25 ng/ml ATc led to 2.4-fold lower GFP activities. These experiments demonstrated that induction is dose-dependent and that maximal induction can be achieved at a concentration of 100 ng/mL ATc. Moreover the maximal induction is reached with an ATc concentration that is 10-fold below the minimal inhibitory concentration (MIC) as measured in liquid culture.

A disc diffusion assay was used to demonstrate induction of GFP expression by ATc. Discs inoculated with ATc were placed onto bacterial lawns containing ptetR2 and uPtetO1-GFP. After 24 hours of incubation, a halo of GFP expression is evident around each disc. Kinetics of uPtetO1-GFP induction was analysed by immunobloting in strains expressing TetR (FIG. 7B). Maximal GFP activities in ptetR2 and ptetR4 containing bacteria were observed at 16 h after the addition of ATc. ptetR6 containing bacteria showed strong but delayed induction.

These experiments show that induction of uPtetO1-GFP was time-dependent and the kinetics of induction depended on ptetR construct.

Example 5

Testing Colonization Ability of Recipient Strains for Conditional Gene Complementation In Vivo In order to rule out the occurrence of secondary mutations that would affect colonization and to assess the expression stability of the GFP reporter gene under the tet inducible transcription, the recombinant strains were evaluated for their ability to colonize C57BL/6J mice. Animals were gavaged with X47 mdaB::ptetR5 recipient strains transformed with pTrpA-uPtetO1-GFP, pGltDH-uPtetO1-GFP or pHdapB-uPtetO1-GFP. Bacteria expressing GFP were successfully re-isolated 1 week after infection for all strains tested (Data not shown).

Example 6

Regulation of Urease Expression Based on the Tetracycline Inducible Expression in *H. pylori*

Regulation of urease expression was investigated in X47 mdaB::ptetR recipient strains transformed with urePtetO constructs to generate a panel of strains containing modified ureA promoters and expressing TetRs (Table 2).

TABLE 2

X47 Strains with Tetracycline Responsive ureA and ureB Expression

| Strain promoter | expression state | Tetracycline − | Tetracycline + |
|---|---|---|---|
| mdaB::ptetR2; urePtetO I | amiE | OFF | ON |
| mdaB::ptetR2; urePtetO II | amiE | OFF | ON |
| mdaB::ptetR2; urePtetO III | amiE | OFF | ON |
| mdaB::ptetR2; urePtetO IV | amiE | OFF | ON |
| mdaB::ptetR2; urePtetO V | amiE | OFF | ON |
| mdaB::ptetR3; urePtetO I | flaA | ON | OFF |
| mdaB::ptetR3; urePtetO II | flaA | ON | OFF |
| mdaB::ptetR3; urePtetO III | flaA | ON | OFF |
| mdaB::ptetR3; urePtetO IV | flaA | ON | OFF |
| mdaB::ptetR3; urePtetO V | flaA | ON | OFF |
| mdaB::ptetR4; urePtetO I | flaA | OFF | ON |
| mdaB::ptetR4; urePtetO II | flaA | OFF | ON |
| mdaB::ptetR4; urePtetO III | flaA | OFF | ON |
| mdaB::ptetR4; urePtetO IV | flaA | OFF | ON |
| mdaB::ptetR4; urePtetO V | flaA | OFF | ON |
| mdaB::ptetR5; urePtetO I | taTaat | ON | OFF |
| mdaB::ptetR5; urePtetO II | taTaat | ON | OFF |
| mdaB::ptetR5; urePtetO III | taTaat | ON | OFF |
| mdaB::ptetR5; urePtetO IV | taTaat | ON | OFF |
| mdaB::ptetR5; urePtetO V | taTaat | ON | OFF |
| mdaB::ptetR6; urePtetO III | taTaat | OFF | ON |
| mdaB::ptetR6; urePtetO IV | taTaat | OFF | ON |
| mdaB::ptetR6; urePtetO V | taTaat | OFF | ON |
| mdaB::ptetR7; urePtetO I | taCaat | ON | OFF |
| mdaB::ptetR7; urePtetO II | taCaat | ON | OFF |
| mdaB::ptetR7; urePtetO III | taCaat | ON | OFF |
| mdaB::ptetR7; urePtetO IV | taCaat | ON | OFF |
| mdaB::ptetR7; urePtetO V | taCaat | ON | OFF |

Figure 8:
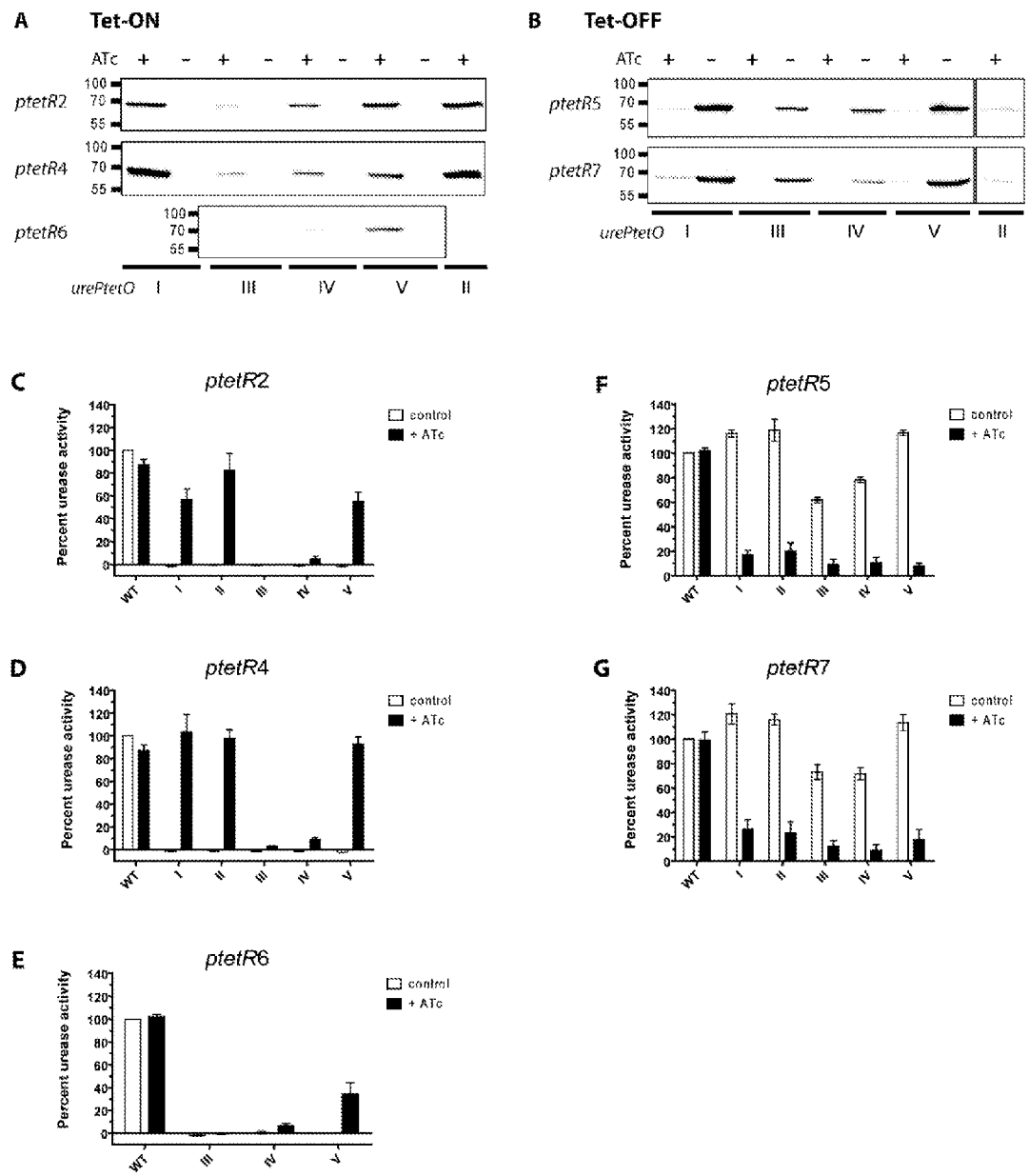
FIG. 8 shows tet regulation of urePtetO in *H. pylori*. Bacteria were cultured in the absence or presence of 50 ng/mL ATc. Immunoblotting (A) Induction of UreB expression by Tet-ON strains. (B) Repression of urease expression in Tet-OFF strains. Urease activity assays. Urease activity is expressed as a percentage of wild-type parent (WT) urease activity. The urePtetO construct is specified under the bars. (C-E) Urease activity of urePtetO strains expressing TetR (F-G) Urease activity of urePtetO strains expressing revTetR.

Regulation of urePtetO promoters by ATc was analysed by immunoblotting and urease activity assays. Immunoblotting revealed that the abundance of the UreB subunit was reduced below the detection limit upon the restriction of ATc in strains harbouring the TetR repressor (Tet-ON system) (FIG. 8A), and upon the addition of ATc in strains harbouring the revTetR repressor (Tet-OFF system) (FIG. 8B). Incomplete repression was observed for constructs I, II and V of the Tet-OFF system (FIG. 8B). Strains harbouring ptetR3 did not display response to ATc (Data not shown).

In the absence of ATc, the urease activity of Tet-ON strains (FIG. 8C-E) was reduced below the detection limit of 2 U/mL. Addition of ATc completely restored urease activity in strains: ptetR2; urePtetOII (FIG. 8C), ptetR3; urePtetOI, II and III (FIG. 8D). Urease activity was only partially restored in strains: ptetR2; urePtetOI and V (FIG. 8C), ptetR3; urePtetOIV (FIG. 8D) and ptetR6; urePtetOV (FIG. 8E). Urease activity of the other Tet-ON strains was below 10% of wild-type urease activity. The urease activity of Tet-OFF strains was reduced to between 35% and 10% to that of the wild-type parent X47 strain (FIG. 8F-G).

Example 7

Induction of urePtetO by ATc in *H. pylori* is Dose- and ptetR-Dependent

A more sensitive urease plate assay was used to detect residual urease activity and low levels of urePtetO induction of Tet-ON strains in the presence of different concentrations of ATc. For ptetR4 strains, ATc at a concentration of 1 ng/mL is sufficient to induce all five urePtetO promoters, but urease activity decreases at concentrations above 25 ng/mL. In the absence of ATc, very low levels of urease activity are seen after 24 h and this is more prominent after 48 h. For ptetR6 strains, significant urease activity is detected after 24 h at ATc concentrations of 5 ng/mL and 10 ng/mL for urePtetOV and urePtetOIV respectively. Urease activity due to induction of urePtetOIII is only evident after 48 hr at 25 ng/mL and 50 ng/mL. Urease activity decreases at concentrations above 50 ng/mL and in absence of ATc, very low levels of urease activity are seen for all three urePtetO promoters after 48 h.

The observed colour change in the urease plates is due to the activity of urease, as a plate inoculated with a pre-induced mdaB::ptetR2; urePtetOV strain will change colour within 30 min of inoculation. Urease activity is induced by the diffusion of ATc from disc placed on a plate inoculated with untreated bacteria, and plates stay yellow when inoculated with a urease negative X47 ureA::rpsL-CAT strain.

Example 8

*H. pylori* Tolerates Low Levels of Doxycycline In Vivo

A literature survey revealed that most studies using the tetracycline system to regulate gene expression in vivo used doxycycline (dox) rather than ATc as the inducer. For cost reasons, dox was selected for the in vivo evaluation of the *H. pylori* tet system and pilot experiments were carried out to identify the maximum dose of dox that wild-type *H. pylori* would tolerate during colonization of C57BL/6J mice. Animals were orally gavaged with wild-type parent X47 strain and drinking water was supplemented with a range of dox concentrations. After one week of infection the bacterial load was significantly reduced at dox concentration of 100 µg/mL and bacteria could not be isolated from mice supplemented with 1000 µg/mL (FIG. 9A). At dox concentrations above 1 µg/mL, the bacterial load decreased by two logs, however at longer infection time points (two and four weeks), the bacterial load in mice supplemented with 5 µg/mL dox is similar to untreated mice (FIG. 9B).

Example 9

In Vivo Induction of the Tet-Inducible Urease by Doxycycline in *H. pylori*

Figure 9:
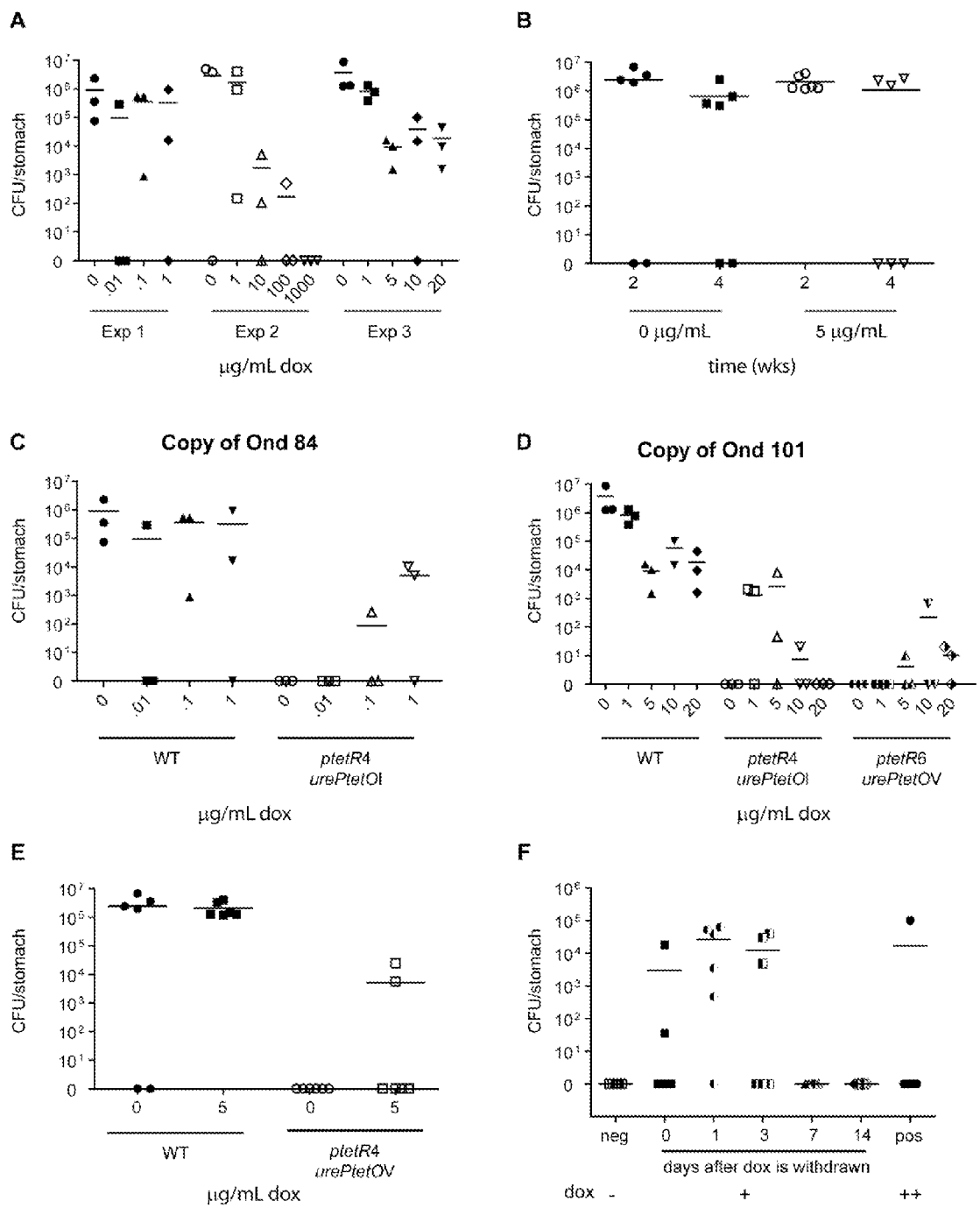
FIG. 9 shows Tet regulation of urePtetO in vivo. (A) X47 tolerance to tetracycline. Bacterial load of mouse infected with wild-type parent X47strain and supplemented with range of dox concentrations for one week. This is the combined data from three separate experiments, animal groups n=3. (B) Bacterial load of mice infected with wild-type X47 and supplemented with 5 μg/mL, evaluated at two and four weeks after infection. Animal groups n=6. (C-D) Bacterial load of mice one week (n=3) and (E) two weeks (n=6) after infection with wild type X47 (WT) or urePtetO strains. Mice were supplemented with different concentrations of dox in their drinking water and urePtetO strains were induced prior to start of infection. (F) Infection of urePtetO strains is dependent on dox supplementation. Mice were supplemented with dox for two weeks after oral gavage with mdaB::ptetR4; urePtetOI. Dox supplement was then removed and bacterial load was evaluated on days 0, 1, 3, 7 and 14. One group of mice did not receive any dox supplementation (neg) and a second group received dox for the duration of the experiment (pos). Animal groups n=6.

Regulation of urePtetO to drive the expression of urease by dox was evaluated using a C57BL/6J infection model. Mice were orally challenged with one of several Tet-ON, mdaB:: ptetR; urePtetO strains and supplemented with a range of dox concentrations that were within the tolerance of X47. Urease is known to be an essential gene required for colonization, and therefore Tet-ON urePtetO strains should not be able to colonize in the absence of the inducer. Several preliminary experiments demonstrated that dox can induce urePtetO in vivo (FIG. 9 C-D). Strains mdaB::ptetR4; urePtetOI and mdaB:: ptetR6; urePtetOV could be re-isolated after one week of infection when animals were supplemented with 0.1-5 μg/mL and 5-20 μg/mL dox respectively. After two weeks of infection, strain mdaB:: ptetR4; urePtetO V could be re-isolated from animals supplemented with 5 μg/mL dox (FIG. 9E). Infection of urePtetO strains is dependent on dox supplementation (FIG. 9F). Mice were supplemented with dox for two weeks after infection to establish successful colonization of mdaB:: ptetR4; urePtetOI. The strain could be re-isolated one and three days after withdrawal of dox supplement but could not be isolated after 7 days (FIG. 9F). Infection by strain mdaB::ptetR4; urePtetOI could be maintained for at least 4 weeks with dox supplementation.

Example 10

Eradication Strategies

We have found that the metabolism of mannose is a promising candidate pathway to achieve *H. pylori* eradication. Indeed, *Helicobacter* genome analysis suggests that mannose is made from glucose only. It is known that *H. pylori* LPS is decorated with Lewis antigens (fucose and galactose) that are essential for colonisation and immune-modulation through the DC sign receptor of dendritic cells. Thus, metabolic control of the Lewis antigen of the LPS can provide control of *H. pylori* colonisation/eradication and immune-modulation, respectively.

Figure 17:
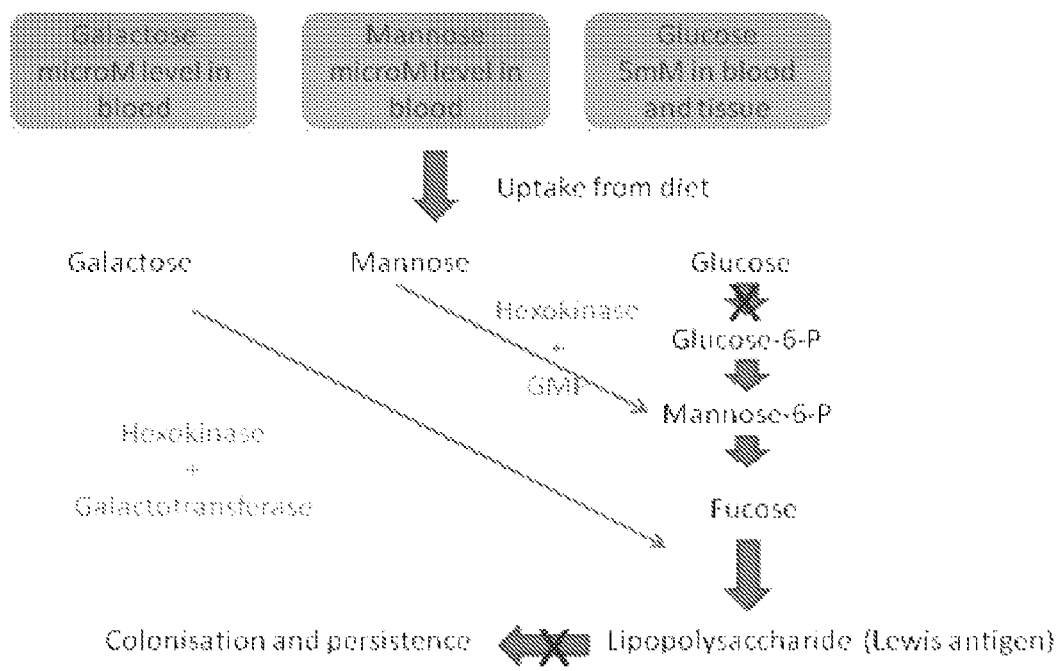
FIG. 17 shows the process of making a sugar shunt for *H. pylori* eradication in which mannose and galactose supplementation in the diet maintains *H. pylori* knock in mutants.

FIG. 17, shows the process of making a sugar shunt for *H. pylori* eradication in which mannose and galactose supplementation in the diet maintains *H. pylori* knock in mutants. To establish the shunt, two enzymes that are missing in *H. pylori* are knocked into the genome: a hexokinase to phosphorylate the mannose upon transport into the cell and a pyrophosphorylase (GMP). Of note, it is known that *H. pylori* can transport mannose allowing diet supplementation. In contrast to glucose, the blood concentration of mannose is very low; micromolar range versus the 5 mM of glucose.

In order to construct the mannose sugar shunt, the phosphomannose isomerase (HP0043) of *H. pylori* is deleted. However, HP0043 is a bifunctional enzyme that also has a pyrophosphorylase function that makes GDP-mannose from mannose-1-phosphate. Thus, the pyrophosphorylase of *E. coli* was knocked-in to restore the metabolic pathway. Also a hexokinase with a broad specificity (yeast hexokinase 1) was also knocked in to phosphorylate the transported mannose into mannose-6-phosphate.

The generation of the HP0043 clean deletion mutant was performed using the counter-selection cassette rpsl-cat as described earlier. Expression of GMP was designed between the UreAB locus and Hxk1 after UreB locus. The sequence of genetic manipulation consisted of the following:

1. X47Δ0043
2. X47Δ0043::rpsL-cat(ureAB)
3. X47Δ0043::gmp(ureAB)
4. X47Δ0043::gmp(ureAB)::rpsL-cat(ureBI)
5. X47Δ0043::gmp(ureAB)::hxk1(ureBI).

Confirmation of genetic manipulation and gene insertion was done by diagnostic PCR on genomic DNA.

Figure 18:
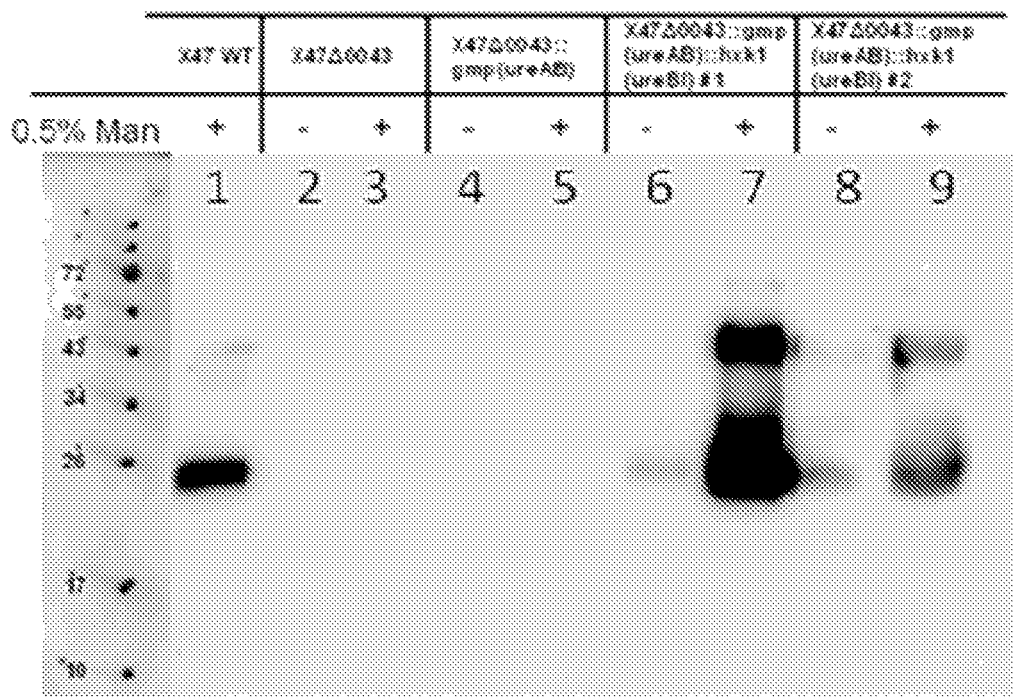
FIG. 18 shows Lewis antigen expression on LPS. *H. pylori* bacteria were grown on blood agar plates with or without mannose (0.5%) and processed for LPS extraction and Western blot using anti-Lewis Y antigen. The presence of Lewis antigen on LPS is detected as a band at about 26 kDa. Lane 1, WT with mannose; lane 2 an 3 HP0043 deletion mutant without and with mannose respectively; lane 4 an 5 HP0043 deletion mutant complemented with the GMP pyrophosphorylase without and with mannose respectively; lane 6 an 7 clone #1 of HP0043 deletion mutant complemented with the GMP pyrophosphorylase and the hexokinase 1 without and with mannose respectively; lane 8 an 9 clone #2 of HP0043 deletion mutant complemented with the GMP pyrophosphorylase and the hexokinase 1 without and with mannose respectively.

Lewis antigen expression of the mannose sugar shunt recombinant strains and wild type were assessed with and without mannose supplementation. FIG. 18 shows clearly that the mannose shunt works based on the Lewis antigen restoration upon mannose supplementation.

The colonization ability of the recombinant strains of *H. pylori* was tested in the mouse model with and without the supplementation of mannose in the diet. Of note, the HP0043 knockout strain was unable to colonize the mouse in a robust manner (data not shown).

A strain knockout of HP0043:gmp(ureAB):hxk1(ureBI) was grown on blood agar containing 0.5% mannose, harvested and used to orally challenge groups of 5 mice. Mice were sacrificed one week after challenge and colonization assessed by growing bacteria on agar Petri dishes from stomach homogenates. Results are shown in Table 3.

TABLE 3

| Diet | Mice Colonized (n = 5) |
|---|---|
| 0% mannose | 1/5 |
| 0.5% mannose in water | 1/5 |
| 0.5% mannose in water and food | 1/5 |
| 5% mannose in water | 3/5 |

Mannose supplementation rescued the colonisation of the knockout of HP0043:gmp (ureAB):hxk1(ureBI) when mannose concentration was as high as 5% in the drinking water. The incomplete rescue of the recombinant strain is likely due to the low urease activity of the strain. Indeed, the insertion of the two genes hxk1 and GMP at the urease operon interfered with urease activity. Thus, re-engineering the shunt by the synthesis of a novel operon composed of the hxk1 and GMP gene was performed and inserted in another location in *H. pylori* genome.

Figure 19:
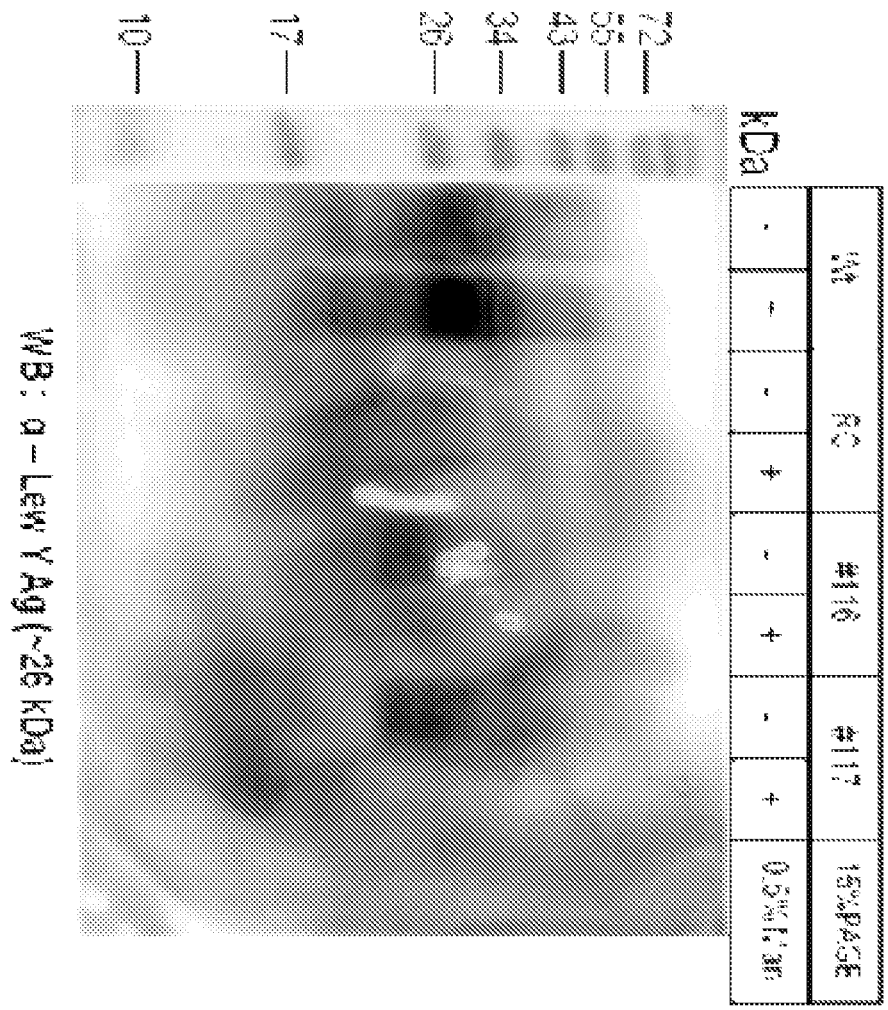
FIG. 19 shows Lewis antigen expression on LPS and growth inhibition. *H. pylori* bacteria were grown in liquid medium with or without mannose (0.5%) and processed for LPS extraction and Western blot using anti-Lewis Y antigen. The presence of Lewis antigen on LPS is detected as a band at about 26 kDa. Wt, Wild-type, RC recipient strain (HP0043 knockout), #116 clone 1 harboring the mannose shunt and #117 clone 2 harboring the mannose shunt.

The recombinant strains harbouring the new mannose shunt were found to be rescued for the biosynthesis of the Lewis antigen on the LPS in absence of mannose supplementation and growth sensitive upon mannose supplementation in vitro (FIGS. 19 and 20, respectively). Although this result was not anticipated, it gives us a better metabolic control as cell growth is inhibited upon mannose addition as well as the Lewis antigen biosynthesis. We reasoned that the mannose shunt is very efficient at utilising mannose traces in the culture medium, but that an excess of mannose is toxic to the cells.

We have further identified the regulated pathway as overexpression of the hexokinase alone inhibits the growth of *H. pylori* in presence of mannose only. Other sugars tested so far failed to inhibit cell growth, highlighting the mannose specificity of the inhibition mechanism. Thus there seems to be a tight regulation of the mannose-6-phosphate required for cell growth in *H. pylori*.

Figure 21:
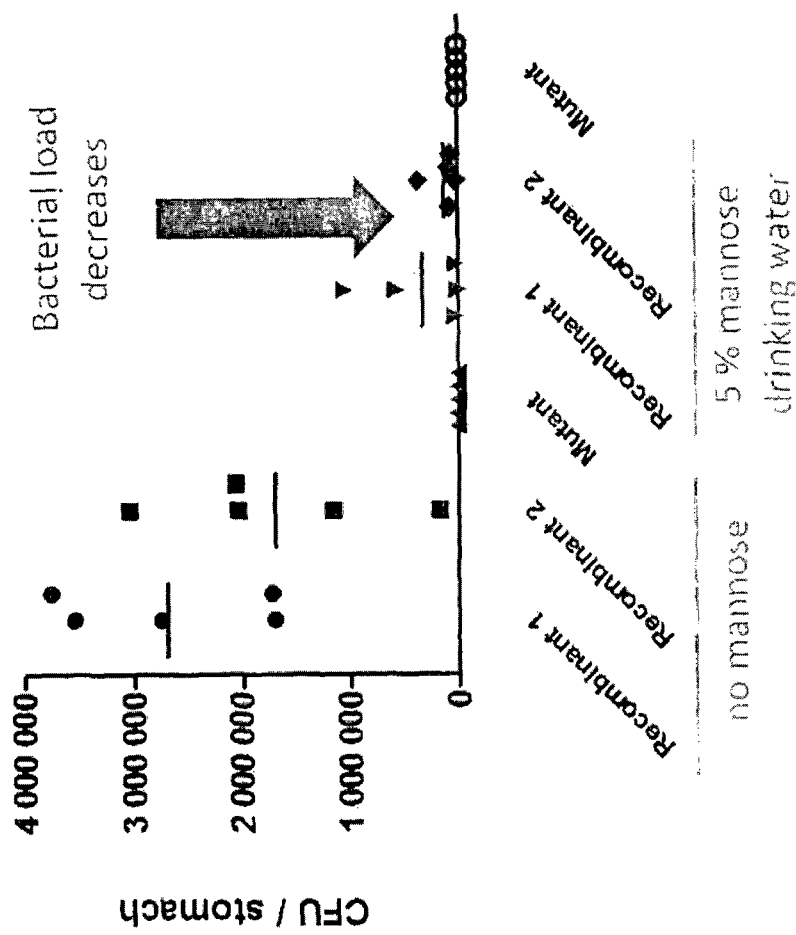
FIG. 21 shows in vivo mediated mannose eradication of recombinant *H. pylori*. Mice were challenged with recombinant *H. pylori* harbouring the mannose shunt, after two weeks of colonisation mice were fed with 5% mannose in the drinking water. After five days of mannose dietary supplementation mice were sacrificed and colony forming unit per stomach was measured.

To evaluate the eradication potential of the new mannose shunt, mice were challenged with recombinant *H. pylori* harbouring the mannose shunt, after two weeks of colonisation mice were fed with 5% mannose in the drinking water and bacterial load evaluated. Bacterial loads were reduced by 1 to 2 Log after the mannose treatment (FIG. 21).

Example 11

Gene Expression System in *Helicobacter pylori*

Figure 22:
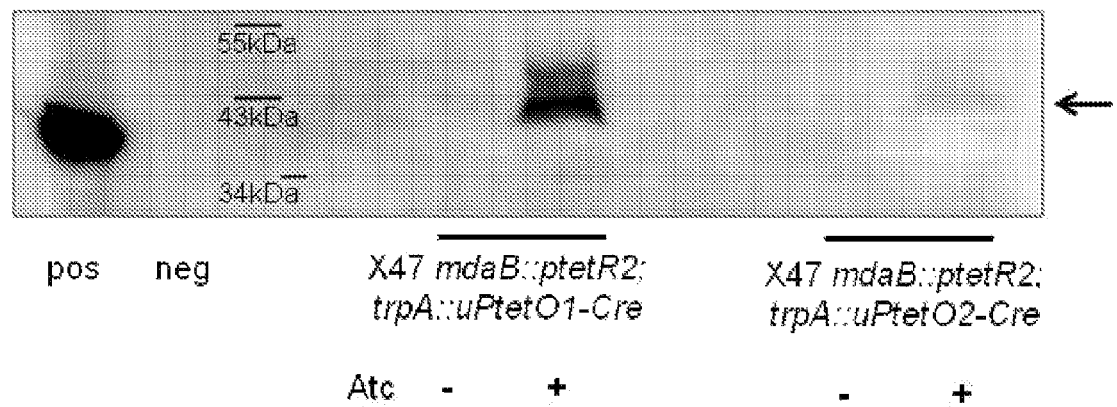
FIG. 22 shows TetRs regulation of cre expression in *H. pylori*. Bacteria were grown in liquid culture with or without 50 ng/ml ATc and analysed by immunoblotting. *E. coli* strain transformed with pMdaB-PtaTaat-TetRs served as positive control (pos). X47 strain served as negative control (neg). Cre was detected using polyclonal rabbit anti-Cre antibody at a concentration of 1 µg/ml.

Construction of *H. pylori* Strains with TetR Regulated Cre Recombinase Expression In order to conditionally express the Cre recombinase in *H. pylori* two Tet responsive promoters uPtetO1 and uPtetO2 were selected to control the cre expression. They consist of the core urease promoter containing a C to T mutation in the −10 box and one tetO site just downstream of the transcriptional start point. uPtetO2 contains a second tetO site between the −35 and −10 box. A synthetic *H. pylori* codon usage optimized version of the cre gene was amplified and cloned into the plasmid pTrpA-uPtetO1-GFP and pTrpA-uPtetO2-GFP to replace GFP. Natural transformation of the recipient strain *H. pylori* X47 mdaB:: ptetR2; trpA:: rpsL-CAT with these plasmids (pTrpA-uPtetO(1/2)-Cre) allowed integration of uPtetO-cre fusions in the chromosome at the trpA locus by homologous recombination. The conditional expression of cre in the constructed strains X47 mdaB:: ptetR2; trpA:: uPtetO-cre was analyzed by immunoblotting. Bacteria were grown in liquid culture the presence of none or 50 ng/ml ATc, respectively. In both strains cre expression is induced in the presence of ATc with expression under control of uPtetO1 is significantly higher compared to uPtetO2 (FIG. 22).

Testing of Cre/Lox Excision in *H. pylori* Strains

A Lox6671 cassette, a promoter-dapA fusion flanked with two lox sites (FIG. 23), was used to test the functionality of the Cre recombinases in *H. pylori*. The cassette was designed and synthesized containing the ureA promoter and the dapA gene. The PureA-dapA fusion is flanked by two lox sites (lox66 and lox71) with their non-palindromic core sequence pointing in the same direction which allows Cre-mediated excision of the sequence between the lox sites. The nucleotide sequences of the lox sites are mutated loxP motives. Cre-mediated recombination between lox66 and lox71 sites generates one wild-type and one double mutant loxP site. Since the double mutant loxP site exhibits much reduced binding affinity for Cre recombinase, Cre-mediated excision using the mutated Cre/loxP system prefers the forward reaction.

The Lox6671 cassette was cloned in the vector pBlu-BI generating the plasmid pBI-Lox6671. Natural transformation of X47 mdaB::ptetR2; trpA::uPtetO(1/2)-cre; ureBI::rpsL-CAT with pBI-Lox6671 resulted in strains X47 mdaB:: ptetR2; trpA::uPtetO(1/2)-cre; ureBI::Lox6671.

Figure 24:
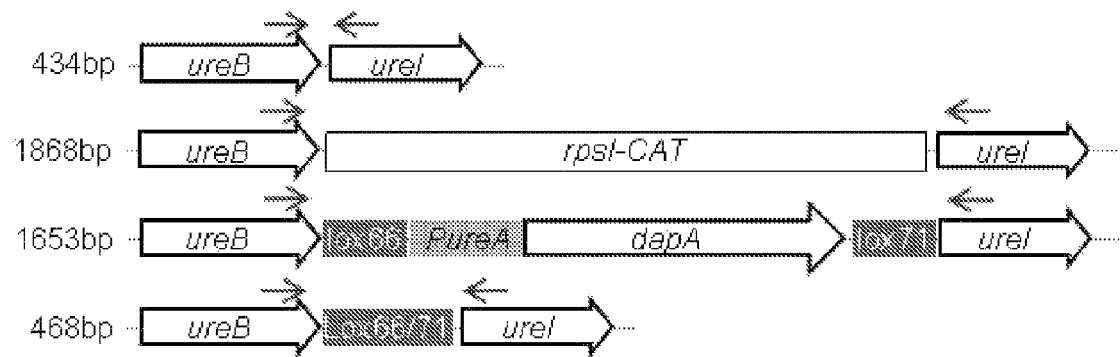
FIG. 24 shows Cre/lox excision in *H. pylori*. Schematic diagram of ureBI locus at different steps of construction of the lox6671 cassette at the ureBI locus. The numbers show the expected PCR fragment sizes using the primer ureB_seqF and ureI_seqR represented by arrows.

A PCR was performed using genomic DNA of the constructed strains to confirm the integration of the cassette at the ureBI locus. Bacteria were grown on blood agar without induction and genomic DNA was isolated. All tested clones showed a PCR band slightly larger than the band of the X47 wild type control (FIG. 24). The band corresponds to the expected size of the ureBI locus with one lox site. This experiment shows that Cre is functional in *H. pylori* and promotes lox mediated gene excision. However the Cre/lox excision took place without induction of TetR meaning the repression of Cre is not sufficient to prevent excision, although Cre levels are below the detection limit of immunoblotting.

Optimization of TetR-Inducible Cre/Lox Excision System

Figure 25:
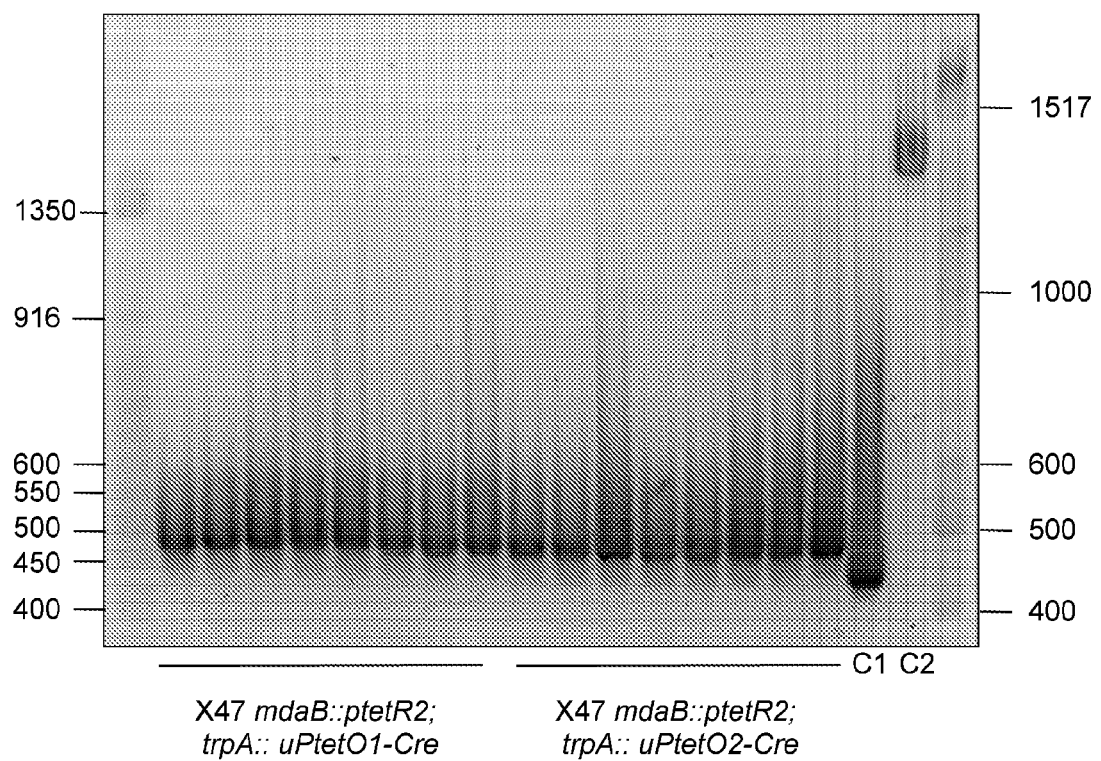
FIG. 25 shows Cre/lox excision in *H. pylori*. DNA electrophoresis showing genomic DNA of *H. pylori* strains X47 mdaB::ptetR2; trpA::uPtetO(1/2)-Cre(clone 1-8) was used as template in a PCR using primer ureB_seqF and ureI_seqR. Genomic DNA of X47 (C1) and plasmid DNA pBI-Lox6671 (C2) were used as control.

To optimize the inducible Cre/lox system in *H. pylori* tetR was exchanged by a *H. pylori* codon optimized version of tetR (tetRs) to improve the expression level of tet repressor. tetRs was cloned into the plasmid pMdaB-PureA-hydA to yield the plasmid pMdaB-PureA-TetR5. The constructed plasmid was used to transform recipient strain X47 mdaB: rpsL-cat by natural transformation to generate X47 mdaB::PureA-tetRs. Expression of tetRs in this strain was analyzed by immunoblotting. The expression of tetRs in the X47 mdaB::PureA-tetRs is higher compared to the strain X47 mdaB::ptetR2 but is lower than the expression in the *E. coli* positive control (pos) (FIG. 25).

Figure 26:
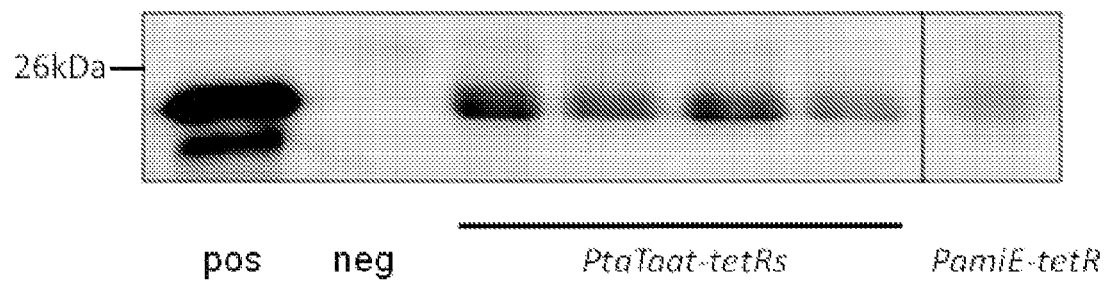
FIG. 26 shows tetRs and tetR expression in *H. pylori*. Western blot analysis of expression of tetRs by strain X47 mdaB::PtaTaat-tetRs clones 1-4 and tetR by strain X47 mdaB::PamiE-tetR. *E. coli* strain transformed with pMdaB-PtaTaat-TetRs served as positive control (pos). X47 strain served as negative control (neg). TetRs was detected using polyclonal rabbit anti-TetR antibody.

Further optimization of the system was done by modifying the promoter uPtetO upstream of cre to lower the basal cre expression. A series of six tet responsive promoters was designed with different translational expression efficiencies (1-6)uPtetO5 (FIG. 26). The promoters are based on uPtetO with two tetO sites located upstream of the −35 box and between the −35 and −10 box similar to urePtetO1). To lower the translation efficiency the start codon was exchanged from ATG to CTG and TTG (4-6) uPtetO5 and in addition the ribosome binding sequence was altered from TAGGAG to TAGCAG (1-3) uPtetO5. The promoter variants were synthesized as fusion with the 5' end of cre and cloned in the plasmid pTrpA-uPtetO2-Cre to generate the six plasmids pTrpA-(1-6)uPtetO5-Cre.

Natural Transformation of the Recipient Strain

X47 trpA:: rpsL-cat with the plasmids was performed to generate the strains X47 mdaB:: (1-6) uPtetO5-cre. These strains and *E. coli* harbouring the plasmids pTrpA-(1-6)uPtetO5-Cre were used to evaluate the strength of the uPtetO promoter variants in the absence of the tet repressor.

Figure 27:
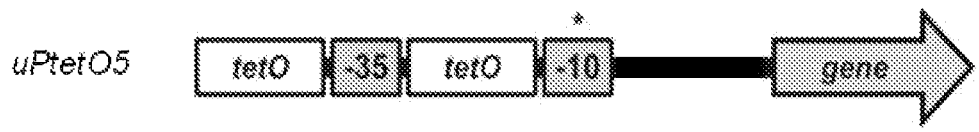
FIG. 27 shows (A) Schematic diagram of tetracycline responsive promoter uPtetO5 construct. The two tetO sites are indicated by white boxes. The star indicates the C to T mutation in the −10 box found in all uPtetO constructs. (B) Nucleotide sequence of (1-6)uPtetO5 constructs: 1uPtetO5 (SEQ ID NO:106), 2uPtetO5 (SEQ ID NO:107), 3uPtetO5 (SEQ ID NO: 108), 4uPtetO5 (SEQ ID NO: 103), 5uPtetO5 (SEQ ID NO: 104), 6uPtetO5 (SEQ ID NO: 105). Ribosome binding site (RBS) and start codon are underlined and mutations of these sequences are indicated in bold letters.

As shown by immunoblotting in FIG. 27 the strength of the uPtetO5 based constructs was much weaker compared to the control strain with pTrpA-uPtetO2-Cre. When altered the start codon from ATG to CTG or TTG in uPtetO5 the expression level of cre gradually decreased and continued to decrease when this alteration is combined with a mutated RBS ((1-3) uPtetO5). In *H. pylori* strains X47 mdaB:: (1-6) uPtetO5-cre the cre expression was reduced below the detection limit except for construct 6uPtetO5 which showed a weak band.

Subsequent rounds of natural transformation of the strain X47 mdaB:: PureA-tetRs were done to first integrate the (1-6)uPtetO5-cre construct and second the Lox6671 cassette. The genomic DNA of the final strains X47 mdaB:: PureA-tetRs; trpA:: (2/4/5/6)uPtetO-cre: ureBI:: Lox6671 was used as template in a PCR to verify the integration of the Lox6671 cassette as done before. All four strains showed a band corresponding to the ureBI locus with one loxP site, indicating that levels of Cre below the Western blot detection limit can promote excision of the of the Lox6671 cassette (data not shown).

Reduction of Basal Cre Expression Using Antisense RNA Expression

Figure 28:
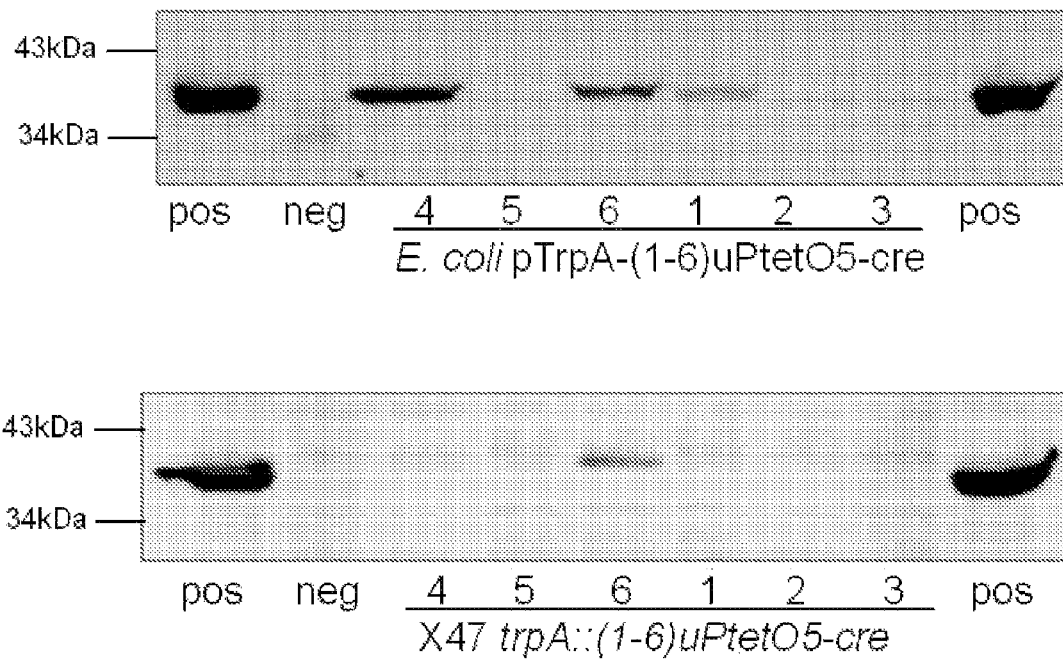
FIG. 28 shows cre expression of constructs 1-6uPtetO5-Cre (A) Western blot analysis of *E. coli* strain harbouring plasmids pTrpA-(1-6)uPtetO5-Cre. *E. coli* strain transformed with pTrpA-uPtetO2-Cre (pos) or pTrpA-RCAT (neg) served as positive and negative control respectively. (B) Western blot of *H. pylori* X47 trpA::(1-6)uPtetO5-cre with *E. coli* harboring pTrpA-uPtetO2-Cre (pos) and X47 trpA::RC (neg) as positive and negative control respectively. Cre was detected using polyclonal rabbit anti-Cre antibody at a concentration of 1 µg/ml.
Figure 29:
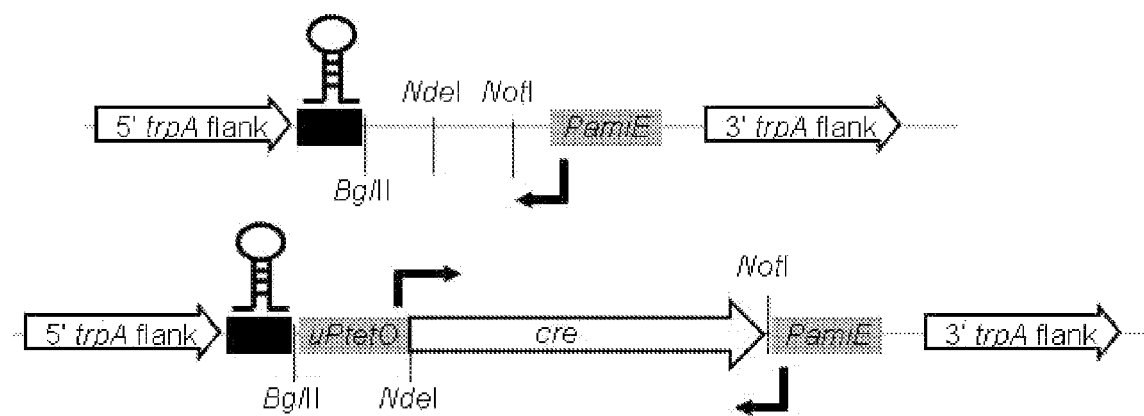
FIG. 29 shows schematic diagram of the construction of the cre sense-antisense cassette. The pMA-Antisense contains 500 bp upstream and downstream sequences of trpA that flank a transcription terminator (black box), a multiple cloning site and the PamiE promoter. The (1-6)uPtetO5-cre fusions were cloned into the MCS of pMA-Antisense to create the final cre inducible sense-antisense cassette. Black arrows indicate transcriptional start points.

In tet repressor systems minimal residual weak basal expression of the silenced gene is commonly observed. In case of the Cre recombinase this expression is sufficient to excise the lox flanked DNA sequence. A second approach was done to optimize the Cre/lox system in *H. pylori* by controlling the cre expression level more tightly with antisense RNA interference. A sense-antisense RNA cassette was designed to inducible transcribe cre mRNA and constitutively transcribe antisense RNA from the same gene (FIG. 28). The cassette was constructed by cloning the six (1-6)uPtetO5-Cre fusions or just the cre gene into pMA-Antisense to generate pTrpA-as(1-6)uPtetO5-Cre and pTrpA-as-Cre. Natural transformation of *H. pylori* recipient strain X47 mdaB::PureA-tetRs; trpA::rpsL-cat with pTrpA-as(1-6)uPtetO5-Cre was performed followed by integration of the Lox6671 cassette at the ureBI locus as described above. The resulting strains X47 mdaB::PureA-tetRs; trpA::as(2/4/6)uPtetO-cre; ureBI:: Lox6671 were tested for integration of the Lox6671 cassette by PCR, but all constructs showed a band corresponding to the ureBI locus with one loxP site (FIG. 29).

Development of a Plasmid Based Tet Inducible Antigen Expression Cassette

Figure 30:
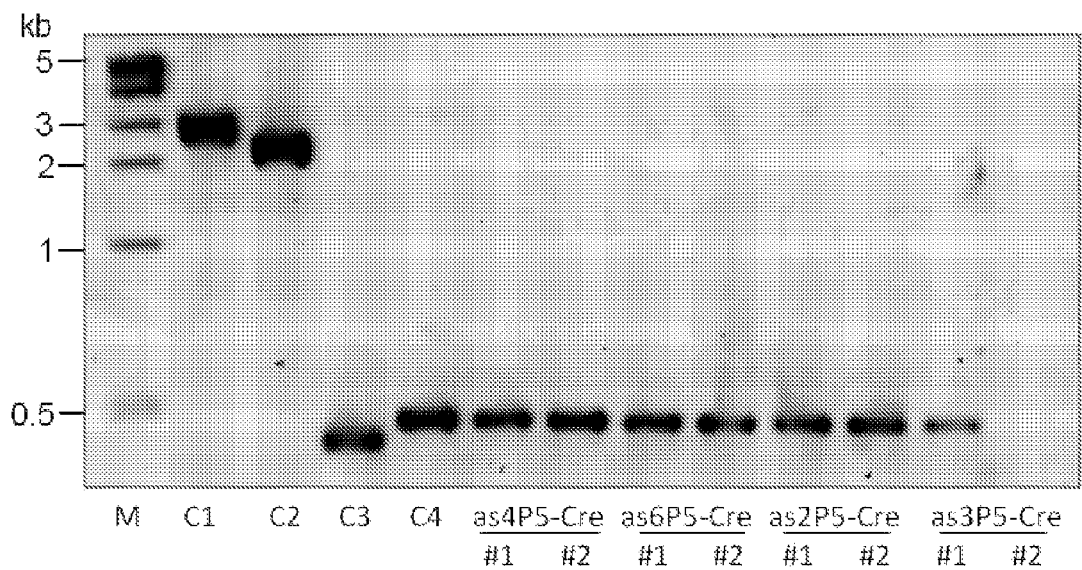
FIG. 30 shows identification of Lox6671 integration in *H. pylori*. Genomic DNA of *H. pylori* strains X47 mdaB::PureA-tetRs; trpA:: as(2/3/4/6)uPtetO-cre; ureBI:: Lox6671 (clone 1+2 each) was used as template in a PCR using primer ureB_seqF and ureI_seqR. Genomic DNA of X47 ureBI::rpsL-CAT (C1), X47 (C3) and X47 mdaB::ptetR2; trpA::uPtetO2-Cre (C4) and plasmid DNA pBI-Lox6671 (C2) were used as control.

An inducible expression cassette (IEC) was designed to comprise two components: a constitutive promoter (flaA promoter) which controls the expression of the tetracycline repressor (tetRs); and an inducible promoter (uPtetO4), negatively regulated by the tetR, controlling the expression of a target gene (FIG. 30). The design of uPtetO4 consists of the core ureA promoter with one tetO site between the −35 and −10 box (similar to urePtetOII). The two elements, facing in opposite direction, are separated by a non-coding spacer sequence. The cassette is flanked by two transcription terminators to isolate the unit when integrated into the shuttle vector pHel2.

Figure 31:
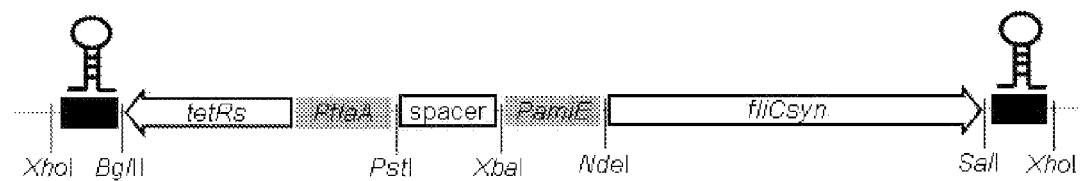
FIG. 31 shows schematic diagram of the synthetic tetracycline inducible gene expression cassette (IEC). The cassette consists of two elements: the tetracycline repressor gene tetRs under control of the flaA promoter (PflaA) and a target gene fliC controlled by tet responsive promoter uPtetO4. TetRs is constitutively expressed and binds to the single tetO site present in uPtetO4 between the −35 and −10 box. TetRs can be induced by ATc to allow expression of fliC. A spacer region of non-coding DNA is present between PflaA and uPtetO4 to separate the two arms of the IEC. The cassette is flanked by two transcription terminators indicated by black boxes. Each element of the IEC is flanked by two unique restriction sites allowing it to be exchanged by other promoters or genes.

The inducible expression cassette was synthesized without the gene for the tetracycline repressor and with the listeriolysin gene as target (pMA-IEC-LLO). To complete the inducible cassette, the gene for H. pylori codon usage optimized (tetRs) was cloned into pMA-IEC-LLO to generate pMA-IEC-Ts-LLO. The listeriolysin gene was exchanged by the H. pylori codon usage optimized Salmonella flagellin subunit C gene (fliCsyn) to create pMA-IEC-Ts-FliCsyn. Finally the whole IEC with fliCsyn was cloned in the shuttle vector pHel2. The resulting plasmid pHel2-IEC-FliCsyn was transformed into E. coli β2150 and subsequently transferred to H. pylori strain B128 by cell to cell plasmid transfer. Transconjugants were examined by restriction mapping but did not show the correct restriction patterns (FIG. 31). Plasmid DNA is modified by H. pylori and restriction enzymes are often inhibited by such modifications. Nevertheless, the presence of two undigested plasmids in all clones can be seen, one of which correspond to B128 endogenous plasmid (pB128) and the other to pHel2-IEC-Ts-FliCsyn in terms of molecular weight.

Figure 32:
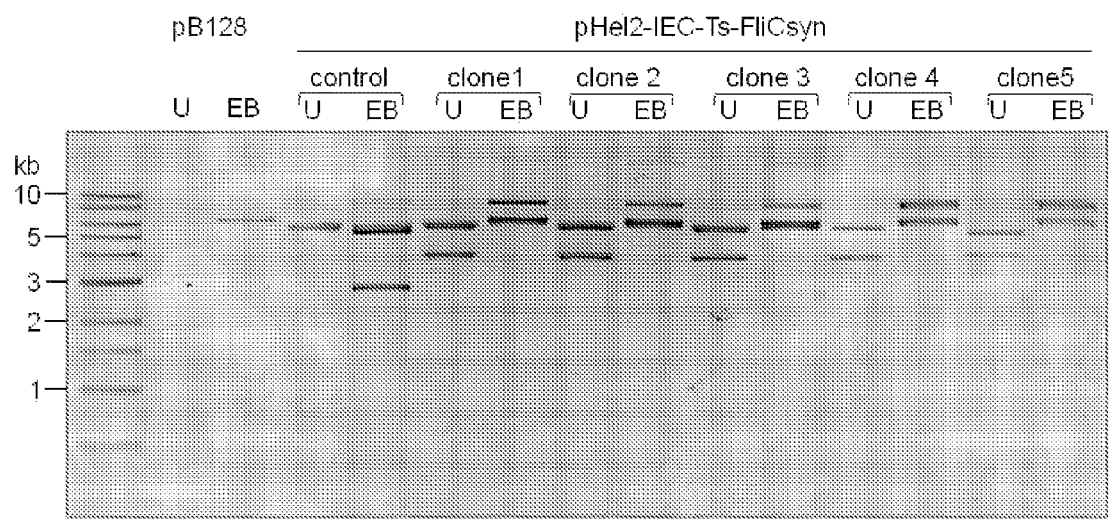
FIG. 32 shows identification of pHel2-IEC-Ts-FliCsyn in *H. pylori* B128. Plasmids extracted from *H. pylori* transconjugants clones 1-5 were digested with EcoRV and BamHI. The expected restriction pattern for pB128 and pHel2-IEC-Ts-FliCsyn comprises of 6 kb, 5 kb, and 2.7 kb DNA fragments. The correct restriction pattern was not observed. As reference, restriction patterns for pB128 (6 kb) and pHel2-IEC-Ts-FliCsyn extracted from *E. coli* (5 kb and 2.7 kb) are present. (U) undigested), (EB) digested with EcoRV and BamHI.
Figure 33:
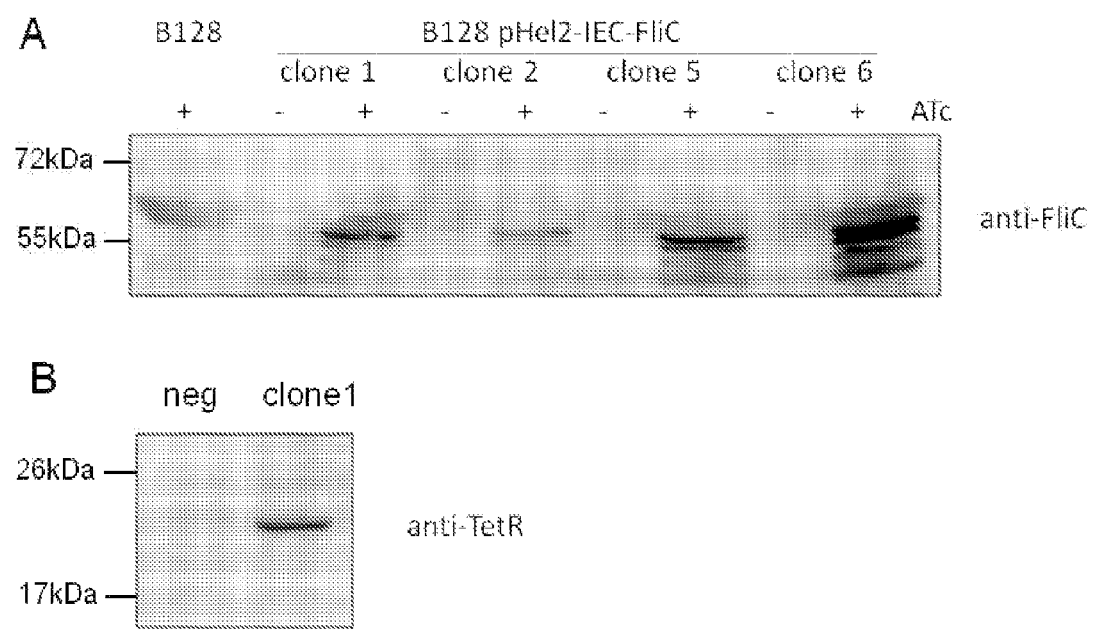
FIG. 33 shows Western blot analysis of B128 pHel2-IEC-Ts-FliCsyn transconjugants. (A) FliCsyn (55 kDa) was detected using polyclonal rabbit anti-FliC antisera at $^{1}/_{1000}$ dilution and (B) TetRs (23 kDa) was detected using polyclonal rabbit anti TetR antibody at 1:1000 dilution. Bacteria were induced by addition of 50 ng/ml anhydrotetracycline (ATc). *H. pylori* B128 served as negative control (neg).
Figure 34:
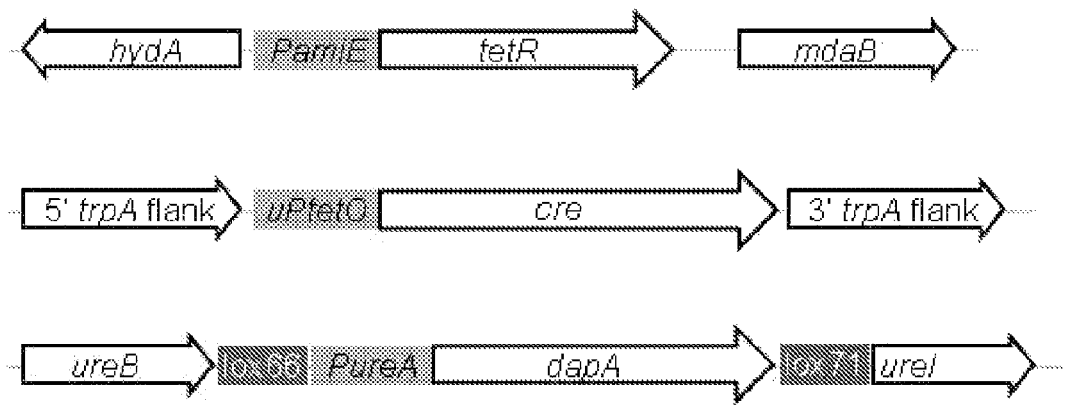
FIG. 34 shows schematic diagram of the TetR regulated Cre/lox excision system in *H. pylori*. Constitutive expression of Tet repressor is driven by PamiE at the mdaB locus. Cre recombinases expression is controlled by the tet responsive promoter uPtetO at the trpA locus. Tetracycline induced expression of Cre would lead to excision of the PureA-dapA fusion flanked by the lox66 and lox71 site (Lox6671 cassette) integrated at the ureBI locus.

The conditional expression of fliCsyn and expression of TetRs in the transconjugants B128 pHel2-IEC-Ts-FliCsyn was analyzed by immunobloting. Bacteria were grown on selective blood agar plates supplemented with none or 50 ng/ml ATc, respectively. tetRs was highly expressed and all tested clones showed expression of FliCsyn when induced with anhydro tetracycline (ATc) (FIG. 32).

Material and Methods

The bacterial strains and plasmids used in this study are listed in Table 4.

TABLE 4

Bacterial Strains and Plasmids Used in this Study

| Strain or plasmid | Description |
|---|---|
| Plasmid: | |
| pUC19-Cre | |
| pTrpA-uPtetO1-GFP | derivative of pTrpA, uPtetO1-GFP |
| pTrpA-uPtetO2-GFP | derivative of pTrpA, uPtetO2-GFP |
| pTrpA-uPtetO1-Cre | derivative of pTrpA-uPtetO2-GFP, uPtetO1-Cre |
| pTrpA-uPtetO2-Cre | derivative of pTrpA-uPtetO2-GFP, uPtetO2-Cre |
| pTrpA-RCAT | derivative of pTrpA, rpsL-CAT |
| pBlu-BI | derivative of pBlu-SK-alt, contains regions of homology to HP0072 and HP0071, contains multiple cloning site (see WO/2010/148459) |
| pMK-RQ-Lox6671 | Derivative of pMK-RQ, contains synthetic Lox6671 cassette |
| pBI-Lox6671 | derivative of pBlu-BI, Lox6671 |
| pMA-T-tetRs | derivative of pMA, contains synthetic H. pylori codon optimised tetRs |
| pMdaB-PureA-hydA | derivative of pMdaB, PureA-hydA |
| pMdaB-PureA-TetRs | derivative of pMdaB-PureA-hydA, PureA-tetRs |
| pMK-1uPtetO5-Cre5' | derivative of pMK, 1uPtetO5-cre5' |
| pMK-2uPtetO5-Cre5' | derivative of pMK, 2uPtetO5-cre5' |
| pMK-3uPtetO5-Cre5' | derivative of pMK, 3uPtetO5-cre5' |
| pMK-4uPtetO5-Cre5' | derivative of pMK, 4uPtetO5-cre5' |
| pMK-5uPtetO5-Cre5' | derivative of pMK, 5uPtetO5-cre5' |
| pMK-6uPtetO5-Cre5' | derivative of pMK, 6uPtetO5-cre5' |
| pTrpA-1uPtetO5-Cre | derivative of pTrpA-uPtetO2-Cre, 1uPtetO5-Cre |
| pTrpA-2uPtetO5-Cre | derivative of pTrpA-uPtetO2-Cre, 2uPtetO5-Cre |
| pTrpA-3uPtetO5-Cre | derivative of pTrpA-uPtetO2-Cre, 3uPtetO5-Cre |
| pTrpA-4uPtetO5-Cre | derivative of pTrpA-uPtetO2-Cre, 4uPtetO5-Cre |
| pTrpA-5uPtetO5-Cre | derivative of pTrpA-uPtetO2-Cre, 5uPtetO5-Cre |
| pTrpA-6uPtetO5-Cre | derivative of pTrpA-uPtetO2-Cre, 6uPtetO5-Cre |
| pMA-Antisense | Derivative of pMA, contains synthetic antisense cassette |
| pTrpA-as1uPtetO5-Cre | Derivative of pMA-Antisense, as1uPtetO5-Cre |
| pTrpA-as2uPtetO5-Cre | Derivative of pMA-Antisense, as1uPtetO5-Cre |
| pTrpA-as3uPtetO5-Cre | Derivative of pMA-Antisense, as1uPtetO5-Cre |
| pTrpA-as4uPtetO5-Cre | Derivative of pMA-Antisense, as1uPtetO5-Cre |
| pTrpA-as6uPtetO5-Cre | Derivative of pMA-Antisense, as1uPtetO5-Cre |
| pMK-RQ-FliCsyn | Derivative of pMK, contains synthetic H. pylori codon optimised fliC gene |
| pMA-IEC-LLOs | Derivative of pMA, contains synthetic inducible antigen expression cassette with H. pylori codon optimised LLO gene as antigen |
| pMA-IEC-TetRs-LLO | Derivative of pMA-IEC-LLOs; tetRs cloned in inducible expression cassette |
| pMA-IEC-TetRs-FliCsyn | Derivative of pMA-IEC-TetRs-LLOs, inducible expression of fliCsyn |
| pHel2 | E. coli-H. pylori shuttle vector |
| pHel2-IEC-FliCsyn | Derivative of pHel2; inducible expression of fliCsyn |
| pHel2-IEC-Ts-FliCsyn | B128 containing pHel2-IEC-T-FliCsyn |
| pWH1925 BD | template for tetR (Schnappinger et al., 1998) |
| pWH1925 r2 | template for revtetR (Scholz et al., 2004) |
| pMdaB | derivative of pBlu-SK-alt, contain regions of homology to HP0630 and HP0631, contains multiple cloning site |

TABLE 4-continued

Bacterial Strains and Plasmids Used in this Study

| Strain or plasmid | Description |
|---|---|
| pMdaB-RCAT | derivative of pMdaB, rpsL-CAT |
| pMdaB-ptetR1 | derivative of pMdaB, PamiE-revtetR |
| pMdaB-ptetR2 | derivative of pMdaB, PamiE-tetR |
| pMdaB-ptetR3 | derivative of pMdaB, PflaA-revtetR |
| pMdaB-ptetR4 | derivative of pMdaB, PflaA-tetR |
| pMdaB-ptetR5 | derivative of pMdaB, PtaTaat-revtetR |
| pMdaB-ptetR6 | derivative of pMdaB, PtaTaat-tetR |
| pMdaB-ptetR7 | derivative of pMdaB, PtaCaat-revtetR |
| pHSG576 | Low copy plasmid (Takeshita et al., 1987) |
| pHRdx | derivative of pHSG576, contains regions of homology to regions flanking HP0954 ORF, contains multiple cloning site (Croxen et al., 2006 |
| pBlu-BI | derivative of pBlu-SK-alt, contain regions of homology to HP0072 and HP0071, contains multiple cloning site (WO/2010/148459) |
| pBlu_uPtetO1-GFP | derivative of pBlu-BI, uPtetO1-GFP |
| pBlu_uPtetO2-GFP | derivative of pBlu-BI, uPtetO2-GFP |
| pBlu_uPtetO3-GFP | derivative of pBlu-BI, uPtetO3-GFP |
| pTrpA | derivative of pBlu-SK-alt, contain regions of homology to HP1277, contains multiple cloning site |
| pTrpA-RCAT | derivative of pTrpA, rpsL-CAT |
| pTrpA-uPtetO1-GFP | derivative of pTrpA, uPtetO1-GFP |
| pTrpA-uPtetO2-GFP | derivative of pTrpA, uPtetO2-GFP |
| pTrpA-uPtetO3-GFP | derivative of pTrpA, uPtetO3-GFP |
| pGltDH | derivative of pBlu-SK-alt, contain regions of homology to HP0379 and HP0380, contains multiple cloning site |
| pGltDH-RCAT | derivative of pGltDH, rpsL-CAT |
| pGltDH-uPtetO1-GFP | derivative of pGltDH, uPtetO1-GFP |
| pGltDH-uPtetO2-GFP | derivative of pGltDH, uPtetO2-GFP |
| pGltDH-uPtetO3-GFP | derivative of pGltDH, uPtetO3-GFP |
| pHdapB | derivative of pHSG576, contains regions of homology to HP0509 and HP0511, contains multiple cloning site |
| pHdapB-RCAT | derivative of pHdapB, rpsL-CAT |
| pHdapB-uPtetO1-GFP | derivative of pHdapB, uPtetO1-GFP |
| pHdapB-uPtetO2-GFP | derivative of pHdapB, uPtetO2-GFP |
| pHdapB-uPtetO3-GFP | derivative of pHdapB, uPtetO3-GFP |
| *E. coli* strain: | |
| DH10β | F-mcrA Δ(mrr-hsdRMS-mcrBC) Φ80dlacZΔM15 ΔlacX74 endA1 recA1 deoR Δ(ara, leu)7697 araD139 galU galK nupG rpsL λ- |
| β2150 | (DdapA::(erm-pir) thrB1004, pro, thi, strA, hsdS, lacZ DM15 (F¢ lacZ DM15 lacIq, traD36, proA−, proB−)) |
| β2150 [pRK2013] | helper strain; β2150 containing pRK2013 |
| β2150 pHel2-IEC-Ts-FliCsyn | donor strain, pHel2-IEC-Ts-FliCsyn |
| DH5α | fhuA2 Δ(argF-lacZ)U169 phoA glnV44 Φ80 Δ(lacZ)M15 gyrA96 recA1 relA1 endA1 thi-1 hsdR17 |
| *H. pylori* strains: | |
| X47 dapB:: rpsL-CAT | HP0510 is replaced with rpsL-CAT |
| X47 dapB:: uPtetO1-GFP | HP0510 is replaced with uPtetO1-GFP |
| X47 dapB:: uPtetO2-GFP | HP0510 is replaced with uPtetO2-GFP |
| X47 gltDH:: rpsL-CAT | rpsL-CAT inserted between HP0379 and HP380 |
| X47 gltDH:: uPtetO1-GFP | uPtetO1-GFP inserted between HP0379 and HP380 |
| X47 gltDH:: uPtetO2-GFP | uPtetO2-GFP inserted between HP0379 and HP380 |
| X47 mdaB:: ptetR(1) | promoter-tetR1 inserted between HP630 and HP631 |
| X47 mdaB:: ptetR(1); dapB:: rpsL-CAT | promoter-tetR1 inserted between HP630 and HP631; HP0510 is replaced with rpsL-CAT |
| X47 mdaB:: ptetR(1); gltDH:: rpsL-CAT | promoter-tetR1 inserted between HP630 and HP631; rpsL-CAT inserted between HP0379 and HP380 |
| X47 mdaB:: ptetR(1); trpA:: rpsL-CAT | promoter-tetR1 inserted between HP630 and HP631; rpsL-CAT inserted into HP1277 |
| X47 mdaB:: ptetR(1); ureA:: rpsL-CAT | promoter-tetR1 inserted between HP630 and HP631; ureA and upstream promoter replaced with rpsL-CAT |
| X47 mdaB:: ptetR(1); ureA:: rpsL-CAT | promoter-tetR1 inserted between HP630 and HP631; ureA and upstream promoter replaced with rpsL-CAT |
| X47 mdaB:: ptetR(1-6); (trpA/gltDH/dapB):: uPtetO(1-2)-GFP | promoter-tetR inserted between HP630 and HP631; uPtetO-GFP inserted at recipient locus |
| X47 mdaB:: ptetR(2) | promoter-tetR2 inserted between HP630 and HP631 |
| X47 mdaB:: ptetR(2); dapB:: rpsL-CAT | promoter-tetR2 inserted between HP630 and HP631; HP0510 is replaced with rpsL-CAT |
| X47 mdaB:: ptetR(2); gltDH:: rpsL-CAT | promoter-tetR2 inserted between HP630 and HP631; rpsL-CAT inserted between HP0379 and HP380 |
| X47 mdaB:: ptetR(2); trpA:: rpsL-CAT | promoter-tetR2 inserted between HP630 and HP631; rpsL-CAT inserted into HP1277 |
| X47 mdaB:: ptetR(2); ureA:: rpsL-CAT | promoter-tetR2 inserted between HP630 and HP631; ureA and upstream promoter replaced with rpsL-CAT |
| X47 mdaB:: ptetR(2); ureA:: rpsL-CAT | promoter-tetR2 inserted between HP630 and HP631; ureA and upstream promoter replaced with rpsL-CAT |

TABLE 4-continued

Bacterial Strains and Plasmids Used in this Study

| Strain or plasmid | Description |
|---|---|
| X47 mdaB:: ptetR(2-7); urePtetO(I-V) | promoter-tetR inserted between HP630 and HP631; tetO operators located in ureA promoter |
| X47 mdaB:: ptetR(3) | promoter-tetR3 inserted between HP630 and HP631 |
| X47 mdaB:: ptetR(3); dapB:: rpsL-CAT | promoter-tetR3 inserted between HP630 and HP631; HP0510 is replaced with rpsL-CAT |
| X47 mdaB:: ptetR(3); gltDH:: rpsL-CAT | promoter-tetR3 inserted between HP630 and HP631; rpsL-CAT inserted between HP0379 and HP380 |
| X47 mdaB:: ptetR(3); trpA:: rpsL-CAT | promoter-tetR3 inserted between HP630 and HP631; rpsL-CAT inserted into HP1277 |
| X47 mdaB:: ptetR(3); ureA:: rpsL-CAT | promoter-tetR3 inserted between HP630 and HP631; ureA and upstream promoter replaced with rpsL-CAT |
| X47 mdaB:: ptetR(4) | promoter-tetR4 inserted between HP630 and HP631 |
| X47 mdaB:: ptetR(4); dapB:: rpsL-CAT | promoter-tetR4 inserted between HP630 and HP631; HP0510 is replaced with rpsL-CAT |
| X47 mdaB:: ptetR(4); gltDH:: rpsL-CAT | promoter-tetR4 inserted between HP630 and HP631; rpsL-CAT inserted between HP0379 and HP380 |
| X47 mdaB:: ptetR(4); trpA:: rpsL-CAT | promoter-tetR4 inserted between HP630 and HP631; rpsL-CAT inserted into HP1277 |
| X47 mdaB:: ptetR(4); ureA:: rpsL-CAT | promoter-tetR4 inserted between HP630 and HP631; ureA and upstream promoter replaced with rpsL-CAT |
| X47 mdaB:: ptetR(5) | promoter-tetR5 inserted between HP630 and HP631 |
| X47 mdaB:: ptetR(5); dapB:: rpsL-CAT | promoter-tetR5 inserted between HP630 and HP631; HP0510 is replaced with rpsL-CAT |
| X47 mdaB:: ptetR(5); gltDH:: rpsL-CAT | promoter-tetR5 inserted between HP630 and HP631; rpsL-CAT inserted between HP0379 and HP380 |
| X47 mdaB:: ptetR(5); trpA:: rpsL-CAT | promoter-tetR5 inserted between HP630 and HP631; rpsL-CAT inserted into HP1277 |
| X47 mdaB:: ptetR(5); ureA:: rpsL-CAT | promoter-tetR5 inserted between HP630 and HP631; ureA and upstream promoter replaced with rpsL-CAT |
| X47 mdaB:: ptetR(6) | promoter-tetR6 inserted between HP630 and HP631 |
| X47 mdaB:: ptetR(6); dapB:: rpsL-CAT | promoter-tetR6 inserted between HP630 and HP631; HP0510 is replaced with rpsL-CAT |
| X47 mdaB:: ptetR(6); gltDH:: rpsL-CAT | promoter-tetR6 inserted between HP630 and HP631; rpsL-CAT inserted between HP0379 and HP380 |
| X47 mdaB:: ptetR(6); trpA:: rpsL-CAT | promoter-tetR6 inserted between HP630 and HP631; rpsL-CAT inserted into HP1277 |
| X47 mdaB:: ptetR(6); ureA:: rpsL-CAT | promoter-tetR6 inserted between HP630 and HP631; ureA and upstream promoter replaced with rpsL-CAT |
| X47 mdaB:: ptetR(6); ureA:: rpsL-CAT | promoter-tetR6 inserted between HP630 and HP631; ureA and upstream promoter replaced with rpsL-CAT |
| X47 mdaB:: ptetR(7) | promoter-tetR7 inserted between HP630 and HP631 |
| X47 mdaB:: ptetR(7); dapB:: rpsL-CAT | promoter-tetR7 inserted between HP630 and HP631; HP0510 is replaced with rpsL-CAT |
| X47 mdaB:: ptetR(7); gltDH:: rpsL-CAT | promoter-tetR7 inserted between HP630 and HP631; rpsL-CAT inserted between HP0379 and HP380 |
| X47 mdaB:: ptetR(7); trpA:: rpsL-CAT | promoter-tetR7 inserted between HP630 and HP631; rpsL-CAT inserted into HP1277 |
| X47 mdaB:: ptetR(7); ureA:: rpsL-CAT | promoter-tetR7 inserted between HP630 and HP631; ureA and upstream promoter replaced with rpsL-CAT |
| X47 mdaB:: ptetR(7); ureA:: rpsL-CAT | promoter-tetR7 inserted between HP630 and HP631; ureA and upstream promoter replaced with rpsL-CAT |
| X47 mdaB:: ptetR2; trpA:: uPtetO1-cre; ureBI:: rpsL-CAT | promoter-tetR2 inserted between HP0630 and HP0631; uPtetO1-cre inserted into HP1277, rpsL-CAT inserted between HP0072 and HP0071 |
| X47 mdaB:: ptetR2; trpA:: uPtetO1-cre; ureBI::Lox6671 | promoter-tetR2 inserted between HP0630 and HP0631; uPtetO1-cre inserted into HP1277, Lox6671 inserted between HP0072 and HP0071 |
| X47 mdaB:: ptetR2; trpA:: uPtetO2-cre; ureBI:: rpsL-CAT | promoter-tetR2 inserted between HP0630 and HP0631; uPtetO2-cre inserted into HP1277, rpsL-CAT inserted between HP0072 and HP0071 |
| X47 mdaB:: ptetR2; trpA:: uPtetO2-cre; ureBI::Lox6671 | promoter-tetR2 inserted between HP0630 and HP0631; uPtetO2-cre inserted into HP1277, Lox6671 inserted between HP0072 and HP0071 |
| X47 mdaB:: PureA-tetRs; trpA:: as1uPtetO5-cre | PureA-tetRs inserted between HP0630 and HP0631; as1uPtetO5-cre inserted between HP1277 |
| X47 mdaB:: PureA-tetRs; trpA:: as1uPtetO5-cre; ureBI:: rpsL-CAT | PureA-tetRs inserted between HP0630 and HP0631; as1uPtetO5-cre inserted between HP1277; rpsL-CAT inserted between HP0072 and HP0071 |
| X47 mdaB:: PureA-tetRs; trpA:: as1uPtetO5-cre; ureBI::Lox6671 | PureA-tetRs inserted between HP0630 and HP0631; as1uPtetO5-cre inserted between HP1277; Lox6671 inserted between HP0072 and HP0071 |
| X47 mdaB:: PureA-tetRs; trpA:: as2uPtetO5-cre | PureA-tetRs inserted between HP0630 and HP0631; as2uPtetO5-cre inserted between HP1277 |
| X47 mdaB:: PureA-tetRs; trpA:: as2uPtetO5-cre; ureBI:: rpsL-CAT | PureA-tetRs inserted between HP0630 and HP0631; as2uPtetO5-cre inserted between HP1277; rpsL-CAT inserted between HP0072 and HP0071 |
| X47 mdaB:: PureA-tetRs; trpA:: as2uPtetO5-cre; ureBI:Lox6671 | PureA-tetRs inserted between HP0630 and HP0631; as2uPtetO5-cre inserted between HP1277; Lox6671 inserted between HP0072 and HP0071 |
| X47 mdaB:: PureA-tetRs; trpA:: as3uPtetO5-cre | PureA-tetRs inserted between HP0630 and HP0631; as3uPtetO5-cre inserted between HP1277 |
| X47 mdaB:: PureA-tetRs; trpA:: as3uPtetO5-cre; ureBI:: rpsL-CAT | PureA-tetRs inserted between HP0630 and HP0631; as3uPtetO5-cre inserted between HP1277; rpsL-CAT inserted between HP0072 and HP0071 |
| X47 mdaB:: PureA-tetRs; trpA:: as3uPtetO5-cre; ureBI::Lox6671 | PureA-tetRs inserted between HP0630 and HP0631; as3uPtetO5-cre inserted between HP1277; Lox6671 inserted between HP0072 and HP0071 |
| X47 mdaB:: PureA-tetRs; trpA:: as4uPtetO5-cre | PureA-tetRs inserted between HP0630 and HP0631; as4uPtetO5-cre inserted between HP1277 |
| X47 mdaB:: PureA-tetRs; trpA:: as4uPtetO5-cre; ureBI:: rpsL-CAT | PureA-tetRs inserted between HP0630 and HP0631; as4uPtetO5-cre inserted between HP1277; rpsL-CAT inserted between HP0072 and HP0071 |
| X47 mdaB:: PureA-tetRs; trpA:: as4uPtetO5-cre; ureBI::Lox6671 | PureA-tetRs inserted between HP0630 and HP0631; as4uPtetO5-cre inserted between HP1277; Lox6671 inserted between HP0072 and HP0071 |
| X47 mdaB:: PureA-tetRs; trpA:: as6uPtetO5-cre | PureA-tetRs inserted between HP0630 and HP0631; as6uPtetO5-cre inserted between HP1277 |
| X47 mdaB:: PureA-tetRs; trpA:: as6uPtetO5-cre; ureBI:: rpsL-CAT | PureA-tetRs inserted between HP0630 and HP0631; as6uPtetO5-cre inserted between HP1277; rpsL-CAT inserted between HP0072 and HP0071 |
| X47 mdaB:: PureA-tetRs; trpA:: as6uPtetO5-cre; ureBI::Lox6671 | PureA-tetRs inserted between HP0630 and HP0631; as6uPtetO5-cre inserted between HP1277; Lox6671 inserted between HP0072 and HP0071 |
| X47 mdaB:: rpsL-CAT | rpsL-CAT inserted between HP0630 and HP0631 |
| X47 mdaB:: rpsL-CAT | rpsL-CAT inserted between HP630 and HP631 |
| X47 mdaB::ptetR2; trpA:: rpsL-CAT | promoter-tetR2 inserted between HP0630 and HP0631; rpsl-CAT inserted into HP1277 |
| X47 mdaB::ptetR2; trpA:: uPtetO1-cre | promoter-tetR2 inserted between HP0630 and HP0631; uPtetO1-cre inserted into HP1277 |
| X47 mdaB::ptetR2; trpA:: uPtetO2-cre | promoter-tetR2 inserted between HP0630 and HP0631; uPtetO2-cre inserted into HP1277 |
| X47 mdaB::PureA-tetRs | PureA-tetRs inserted between HP0630 and HP0631 |
| X47 mdaB::PureA-tetRs; trpA:: 1uPtetO5-cre | PureA-tetRs inserted between HP0630 and HP0631; 1uPtetO5-cre inserted between HP1277 |

TABLE 4-continued

Bacterial Strains and Plasmids Used in this Study

| Strain or plasmid | Description |
| --- | --- |
| X47 mdaB::PureA-tetRs; trpA:: 2uPtetO5-cre | PureA-tetRs inserted between HP0630 and HP0631; 2uPtetO5-cre inserted between HP1277 |
| X47 mdaB::PureA-tetRs; trpA:: 3uPtetO5-cre | PureA-tetRs inserted between HP0630 and HP0631; 3uPtetO5-cre inserted between HP1277 |
| X47 mdaB::PureA-tetRs; trpA:: 4uPtetO5-cre | PureA-tetRs inserted between HP0630 and HP0631; 4uPtetO5-cre inserted between HP1277 |
| X47 mdaB::PureA-tetRs; trpA:: 5uPtetO5-cre | PureA-tetRs inserted between HP0630 and HP0631; 5uPtetO5-cre inserted between HP1277 |
| X47 mdaB::PureA-tetRs; trpA:: 6uPtetO5-cre | PureA-tetRs inserted between HP0630 and HP0631; 6uPtetO5-cre inserted between HP1277 |
| X47 mdaB::PureA-tetRs; trpA:: rpsL-CAT | PureA-tetRs inserted between HP0630 and HP0631; rpsL-CAT inserted between HP1277 |
| X47 mdaB::PureA-tetRs; trpA:: 1uPtetO5-cre; ureBI:: rpsL-CAT | PureA-tetRs inserted between HP0630 and HP0631; 1uPtetO5-cre inserted between HP1277; rpsL-CAT inserted between HP0072 and HP0071 |
| X47 mdaB::PureA-tetRs; trpA:: 1uPtetO5-cre; ureBI::Lox6671 | PureA-tetRs inserted between HP0630 and HP0631; 1uPtetO5-cre inserted between HP1277; Lox6671 inserted between HP0072 and HP0071 |
| X47 mdaB::PureA-tetRs; trpA::2uPtetO5-cre; ureBI:: rpsL-CAT | PureA-tetRs inserted between HP0630 and HP0631; 2uPtetO5-cre inserted between HP1277; rpsL-CAT inserted between HP0072 and HP0071 |
| X47 mdaB::PureA-tetRs; trpA::2uPtetO5-cre; ureBI::Lox6671 | PureA-tetRs inserted between HP0630 and HP0631; 2uPtetO5-cre inserted between HP1277; Lox6671 inserted between HP0072 and HP0071 |
| X47 mdaB::PureA-tetRs; trpA::3uPtetO5-cre; ureBI:: rpsL-CAT | PureA-tetRs inserted between HP0630 and HP0631; 3uPtetO5-cre inserted between HP1277; rpsL-CAT inserted between HP0072 and HP0071 |
| X47 mdaB::PureA-tetRs; trpA::3uPtetO5-cre; ureBI::Lox6671 | PureA-tetRs inserted between HP0630 and HP0631; 3uPtetO5-cre inserted between HP1277; Lox6671 inserted between HP0072 and HP0071 |
| X47 mdaB::PureA-tetRs; trpA::4uPtetO5-cre; ureBI:: rpsL-CAT | PureA-tetRs inserted between HP0630 and HP0631; 4uPtetO5-cre inserted between HP1277; rpsL-CAT inserted between HP0072 and HP0071 |
| X47 mdaB::PureA-tetRs; trpA::4uPtetO5-cre; ureBI::Lox6671 | PureA-tetRs inserted between HP0630 and HP0631; 4uPtetO5-cre inserted between HP1277; Lox6671 inserted between HP0072 and HP0071 |
| X47 mdaB::PureA-tetRs; trpA::5uPtetO5-cre; ureBI:: rpsL-CAT | PureA-tetRs inserted between HP0630 and HP0631; 5uPtetO5-cre inserted between HP1277; rpsL-CAT inserted between HP0072 and HP0071 |
| X47 mdaB::PureA-tetRs; trpA::5uPtetO5-cre; ureBI::Lox6671 | PureA-tetRs inserted between HP0630 and HP0631; 5uPtetO5-cre inserted between HP1277; Lox6671 inserted between HP0072 and HP0071 |
| X47 mdaB::PureA-tetRs; trpA::6uPtetO5-cre; ureBI:: rpsL-CAT | PureA-tetRs inserted between HP0630 and HP0631; 6uPtetO5-cre inserted between HP1277; rpsL-CAT inserted between HP0072 and HP0071 |
| X47 mdaB::PureA-tetRs; trpA::6uPtetO5-cre; ureBI::Lox6671 | PureA-tetRs inserted between HP0630 and HP0631; 6uPtetO5-cre inserted between HP1277; Lox6671 inserted between HP0072 and HP0071 |
| X47 trpA:: rpsL-CAT | rpsL-CAT inserted into HP1277 |
| X47 trpA:: uPtetO1-GFP | uPtetO1-GFP inserted into HP1277 |
| X47 trpA:: uPtetO2-GFP | uPtetO2-GFP inserted into HP1277 |
| X47 ureA:: rpsL-CAT | ureA and upstream promoter replaced with rpsL-CAT |
| X47 ureBI:: rpsL-CAT | rpsL-CAT inserted between HP0072 and HP0071 |
| X47 urePtetO(I) | tetO operaters located in ureA promoter |
| X47 urePtetO(II) | tetO operaters located in ureA promoter |
| X47 urePtetO(III) | tetO operaters located in ureA promoter |
| X47 urePtetO(IV) | tetO operaters located in ureA promoter |
| X47 urePtetO(V) | tetO operaters located in ureA promoter |
| X47 | wild-type strain, also known as X47-2AL (Ermak et al., 1998) |
| B128 | clinical isolate |

*H. pylori* X47 (Ermak et al. 1998) strains were routinely grown at 37° C. under microaerophilic conditions on Columbia blood agar (CBA) plates containing 5% horse blood and Dent's antibiotic supplement (Oxoid). When appropriate, antibiotic selection in *H. pylori* was carried out by supplementing media with chloramphenicol or streptomycin at a final concentration of 10 μg/mL. *H. pylori* liquid culture: Bacteria were grown in Brain Heart Infusion (BHI) medium or Bruccella Broth supplemented with 10% Newborn Calf Serum (NCS) and Dent's antibiotic supplement. Cultures were inoculated with bacteria resuspended in PBS to give a starting $OD_{600}$ of 0.05, and grown under microaerophilic conditions at 37° C. and 120 rpm. Growth studies were performed without any prior adaptation of *H. pylori* strains to liquid media. *Escherichia coli* DH5a was grown in Luria-Bertani broth. When necessary, antibiotics were added to the following final concentrations: ampicillin, 100 μg/ml and chloramphenicol, 20 μg/ml.

Construction of *H. pylori* Strains Expressing TetR and revTetR

Generation if HP Promoter-tetR Fusion Constructs (ptetR).

Four different *H. pylori* promoters were used to generate several different promoter-tetR constructs to drive constitutive expression of TetRs in *H. pylori* (ptetR1-8) FIG. 1). ptetR 1 through 4 were generated by short fusion PCR (Shevchuk et al. 2004). Briefly, for ptetR1, the amiE promoter was amplified from 26695 genomic DNA (NCBI accession number NC_000915) using primers tet1 and tet2, and tetR was amplified from pWH1925 BD (Schnappinger et al. 1998) with primers tet3 and tet9. Primers tet4 and tet10 were used to amplify the fusion PCR product and introduce flanking SalI and BamHI sites. For ptetR2, revtetR was amplified from pWH1925 r2 (Scholz et al. 2004). For ptetR3 and ptetR4, the flaA promoter was used to drive expression of tetR/revtetR and were generated using primers tet5 through tet10. A different strategy was used to generate the core urease promoter-tetR fusions, ptetR5-8. The core promoter is very small, therefore three sequential rounds of PCR, using three long forward primers and one short reverse primer, was used to fuse the promoter to the tetR/revtetR genes in a step wise manner.

Step 1. Long forward primer tet1 with reverse primer tet9, Step 2. forward primers tet12 (ptetR5-6 mutant) or tet13 (ptetR7-8) with primer tet9, followed by Step 3. using forward primer tet14 with reverse primer tet10 to introduce flanking SalI and BamHI sites. All ptetR constructs were cloned into vector pHRdx (Takeshita et al. 1987; Croxen et al. 2006) to generate pH_Rdx-ptetR(1-8). Several attempts to introduce ptetR constructs into the HP0954 locus of the X47 recipient strain by homologous recombination failed. Therefore primers mbtetF and mbtetR were used to amplify the ptetR constructs and introduce flanking SbfI and EcoRI cut sites for cloning into PstI and EcoRI digested pMdaB cloning vector to generate pMdaB-ptetR(1-7) constructs (FIG. 11). Natural transformation of *H. pylori* recipient strain X47 mdaB:: rpsL-CAT with these plasmid constructs was performed to create X47 mdaB:: ptetR(1-7). Chromosomal DNA of the resulting streptomycin-resistant transformants was checked for the correct allelic insertion.

Figure 12:
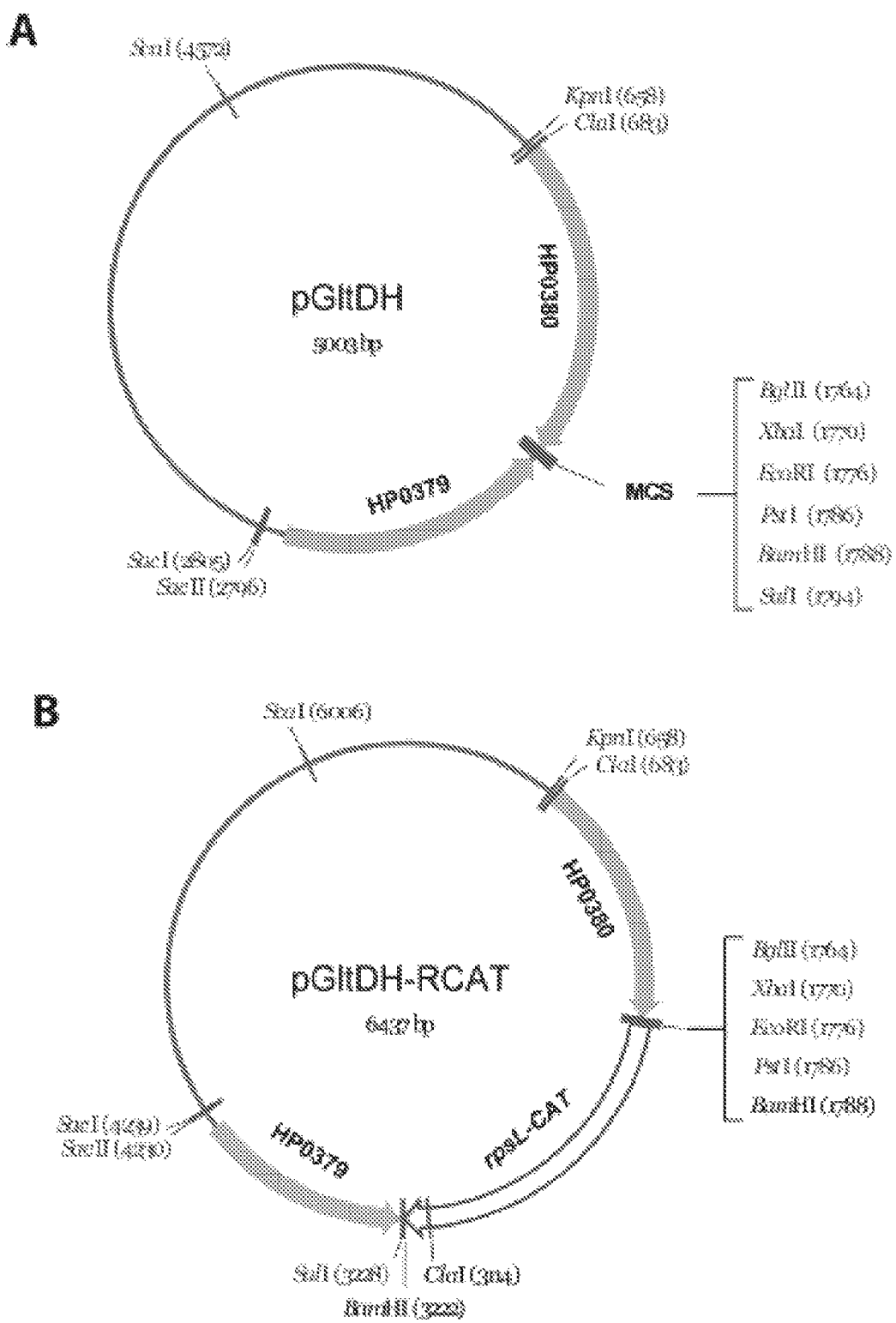
FIG. 12 shows construct maps for vectors used for targeted insertion of DNA into the GltDH locus of the *H. pylori* genome by homologous recombination. (A) pGltDH, cloning vector (B) pGltDH-RCAT, containing rpsL-CAT, used for generating *H. pylori* recipient strains at the GltDH locus.
Figure 13:
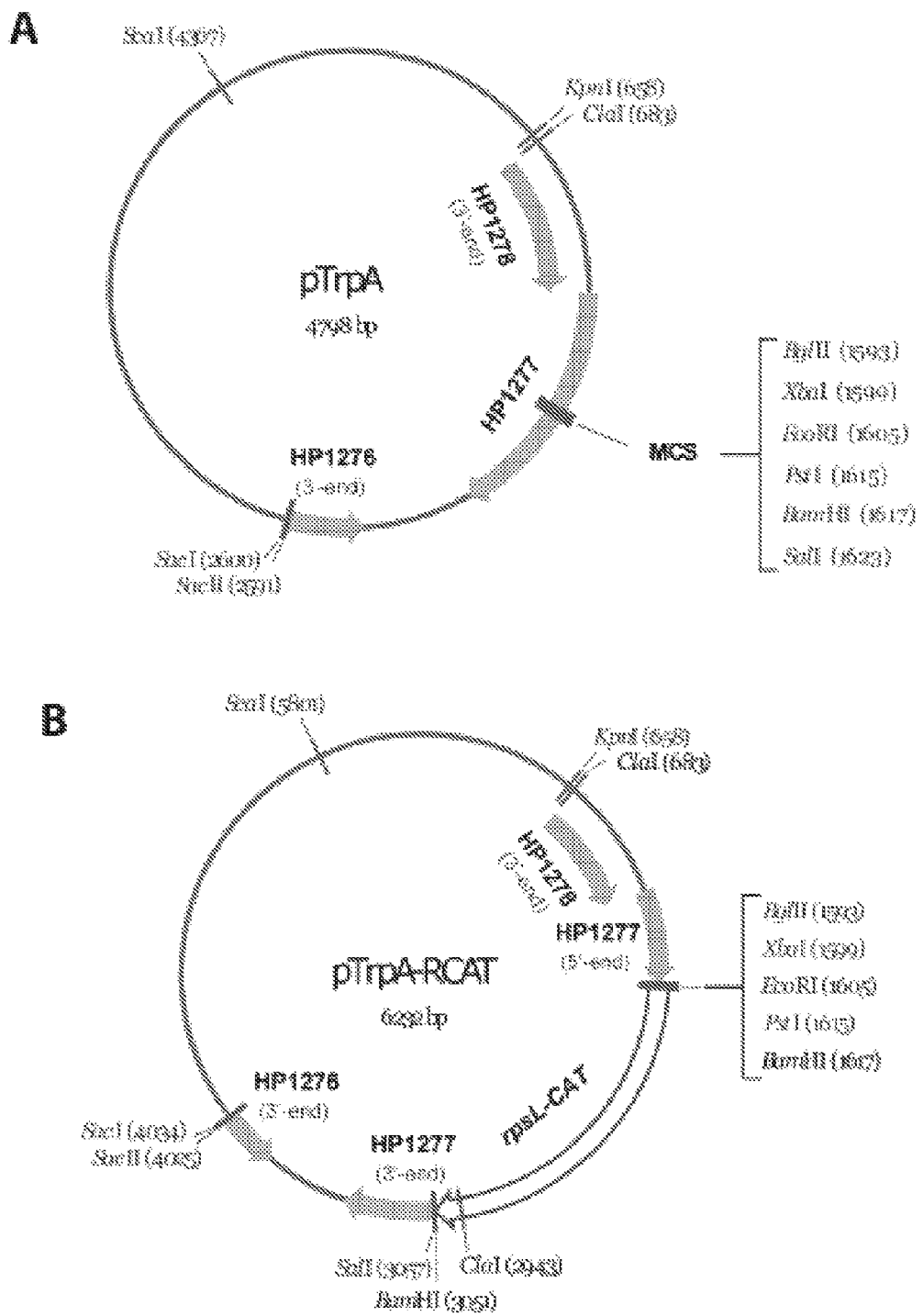
FIG. 13 shows construct maps for vectors used for targeted insertion of DNA into the TrpA locus of the *H. pylori* genome by homologous recombination. (A) pTrpA, cloning vector (B) pTrpA-RCAT, containing rpsL-CAT, used for generating *H. pylori* recipient strains at the TrpA locus.

Construction of Cloning Vectors, for Integration of Genes into Recipient Loci, pMdaB pGltDH, pTrpA and pHdapB pGltDH:

1 kb of the C-terminal end of HP0380 was amplified with primers GltDH1 and GltDH2 and 1 kb of HP00379 was amplified with primers GltDH3 and GltDH4. These two fragments were joined together by short fusion PCR, using primers GltDH1 and GltDH4, to generate a 2 kb PCR product, containing a small MCS site inserted between $HPO_{380}$ and $HPO_{378}$, flanked by ClaI and SacII restriction sites. This fragment was cloned into vector back bone of pBlu-SK-alt (xhoI and SalI sites in pBluescript SK (–) were deleted by restriction enzyme digest and religation) to give pGltDH, a cloning vector where DNA of interest could be cloned into the unique restriction sites of the mini MCS and incorporated by homologous recombination into the *H. pylori* genome between HP0380 and HP0379 (FIG. 12A).

pTrpA:

A similar strategy was used to generate pTrpA, using primers TrpA1 through TrpA4 with the final construct containing a small MCS inserted into the center of HP1277. This vector is used to introduce DNA sequences of interest into the center of HP1277 (FIG. 13A).

pMdaB:

Two 1 kb regions flanking the mdaB gene (HP0630) were amplified from using primers MdaB1 and MdaB2, and MdaB3 and MdaB4. These two fragments were joined together by short fusion PCR, using primers using primers MdaB1 and MdaB4, to generate a 2.1 kb PCR product, containing a small MCS site inserted between HP0630 and HP0631, flanked by ClaI and NotI restriction sites. This fragment was cloned into vector back bone of pBlu-SK-alt to give pMdaB, a cloning vector where DNA of interest could be cloned into the unique restriction sites of the mini MCS and incorporated by homologous recombination into the *H. pylori* genome between HP0630 and HP0631.

pHdapB:

Two 600 bp regions flanking HP0510 were amplified using primers DapB1 and DapB2, and DapB3 and DapB4, and joined together by fusion PCR resulting in a 1.2 kb product where HP0510 was replaced with a small MCS. Primers DapB5 and DapB6 were used to amplify the fusion product and introduce HindIII and EcoRI restriction sites. The final product was cloned into pHSG576 to create pHdapB, a cloning vector where DNA of interest could be cloned into the unique restriction sites of the MCS and then transformed into *H. pylori*, to generate a strain where HP0510 is replaced with the DNA sequence of interest. (FIG. 14A).

Plasmid Constructs for Generating Recipient X47 Strains for Introduction of Foreign DNA at Recipient Locus.

Figure 14:
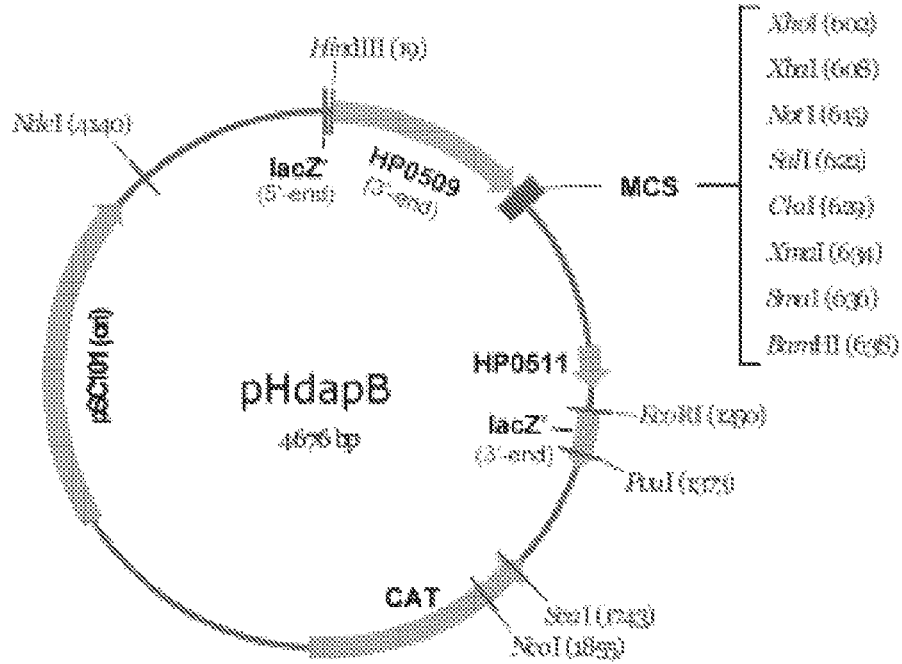
FIG. 14 shows construct maps for vectors used for targeted insertion of DNA into the DapB locus of the *H. pylori* genome by homologous recombination. (A) pHdapB, cloning vector (B) pHdapB-RCAT, containing rpsL-CAT, used for generating *H. pylori* recipient strains at the DapB locus.
Figure 14:
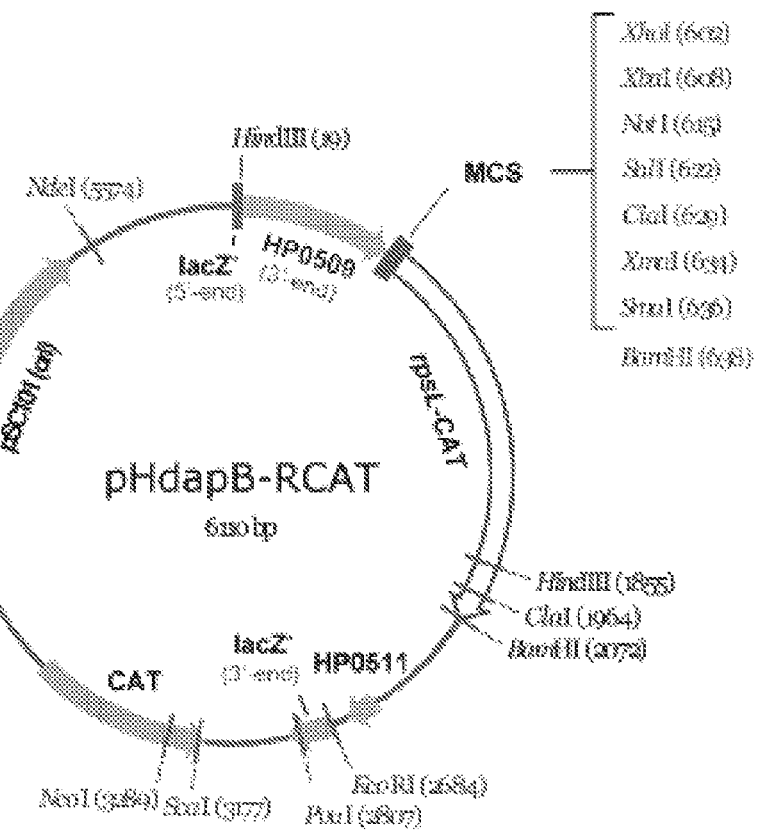

A counter-selection cassette, rpsL-CAT, flanked by BamHI restriction sites was clone into BamHI site of pGltDH, pTrpA, pMdaB and pHdapB to generate pGltDH-RCAT, pTrpA-RCAT, pMdaB-RCAT and pHdapB-RCAT respectively (FIGS. 12B, 13B and 14B). These constructs are used to make the recipient X47 strains, gltDH::rpsL-CAT, trpA::rpsL-CAT, mdaB::rpsL-CAT and dapB::rpsL-CAT, required for introducing DNA sequence of interest into the appropriate recipient locus.

Figure 15:
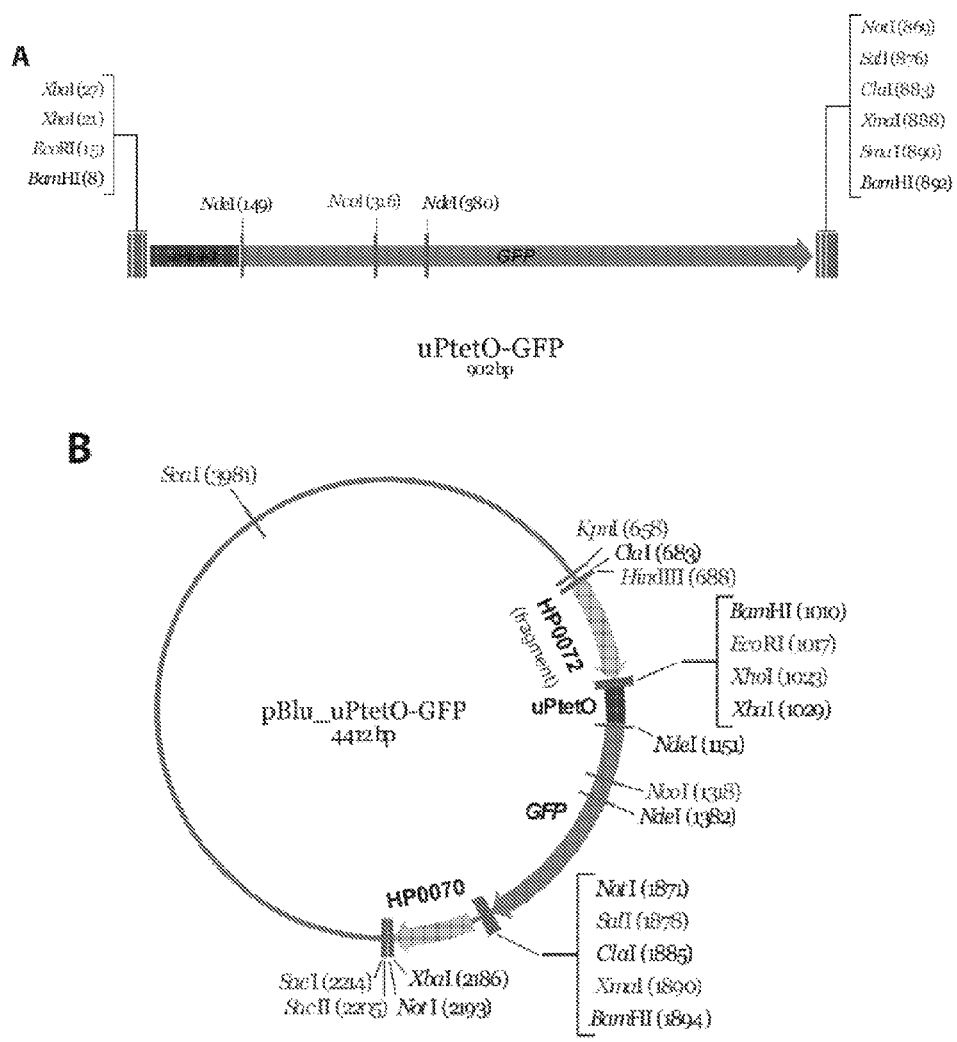
FIG. 15 shows construct maps of tet responsive uPtetO fused to GFP. (A) Detailed map of uPtetO-GFP. (B) uPtetO-GFP cloned into pBluscript variant.

Construction of Tetracycline Responsive Promoter, uPtetO, with GFP as Reporter Gene; pBlu_uPtetO-GFP A similar 3 step PCR methodology used to make ptetR(5-8) was used to make uPtetO(1-3)-GFP constructs. Briefly, gfp-mut2 was amplified using primers tetOGFP1 and tetOGFP5 (step1). In step 2, forward primers tetOGFP2, tetOGFP3 and tetOGFP4 were used with reverse primer tetOGFP5 for uPtetO1-GFP, uPtetO2-GFP and uPtetO3-GFP respectively, and finally primers tetOGFP5 and tetOGFP6 were used to complete the three constructs (step3), where the final constructs contained a modified core mutant urease promoter (containing one or more tetO binding sites FIG. 3B) fused to gfp-mut2, separated by NdeI cut site, and flanked on both ends by several unique restriction sites. (FIG. 15A) Each construct was digested with BamHI and ligated into the vector backbone of BamHI digested pBlu_BI plasmid (Benghezal et al. 2010) to generate the vectors pBlu_uPtetO(1-3)-GFP (FIG. 15B).

Construction of *H. pylori* Tetracycline Responsive Promoter, urePtetO

Several tetO modified ureA promoter constructs (urePtetOI-V), containing up to three tetO sites in different locations, were designed and constructed using short fusion PCR (FIG. 3C). Primer pairs used to make each urePtetO construct are listed in Table 6.

TABLE 5

Oligonucleotide primers used in this study

| Name | Sequence (5'--> 3') | Function of PCR product | SEQ ID NO: |
|---|---|---|---|
| tet1 | CCGTCGACTTGCAAAAAGCGTCTAAAATCTATTGTATTAACG | ptetR construction | SEQ ID NO: 24 |
| tet2 | GACATATTATGTTCCTTGTTTTTTGATGAGAGTTC | | SEQ ID NO: 25 |
| tet3 | CATCAAAAAACAAGGAACATAATATCTCTAGATTAGATAAAAGTAAAGTGATTAACAG | | SEQ ID NO: 26 |
| tet4 | GCTACCGTCGACTTGCAAAAAGCGTC | | SEQ ID NO: 27 |
| tet5 | ACCGTCGACCAATAAGATTTGGTATAAATTTTCTTTATTATAGC | | SEQ ID NO: 28 |
| tet6 | CTAATCTAGACATTGTTGTTACTCCTTGTTATAAAAAACCCAAAG | | SEQ ID NO: 29 |
| tet7 | CAAGGAGTTACAACAATGTCTAGATTAGATAAAAGTAAAGTGATTAACAG | | SEQ ID NO: 30 |
| tet8 | GCTACCGTCGACCAATAAGATTTGG | | SEQ ID NO: 31 |
| tet9 | TCGGATCCTTATCAGACTATTTGCAACAGTGCCGTAAG | | SEQ ID NO: 32 |

TABLE 5-continued

Oligonucleotide primers used in this study

| Name | Sequence (5'--> 3') | Function of PCR product | SEQ ID NO: |
|---|---|---|---|
| tet10 | CTCATCGGATCCTTATCAGACTATTTGC | | SEQ ID NO: 33 |
| tet11 | CAACCTTGATTTCGTTATGTCTTCAAGGAAAAACACTTTAAGAATAGGAGAATAAGATGTCTAGATTAGATAAAAGTAAAGTGATTAACAG | | SEQ ID NO: 34 |
| tet12 | ACCGTCGACAATGAACGCTTCTGTTAATCTTAGTAAATCAAAACATTGCTATAATTACATCCAACCTTGATTTCGTTATGTCTTCAAG | | SEQ ID NO: 35 |
| tet13 | ACCGTCGACAATGAACGCTTCTGTTAATCTTAGTAAATCAAAACATTGCTACAATTACATCCAACCTTGATTTCGTTATGTCTTCAAG | | SEQ ID NO: 36 |
| tet14 | GCTACCGTCGACAATGAACGCTTCTG | | SEQ ID NO: 37 |
| mbtetF | TCTAGAGAATTCGTACCCTCGAGTCTAGAGCATG | cloning ptetR into pBlu_mdaB | SEQ ID NO: 38 |
| mbtetR | CGGATCCCTGCAGGCCTTATCAGACTATTTGCAACAGTG | | SEQ ID NO: 39 |
| ureArcat1 | CGTTAGTGTTAGAAAGCAAGCAG | Inactivation of ureA with rpsL-CAT | SEQ ID NO: 40 |
| ureArcat2 | CATAGTTATAAAGCATCTTTAAAATGAATTAGTGTTATATCTTTGAAG | | SEQ ID NO: 41 |
| ureArcat3 | CTGAATAAATAAAATCCTAATGTTGCCGACAGACCGGTTC | | SEQ ID NO: 42 |
| ureArcat4 | ACGCATGATTGATTGCAGAAGGAG | | SEQ ID NO: 43 |
| ureArcat5 | CACTAATTCATTTTAAAGATGCTTTATAACTATGGATTAAACAC | | SEQ ID NO: 44 |
| ureArcat6 | CCAACATTTTTAGGATTTTATTTATTCAGCAAGTCTTG | | SEQ ID NO: 45 |
| ureArcat7 | CCAAAGCCTAGTGAATTTGAATGTC | | SEQ ID NO: 46 |
| ureArcat8 | ATCGCACCAGCTTCAATTTGATC | | SEQ ID NO: 47 |
| ureAtet01 | GATGTAATTGTAGCATCTCTATCACTGATAGGGATTAACATCTCTATCACTGATAGGGATATTATTTAAAATGAATTAGTGTTATATCTTTGAAG | reconstruction of ureA promoter | SEQ ID NO: 48 |
| ureAtet02 | CAGTGATAGAGATGCTACAATTACATCCAACCTTG | | SEQ ID NO: 49 |
| ureAtet03 | GATGTAATTGTAGCATCTCTATCACTGATAGGGATTAACAGAAGCGTTCATTAAC | | SEQ ID NO: 50 |
| ureAtet04 | GATAGGGATGTAATTGTAGCATCTCTATCACTGATAGGGATTAACATCTCTATCACTGATAGGGATATTATTTAAAATGAATTAGTGTTATATCTTTGAAG | | SEQ ID NO: 51 |
| ureAtet05 | GAGATGCTACAATTACATCCCTATCAGTGATAGAGATGTCTTCAAGGAAAAACACTTTAAGAATAGG | | SEQ ID NO: 52 |
| ureAtet06 | GACATCTCTATCACTGATAGGGATGTAATTGTAGCATCTCTATCACTGATAGGGATTAACAGAAGCGTTCATTAAC | | SEQ ID NO: 53 |
| ureAtet07 | CATCCCTATCAGTGATAGAGATGTCTTCAAGGAAAAACACTTTAAGAATAGG | | SEQ ID NO: 54 |
| ureAtet08 | GACATCTCTATCACTGATAGGGATGTAATTGTAGCAATGTTTTGATTTACTAAG | | SEQ ID NO: 55 |
| urePseq | GTCTTTTTACCAGCTCTCGCTTC | Sequencing ureAB promoter | SEQ ID NO: 56 |
| tetOGFP1 | TGCTATAATTACATCCCTATCAGTGATAGAGATGTCTTCAAGGAAAAACACTTTAAGAATAGGAGAATAACATATGAGTAAAGGAGAAGAACTTTTCAC | construction of uPtetO-GFP | SEQ ID NO: 57 |
| tetOGFP2 | TCCAGAATTCCTCGAGTCTAGAGATTAGTTAATGAACGCTTCTGTTAATCTTAGTAAATCAAAACATTGCTATAATTACATCCCTATCAGT | | SEQ ID NO: 58 |
| tetOGFP3 | TCCAGAATTCCTCGAGTCTAGAGATTACTTAATGAACGCTTCTGTTAATCCCTATCAGTGATAGAGATGCTATAATTACATCCCTATCAGTG | | SEQ ID NO: 59 |
| tetOGFP4 | TCCAGAATTCCTCGAGTCTAGAGTCCCTATCAGTGATAGAGATGTTAATCCCTATCAGTGATAGAGATGCTATAATTACATCCCTATCAGTG | | SEQ ID NO: 60 |
| tetOGFP5 | CGCTATGGATCCCGGGATCGATGTCGACGCGGCCGCTTATTTGTATAGTTCATCCATGCCATG | | SEQ ID NO: 61 |
| tetOGFP6 | GCTTCAGGATCCAGAATTCCTCGAGTCTAGAG | | SEQ ID NO: 62 |

TABLE 5-continued

Oligonucleotide primers used in this study

| Name | Sequence (5'--> 3') | Function of PCR product | SEQ ID NO: |
|---|---|---|---|
| MdaB1 | GACGGTATCGATGCGTTTTCATCGCCAAAATGCTC | pMdaB cloning vector | SEQ ID NO: 63 |
| MdaB2 | CGGATCCCTGCAGGAATTCTCTAGAAGATCTCTAATTAAGGAGTGGTCATGTTC | | SEQ ID NO: 64 |
| MdaB3 | CTTCTAGAGAATTCCTGCAGGGATCCGTCGACAAATTTTCATTATCTTAACATAATAAAAATAATACAG | | SEQ ID NO: 65 |
| MdaB4 | CGCGGTGGCGGCCGCGAGCTTATGGAAGAATACAGCTC | | SEQ ID NO: 66 |
| GltDH1 | GACGGTATCGATATTCCACCCTAGCGTGAATGAAAG | pGltDH cloning vector | SEQ ID NO: 67 |
| GltDH2 | CTGCAGGAATTCTCTAGAAGATCTGTAATCAAACCCCTTGCGCTATC | | SEQ ID NO: 68 |
| GltDH3 | CAGATCTTCTAGAGAAETCCTGCAGGGATCCGTCGACCAATTTTACAAACCCAATTTTTTAACCAAC | | SEQ ID NO: 69 |
| GltDH4 | GCTCCACCGCGGCGAATCACCTAATTTCAACCTCTTTG | | SEQ ID NO: 70 |
| TrpA1 | GACGGTATCGATTTGCCTGATTATGTGATCGCATG | pTrpA cloning vector | SEQ ID NO: 71 |
| TrpA2 | GAGATCTTCTAGAGAATTCCTGCAGGGATCCGTCGACATCCGCTCAAAAACACCAAATCAAG | | SEQ ID NO: 72 |
| TrpA3 | CTGCAGGAATTCTCTAGAAGATCTCATGTCCGCTATTAAAACCCTATC | | SEQ ID NO: 73 |
| TrpA4 | GCTCCACCGCGGAAATGAAAAAGGAACACGGAGGTC | | SEQ ID NO: 74 |
| DapB1 | CCAAGCTTGATACTCATCACTCAAGTGGATG | pHdapB cloning vector | SEQ ID NO: 75 |
| DapB2 | CTCTAGACTCGAGGCGCTTTCCTTGCTTTAAATCTTAC | | SEQ ID NO: 76 |
| DapB3 | GAAAGCGCCTCGAGTCTAGAGCGGCCGCGTCGACATCGATCCCGGGATCCTGAATGTTTTAATTCTTTTTGTATAAATAATTCACG | | SEQ ID NO: 77 |
| DapB4 | GCGAATTCTGGETTAGTCAGTGTGGTAAGG | | SEQ ID NO: 78 |
| DapB5 | GCTACCAACCTTGATACTCATCACTC | | SEQ ID NO: 79 |
| DapB6 | GGTAGCGAATTCTGGTTTAGTCAGTG | | SEQ ID NO: 80 |
| MS_NdeI-Cre F | GCTAACATATGTCCAATTTACTGACCGT | Construction of pTrpA-uPtetO2-Cre | SEQ ID NO: 81 |
| MS_Cre-SalI R | GCTAAGTCGACGCGGCCGCTTAATCGCCATCTTCCAGCA | | SEQ ID NO: 82 |
| MS_ureBseq F | CGACACTACCGCTCACATTG | PCR of Lox cassette | SEQ ID NO: 83 |
| MS_ureIseq R | CCACAAAAAGTTCATCACCGCAG | | SEQ ID NO: 84 |
| MS_NdeI-FliC F | GCTAACATATGGCTCAAGTGATTAATACCAATAGCT | Construction of pMA-IEC-Ts-FliCsyn | SEQ ID NO: 85 |
| MS_FliC-SalI R | GCTAAGTCGACCAGGGATCCTTATTCTTTAGGAAAAATTTCA | | SEQ ID NO: 86 | a Based on sequence of *H. pylori* strain 26695

Briefly, 1 kb upstream and 2 kb downstream of the ureA promoter were amplified separately. Long primer tails were used to reconstruct the ureA promoter region upon fusion of the two amplified fragments by PCR. Primers ureArcat7 and ureArcat8 were used to amplify the final 3 kb products, ure-PtetO(I-V).

Construction of ureA Knockout Strain:

The ureA:: rpsL-CAT construct was generated by short multiple fusion PCR. Briefly, fragments 1 and 3 were amplified from 26695 genomic DNA using primers ureArcat1 and ureArcat2, and ureArcat3 and ureArcat4 respectively and rpsL-CAT selection cassette (middle fragment) was amplified using primers ureArcat5 and ureArcat6. Nested primers ureArcat7 and ureArcat8 were used to amplify the fusion PCR product. Natural transformation of the *H. pylori* strain X47 with the final PCR fusion product was performed to create the recipient strain X47 ureA:: rpsL-CAT, were ureA and the ureA promoter are replaced by rpsL-CAT.

Construction of urePtetO Strains:

Natural transformation of the recipient strain X47 ureA:: rpsL-CAT with urePtetO(I-V) constructs resulted in strains X47 urePtetO(I-V). Correct allelic replacement of the resulting streptomycin-resistant transformants was confirmed by sequencing using primer urePseq.

Figure 16:
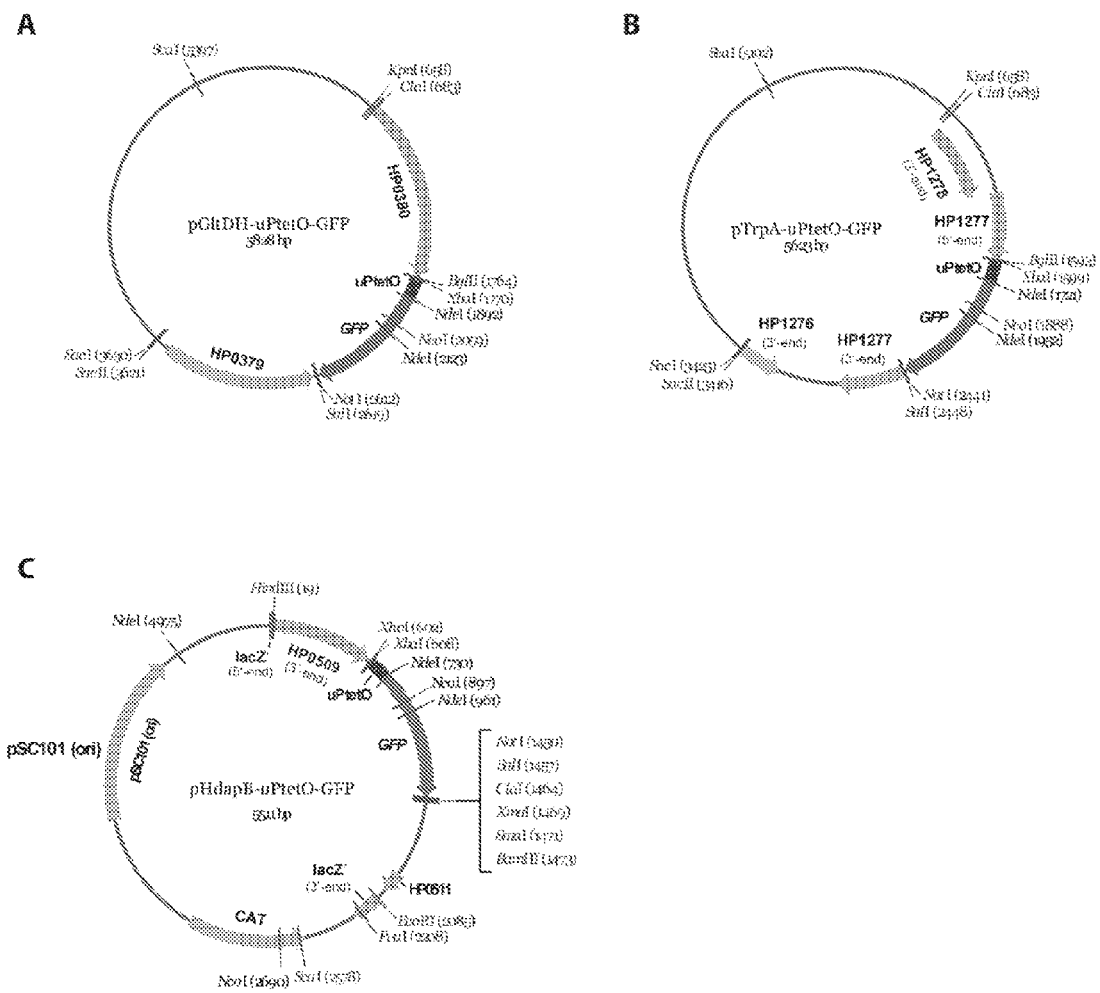
FIG. 16 shows construct maps of tet responsive uPtetO-GFP cloned into recipient vectors for targeted integration into the *H. pylori* genome at (A) the GltDH locus, (B) the trpA locus and (C) the dapB locus.

Construction of GFP Reporter Strains to Characterize the Tetracycline Regulation of uPtetO in *H. pylori*.

uptetO-GFP(1-3) constructs were excised form pBlu_uPtetO-GFP(1-3) by double restriction digest with SalI and XbaI and cloned into similarly digested pGltDH, pTrpA and pHdapB vectors to yield pGltDH-uPtetO-GFP(1-3), pTrpA-uPtetO-GFP(1-3) and pHdapB-uPtetO-GFP(1-3) plasmids (FIG. 16A-C). X47 mdaB:: ptetR(1-6) strains were transformed with pTrpA-RCAT, pGltDH-RCAT and pHdapB-RCAT to generate the respective recipient strains. The recipient strains were then transformed with the appropriate uPtetO-GFP containing plasmids to create a panel of X47 mdaB:: ptetR; uPtetO-GFP strains (Table 4) that express GFP under the control of a tetracycline inducible promoter from one of three recipient loci and also express either TetR or revTetR. Strains that express revTetR, will express GFP in the absence of the inducer molecule and strains expressing TetR will only express GFP when grown in the presence of the inducer.

Construction of X47 mdaB::ptetR; urePtetO Strains

Natural transformation of strains X47 mdaB::ptetRI(1-7) with ureA:: rpsL-CAT construct resulted in the recipient strains, X47 mdaB:: ptetR; ureA:: rpsL-CAT (1-7). These strains were all transformed with the urePtetO(I-V) constructs, generating a whole series of X47 mdaB:: ptetR; urePtetO strains (Table 4).

TABLE 6

Primer pairs for making urePtetO constructs

| Construct | upstream | downstream |
|---|---|---|
| urePtetOI | ureArcat1 & ureAtetO1 | ureAtetO2 & ureArcat4 |
| urePtetOII | ureArcat1 & ureAtetO3 | ureAtetO2 & ureArcat4 |
| urePtetOIII | ureArcat1 & ureAtetO4 | ureAtetO5 & ureArcat4 |
| urePtetOIV | ureArcat1 & ureAtetO6 | ureAtetO7 & ureArcat4 |
| urePtetOV | ureArcat1 & ureAtetO8 | ureAtetO7 & ureArcat4 |

Immunoassays—SDS-PAGE and Western Blot Analysis

Whole cell lysates of bacteria growing on either chloramphenicol or streptomycin plates was resuspended in phosphate-buffered saline (PBS) buffer. Cells were pelleted and resuspended in lysis buffer (50 mM Tris-HCl, 250 mM NaCl, 1% triton X-100) and incubated on ice for 15 min. Samples were then sonicated for 10 sec. Insoluble cell debris was removed by centrifugation at 13,000 rpm form 10 min at 4° C. Cell lysates were mixed with sodium dodecyl sulfate (SDS) sample buffer and incubated at 95° C. for 10 min. The proteins were separated by 10% SDS-polyacrylamide gel electrophoresis (PAGE) and electrotransferred to a pvdf (0.22 μm Immobulon, Millipore) membrane at 4° C. with a constant voltage of 90 V in transfer buffer (192 mM glycine, 25 mM Tris, 20% [vol/vol] methanol) for 2 hours. The membrane was blocked by using 2% BSA (Sigma) in PBST (150 mM NaCl, 10 mM Tris-C1, pH 7.0, 0.1% [vol/vol] Tween 20) and then incubated with the appropriate primary antibody, washed and then incubated with a secondary antibody containing a horseradish peroxidise (HRP) conjugate. The membrane was washed again and detection of secondary HRP conjugate was accomplished by chemiluminescence (Sigma). For detection of TetR and revTetR, rabbit polyclonal IgG anti TetR (Mo-BiTec) at a dilution of 1:2000 was used as the primary. For detection of UreB subunit, mouse monoclonal IgG anti UreB (Austral Biologicals) was used at a dilution of 1:8000. For detection of GFP, rabbit polyclonal anti GFP (Ondek) was used at a dilution of 1:2000. Secondary antibodies, mouse anti-rabbit-HRP and rabbit anti-mouse-HRP (Jackson ImmunoResearch Laboratories) were used at a dilution of 1:10,000. Chemiluminescence was detected using LAS 3000 (Fujifilm) (software Image reader LAS 3000 V2.2)

Urease Activity Assay

Urease Plate Assay:

Bacteria were resuspended in PBS to 0.1 $OD_{600}$ and 20 μL of suspension was spotted onto fresh urease plates (Brucella broth, 7% NCS, 1 mM urea, phenol red 100 mg/L, vancomycin 6 mg/L, pH ~6.2—enough to see the change in plate colour, due to the pH indicator, but not acidic enough to inhibit growth of urease negative strains.) containing ATc with concentrations ranging from 0 to 250 ng/mL. Plates were incubated under microaerophilic conditions and examined for colour change every 24 h.

Disc Diffusion Assay:

Bacteria were plated onto urease plates, and blank discs were placed onto the inoculated plate. 10 μL of ATc was placed onto each disc and plates were incubated under microaerophilic conditions and examined for colour change every 30 h.

Liquid Urease Assay:

Bacteria were grown on CBA plates with or without 50 ng/mL ATc for two successive passages. Bacteria were resuspended in cold buffer A (25 mM phosphate buffer, pH 6.8) and standardized to an $OD_{600}$ of 4.0. 50 μL of standardized bacterial suspension was diluted with 50 μL of buffer B (25 mM phosphate buffer, pH 6.8, 0.2% tween-20). In 96 well plate, 25 μL of diluted bacterial suspension was diluted with 150 μL of buffer C (25 mM phosphate buffer, pH 6.8, 250 μM phenol red) and incubated for 5 min at 37° C. 75 μL of urea solution (0.5 M) was then added and the absorbance at 560 nm was measured every 72 seconds for 75 cycles using a POLARstar Omega (BGM Labtech) platereader. Activity was measured as the rate of change in absorbance over time and expressed as percent of urease activity of the wild-type parent strain. All urease activity measurements were carried out in triplicate and experiments were repeated three times.

GFP Reporter Assay

Disc Diffusion Assay:

Bacteria were plated onto CBA plates, and incubated for 14 hr at 37° C. Blank discs were placed onto bacterial lawn and inoculated with 30 μL ATc solution and incubated for 48 h before visualization of GFP expression using the LAS 3000 (Fujifilm)(light source—Blue-460 nm EPI, Filter GFP510DF10).

GFP Fluorescence:

Bacteria were plated onto fresh CBA plates with or without 50 ng/mL ATc and visualized after 24 hr incubation. For Tet-OFF strains, ptetR(2,4,6) bacteria were passaged twice on CBA plates containing ATc prior to the experiments, to allow strains enough time to repress GFP expression.

Liquid Culture:

5 mL cultures were grown for 14 h and then induced with 200 ng/mL ATc unless otherwise stated. Bacteria were harvested by centrifugation, washed twice with PBS and resuspended to a density of $20D_{600}$. Then, 0.1 ml of the bacterial suspension was transferred into black 96-well plates, and fluorescence at 520 nm after excitation at 485 nm was measured in using the POLARstar Omega platereader.

Animal Experiments 6-7 week old C57BL/6J female mice were orally gavaged once with 200 μL of 1×10$^9$ CFU/mL bacteria, that had been passaged on CBA plates containing 50 ng/mL ATc to induce expression of tetracycline responsive genes. Mice were supplemented with doxycycline in their drinking water containing 5% sucrose. Mice were sacrificed at indicated time points and stomachs were removed and homogenized in 1 mL BHI using a tissue lysing agent (Retch). Homogenates were serially diluted and plated out on *H. pylori* selective plates, (CBA containing 5% Horse blood, Dent, polymyxin B 2500 U/L or 0.2975 mg/L, nalidixic acid 10 mg/L and Bacitracin 100 mg/L). Colonies were counted to calculate bacteria load. Re-isolated clones were checked for tet responsive gene expression and sequenced when appropriate.

The *H. pylori* strains and plasmids used in this study are listed in Table 4. *H. pylori* X47 strains were routinely grown at 37° C. under microaerobic conditions on Brain Heart Infusion (BHI) blood agar (BHIB) or Heart Infusion (HI) blood agar (HIB) plates containing 5% horse blood and 5% Newborn Calf Serum (NCS). When appropriate, *H. pylori* antibiotic selection was carried out by supplementing media with chloramphenicol or streptomycin at a final concentration of 10 μg/mL. *H. pylori* liquid culture: Bacteria were grown in Brain Heart Infusion (BHI) medium supplemented with 10% Newborn Calf Serum (NCS) and Dent's antibiotic supplement. Cultures were inoculated with bacteria resuspended in PBS to give a starting $OD_{600}$ of 0.05, and grown under microaerobic conditions at 37° C. and 120 rpm. *Escherichia coli* DH10β was grown in Luria-Bertani broth at 37° C. and 180 rpm. When necessary, antibiotics were added to the following final concentrations: ampicillin, 100 μg/ml and chloramphenicol, 20 μg/ml.

The *H. pylori* 26695 codon usage optimized cre recombinase (SEQ ID NO:87) gene was amplified from pUC19-Cre by using the primer MS_NdeI-Cre F and MS_Cre-SalI R. The 1 kb PCR fragment was digested with NdeI and SalI and cloned into the similarly digested vectors pTrpA-uPtetO1-GFP or pTrpA-uPtetO2-GFP (Table 4) to generate pTrpA-uPtetO1-Cre and pTrpA-uPtetO2-Cre.

Natural transformation of the *H. pylori* recipient strains X47 mdaB:: ptetR2; trpA:: rpsL-CAT with the plasmids pTrpA-uPtetO1-Cre or pTrpA-uPtetO2-Cre, generating strains X47 mdaB::ptetR2; trpA::uPtetO(1/2)-cre (Table 4).

A synthetic cassette Lox6671 (SEQ ID NO:88) was designed and synthesized containing a PureA-dapA fusion flanked by lox66 and lox71 cre recombinases recognition sites (pMK-RQ-Lox6671) (FIG. 22). The cassette was excised by double restriction digest with EcoRI and BglII and cloned into the similar digested vector pBlu_BI to yield the plasmid pBI-Lox6671.

Genomic DNA of the strain X47 ureBI::rpsL-CAT was used as template to amplify the counterselection cassette, rpsL-CAT, integrated between the ureB and ureI gene. Natural transformations of the *H. pylori* strains X47 mdaB:: ptetR2; trpA:: uPtetO(1/2)-cre with ureBI-RCAT PCR product were performed to generate the recipient strains X47 mdaB::ptetR2; trpA:: uPtetO(1/2)-cre; ureBI:: rpsL-CAT to introduce the Lox6671 cassette into the ureBI locus. These strains were transformed with pBI-Lox6671, generating X47 mdaB:: ptetR2; trpA:: uPtetO(1/2)-cre; ureBI::Lox6671 strain (Table 4). In addition recipient strain X47 ureBI:: rpsL-CAT was transformed with pBI-Lox6671 to generate a control strain X47 ureBI:: lox6671.

The gene sequence of tetR was codon optimized for *H. pylori* 26695 codon usage and synthesized. The synthetic tetRs (SEQ ID NO:89) was excised form pMA-T-TetRs by double restriction digest with EcoRI and BglII and cloned into the similarly digested vector pMdaB-PureA-hydA to yield the plasmid pMdaB-PureA-TetR5. Natural transformation of the recipient strain X47 mdaB::rpsL-CAT with this plasmid was performed to generate X47 mdaB::PureA-tetRs.

Figure 23:
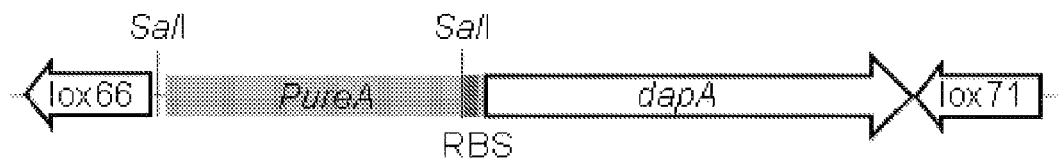
FIG. 23 shows schematic diagram of the Lox6671 cassette. The cassette is flanked by two lox sites (Lox66 and Lox71) with their non-palindromic core sequence pointing in the same direction to allow cre mediated excision of the sequence between the lox sites. The core urease promoter and the dapA gene are between the lox sites. PureA can be excised by SalI leaving a RBS upstream of dapA.

Construction of *H. pylori* Strains with TetRs Regulated Cre-Lox System and Different Cre Expression Efficiencies
Construction of pTrpA-(1-6)uPtetO5-Cre A set of six different inducible promoter-cre5' variants designed and synthesized (pMK-(1-6)uPtetO5-Cre5'). The promoter variants contain two tetO sites, a wt or mutated RBS and ATG, CTG or TTG as start codon (FIG. 23). The uPtetO5-Cre5' fusions were excised form pMK-(1-6)uPtetO5-Cre5' by double restriction digest with BglII and BamHI and cloned into the similarly digested vector pTrpA-uPtetO2-Cre to yield pTrpA-(1-6)uPtetO5-Cre plasmids (SEQ ID NOs:90 to 95). The construction was confirmed by restriction digest with NdeI. The fusions (1/4)uPtetO5-Cre5' were cloned similarly into pTrpA-6uPtetO5-Cre to generate the plasmids pTrpA-(1,4)uPtetO5-Cre.

Construction of *H. pylori* Strains with TetRs Regulated Cre-Lox System

Natural transformation of X47 mdaB:: PureA-tetRs with pTrpA-RCAT was performed to generate recipient strain X47 mdaB:: PureA-tetRs; trpA:: rpsL-CAT. This strain was transformed with the constructed plasmids pTrpA-(1-6)uPtetO5-Cre. The resulting strains were sequentially transformed with pBI-RCAT and pBI-Lox6671 to create the strains X47 mdaB:: PureA-tetRs; trpA::(1-6)uPtetO5-cre; ureBI:: Lox6671.

Construction of Cre Antisense RNA Expressing *H. pylori* Strains with TetRs Regulated Cre-Lox System
Construction of pTrpA-as(1-6)uPtetO5-Cre (SEQ ID NO:96)

A cassette was designed and synthesized to inducible transcribe mRNA of a gene of interest and constantly express antisense RNA from the same gene copy at the trpA locus (pMA-Antisense) (FIG. 28). The (1-6) uPtetO5-cre variants of pTrpA-(1-6)uPtetO5-Cre were excised and cloned into pMA-Antisense by digest with BglII and NotI to generate pTrpA-as(1-6)uPtetO5-Cre. The plasmids were used to transform the recipient strains X47 mdaB:: PureA-tetRs; trpA:: rpsL-CAT and to generate X47 mdaB:: PureA-tetRs; trpA:: as(1-6)uPtetO5-cre. Following, the strains were sequentially transformed with pBI-RCAT and pBI-Lox6671 to create the strains X47 mdaB:: PureA-tetRs; trpA:: as-(1-6)uPtetO5-cre; ureBI::Lox6671.

Immunoassay—SDS-PAGE and Western Blot Analysis.

Bacteria were grown for 24 hours on selective plates or in selective liquid media. Cells were harvested and resuspended in phosphate-buffered saline (PBS) buffer. Samples were then sonicated for 10 seconds, mixed with sodium dodecyl sulfate (SDS) sample buffer and incubated at 37° C. for 15 min. Insoluble cell debris was removed by centrifugation at 13,000 rpm for 1 min. The proteins were separated by 10% SDS-polyacrylamide gel electrophoresis (PAGE) and electrotransferred to a PVDF membrane (Immobilon-P Transfer (0.45 μm, Millipore) with a constant voltage of 100 V in transfer buffer (192 mM glycine, 25 mM Tris, 20% [vol/vol] methanol) for 1 hour. The membranes were blocked with 3% BSA (Sigma) in PBST (150 mM NaCl, 10 mM Tris-C1, pH 7.0, 0.1% [vol/vol] Tween 20) and then incubated with the appropriate primary antibody, washed and then incubated with a secondary antibody containing a horseradish peroxidise (HRP) conjugate. The membrane was washed again and detection of secondary HRP conjugate was accomplished by chemiluminescence (Sigma). For detection of Cre recombinase, rabbit polyclonal IgG anti Cre (abcam) was used at a dilution of 1:1000. For detection of TetR rabbit polyclonal IgG anti TetR (abcam) at a dilution of 1:1000 was used as the primary. Secondary antibody rabbit anti-mouse-HRP (Jackson ImmunoResearch Laboratories) was used at a dilution of 1:5000. Chemiluminescence was detected using LAS 3000 (Fujifilm)(software Image reader LAS 3000 V2.2)

Construction of a pHel2 Based Shuttle Vector Containing Tet Inducible Antigen Expression Cassette A tet inducible expression cassette was designed containing the tetRsyn gene under control of PflaA and a target gene under control of uPtetO4. The cassette was synthesized with the *H. pylori* codon usage optimized listeriosylin gene as target gene and without the tetRsyn gene (pMA-IEC-LLO) (SEQ ID NO:97). In a first cloning step tetRsyn was excised from pMA-T-TetRsyn by double restriction digest with EcoRI and BglII and cloned into the similar digested vector pMA-IEC-LLO to yield the plasmid pMA-IEC-Ts-LLO. Second fliCsyn (SEQ ID NO:98) was amplified using primers MS_NdeI-FliC F and MS_FliC-SalI R and plasmid pMK-RQ-FliCsyn as template. The resulting PCR fragment and pMA-IEC-Ts-LLO were digested with NdeI and SalI to clone fliCsyn in the vector replacing the LLO gene (pMA-IEC-Ts-FliCsyn) (SEQ ID NO:99). Finally the constructed plasmid was digested with XhoI to excise the whole inducible expression cassette. The cassette was cloned in the similar digested vector pHel2 to yield the shuttle vector pHel2-IEC-Ts-FliCsyn (SEQ ID NO:100).

Cell to Cell Transfer of pHel2-IEC-Ts-FLiCsyn from *E. Coli* to *H. pylori*

The recombinant shuttle vector pHel2-IEC-Ts-FliCsyn was conjugated from *E. coli* to *H. pylori* with *E. coli* strain β2150 as donor and β2150 [pRK2013] as helper strain. *H. pylori* recipient strain B128 was grown for 24 hours on selective blood agar plates. Both *E. coli* β2150 containing the recombinant shuttle vector and β2150 [pRK2013] were grown overnight in liquid culture containing 1 mM DAP. All bacteria were harvested and resuspended in phosphate-buffered saline or LB media respectively. The bacteria strains were mixed together following relative $OD_{600}$: 25 µl of 10 $OD_{600}$ units of donor; 25 µl of 10 $OD_{600}$ units of helper; and 250 µl of 10 $OD_{600}$ units of recipient. The cell mixture was spotted on a blood agar plate supplemented with 1 mM DAP and incubated at 37° C. for 4 h under microaerophilic conditions. The bacterial mixture was then spread onto a fresh blood agar plate supplemented with selective antibiotics and Dent and incubated at 37° C. under microaerophilic conditions. Resulting transconjugants B128 pHel2-IEC-Ts-FliCsyn were observed after 3-5 days.

REFERENCES

Algood & Cover (2006), Clin Microbiol Rev., 19(4): 597-613.
Amieva & El-Omar (2008), Gastroenterology, 134(1): 306-323.
Bauerfeind et al., (1997), Gut, 40(1): 25-30.
Benghezal et al., (2010), WO/2010/148459.
Boneca et al., (2008), Appl Environ Microbiol., 74(7): 2095-2102.
Cormack et al., (1996), Gene, 173 (1 Spec No): 33-38.
Croxen et al., (2006), J. Bacteriol., 188(7): 2656-2665.
Davies et al., (2002), FEMS Microbiol Lett 213(1): 27-32.
Eaton et al. (1991), Infect Immun., 59(7): 2470-2475.
Eaton & Krakowka (1994), Infect Immun., 62(9): 3604-3607.
Ehrt et al., (2005), Nucleic Acids Res., 33 (2): e21.
Ermak et al., (1998). J Exp Med., 188(12): 2277-2288.
Gandotra et al., (2007), Nat. Med., 13(12): 1515-1520.
Gossen & Bujard (1993), Nucleic Acids Res., 21(18): 4411-4412.
Graham & Shiotani (2008), Nat Clin Pract Gastroenterol Hepatol., 5(6): 321-331.
Ji et al., (2001), Science, 293(5538): 2266-2269.
Kamionka et al., (2004), Nucleic Acids Res., 32(2): 842-847.
Kavermann et al., (2003), J Exp Med., 197(7): 813-822.
Klotzsche et al., (2009), Nucleic Acids Res., 37(6): 1778-1788.
Kuipers et al., (1995), Aliment Pharmacol Ther., 9 Suppl 2: 59-69.
Langford et al. (2006). "In vitro and in vivo complementation of the *Helicobacter pylori* arginase mutant using an intergenic chromosomal site." *Helicobacter* 11(5): 477-493.
Lathem et al., (2007), Science, 315(5811): 509-513.
Liu et al., (2008), Proc Natl Acad Sci USA 105(27): 9385-9390.
McGowan et al., (2003), Mol. Microbiol., 48(5): 1225-1239.
Pflock et al. (2005), Infect Immun., 73(10): 6437-6445.
Schnappinger et al. (1998), EMBO J., 17(2): 535-543.
Scholz et al. (2004), Mol. Microbiol., 53(3): 777-789.
Sharma et al., (2010), Nature, 464(7286): 250-255.
Shevchuk et al., (2004), Nucleic Acids Res., 32 (2): e19.
Takeshita et al., (1987), Gene, 61(1): 63-74.
Tsuda et al. (1994), Infect Immun., 62(8): 3586-3589.
van Vliet et al., (2002), Infect Immun., 70(6): 2846-2852.
Wilson & Crabtree (2007), Gastroenterology, 133(1): 288-308.
Wroblewski et al., (2010), Clin Microbiol Rev., 23(4): 713-739.
Zhang et al., (2000), Gene, 255(2): 297-305.
Zhu et al., (2002), Semin Cell Dev Biol 13(2): 121-128.
Zullo et al., (2007), Gut, 56(10): 1353-1357.

SEQUENCE LISTING

```
<160> NUMBER OF SEQ ID NOS: 109

<210> SEQ ID NO 1
<211> LENGTH: 5087
<212> TYPE: DNA
<213> ORGANISM: Helicobacter pylori

<400> SEQUENCE: 1
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg ggggctccct ttagggttcc     180
```

```
gatttagtgc tttacggcac ctcgacccca aaaaacttga ttagggtgat ggttcacgta    240
gtgggccatc gccctgatag acggtttttc gcccttttgac gttggagtcc acgttcttta    300
atagtggact cttgttccaa actggaacaa cactcaaccc tatctcggtc tattcttttg    360
atttataagg gattttgccg atttcggcct attggttaaa aatgagctg atttaacaaa    420 aatttaacgc gaattttaac aaaatattaa cgcttacaat ttccattcgc cattcaggct    480
gcgcaactgt tggaagggc gatcggtgcg ggcctcttcg ctattacgcc agctggcgaa    540 aggggatgt gctgcaaggc gattaagttg gtaacgcca gggttttccc agtcacgacg    600
ttgtaaaacg acggccagtg aattgtaata cgactcacta tagggcgaat gggtaccgg    660 gccccccctc gatcgacggt atcgatgcgt tttcatcgcc aaaatgctcc acaaattcgc    720
ccgcatcaaa atgccctctc ctttcgcaca atcatggat cctgttccca taagcccaag    780 agggcggtt atacgcatcc aatttaggga gagcccccaa catcaagtaa taaagcacat    840
tacccacgat attttttttca ctaggcgggc aaccaggaac attgatcacg ggtttatcaa    900
tgattttatg caagggttgc gcgttagagg ggttagggta agccgcttga acgccccaa    960 aacttgagca tgtgcctatg gcaaaaatag cggctgcgta ttgagcggct ttcctacact   1020
cttcagctcc cgtttcagcg tttgggcctt gagtgaggaa gtattccgtg ccttggggga   1080
tacccccttc taccattaaa atgtaattgt ttttatgctt ttctatggcg tcatgcaagc   1140 tttttttcagc ttgaaaaccg ctcgctacca tgatggtctc atggtattct aggttgatgt   1200
aatcaaagat aatgctatca atggtggggt ctgcgctcct taacaaactt tcgctacaac   1260
cggtgcattc tgccatgtgc aaccaaatca cgggcaatct gttagccact tccaccgcct   1320
tcaaagtcaa gggagcaaaa ctagccggca aggctaacgc tgtgctcatc atgcccgccc   1380
acttcaataa atcgcgccta gaaatgcccg ccccttttaaa ctcgtcttgc aagttttttat   1440 gctcgttgtg agcgttaaac gaacggacta tatcaaggcg ttcttcaatc ttttgatagg   1500
tctttttttc atcgtagaac atgaccactc cttaattaga gatcttctag agaattcctg   1560
cagggatccg tcgacaaatt ttcattatct taacataata aaaataatac agctgcaatt   1620
gattgttttt tagttttttat tgagattgag ggaatttctt taatattaag tttcatttgg   1680
atagaatgcc accctatttt attagaaaag gaacaaatg aaaaaagtac tcatcattaa   1740
cggggccaaa gcgttcggga gctctggagg gaaactcaat gaaaccttga ctgaccatgc   1800
aaaaaagact ctagagtctt tggggctaga agtggatact acgatcgtgg ataaaggcta   1860
tgaacatgct caagaagtgg agaaagtctt tagcgctgat gcgacgattt ggcaaatgcc   1920
tggctggtgg atgggagagc cttggattgt gaaaaatac attgatgaag tctttagcgt   1980
agggcatgga aagcttttatg ctagcgatgg cagaagctcg caaaacccca ctaaaaacta   2040
cgggaaaggg ggcttgatgc aaggcaaaaa atacatgttg agcttgactt ggaacgctcc   2100
cattgaagcc tttaatgatc ctagtgaatt ttttgaaggg gtgggtgtgg atgttgtgta   2160
tttgcatttg cataaagcgt tccaatttt agggctttca gcgttgccca cttttatttg   2220
caacgatgtg gtgaaaaacc cccaagtgga gcagtatctt aactctctca ccacgcattt   2280
gcgccaagct tttggcaagt gattttaaaa ttttttttaac cccccatttt ctttgggggg   2340
gcttgtttat tccacaataa agtctctggg attgagatcg cagcctaaga taagatccct   2400
aagattactg cccaccgttt gataactcgc attgctcaca agtagaaatc cgtatttttc   2460
aaaaggcaca acaagagtgc cgtctctatc ccttaattgc gcttttgctt tatcccaaca   2520
aatatatctt ggctcttcat ctgtgtagct ttcaaaggct tctctggcgt tttctagcaa   2580
```

```
gtagtctatg acagcgctag ccaattcctt agcgtttctt gctatttcc tttgatgatt    2640
ggggagctta acgctttgaa gattatggga agttaagtca tcatcaaggg ttttactaat    2700
ctctctggtg cggtattctt taggcaaatc tttaaacaat cccacttgac agaattgatc    2760
cgctaaatat tcgctcctat tcttcacttc ctctatcccc caagaatggg tgttattgat    2820
gaaatagtcg tttaaatgca aggagctgta ttcttccata agctcgcggc cgccaccgcg    2880
gtggagctcc agcttttgtt ccctttagtg agggttaatt tcgagcttgg cgtaatcatg    2940
gtcatagctg tttcctgtgt gaaattgtta tccgctcaca attccacaca atacgagc     3000
cggaagcata aagtgtaaag cctggggtgc ctaatgagtg agctaactca cattaattgc    3060
gttgcgctca ctgcccgctt tccagtcggg aaacctgtcg tgccagctgc attaatgaat    3120
cggccaacgc gcggggagag gcggtttgcg tattgggcgc tcttccgctt cctcgctcac    3180
tgactcgctg cgctcggtcg ttcggctgcg gcgagcggta tcagctcact caaaggcggt    3240
aatacggtta tccacagaat caggggataa cgcaggaaag aacatgtgag caaaaggcca    3300
gcaaaaggcc aggaaccgta aaaaggccgc gttgctggcg ttttttccata ggctccgccc    3360
ccctgacgag catcacaaaa atcgacgctc aagtcagagg tggcgaaacc cgacaggact    3420
ataaagatac caggcgtttc ccctggaag ctccctcgtg cgctctcctg ttccgaccct    3480
gccgcttacc ggatacctgt ccgcctttct cccttcggga agcgtggcgc tttctcatag    3540
ctcacgctgt aggtatctca gttcggtgta ggtcgttcgc tccaagctgg gctgtgtgca    3600
cgaaccccc gttcagcccg accgctgcgc cttatccggt aactatcgtc ttgagtccaa    3660
cccggtaaga cacgacttat cgccactggc agcagccact ggtaacagga ttagcagagc    3720
gaggtatgta ggcggtgcta cagagttctt gaagtggtgg cctaactacg gctacactag    3780
aaggacagta tttggtatct gcgctctgct gaagccagtt accttcggaa aaagagttgg    3840
tagctcttga tccggcaaac aaaccaccgc tggtagcggt ggttttttg tttgcaagca    3900
gcagattacg cgcagaaaaa aaggatctca agaagatcct ttgatctttt ctacggggtc    3960
tgacgctcag tggaacgaaa actcacgtta agggattttg gtcatgagat tatcaaaaag    4020
gatcttcacc tagatccttt taaattaaaa atgaagtttt aaatcaatct aaagtatata    4080
tgagtaaact tggtctgaca gttaccaatg cttaatcagt gaggcaccta tctcagcgat    4140
ctgtctattt cgttcatcca tagttgcctg actccccgtc gtgtagataa ctacgatacg    4200
ggagggctta ccatctggcc ccagtgctgc aatgataccg cgagacccac gctcaccggc    4260
tccagattta tcagcaataa accagccagc cggaagggcc gagcgcagaa gtggtcctgc    4320
aactttatcc gcctccatcc agtctattaa ttgttgccgg gaagctagag taagtagttc    4380
gccagttaat agtttgcgca acgttgttgc cattgctaca ggcatcgtgg tgtcacgctc    4440
gtcgtttggt atggcttcat tcagctccgg ttcccaacga tcaaggcgag ttacatgatc    4500
ccccatgttg tgcaaaaaag cggttagctc cttcggtcct ccgatcgttg tcagaagtaa    4560
gttggccgca gtgttatcac tcatggttat ggcagcactg cataattctc ttactgtcat    4620
gccatccgta agatgctttt ctgtgactgg tgagtactca accaagtcat tctgagaata    4680
gtgtatgcgg cgaccgagtt gctcttgccc ggcgtcaata cgggataata ccgcgccaca    4740
tagcagaact ttaaaagtgc tcatcattgg aaaacgttct cggggcgaa aactctcaag    4800
gatcttaccg ctgttgagat ccagttcgat gtaaccccact cgtgcaccca actgatcttc    4860
agcatctttt actttcacca gcgtttctgg gtgagcaaaa acaggaaggc aaaatgccgc    4920
```

-continued

| | |
|---|---|
| aaaaaaggga ataagggcga cacggaaatg ttgaatactc atactcttcc tttttcaata | 4980 |
| ttattgaagc atttatcagg gttattgtct catgagcgga tacatatttg aatgtattta | 5040 |
| gaaaaataaa caaataggg ttccgcgcac atttccccga aaagtgc | 5087 |

<210> SEQ ID NO 2
<211> LENGTH: 6521
<212> TYPE: DNA
<213> ORGANISM: Helicobacter pylori

<400> SEQUENCE: 2

| | |
|---|---|
| cacctgacgc gccctgtagc ggcgcattaa gcgcggcggg tgtggtggtt acgcgcagcg | 60 |
| tgaccgctac acttgccagc gccctagcgc ccgctccttt cgctttcttc ccttcctttc | 120 |
| tcgccacgtt cgccggcttt ccccgtcaag ctctaaatcg gggctccct ttagggttcc | 180 |
| gatttagtgc tttacggcac ctcgacccca aaaaacttga ttagggtgat ggttcacgta | 240 |
| gtgggccatc gccctgatag acggtttttc gccctttgac gttggagtcc acgttcttta | 300 |
| atagtggact cttgttccaa actggaacaa cactcaaccc tatctcggtc tattcttttg | 360 |
| atttataagg gattttgccg atttcggcct attggttaaa aaatgagctg atttaacaaa | 420 |
| aatttaacgc gaattttaac aaaatattaa cgcttacaat ttccattcgc cattcaggct | 480 |
| gcgcaactgt tgggaagggc gatcggtgcg ggcctcttcg ctattacgcc agctggcgaa | 540 |
| aggggatgt gctgcaaggc gattaagttg gtaacgcca gggttttccc agtcacgacg | 600 |
| ttgtaaaacg acggccagtg aattgtaata cgactcacta tagggcgaat tgggtaccgg | 660 |
| gcccccctc gatcgacggt atcgatgcgt tttcatcgcc aaaatgctcc acaaattcgc | 720 |
| ccgcatcaaa atgccctctc ctttcgcaca aatcatggat cctgttccca taagcccaag | 780 |
| aggggcggtt atacgcatcc aatttaggga gagccccaaa catcaagtaa taaagcacat | 840 |
| tacccacgat attttttca ctaggcgggc aaccaggaac attgatcacg ggtttatcaa | 900 |
| tgattttatg caagggttgc gcgttagagg ggttagggta agccgcttga acgccccaa | 960 |
| aacttgagca tgtgcctatg gcaaaaatag cggctgcgta ttgagcggct ttcctacact | 1020 |
| cttcagctcc cgtttcagcg tttgggcctt gagtgaggaa gtattccgtg ccttggggga | 1080 |
| tacccccttc taccattaaa atgtaattgt ttttatgctt ttctatggcg tcatgcaagc | 1140 |
| ttttttcagc ttgaaaaccg ctcgctacca tgatggtctc atggtattct aggttgatgt | 1200 |
| aatcaaagat aatgctatca atggtggggt ctgcgctcct taacaaactt cgctacaac | 1260 |
| cggtgcattc tgccatgtgc aaccaaatca cgggcaatct gttagccact tccaccgcct | 1320 |
| tcaaagtcaa gggagcaaaa ctagccggca aggctaacgc tgtgctcatc atgcccgccc | 1380 |
| acttcaataa atcgcgccta gaaatgcccg ccccttaaa ctcgtcttgc aagtttttat | 1440 |
| gctcgttgtg agcgttaaac gaacggacta tatcaaggcg ttcttcaatc ttttgatagg | 1500 |
| tcttttttc atcgtagaac atgaccactc cttaattaga gatccgatgc tttataacta | 1560 |
| tggattaaac actttttag taattctta aaatcaattt tggaattttt cattttgtct | 1620 |
| aaaatgagta agattatttt tataagtaaa acaataatta aaaattagtt tatgttttat | 1680 |
| aaatattaat gtaaattatg tagggtttat tttataaaaa ttttaaaag catttaaatt | 1740 |
| atttctagtt tatattttg taagtaaatt ttagatatca tccaaagttt attacatttt | 1800 |
| taaagaaagg aattattgtg cctaccataa atcaattggt tagaaaagag cgcaaaaaag | 1860 |
| ttttagaaaa atctaaatct ccagcgctta aaaattgtcc acaagaagg ggagtttgca | 1920 |
| ctagggttta tactacaaca cctaaaaaac caaactcagc gttaagaaaa gttgccaaag | 1980 |

```
taagacttac tagtggcttt gaagtgatca gctatatcgg cggtgaaggt cataacttgc    2040
aagaacacag cattgtttta gtgcgtggtg gtagggtaaa agacttacca ggggttaaat    2100
atcacatcgt tcgtggtgct cttgatacag caggtgttgc aaaaagaaca gtttctcgtt    2160
ctaaatatgg tgctaaacgt cctaaagcag gcgctgcaaa ataatcattc atacagacaa    2220
atccgttaga tgatatagat tgaaaagtgg atagatttat gatatagtgg atagatttat    2280
gatataatga gttatcaaca aatcggaatt tacggaggat aaatgatgca attcacaaag    2340
attgatataa ataattggac acgaaagag tatttcgacc actattttgg caatacgccc     2400
tgcacatata gtatgacggt aaaactcgat atttctaagt tgaaaaagga tggaaaaaag    2460
ttatacccaa ctcttttata tggagttaca acgatcatca atcgacatga agagttcagg    2520
accgcattag atgaaaacgg acaggtaggc gttttttcag aaatgctgcc ttgctacaca    2580 gttttttcata aggaaactga aaccttttcg agtatttgga ctgagtttac agcagactat    2640
actgagtttc ttcagaacta tcaaaaggat atagacgctt ttggtgaacg aatgggaatg    2700
tccgcaaagc ctaatcctcc ggaaaacact ttccctgttt ctatgatacc gtggacaagc    2760
tttgaaggct ttaacttaaa tctaaaaaaa ggatatgact atctactgcc gatatttacg    2820
tttgggaagt attatgagga gggcggaaaa tactatattc ccttatcgat tcaagtgcat    2880
catgccgttt tgtgacggctt tcatgttttgc cgttttttgg atgaattaca agacttgctg    2940
aataaataaa atcccagttt gtcgcactga taaggatctt ctagagaatt cctgcaggga    3000
tccgtcgaca aatttttcatt atcttaacat aataaaaata atacagctgc aattgattgt    3060
tttttagttt ttattgagat tgagggaatt tctttaatat taagtttcat ttggatagaa    3120
tgccacccta ttttattaga aaaggaacaa aatgaaaaaa gtactcatca ttaacggggc    3180
caaagcgttc gggagctctg gagggaaact caatgaaacc ttgactgacc atgcaaaaaa    3240
gactctagag tctttggggc tagaagtgga tactacgatc gtggataaag gctatgaaca    3300
tgctcaagaa gtggagaaag tctttagcgc tgatgcgacg atttggcaaa tgcctggctg    3360
gtggatggga gagccttgga ttgtgaaaaa atacattgat gaagtcttta gcgtagggca    3420
tggaaagctt tatgctagcg atggcagaag ctcgcaaaac cccactaaaa actacgggaa    3480 aggggggcttg atgcaaggca aaaatacat gttgagcttg acttggaacg ctcccattga    3540
agcctttaat gatcctagtg aatttttttga aggggtgggt gtggatgttg tgtatttgca    3600
tttgcataaa gcgttccaat ttttagggct ttcagcgttg cccactttta tttgcaacga    3660
tgtggtgaaa aaccccccaag tggagcagta tcttaactct ctcaccacgc atttgcgcca    3720
agcttttggc aagtgatttt aaaattttt taacccccccc atttctttgg ggggcttgt     3780 ttattccaca ataaagtctc tgggattgag atcgcagcct aagataagat ccctaagatt    3840
actgcccacc gtttgataac tcgcattgct cacaaagtag aatccgtatt tttcaaaagg    3900
cacaacaaga gtgccgtctc tatcccttaa ttgcgctttt gctttatccc aacaaatata    3960
tcttggctct tcatctgtgt agctttcaaa ggcttctctg gcgttttcta gcaagtagtc    4020
tatgacagcg ctagccaatt ccttagcgtt tcttgctatt ttcctttgat gattggggag    4080
cttaacgctt tgaagattat gggaagttaa gtcatcatca agggttttac taatctctct    4140
ggtgcggtat tctttaggca aatctttaaa caatcccact tgacagaatt gatccgctaa    4200
atattcgctc ctattcttca cttcctctat cccccaagaa tgggtgttat tgatgaaata    4260
gtcgtttaaa tgcaaggagc tgtattcttc cataagctcg cggccgccac cgcggtggag    4320
```

| | |
|---|---|
| ctccagcttt tgttcccttt agtgagggtt aatttcgagc ttggcgtaat catggtcata | 4380 |
| gctgtttcct gtgtgaaatt gttatccgct cacaattcca cacaacatac gagccggaag | 4440 |
| cataaagtgt aaagcctggg gtgcctaatg agtgagctaa ctcacattaa ttgcgttgcg | 4500 |
| ctcactgccc gctttccagt cgggaaacct gtcgtgccag ctgcattaat gaatcggcca | 4560 |
| acgcgcgggg agaggcggtt tgcgtattgg gcgctcttcc gcttcctcgc tcactgactc | 4620 |
| gctgcgctcg gtcgttcggc tgcggcgagc ggtatcagct cactcaaagg cggtaatacg | 4680 |
| gttatccaca gaatcagggg ataacgcagg aaagaacatg tgagcaaaag gccagcaaaa | 4740 |
| ggccaggaac cgtaaaaagg ccgcgttgct ggcgtttttc cataggctcc gcccccctga | 4800 |
| cgagcatcac aaaaatcgac gctcaagtca gaggtggcga acccgacag gactataaag | 4860 |
| ataccaggcg tttcccctg gaagctccct cgtgcgctct cctgttccga ccctgccgct | 4920 |
| taccggatac ctgtccgcct ttctcccttc gggaagcgtg gcgctttctc atagctcacg | 4980 |
| ctgtaggtat ctcagttcgg tgtaggtcgt tcgctccaag ctgggctgtg tgcacgaacc | 5040 |
| ccccgttcag cccgaccgct gcgccttatc cggtaactat cgtcttgagt ccaacccggt | 5100 |
| aagacacgac ttatcgccac tggcagcagc cactggtaac aggattagca gagcgaggta | 5160 |
| tgtaggcggt gctacagagt tcttgaagtg gtggcctaac tacggctaca ctagaaggac | 5220 |
| agtatttggt atctgcgctc tgctgaagcc agttaccttc ggaaaaagag ttggtagctc | 5280 |
| ttgatccggc aaacaaacca ccgctggtag cggtggtttt tttgtttgca agcagcagat | 5340 |
| tacgcgcaga aaaaaggat ctcaagaaga tcctttgatc ttttctacgg ggtctgacgc | 5400 |
| tcagtggaac gaaaactcac gttaagggat tttggtcatg agattatcaa aaaggatctt | 5460 |
| cacctagatc cttttaaatt aaaaatgaag ttttaaatca atctaaagta tatatgagta | 5520 |
| aacttggtct gacagttacc aatgcttaat cagtgaggca cctatctcag cgatctgtct | 5580 |
| atttcgttca tccatagttg cctgactccc cgtcgtgtag ataactacga tacgggaggg | 5640 |
| cttaccatct ggccccagtg ctgcaatgat accgcgagac ccacgctcac cggctccaga | 5700 |
| tttatcagca ataaaccagc cagccggaag ggccgagcgc agaagtggtc ctgcaacttt | 5760 |
| atccgcctcc atccagtcta ttaattgttg ccgggaagct agagtaagta gttcgccagt | 5820 |
| taatagtttg cgcaacgttg ttgccattgc tacaggcatc gtggtgtcac gctcgtcgtt | 5880 |
| tggtatggct tcattcagct ccggttccca acgatcaagg cgagttacat gatcccccat | 5940 |
| gttgtgcaaa aaagcggtta gctccttcgg tcctccgatc gttgtcagaa gtaagttggc | 6000 |
| cgcagtgtta tcactcatgg ttatggcagc actgcataat tctcttactg tcatgccatc | 6060 |
| cgtaagatgc ttttctgtga ctggtgagta ctcaaccaag tcattctgag aatagtgtat | 6120 |
| gcggcgaccg agttgctctt gcccggcgtc aatacgggat aataccgcgc cacatagcag | 6180 |
| aactttaaaa gtgctcatca ttggaaaacg ttcttcgggg cgaaaactct caaggatctt | 6240 |
| accgctgttg agatccagtt cgatgtaacc cactcgtgca cccaactgat cttcagcatc | 6300 |
| ttttactttc accagcgttt ctgggtgagc aaaaacagga aggcaaaatg ccgcaaaaaa | 6360 |
| gggaataagg gcgacacgga aatgttgaat actcatactc ttcctttttc aatattattg | 6420 |
| aagcatttat cagggttatt gtctcatgag cggatacata tttgaatgta tttagaaaaa | 6480 |
| taaacaaata gggttccgc gcacatttcc ccgaaaagtg c | 6521 |

<210> SEQ ID NO 3
<211> LENGTH: 6010
<212> TYPE: DNA
<213> ORGANISM: Helicobacter pylori

<400> SEQUENCE: 3

```
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg ggggctccct ttagggttcc     180
gatttagtgc tttacggcac ctcgacccca aaaacttga ttagggtgat ggttcacgta      240
gtgggccatc gccctgatag acggttttc gcccttgac gttggagtcc acgttcttta      300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaatttaac aaaatattaa cgcttacaat ttccattcgc cattcaggct      480
gcgcaactgt tgggaagggc gatcggtgcg ggcctcttcg ctattacgcc agctggcgaa     540
agggggatgt gctgcaaggc gattaagttg ggtaacgcca gggttttccc agtcacgacg     600
ttgtaaaacg acggccagtg aattgtaata cgactcacta tagggcgaat gggtaccgg      660
gccccccctc gatcgacggt atcgatgcgt tttcatcgcc aaaatgctcc acaaattcgc     720
ccgcatcaaa atgccctctc cttcgcaca aatcatggat cctgttccca taagcccaag      780
aggggcggtt atacgcatcc aatttaggga gagccccaaa catcaagtaa taaagcacat     840
tacccacgat atttttttca ctaggcgggc aaccaggaac attgatcacg ggtttatcaa     900
tgattttatg caagggttgc gcgttagagg ggttagggta agccgcttga acgcccccaa     960
aacttgagca tgtgcctatg gcaaaaatag cggctgcgta ttgagcggct ttcctacact    1020
cttcagctcc cgtttcagcg tttgggcctt gagtgaggaa gtattccgtg ccttgggga    1080
tacccccttc taccattaaa atgtaattgt ttttatgctt ttctatggcg tcatgcaagc    1140
ttttttcagc ttgaaaaccg ctcgctacca tgatggtctc atggtattct aggttgatgt    1200
aatcaaagat aatgctatca atggtggggt ctgcgctcct taacaaactt tcgctacaac    1260
cggtgcattc tgccatgtgc aaccaaatca cgggcaatct gttagccact tccaccgcct    1320
tcaaagtcaa gggagcaaaa actagccggca aggctaacgc tgtgctcatc atgcccgccc   1380
acttcaataa atcgcgccta gaaatgcccg ccccttaaa ctcgtcttgc aagttttat     1440
gctcgttgtg agcgttaaac gaacggacta tatcaaggcg ttcttcaatc ttttgatagg    1500
tctttttttc atcgtagaac atgaccactc cttaattaga gatcttctag agaattcgta    1560
ccctcgagtc tagagcatgc gtcgacttgc aaaaagcgtc taaaatctat tgtattaacg    1620
cgctatatgg cttagtggaa gtgaaaataa aataactata aaacagagc ggctaaaacc     1680
tcatttttag aaataggtta cccaatggag caaaaaagtt aaaactcgcc cacaataatc    1740
ataatgatta aagttttcat attcattata aatccgttta cacaattatt ttataaattc    1800
aagtagaggg tttgtaggaa ctctcatcaa aaaacaagga acataatatg tctagattag    1860
ataaaagtaa agtgattaac agcgcattag cgctggggaa tgaggtcgga atcgaaggtg    1920
taacaacccg taaactcgcc cagaagcttg gtgtagagca gcctacattg tattggcatg    1980
taaaaaataa gcgggcccta ctggatgcgc tggcggtgga gatcttggcg cgtcatcatg    2040
attattcact gcctgcggcg ggggaatcct ggcagtcatt tctgcgcaat aatgcaatga    2100
gtttccgccg cgcgctgctg cgttaccgtg acggggcaaa agtgcacctc ggcacgcgtc    2160
ctgatgaaaa acagtatgat acggtggaaa cccagttacg ctttatgaca gaaaacggct    2220
tttcactgcg cgacgggcta tatgcgattt cagcggtcag tcatttacc ttaggtgccg     2280
```

```
tactggagca gcaggagcat actgccgccc tgaccgaccg ccctgcagca ccggacgaaa    2340
acctgccgcc gctattgcgg gaagcgctgc agattatgga cagtgatgat ggtgagcagg    2400
cctttctgca tggcctggag agcctgatcc ggggggtttga ggtgcagctt acggcactgt    2460
tgcaaatagt ctgataaggc ctgcagggat ccgtcgacaa attttcatta tcttaacata    2520
ataaaaataa tacagctgca attgattgtt ttttagtttt tattgagatt gagggaattt    2580
ctttaatatt aagtttcatt tggatagaat gccaccctat tttattagaa aaggaacaaa    2640
atgaaaaaag tactcatcat taacggggcc aaagcgttcg ggagctctgg agggaaactc    2700
aatgaaacct tgactgacca tgcaaaaaag actctagagt ctttgggggct agaagtggat    2760 actacgatcg tggataaagg ctatgaacat gctcaagaag tggagaaagt ctttagcgct    2820
gatgcgacga tttggcaaat gcctggctgg tggatgggag agccttggat tgtgaaaaaa    2880
tacattgatg aagtctttag cgtagggcat ggaaagcttt atgctagcga tggcagaagc    2940
tcgcaaaacc ccactaaaaa ctacgggaaa ggggcttga tgcaaggcaa aaaatacatg    3000
ttgagcttga cttggaacgc tcccattgaa gcctttaatg atcctagtga atttttttgaa    3060 ggggtgggtg tggatgttgt gtatttgcat ttgcataaag cgttccaatt tttagggctt    3120
tcagcgttgc ccacttttat ttgcaacgat gtggtgaaaa accccaagt ggagcagtat    3180 cttaactctc tcaccacgca tttgcgccaa gcttttggca agtgatttta aaattttttt    3240 aacccccca tttctttggg ggggcttgtt tattccacaa taaagtctct gggattgaga    3300
tcgcagccta agataagatc cctaagatta ctgcccaccg tttgataact cgcattgctc    3360
acaaagtaga atccgtattt ttcaaaaggc acaacaagag tgccgtctct atcccttaat    3420
tgcgcttttg ctttatccca acaaatatat cttggctctt catctgtgta gctttcaaag    3480
gcttctctgg cgttttctag caagtagtct atgacagcgc tagccaattc cttagcgttt    3540
cttgctattt tcctttgatg attggggagc ttaacgcttt gaagattatg ggaagttaag    3600
tcatcatcaa gggttttact aatctctctg gtgcggtatt cttttaggcaa atctttaaac    3660 aatcccactt gacagaattg atccgctaaa tattcgctcc tattcttcac ttcctctatc    3720
ccccaagaat gggtgttatt gatgaaatag tcgtttaaat gcaaggagct gtattcttcc    3780
ataagctcgc ggccgccacc gcggtggagc tccagctttt gttccctta gtgagggtta    3840 atttcgagct tggcgtaatc atggtcatag ctgtttcctg tgtgaaattg ttatccgctc    3900
acaattccac acaacatacg agccggaagc ataaagtgta aagcctgggg tgcctaatga    3960
gtgagctaac tcacattaat tgcgttgcgc tcactgcccg ctttccagtc gggaaacctg    4020
tcgtgccagc tgcattaatg aatcggccaa cgcgcgggga gaggcggttt gcgtattggg    4080
cgctcttccg cttcctcgct cactgactcg ctgcgctcgg tcgttcggct gcggcgagcg    4140
gtatcagctc actcaaaggc ggtaatacgg ttatccacag aatcagggga taacgcagga    4200
aagaacatgt gagcaaaagg ccagcaaaag gccaggaacc gtaaaaaggc cgcgttgctg    4260 gcgttttttcc ataggctccg ccccccctgac gagcatcaca aaaatcgacg ctcaagtcag    4320
aggtggcgaa acccgacagg actataaaga taccaggcgt ttccccctgg aagctccctc    4380
gtgcgctctc ctgttccgac cctgccgctt accggatacc tgtccgcctt ctcccttcg    4440 ggaagcgtgg cgctttctca tagctcacgc tgtaggtatc tcagttcggt gtaggtcgtt    4500
cgctccaagc tgggctgtgt gcacgaaccc cccgttcagc ccgaccgctg cgccttatcc    4560
ggtaactatc gtcttgagtc aacccggta agacacgact tatcgccact ggcagcagcc    4620
actggtaaca ggattagcag agcgaggtat gtaggcggtg ctacagagtt cttgaagtgg    4680
```

```
tggcctaact acggctacac tagaaggaca gtatttggta tctgcgctct gctgaagcca   4740
gttaccttcg gaaaaagagt tggtagctct tgatccggca acaaaccac cgctggtagc   4800 ggtggttttt ttgtttgcaa gcagcagatt acgcgcagaa aaaaggatc tcaagaagat   4860 cctttgatct tttctacggg gtctgacgct cagtggaacg aaaactcacg ttaagggatt   4920
ttggtcatga gattatcaaa aaggatcttc acctagatcc tttaaatta aaaatgaagt   4980 tttaaatcaa tctaaagtat atatgagtaa acttggtctg acagttacca atgcttaatc   5040
agtgaggcac ctatctcagc gatctgtcta tttcgttcat ccatagttgc ctgactcccc   5100
gtcgtgtaga taactacgat acgggagggc ttaccatctg gccccagtgc tgcaatgata   5160
ccgcgagacc cacgctcacc ggctccagat ttatcagcaa taaccagcc agccggaagg   5220 gccgagcgca gaagtggtcc tgcaactta tccgcctcca tccagtctat taattgttgc   5280
cgggaagcta gagtaagtag ttcgccagtt aatagtttgc gcaacgttgt tgccattgct   5340
acaggcatcg tggtgtcacg ctcgtcgttt ggtatggctt cattcagctc cggttcccaa   5400
cgatcaaggc gagttacatg atccccatg ttgtgcaaaa aagcggttag ctccttcggt   5460
cctccgatcg ttgtcagaag taagttggcc gcagtgttat cactcatggt tatggcagca   5520
ctgcataatt ctcttactgt catgccatcc gtaagatgct tttctgtgac tggtgagtac   5580
tcaaccaagt cattctgaga atagtgtatg cggcgaccga gttgctcttg cccggcgtca   5640
atacgggata ataccgcgcc acatagcaga actttaaaag tgctcatcat tggaaaacgt   5700
tcttcggggc gaaaactctc aaggatctta ccgctgttga tccagttc gatgtaaccc   5760 actcgtgcac ccaactgatc ttcagcatct tttactttca ccagcgtttc tgggtgagca   5820
aaaacaggaa ggcaaaatgc cgcaaaaaag gaataaggg cgacacggaa atgttgaata   5880
ctcatactct tcctttttca atattattga agcatttatc agggttattg tctcatgagc   5940
ggatacatat ttgaatgtat ttagaaaaat aaacaaatag gggttccgcg cacatttccc   6000
cgaaaagtgc                                                         6010
```

<210> SEQ ID NO 4
<211> LENGTH: 6010
<212> TYPE: DNA
<213> ORGANISM: Helicobacter pylori

<400> SEQUENCE: 4

```
cacctgacgc gccctgtagc ggcgcattaa gcgcggcggg tgtggtggtt acgcgcagcg     60
tgaccgctac acttgccagc gccctagcgc ccgctccttt cgctttcttc ccttcctttc    120
tcgccacgtt cgccggcttt ccccgtcaag ctctaaatcg gggctccct ttagggttcc    180 gatttagtgc tttacggcac ctcgacccca aaaaacttga ttagggtgat ggttcacgta    240
gtgggccatc gccctgatag acggttttc gcccttgac gttggagtcc acgttcttta    300
atagtggact cttgttccaa actggaacaa cactcaaccc tatctcggtc tattcttttg    360
atttataagg gattttgccg atttcggcct attggttaaa aaatgagctg atttaacaaa    420
aatttaacgc gaattttaac aaaatattaa cgcttacaat ttccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tgggtaccgg    660
gccccccctc gatcgacggt atcgatgcgt tttcatcgcc aaaatgctcc acaaattcgc    720
```

```
ccgcatcaaa atgccctctc ctttcgcaca aatcatggat cctgttccca taagcccaag    780
aggggcggtt atacgcatcc aatttaggga gagccccaaa catcaagtaa taaagcacat    840
tacccacgat attttttca ctaggcgggc aaccaggaac attgatcacg ggtttatcaa     900
tgattttatg caagggttgc gcgttagagg ggttagggta agccgcttga acgcccccaa    960
aacttgagca tgtgcctatg gcaaaaatag cggctgcgta ttgagcggct ttcctacact   1020
cttcagctcc cgtttcagcg tttgggcctt gagtgaggaa gtattccgtg ccttggggga   1080
tacccccttc taccattaaa atgtaattgt ttttatgctt ttctatggcg tcatgcaagc   1140
tttttttcagc ttgaaaaccg ctcgctacca tgatggtctc atggtattct aggttgatgt  1200
aatcaaagat aatgctatca atggtggggt ctgcgctcct taacaaactt cgctacaac   1260
cggtgcattc tgccatgtgc aaccaaatca cgggcaatct gttagccact tccaccgcct  1320
tcaaagtcaa gggagcaaaa ctagccggca aggctaacgc tgtgctcatc atgcccgccc  1380
acttcaataa atcgcgccta gaaatgcccg cccctttaaa ctcgtcttgc aagttttttat 1440
gctcgttgtg agcgttaaac gaacggacta tatcaaggcg ttcttcaatc tttttgatagg 1500
tcttttttc atcgtagaac atgaccactc cttaattaga gatcttctag agaattcgta    1560
ccctcgagtc tagagcatgc gtcgacttgc aaaaagcgtc taaaatctat tgtattaacg   1620
cgctatatgg cttagtggaa gtgaaaataa aataactata aaaacagagc ggctaaaacc   1680
tcattttag aaataggtta cccaatggag caaaaaagtt aaaactcgcc cacaataatc    1740
ataatgatta aagttttcat attcattata aatccgttta cacaattatt ttataaattc   1800
aagtagaggg tttgtaggaa ctctcatcaa aaaacaagga acataatatg tctagattag   1860
ataaaagtaa agtgattaac agcgcattag agctgcttaa tgaggtcgga atcgaaggtt   1920
taacaacccg taaactcgcc cagaagcttg gtgtagagca gcctacattg tattggcatg   1980
taaaaaataa gcgggcccta ctggatgcgc tggcggtgga gatcttggcg cgtcatcatg   2040
attattcact gcctgcggcg ggggaatcct ggcagtcatt tctgcgcaat aatgcaatga   2100
gtttccgccg cgcgctgctg cgttaccgtg acggggcaaa agtgcacctc ggcacgcgtc   2160
ctgatgaaaa acagtatgat acggtggaaa cccagttacg ctttatgaca gaaaacggct   2220
tttcactgcg cgacgggcta tatgcgattt cagcggtcag tcattttacc ttaggtgccg   2280
tactggagca gcaggagcat actgccgccc tgaccgaccg ccctgcagca ccggacgaaa   2340
acctgccgcc gctattgcgg gaagcgctgc agattatgga cagtgatgat ggtgagcagg   2400
cctttctgca tggcctggag agcctgatcc gggggtttga ggtgcagctt acggcactgt   2460
tgcaaatagt ctgataaggc ctgcagggat ccgtcgacaa attttcatta tcttaacata   2520
ataaaaataa tacagctgca attgattgtt ttttagtttt tattgagatt gagggaattt   2580
ctttaatatt aagtttcatt tggatagaat gccaccctat tttattagaa aaggaacaaa   2640
atgaaaaaag tactcatcat taacggggcc aaagcgttcg ggagctctgg agggaaactc   2700
aatgaaacct tgactgacca tgcaaaaaag actctagagt ctttgggct agaagtggat   2760
actacgatcg tggataaagg ctatgaacat gctcaagaag tggagaaagt ctttagcgct   2820
gatgcgacga tttggcaaat gcctggctgg tggatgggag agccttggat tgtgaaaaaa   2880
tacattgatg aagtctttag cgtagggcat ggaaagcttt atgctagcga tggcagaagc   2940
tcgcaaaacc ccactaaaaa ctacgggaaa ggggcttga tgcaaggcaa aaaatacatg    3000
ttgagcttga cttggaacgc tcccattgaa gcctttaatg atcctagtga atttttgaa    3060
ggggtgggtg tggatgttgt gtatttgcat ttgcataaag cgttccaatt tttagggctt   3120
```

```
tcagcgttgc ccactttat ttgcaacgat gtggtgaaaa accccaagt ggagcagtat    3180
cttaactctc tcaccacgca tttgcgccaa gcttttggca agtgatttta aattttttt    3240
aacccccccca tttctttggg ggggcttgtt tattccacaa taaagtctct gggattgaga   3300
tcgcagccta agataagatc cctaagatta ctgcccaccg tttgataact cgcattgctc    3360
acaaagtaga atccgtattt ttcaaaaggc acaacaagag tgccgtctct atcccttaat    3420
tgcgcttttg ctttatccca acaaatatat cttggctctt catctgtgta gctttcaaag    3480
gcttctctgg cgttttctag caagtagtct atgacagcgc tagccaattc cttagcgttt    3540
cttgctattt ccctttgatg attggggagc ttaacgcttt gaagattatg gaagttaag    3600
tcatcatcaa gggttttact aatctctctg gtgcggtatt ctttaggcaa atctttaaac    3660
aatcccactt gacagaattg atccgctaaa tattcgctcc tattcttcac ttcctctatc    3720
ccccaagaat gggtgttatt gatgaaatag tcgtttaaat gcaaggagct gtattcttcc    3780
ataagctcgc ggccgccacc gcggtggagc tccagctttt gttccctta gtgagggtta    3840
atttcgagct tggcgtaatc atggtcatag ctgtttcctg tgtgaaattg ttatccgctc    3900
acaattccac acaacatacg agccggaagc ataaagtgta aagcctgggg tgcctaatga    3960
gtgagctaac tcacattaat tgcgttgcgc tcactgcccg ctttccagtc gggaaacctg    4020
tcgtgccagc tgcattaatg aatcggccaa cgcgcgggga gaggcggttt gcgtattggg    4080
cgctcttccg cttcctcgct cactgactcg ctgcgctcgg tcgttcggct gcggcgagcg    4140
gtatcagctc actcaaaggc ggtaatacgg ttatccacag aatcagggga taacgcagga    4200
aagaacatgt gagcaaaagg ccagcaaaag gccaggaacc gtaaaaaggc cgcgttgctg    4260
gcgtttttcc ataggctccg ccccctgac gagcatcaca aaaatcgacg ctcaagtcag    4320
aggtggcgaa acccgacagg actataaaga taccaggcgt ttccccctgg aagctccctc    4380
gtgcgctctc ctgttccgac cctgccgctt accggatacc tgtccgcctt tctcccttcg    4440
ggaagcgtgg cgctttctca tagctcacgc tgtaggtatc tcagttcggt gtaggtcgtt    4500
cgctccaagc tgggctgtgt gcacgaaccc cccgttcagc ccgaccgctg cgccttatcc    4560
ggtaactatc gtcttgagtc aacccggta agacacgact tatcgccact ggcagcagcc    4620
actggtaaca ggattagcag agcgaggtat gtaggcggtg ctacagagtt cttgaagtgg    4680
tggcctaact acggctacac tagaaggaca gtatttggta tctgcgctct gctgaagcca    4740
gttaccttcg gaaaaagagt tggtagctct tgatccggca acaaaccac cgctggtagc    4800
ggtggttttt ttgtttgcaa gcagcagatt acgcgcagaa aaaaggatc tcaagaagat    4860
cctttgatct tttctacggg gtctgacgct cagtggaacg aaaactcacg ttaagggatt    4920
ttggtcatga gattatcaaa aaggatcttc acctagatcc tttaaatta aaatgaagt    4980
tttaaatcaa tctaaagtat atatgagtaa acttggtctg acagttacca atgcttaatc    5040
agtgaggcac ctatctcagc gatctgtcta tttcgttcat ccatagttgc ctgactcccc    5100
gtcgtgtaga taactacgat acgggagggc ttaccatctg gccccagtgc tgcaatgata    5160
ccgcgagacc cacgctcacc ggctccagat ttatcagcaa taaaccagcc agccggaagg    5220
gccgagcgca gaagtggtcc tgcaacttta tccgcctcca tccagtctat taattgttgc    5280
cgggaagcta gagtaagtag ttcgccagtt aatagtttgc gcaacgttgt tgccattgct    5340
acaggcatcg tggtgtcacg ctcgtcgttt ggtatggctt cattcagctc cggttcccaa    5400
cgatcaaggc gagttacatg atcccccatg ttgtgcaaaa aagcggttag ctccttcggt    5460
```

| | |
|---|---|
| cctccgatcg ttgtcagaag taagttggcc gcagtgttat cactcatggt tatggcagca | 5520 |
| ctgcataatt ctcttactgt catgccatcc gtaagatgct tttctgtgac tggtgagtac | 5580 |
| tcaaccaagt cattctgaga atagtgtatg cggcgaccga gttgctcttg cccggcgtca | 5640 |
| atacgggata ataccgcgcc acatagcaga actttaaaag tgctcatcat tggaaaacgt | 5700 |
| tcttcgggc gaaaactctc aaggatctta ccgctgttga gatccagttc gatgtaaccc | 5760 |
| actcgtgcac ccaactgatc ttcagcatct tttactttca ccagcgtttc tgggtgagca | 5820 |
| aaaacaggaa ggcaaaatgc cgcaaaaaag gaataaggg cgacacggaa atgttgaata | 5880 |
| ctcatactct tcctttttca atattattga agcatttatc agggttattg tctcatgagc | 5940 |
| ggatacatat ttgaatgtat ttagaaaaat aaacaaatag gggttccgcg cacatttccc | 6000 |
| cgaaaagtgc | 6010 |

<210> SEQ ID NO 5
<211> LENGTH: 5911
<212> TYPE: DNA
<213> ORGANISM: Helicobacter pylori

<400> SEQUENCE: 5

| | |
|---|---|
| cacctgacgc gccctgtagc ggcgcattaa gcgcggcggg tgtggtggtt acgcgcagcg | 60 |
| tgaccgctac acttgccagc gccctagcgc ccgctccttt cgctttcttc ccttcctttc | 120 |
| tcgccacgtt cgccggcttt ccccgtcaag ctctaaatcg ggggctccct ttagggttcc | 180 |
| gatttagtgc tttacggcac ctcgacccca aaaaacttga ttagggtgat ggttcacgta | 240 |
| gtgggccatc gccctgatag acggtttttc gccctttgac gttggagtcc acgttcttta | 300 |
| atagtggact cttgttccaa actggaacaa cactcaaccc tatctcggtc tattcttttg | 360 |
| atttataagg gattttgccg atttcggcct attggttaaa aaatgagctg atttaacaaa | 420 |
| aatttaacgc gaattttaac aaaatattaa cgcttacaat ttccattcgc cattcaggct | 480 |
| gcgcaactgt tgggaagggc gatcggtgcg ggcctcttcg ctattacgcc agctggcgaa | 540 |
| agggggatgt gctgcaaggc gattaagttg ggtaacgcca gggttttccc agtcacgacg | 600 |
| ttgtaaaacg acggccagtg aattgtaata cgactcacta tagggcgaat tgggtaccgg | 660 |
| gccccccctc gatcgacggt atcgatgcgt tttcatcgcc aaaatgctcc acaaattcgc | 720 |
| ccgcatcaaa atgccctctc ctttcgcaca aatcatggat cctgttccca taagcccaag | 780 |
| agggggcggtt atacgcatcc aatttaggga gagccccaaa catcaagtaa taaagcacat | 840 |
| tacccacgat attttttca ctaggcgggc aaccaggaac attgatcacg ggtttatcaa | 900 |
| tgattttatg caagggttgc gcgttagagg ggttagggta agccgcttga acgccccaa | 960 |
| aacttgagca tgtgcctatg gcaaaaatag cggctgcgta ttgagcggct ttcctacact | 1020 |
| cttcagctcc cgtttcagcg tttgggcctt gagtgaggaa gtattccgtg ccttggggga | 1080 |
| tacccccttc taccattaaa atgtaattgt ttttatgctt ttctatggcg tcatgcaagc | 1140 |
| ttttttcagc ttgaaaaccg ctcgctacca tgatggtctc atggtattct aggttgatgt | 1200 |
| aatcaaagat aatgctatca atggtgggt ctgcgctcct taacaaactt cgctacaac | 1260 |
| cggtgcattc tgccatgtgc aaccaaatca cgggcaatct gttagccact ccaccgcct | 1320 |
| tcaaagtcaa gggagcaaaa ctagccggca aggctaacgc tgtgctcatc atgcccgccc | 1380 |
| acttcaataa atcgcgccta gaaatgcccg ccccttaaa ctcgtcttgc aagtttttat | 1440 |
| gctcgttgtg agcgttaaac gaacggacta tatcaaggcg ttcttcaatc ttttgatagg | 1500 |
| tctttttttc atcgtagaac atgaccactc cttaattaga gatcttctag agaattcgta | 1560 |

```
ccctcgagtc tagagcatgc gtcgaccaat aagatttggt ataaattttc tttattatag    1620
cccattttca tgctccttta aattttgctt ttaaaacaaa gcccttttaaa atttcaaact   1680 ttaaccgatt atagttccaa ccaaaagcaa ggatgccttt gggttttta taacaaggag    1740 ttacaacaat gtctagatta gataaaagta aagtgattaa cagcgcatta gcgctgggga   1800
atgaggtcgg aatcgaaggt gtaacaaccc gtaaactcgc ccagaagctt ggtgtagagc   1860
agcctacatt gtattggcat gtaaaaaata agcgggccct actggatgcg ctggcggtgg   1920
agatcttggc gcgtcatcat gattattcac tgcctgcggc gggggaatcc tggcagtcat   1980
ttctgcgcaa taatgcaatg agtttccgcc gcgcgctgct gcgttaccgt gacgggcaa    2040 aagtgcacct cggcacgcgt cctgatgaaa acagtatga tacggtggaa acccagttac    2100
gctttatgac agaaaacggc ttttcactgc gcgacgggct atatgcgatt tcagcggtca   2160
gtcattttac cttaggtgcc gtactggagc agcaggagca tactgccgcc ctgaccgacc   2220
gccctgcagc accggacgaa aacctgccgc cgctattgcg ggaagcgctg cagattatgg   2280
acagtgatga tggtgagcag gcctttctgc atggcctgga gagcctgatc cggggggtttg  2340 aggtgcagct tacggcactg ttgcaaatag tctgataagg cctgcaggga tccgtcgaca   2400
aattttcatt atcttaacat aataaaaata atacagctgc aattgattgt ttttttagttt  2460 ttattgagat tgagggaatt tctttaatat taagtttcat ttggatagaa tgccaccctaa  2520 ttttattaga aaaggaacaa aatgaaaaaa gtactcatca ttaacggggc caaagcgttc    2580
gggagctctg gagggaaact caatgaaacc ttgactgacc atgcaaaaaa gactctagag   2640
tctttggggc tagaagtgga tactacgatc gtggataaag gctatgaaca tgctcaagaa   2700
gtggagaaag tctttagcgc tgatgcgacg atttggcaaa tgcctggctg gtggatggga   2760
gagccttgga ttgtgaaaaa atacattgat gaagtcttta gcgtagggca tggaaagctt   2820
tatgctagcg atggcagaag ctcgcaaaac cccactaaaa actacgggaa aggggcttg   2880 atgcaaggca aaaaatacat gttgagcttg acttggaacg ctcccattga agcctttaat   2940
gatcctagtg aatttttga aggggtgggt gtggatgttg tgtatttgca tttgcataaa    3000
gcgttccaat ttttagggct ttcagcgttg cccacttta tttgcaacga tgtggtgaaa   3060
aacccccaag tggagcagta tcttaactct ctcaccacgc atttgcgcca agcttttggc    3120
aagtgatttt aaaattttt taacccccc atttctttgg gggggcttgt ttattccaca    3180
ataaagtctc tgggattgag atcgcagcct aagataagat ccctaagatt actgcccacc   3240
gtttgataac tcgcattgct cacaaagtag aatccgtatt tttcaaaagg cacaacaaga   3300
gtgccgtctc tatcccttaa ttgcgctttt gctttatccc aacaaatata tcttggctct   3360
tcatctgtgt agctttcaaa ggcttctctg gcgttttcta gcaagtagtc tatgacagcg   3420
ctagccaatt ccttagcgtt tcttgctatt ttcctttgat gattggggag cttaacgctt   3480
tgaagattat gggaagttaa gtcatcatca agggttttac taatctctct ggtgcggtat   3540
tctttaggca aatctttaaa caatcccact tgacagaatt gatccgctaa atattcgctc   3600
ctattcttca cttcctctat cccccaagaa tgggtgttat tgatgaaata gtcgtttaaa   3660
tgcaaggagc tgtattcttc cataagctcg cggccgccac cgcggtggag ctccagcttt   3720
tgttcccttt agtgagggtt aatttcgagc ttggcgtaat catggtcata gctgtttcct   3780
gtgtgaaatt gttatccgct cacaattcca cacaacatac gagccggaag cataaagtgt   3840
aaagcctggg gtgcctaatg agtgagctaa ctcacattaa ttgcgttgcg ctcactgccc   3900
```

```
gctttccagt cgggaaacct gtcgtgccag ctgcattaat gaatcggcca acgcgcgggg    3960
agaggcggtt tgcgtattgg gcgctcttcc gcttcctcgc tcactgactc gctgcgctcg    4020
gtcgttcggc tgcggcgagc ggtatcagct cactcaaagg cggtaatacg gttatccaca    4080
gaatcagggg ataacgcagg aaagaacatg tgagcaaaag gccagcaaaa ggccaggaac    4140
cgtaaaaagg ccgcgttgct ggcgtttttc cataggctcc gcccccctga cgagcatcac    4200
aaaaatcgac gctcaagtca gaggtggcga aacccgacag gactataaag ataccaggcg    4260
tttccccctg gaagctccct cgtgcgctct cctgttccga ccctgccgct taccggatac    4320
ctgtccgcct ttctcccttc gggaagcgtg gcgctttctc atagctcacg ctgtaggtat    4380
ctcagttcgg tgtaggtcgt tcgctccaag ctgggctgtg tgcacgaacc cccgttcag    4440
cccgaccgct gcgccttatc cggtaactat cgtcttgagt ccaacccggt aagacacgac    4500
ttatcgccac tggcagcagc cactggtaac aggattagca gagcgaggta tgtaggcggt    4560
gctacagagt tcttgaagtg gtggcctaac tacggctaca ctagaaggac agtatttggt    4620
atctgcgctc tgctgaagcc agttaccttc ggaaaaagag ttggtagctc ttgatccggc    4680
aaacaaacca ccgctggtag cggtggtttt tttgtttgca agcagcagat tacgcgcaga    4740
aaaaaaggat ctcaagaaga tcctttgatc ttttctacgg ggtctgacgc tcagtggaac    4800
gaaaactcac gttaagggat tttggtcatg agattatcaa aaaggatctt cacctagatc    4860
cttttaaatt aaaaatgaag ttttaaatca atctaaagta tatatgagta aacttggtct    4920
gacagttacc aatgcttaat cagtgaggca cctatctcag cgatctgtct atttcgttca    4980
tccatagttg cctgactccc cgtcgtgtag ataactacga tacgggaggg cttaccatct    5040
ggccccagtg ctgcaatgat accgcgagac ccacgctcac cggctccaga tttatcagca    5100
ataaccagc cagccggaag ggccgagcgc agaagtggtc ctgcaacttt atccgcctcc    5160
atccagtcta ttaattgttg ccgggaagct agagtaagta gttcgccagt taatagtttg    5220
cgcaacgttg ttgccattgc tacaggcatc gtggtgtcac gctcgtcgtt tggtatggct    5280
tcattcagct ccggttccca acgatcaagg cgagttacat gatccccat gttgtgcaaa    5340
aaagcggtta gctccttcgg tcctccgatc gttgtcagaa gtaagttggc cgcagtgtta    5400
tcactcatgg ttatggcagc actgcataat tctcttactg tcatgccatc cgtaagatgc    5460
ttttctgtga ctggtgagta ctcaaccaag tcattctgag aatagtgtat gcggcgaccg    5520
agttgctctt gcccggcgtc aatacgggat aataccgcgc cacatagcag aactttaaaa    5580
gtgctcatca ttggaaaacg ttcttcgggg cgaaaactct caaggatctt accgctgttg    5640
agatccagtt cgatgtaacc cactcgtgca cccaactgat cttcagcatc ttttactttc    5700
accagcgttt ctgggtgagc aaaaacagga aggcaaaatg ccgcaaaaaa gggaataagg    5760
gcgacacgga aatgttgaat actcatactc ttcctttttc aatattattg aagcatttat    5820
cagggttatt gtctcatgag cggatacata tttgaatgta tttagaaaaa taaacaaata    5880
ggggttccgc gcacatttcc ccgaaaagtg c                                   5911

<210> SEQ ID NO 6
<211> LENGTH: 5911
<212> TYPE: DNA
<213> ORGANISM: Helicobacter pylori

<400> SEQUENCE: 6
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
```

```
tcgccacgtt cgccggcttt ccccgtcaag ctctaaatcg ggggctccct ttagggttcc      180
gatttagtgc tttacggcac ctcgacccca aaaaacttga ttagggtgat ggttcacgta      240
gtgggccatc gccctgatag acggttttc gcccttgac gttggagtcc acgttcttta       300
atagtggact cttgttccaa actggaacaa cactcaaccc tatctcggtc tattcttttg      360
atttataagg gattttgccg atttcggcct attggttaaa aaatgagctg atttaacaaa      420
aatttaacgc gaattttaac aaaatattaa cgcttacaat ttccattcgc cattcaggct      480
gcgcaactgt tgggaagggc gatcggtgcg ggcctcttcg ctattacgcc agctggcgaa      540 aggggatgt gctgcaaggc gattaagttg gtaacgcca gggttttccc agtcacgacg       600
ttgtaaaacg acggccagtg aattgtaata cgactcacta tagggcgaat tgggtaccgg     660
gccccccctc gatcgacggt atcgatgcgt tttcatcgcc aaaatgctcc acaaattcgc     720
ccgcatcaaa atgccctctc ctttcgcaca aatcatggat cctgttccca taagcccaag    780
aggggcggtt atacgcatcc aatttaggga gagccccaaa catcaagtaa taagcacat     840 tacccacgat attttttca ctaggcgggc aaccaggaac attgatcacg ggtttatcaa      900
tgattttatg caaggttgc gcgttagagg ggttagggta agccgcttga acgccccaa      960 aacttgagca tgtgcctatg gcaaaaatag cggctgcgta ttgagcggct ttcctacact     1020
cttcagctcc cgtttcagcg tttgggcctt gagtgaggaa gtattccgtg ccttggggga    1080 taccccttc taccattaaa atgtaattgt ttttatgctt ttctatggcg tcatgcaagc      1140
ttttttcagc ttgaaaaccg ctcgctacca tgatggtctc atggtattct aggttgatgt    1200
aatcaaagat aatgctatca atggtggggt ctgcgctcct taacaaactt cgctacaac    1260 cggtgcattc tgccatgtgc aaccaaatca cgggcaatct gttagccact tccaccgcct    1320
tcaaagtcaa gggagcaaaa ctagccggca aggctaacgc tgtgctcatc atgcccgccc    1380
acttcaataa atcgcgccta gaaatgcccg ccccttttaaa ctcgtcttgc aagttttat    1440 gctcgttgtg agcgttaaac gaacggacta tatcaaggcg ttcttcaatc ttttgatagg    1500 tcttttttc atcgtagaac atgaccactc cttaattaga gatcttctag agaattcgta    1560
ccctcgagtc tagagcatgc gtcgaccaat aagatttggt ataaattttc tttattatag    1620 cccatttca tgctccttta aattttgctt ttaaaacaaa gccctttaaa atttcaaact    1680
ttaaccgatt atagttccaa ccaaaagcaa ggatgccttt gggttttta taacaaggag    1740 ttacaacaat gtctagatta gataaaagta aagtgattaa cagcgcatta gagctgctta    1800
atgaggtcgg aatcgaaggt ttaacaaccc gtaaactcgc ccagaagctt ggtgtagagc    1860
agcctacatt gtattggcat gtaaaaaata agcgggccct actggatgcg ctggcggtgg    1920
agatcttggc gcgtcatcat gattattcac tgcctgcggc ggggaatcc tggcagtcat    1980 ttctgcgcaa taatgcaatg agtttccgcc gcgcgctgct gcgttaccgt gacggggcaa    2040
aagtgcacct cggcacgcgt cctgatgaaa aacagtatga tacggtggaa acccagttac    2100
gctttatgac agaaaacggc ttttcactgc gcgacgggct atatgcgatt tcagcggtca    2160
gtcattttac cttaggtgcc gtactggagc agcaggagca tactgccgcc ctgaccgacc    2220
gccctgcagc accggacgaa aacctgccgc cgctattgcg ggaagcgctg cagattatgg    2280
acagtgatga tggtgagcag gcctttctgc atggcctgga gagcctgatc cggggggttg    2340
aggtgcagct tacggcactg ttgcaaatag tctgataagg cctgcaggga tccgtcgaca    2400
aattttcatt atcttaacat aataaaaata atacagctgc aattgattgt ttttagttt    2460
```

```
ttattgagat tgagggaatt tctttaatat taagtttcat ttggatagaa tgccaccta      2520 ttttattaga aaaggaacaa aatgaaaaaa gtactcatca ttaacggggc caaagcgttc      2580
gggagctctg gagggaaact caatgaaacc ttgactgacc atgcaaaaaa gactctagag      2640
tctttggggc tagaagtgga tactacgatc gtggataaag gctatgaaca tgctcaagaa      2700
gtggagaaag tctttagcgc tgatgcgacg atttggcaaa tgcctggctg gtggatggga      2760
gagccttgga ttgtgaaaaa atacattgat gaagtcttta gcgtagggca tggaaagctt      2820
tatgctagcg atggcagaag ctcgcaaaac cccactaaaa actacgggaa aggggggcttg     2880 atgcaaggca aaaatacat gttgagcttg acttggaacg ctcccattga agcctttaat       2940
gatcctagtg aatttttga aggggtgggt gtggatgttg tgtatttgca tttgcataaa       3000
gcgttccaat ttttagggct ttcagcgttg cccactttta tttgcaacga tgtggtgaaa      3060 aaccccaag tggagcagta tcttaactct ctcaccacgc atttgcgcca agcttttggc       3120
aagtgatttt aaaatttttt taaccccccc atttctttgg gggggcttgt ttattccaca      3180
ataaagtctc tgggattgag atcgcagcct aagataagat ccctaagatt actgccacc      3240 gtttgataac tcgcattgct cacaaagtag aatccgtatt tttcaaaagg cacaacaaga     3300
gtgccgtctc tatcccttaa ttgcgctttt gctttatccc aacaaatata tcttggctct     3360
tcatctgtgt agctttcaaa ggcttctctg gcgttttcta gcaagtagtc tatgacagcg     3420
ctagccaatt ccttagcgtt tcttgctatt ttcctttgat gattggggag cttaacgctt     3480
tgaagattat gggaagttaa gtcatcatca agggttttac taatctctct ggtgcggtat     3540
tctttaggca aatcttttaaa caatcccact tgacagaatt gatccgctaa atattcgctc    3600
ctattcttca cttcctctat cccccaagaa tgggtgttat tgatgaaata gtcgtttaaa     3660
tgcaaggagc tgtattcttc cataagctcg cggccgccac cgcggtggag ctccagcttt     3720
tgttcccttt agtgagggtt aatttcgagc ttggcgtaat catggtcata gctgtttcct     3780
gtgtgaaatt gttatccgct cacaattcca cacaacatac gagccggaag cataaagtgt     3840
aaagcctggg gtgcctaatg agtgagctaa ctcacattaa ttgcgttgcg ctcactgccc     3900
gctttccagt cgggaaacct gtcgtgccag ctgcattaat gaatcggcca acgcgcgggg     3960
agaggcggtt tgcgtattgg gcgctcttcc gcttcctcgc tcactgactc gctgcgctcg     4020
gtcgttcggc tgcggcgagc ggtatcagct cactcaaagg cggtaatacg gttatccaca     4080
gaatcagggg ataacgcagg aaagaacatg tgagcaaaag gccagcaaaa ggccaggaac     4140
cgtaaaaagg ccgcgttgct ggcgtttttc cataggctcc gccccctga cgagcatcac      4200 aaaaatcgac gctcaagtca gaggtggcga aacccgacag gactataaag ataccaggcg     4260
tttccccctg gaagctccct cgtgcgctct cctgttccga ccctgccgct taccggatac     4320
ctgtccgcct ttctcccttc gggaagcgtg gcgctttctc atagctcacg ctgtaggtat     4380
ctcagttcgg tgtaggtcgt tcgctccaag ctgggctgtg tgcacgaacc ccccgttcag     4440
cccgaccgct gcgccttatc cggtaactat cgtcttgagt ccaacccggt aagacacgac     4500
ttatcgccac tggcagcagc cactggtaac aggattagca gagcgaggta tgtaggcggt     4560
gctacagagt tcttgaagtg gtggcctaac tacggctaca ctagaaggac agtatttggt     4620
atctgcgctc tgctgaagcc agttaccttc ggaaaaagag ttggtagctc ttgatccggc     4680
aaacaaacca ccgctggtag cggtggtttt tttgtttgca agcagcagat tacgcgcaga     4740
aaaaaaggat ctcaagaaga tcctttgatc ttttctacgg ggtctgacgc tcagtggaac     4800
gaaaactcac gttaagggat tttggtcatg agattatcaa aaaggatctt cacctagatc     4860
```

```
cttttaaatt aaaaatgaag ttttaaatca atctaaagta tatatgagta aacttggtct    4920
gacagttacc aatgcttaat cagtgaggca cctatctcag cgatctgtct atttcgttca    4980
tccatagttg cctgactccc cgtcgtgtag ataactacga tacgggaggg cttaccatct    5040
ggccccagtg ctgcaatgat accgcgagac ccacgctcac cggctccaga tttatcagca    5100
ataaaccagc cagccggaag ggccgagcgc agaagtggtc ctgcaacttt atccgcctcc    5160
atccagtcta ttaattgttg ccgggaagct agagtaagta gttcgccagt taatagtttg    5220
cgcaacgttg ttgccattgc tacaggcatc gtggtgtcac gctcgtcgtt tggtatggct    5280
tcattcagct ccggttccca acgatcaagg cgagttacat gatcccccat gttgtgcaaa    5340
aaagcggtta gctccttcgg tcctccgatc gttgtcagaa gtaagttggc cgcagtgtta    5400
tcactcatgg ttatggcagc actgcataat tctcttactg tcatgccatc cgtaagatgc    5460
ttttctgtga ctggtgagta ctcaaccaag tcattctgag aatagtgtat gcggcgaccg    5520
agttgctctt gcccggcgtc aatacggat aataccgcgc cacatagcag aactttaaaa    5580
gtgctcatca ttggaaaacg ttcttcgggg cgaaaactct caaggatctt accgctgttg    5640
agatccagtt cgatgtaacc cactcgtgca cccaactgat cttcagcatc ttttactttc    5700
accagcgttt ctgggtgagc aaaaacagga aggcaaaatg ccgcaaaaaa gggaataagg    5760
gcgacacgga aatgttgaat actcatactc ttcctttttc aatattattg aagcatttat    5820
cagggttatt gtctcatgag cggatacata tttgaatgta tttagaaaaa taaacaaata    5880
ggggttccgc gcacatttcc ccgaaaagtg c                                  5911

<210> SEQ ID NO 7
<211> LENGTH: 5857
<212> TYPE: DNA
<213> ORGANISM: Helicobacter pylori

<400> SEQUENCE: 7
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg gggctccct ttagggttcc      180 gatttagtgc tttacggcac ctcgacccca aaaaacttga ttagggtgat ggttcacgta     240
gtgggccatc gccctgatag acggtttttc gccctttgac gttggagtcc acgttcttta     300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat ttccattcgc cattcaggct     480
gcgcaactgt tgggaagggc gatcggtgcg ggcctcttcg ctattacgcc agctggcgaa     540
agggggatgt gctgcaaggc gattaagttg ggtaacgcca gggttttccc agtcacgacg     600
ttgtaaaacg acggccagtg aattgtaata cgactcacta tagggcgaat ggggaccgg      660 gccccccctc gatcgacggt atcgatgcgt tttcatcgcc aaaatgctcc acaaattcgc     720
ccgcatcaaa atgccctctc ctttcgcaca aatcatggat cctgttccca taagcccaag     780
aggggcggtt atacgcatcc aatttaggga gagccccaaa catcaagtaa taagcacat     840 tacccacgat atttttttca ctaggcgggc aaccaggaac attgatcacg ggtttatcaa     900 tgatttttatg caagggttgc gcgttagagg ggttagggta agccgcttga acgccccaa     960 aacttgagca tgtgcctatg gcaaaaatag cggctgcgta ttgagcggct ttcctacact    1020
```

```
cttcagctcc cgtttcagcg tttgggcctt gagtgaggaa gtattccgtg ccttggggga    1080
tacccccttc taccattaaa atgtaattgt ttttatgctt ttctatggcg tcatgcaagc    1140 tttttttcagc ttgaaaaccg ctcgctacca tgatggtctc atggtattct aggttgatgt   1200
aatcaaagat aatgctatca atggtggggt ctgcgctcct taacaaactt tcgctacaac    1260
cggtgcattc tgccatgtgc aaccaaatca cgggcaatct gttagccact tccaccgcct    1320
tcaaagtcaa gggagcaaaa ctagccggca aggctaacgc tgtgctcatc atgcccgccc    1380
acttcaataa atcgcgccta gaaatgcccg cccctttaaa ctcgtcttgc aagttttttat   1440 gctcgttgtg agcgttaaac gaacggacta tatcaaggcg ttcttcaatc ttttgatagg    1500 tcttttttttc atcgtagaac atgaccactc cttaattaga gatcttctag agaattcgta   1560
ccctcgagtc tagagcatgc gtcgacaatg aacgcttctg ttaatcttag taaatcaaaa    1620
cattgctata attacatcca accttgattt cgttatgtct tcaaggaaaa acactttaag    1680
aataggagaa taagatgtct agattagata aagtaaagt gattaacagc gcattagcgc     1740
tggggaatga ggtcggaatc gaaggtgtaa caacccgtaa actcgcccag aagcttggtg    1800
tagagcagcc tacattgtat tggcatgtaa aaaataagcg ggccctactg gatgcgctgg    1860
cggtggagat cttggcgcgt catcatgatt attcactgcc tgcggcgggg gaatcctggc    1920
agtcatttct gcgcaataat gcaatgagtt tccgccgcgc gctgctgcgt taccgtgacg    1980
gggcaaaagt gcacctcggc acgcgtcctg atgaaaaaca gtatgatacg gtggaaaccc    2040
agttacgctt tatgacagaa aacggctttt cactgcgcga cgggctatat gcgatttcag    2100
cggtcagtca ttttacctta ggtgccgtac tggagcagca ggagcatact gccgccctga    2160
ccgaccgccc tgcagcaccg gacgaaaacc tgccgccgct attgcgggaa gcgctgcaga    2220
ttatggacag tgatgatggt gagcaggcct ttctgcatgg cctggagagc ctgatccggg    2280
ggtttgaggt gcagcttacg gcactgttgc aaatagtctg ataaggcctg cagggatccg    2340
tcgacaaatt tcattatct taacataata aaaataatac agctgcaatt gattgttttt     2400 tagttttttat tgagattgag ggaatttctt taatattaag tttcatttgg atagaatgcc   2460
accctatttt attagaaaag gaacaaaatg aaaaagtac tcatcattaa cggggccaaa     2520
gcgttcggga gctctggagg gaaactcaat gaaaccttga ctgaccatgc aaaaaagact    2580
ctagagtctt tggggctaga agtggatact acgatcgtgg ataaaggcta tgaacatgct    2640
caagaagtgg agaaagtctt tagcgctgat gcgacgattt ggcaaatgcc tggctggtgg    2700
atgggagagc cttggattgt gaaaaaatac attgatgaag tctttagcgt agggcatgga    2760
aagctttatg ctagcgatgg cagaagctcg caaaacccca ctaaaaacta cgggaaaggg    2820
ggcttgatgc aaggcaaaaa atacatgttg agcttgactt ggaacgctcc cattgaagcc    2880
tttaatgatc ctagtgaatt ttttgaaggg gtgggtgtgg atgttgtgta tttgcatttg    2940
cataaagcgt tccaattttt agggctttca gcgttgccca cttttatttg caacgatgtg    3000
gtgaaaaacc cccaagtgga gcagtatctt aactctctca ccacgcattt gcgccaagct    3060
tttggcaagt gattttaaaa ttttttttaac cccccatttt cttgggggg gcttgtttat    3120 tccacaataa agtctctggg attgagatcg cagcctaaga taagatccct aagattactg    3180
cccaccgttt gataactcgc attgctcaca agtagaaatc cgtatttttc aaaaggcaca    3240
acaagagtgc cgtctctatc ccttaattgc gcttttgctt tatcccaaca aatatatctt    3300
ggctcttcat ctgtgtagct ttcaaaggct tctctggcgt tttctagcaa gtagtctatg    3360
acagcgctag ccaattcctt agcgtttctt gctattttcc tttgatgatt ggggagctta    3420
```

```
acgctttgaa gattatggga agttaagtca tcatcaaggg ttttactaat ctctctggtg   3480
cggtattctt taggcaaatc tttaaacaat cccacttgac agaattgatc cgctaaatat   3540
tcgctcctat tcttcacttc ctctatcccc caagaatggg tgttattgat gaaatagtcg   3600
tttaaatgca aggagctgta ttcttccata agctcgcggc cgccaccgcg gtggagctcc   3660
agcttttgtt cccttttagtg agggttaatt tcgagcttgg cgtaatcatg gtcatagctg   3720
tttcctgtgt gaaattgtta tccgctcaca attccacaca acatacgagc cggaagcata   3780
aagtgtaaag cctggggtgc ctaatgagtg agctaactca cattaattgc gttgcgctca   3840
ctgcccgctt tccagtcggg aaacctgtcg tgccagctgc attaatgaat cggccaacgc   3900
gcggggagag gcggtttgcg tattgggcgc tcttccgctt cctcgctcac tgactcgctg   3960
cgctcggtcg ttcggctgcg gcgagcggta tcagctcact caaaggcggt aatacggtta   4020
tccacagaat caggggataa cgcaggaaag aacatgtgag caaaaggcca gcaaaaggcc   4080
aggaaccgta aaaaggccgc gttgctggcg ttttccata ggctccgccc ccctgacgag   4140
catcacaaaa atcgacgctc aagtcagagg tggcgaaacc cgacaggact ataaagatac   4200
caggcgtttc cccctggaag ctccctcgtg cgctctcctg ttccgaccct gccgcttacc   4260
ggatacctgt ccgcctttct cccttcggga agcgtggcgc tttctcatag ctcacgctgt   4320
aggtatctca gttcggtgta ggtcgttcgc tccaagctgg gctgtgtgca cgaaccccc   4380 gttcagcccg accgctgcgc cttatccggt aactatcgtc ttgagtccaa cccggtaaga   4440
cacgacttat cgccactggc agcagccact ggtaacagga ttagcagagc gaggtatgta   4500
ggcggtgcta cagagttctt gaagtggtgg cctaactacg gctacactag aaggacagta   4560
tttggtatct gcgctctgct gaagccagtt accttcggaa aaagagttgg tagctcttga   4620
tccggcaaac aaaccaccgc tggtagcggt ggtttttttg tttgcaagca gcagattacg   4680
cgcagaaaaa aaggatctca agaagatcct ttgatctttt ctacggggtc tgacgctcag   4740
tggaacgaaa actcacgtta agggattttg gtcatgagat tatcaaaaag gatcttcacc   4800
tagatccttt taaattaaaa atgaagtttt aaatcaatct aaagtatata tgagtaaact   4860
tggtctgaca gttaccaatg cttaatcagt gaggcaccta tctcagcgat ctgtctattt   4920
cgttcatcca tagttgcctg actccccgtc gtgtagataa ctacgatacg ggagggctta   4980
ccatctggcc ccagtgctgc aatgataccg cgagacccac gctcaccggc tccagattta   5040
tcagcaataa accagccagc cggaagggcc gagcgcagaa gtggtcctgc aactttatcc   5100
gcctccatcc agtctattaa ttgttgccgg gaagctagag taagtagttc gccagttaat   5160
agtttgcgca acgttgttgc cattgctaca ggcatcgtgg tgtcacgctc gtcgtttggt   5220
atggcttcat tcagctccgg ttcccaacga tcaaggcgag ttacatgatc ccccatgttg   5280
tgcaaaaaag cggttagctc cttcggtcct ccgatcgttg tcagaagtaa gttggccgca   5340
gtgttatcac tcatggttat ggcagcactg cataattctc ttactgtcat gccatccgta   5400
agatgctttt ctgtgactgg tgagtactca accaagtcat tctgagaata gtgtatgcgg   5460
cgaccgagtt gctcttgccc ggcgtcaata cgggataata ccgcgccaca tagcagaact   5520
ttaaaagtgc tcatcattgg aaaacgttct tcggggcgaa aactctcaag gatcttaccg   5580
ctgttgagat ccagttcgat gtaacccact cgtgcaccca actgatcttc agcatctttt   5640
actttcacca gcgtttctgg gtgagcaaaa acaggaaggc aaaatgccgc aaaaaaggga   5700
ataagggcga cacggaaatg ttgaatactc atactcttcc ttttttcaata ttattgaagc   5760
```

```
atttatcagg gttattgtct catgagcgga tacatatttg aatgtattta gaaaaataaa    5820
caaatagggg ttccgcgcac atttccccga aaagtgc                             5857

<210> SEQ ID NO 8
<211> LENGTH: 5971
<212> TYPE: DNA
<213> ORGANISM: Helicobacter pylori

<400> SEQUENCE: 8
cacctgacgc gccctgtagc ggcgcattaa gcgcggcggg tgtggtggtt acgcgcagcg     60
tgaccgctac acttgccagc gccctagcgc ccgctccttt cgctttcttc ccttcctttc    120
tcgccacgtt cgccggcttt ccccgtcaag ctctaaatcg ggggctccct ttagggttcc    180
gatttagtgc tttacggcac ctcgacccca aaaaacttga ttagggtgat ggttcacgta    240
gtgggccatc gccctgatag acggtttttc gcccttt gac gttggagtcc acgttcttta    300
atagtggact cttgttccaa actgaacaa cactcaaccc tatctcggtc tattcttttg    360
atttataagg gattttgccg atttcggcct attggttaaa aaatgagctg atttaacaaa    420
aatttaacgc gaattttaac aaaatattaa cgcttacaat ttccattcgc cattcaggct    480
gcgcaactgt tgggaagggc gatcggtgcg ggcctcttcg ctattacgcc agctggcgaa    540 aggggatgt gctgcaaggc gattaagttg ggtaacgcca gggttttccc agtcacgacg    600
ttgtaaaacg acgccagtg aattgtaata cgactcacta tagggcgaat tgggtaccgg    660
gccccccctc gatcgacggt atcgatgcgt tttcatcgcc aaaatgctcc acaaattcgc    720
ccgcatcaaa atgccctctc ctttcgcaca atcatggat cctgttccca taagcccaag    780
aggggcggtt atacgcatcc aatttaggga gagccccaaa catcaagtaa taaagcacat    840
tacccacgat attttttttca ctaggcgggc aaccaggaac attgatcacg ggtttatcaa    900
tgattttatg caagggttgc gcgttagagg ggttagggta agccgcttga acgccccaa    960 aacttgagca tgtgcctatg gcaaaaatag cggctgcgta ttgagcggct ttcctacact   1020
cttcagctcc cgtttcagcg tttgggcctt gagtgaggaa gtattccgtg ccttggggga   1080
tacccccttc taccattaaa atgtaattgt ttttatgctt ttctatggcg tcatgcaagc   1140
ttttttcagc ttgaaaaccg ctcgctacca tgatggtctc atggtattct aggttgatgt   1200
aatcaaagat aatgctatca atggtggggt ctgcgctcct taacaaactt tcgctacaac   1260
cggtgcattc tgccatgtgc aaccaaatca cgggcaatct gttagccact tccaccgcct   1320
tcaaagtcaa gggagcaaaa ctagccggca aggctaacgc tgtgctcatc atgcccgccc   1380
acttcaataa atcgcgccta gaaatgcccg cccctttaaa ctcgtcttgc aagtttttat   1440
gctcgttgtg agcgttaaac gaacggacta tatcaaggcg ttcttcaatc ttttgatagg   1500 tcttttttttc atcgtagaac atgaccactc cttaattaga gatcttctag agaattcgta   1560
ccctcgagtc tagagcatgc gtcgacaatg aacgcttctg ttaatcttag taaatcaaaa   1620
cattgctata attacatcca accttgattt cgttatgtct tcaaggaaaa acactttaag   1680
aataggagaa taaggtcgac aatgaacgct tctgttaatc ttagtaaatc aaaacattgc   1740
tacaattaca tccaaccttg atttcgttat gtcttcaagg aaaaacactt taagaatagg   1800
agaataagat gtctagatta gataaaagta aagtgattaa cagcgcatta gagctgctta   1860
atgaggtcgg aatcgaaggt ttaacaaccc gtaaactcgc ccagaagctt ggtgtagagc   1920
agcctacatt gtattggcat gtaaaaaata agcgggccct actggatgcg ctggcggtgg   1980
agatcttggc gcgtcatcat gattattcac tgcctgcggc ggggaatcc tggcagtcat   2040
```

```
ttctgcgcaa taatgcaatg agtttccgcc gcgcgctgct gcgttaccgt gacggggcaa    2100
aagtgcacct cggcacgcgt cctgatgaaa aacagtatga tacggtggaa acccagttac    2160
gctttatgac agaaaacggc ttttcactgc gcgacgggct atatgcgatt tcagcggtca    2220
gtcattttac cttaggtgcc gtactggagc agcaggagca tactgccgcc ctgaccgacc    2280
gccctgcagc accggacgaa aacctgccgc cgctattgcg ggaagcgctg cagattatgg    2340
acagtgatga tggtgagcag gcctttctgc atggcctgga gagcctgatc cgggggtttg    2400
aggtgcagct tacggcactg ttgcaaatag tctgataagg cctgcaggga tccgtcgaca    2460 aatttttcatt atcttaacat aataaaaata atacagctgc aattgattgt tttttagttt    2520
ttattgagat tgagggaatt tctttaatat taagtttcat ttggatagaa tgccaccta    2580 ttttattaga aaaggaacaa aatgaaaaaa gtactcatca ttaacggggc caaagcgttc    2640
gggagctctg gagggaaact caatgaaacc ttgactgacc atgcaaaaaa gactctagag    2700
tctttggggc tagaagtgga tactacgatc gtggataaag gctatgaaca tgctcaagaa    2760
gtggagaaag tctttagcgc tgatgcgacg atttggcaaa tgcctggctg gtggatggga    2820
gagccttgga ttgtgaaaaa atacattgat gaagtcttta gcgtaggggca tggaaagctt    2880 tatgctagcg atggcagaag ctcgcaaaac cccactaaaa actacgggaa aggggcttg    2940 atgcaaggca aaaatacat gttgagcttg acttggaacg ctcccattga agcctttaat    3000
gatcctagtg aattttttga aggggtgggt gtggatgttg tgtatttgca tttgcataaa    3060
gcgttccaat ttttagggct ttcagcgttg cccactttta tttgcaacga tgtggtgaaa    3120
aacccccaag tggagcagta tcttaactct ctcaccacgc atttgcgcca agcttttggc    3180
aagtgatttt aaaatttttt taacccccc atttctttgg ggggcttgt ttattccaca    3240 ataaagtctc tgggattgag atcgcagcct aagataagat ccctaagatt actgcccacc    3300
gtttgataac tcgcattgct cacaaagtag aatccgtatt tttcaaaagg cacaacaaga    3360
gtgccgtctc tatcccttaa ttgcgctttt gctttatccc aacaaatata tcttggctct    3420
tcatctgtgt agcttcaaa ggcttctctg gcgttttcta gcaagtagtc tatgacagcg    3480
ctagccaatt ccttagcgtt tcttgctatt ttcctttgat gattggggag cttaacgctt    3540
tgaagattat gggaagttaa gtcatcatca agggttttac taatctctct ggtgcggtat    3600
tctttaggca aatcttttaaa caatcccact tgacagaatt gatccgctaa atattcgctc    3660
ctattcttca cttcctctat cccccaagaa tgggtgttat tgatgaaata gtcgtttaaa    3720
tgcaaggagc tgtattcttc cataagctcg cggccgccac cgcggtggag ctccagcttt    3780
tgttcccttt agtgagggtt aatttcgagc ttggcgtaat catggtcata gctgtttcct    3840
gtgtgaaatt gttatccgct cacaattcca cacaacatac gagccggaag cataaagtgt    3900
aaagcctggg gtgcctaatg agtgagctaa ctcacattaa ttgcgttgcg ctcactgccc    3960
gctttccagt cgggaaacct gtcgtgccag ctgcattaat gaatcggcca acgcgcgggg    4020
agaggcggtt tgcgtattgg gcgctcttcc gcttcctcgc tcactgactc gctgcgctcg    4080
gtcgttcggc tgcggcgagc ggtatcagct cactcaaagg cggtaatacg ttatccaca    4140 gaatcagggg ataacgcagg aaagaacatg tgagcaaaag gccagcaaaa ggccaggaac    4200
cgtaaaaagg ccgcgttgct ggcgtttttc cataggctcc gcccccctga cgagcatcac    4260
aaaaatcgac gctcaagtca gaggtggcga aacccgacag gactataaag ataccaggcg    4320
tttccccctg gaagctccct cgtgcgctct cctgttccga ccctgccgct taccggatac    4380
```

```
ctgtccgcct ttctcccttc gggaagcgtg gcgctttctc atagctcacg ctgtaggtat    4440
ctcagttcgg tgtaggtcgt tcgctccaag ctgggctgtg tgcacgaacc ccccgttcag    4500
cccgaccgct gcgccttatc cgtaactat cgtcttgagt ccaacccggt aagacacgac     4560
ttatcgccac tggcagcagc cactggtaac aggattagca gagcgaggta tgtaggcggt    4620
gctacagagt tcttgaagtg gtggcctaac tacggctaca ctagaaggac agtatttggt    4680
atctgcgctc tgctgaagcc agttaccttc ggaaaaagag ttggtagctc ttgatccggc    4740
aaacaaacca ccgctggtag cggtggtttt tttgtttgca agcagcagat tacgcgcaga    4800
aaaaaaggat ctcaagaaga tcctttgatc ttttctacgg ggtctgacgc tcagtggaac    4860
gaaaactcac gttaagggat tttggtcatg agattatcaa aaaggatctt cacctagatc    4920
cttttaaatt aaaaatgaag ttttaaatca atctaaagta tatatgagta aacttggtct    4980
gacagttacc aatgcttaat cagtgaggca cctatctcag cgatctgtct atttcgttca    5040
tccatagttg cctgactccc cgtcgtgtag ataactacga tacggagggc ttaccatct    5100 ggccccagtg ctgcaatgat accgcgagac ccacgctcac cggctccaga tttatcagca    5160
ataaaccagc cagccggaag ggccgagcgc agaagtggtc ctgcaactt atccgcctcc     5220 atccagtcta ttaattgttg ccgggaagct agagtaagta gttcgccagt taatagtttg    5280
cgcaacgttg ttgccattgc tacaggcatc gtggtgtcac gctcgtcgtt tggtatggct    5340
tcattcagct ccggttccca acgatcaagg cgagttacat gatcccccat gttgtgcaaa    5400
aaagcggtta gctccttcgg tcctccgatc gttgtcagaa gtaagttggc cgcagtgtta    5460
tcactcatgg ttatggcagc actgcataat tctcttactg tcatgccatc cgtaagatgc    5520
ttttctgtga ctggtgagta ctcaaccaag tcattctgag aatagtgtat gcggcgaccg    5580
agttgctctt gccggcgtc aatacggat aataccgcgc cacatagcag aactttaaaa     5640
gtgctcatca ttggaaaacg ttcttcgggg cgaaaactct caaggatctt accgctgttg    5700
agatccagtt cgatgtaacc cactcgtgca cccaactgat cttcagcatc ttttactttc    5760
accagcgttt ctgggtgagc aaaaacagga aggcaaaatg ccgcaaaaaa gggaataagg    5820
gcgacacgga aatgttgaat actcatactc ttccttttc aatattattg aagcatttat     5880
cagggttatt gtctcatgag cggatacata tttgaatgta tttagaaaaa taaacaaata    5940
ggggttccgc gcacatttcc ccgaaaagtg c                                   5971
```

<210> SEQ ID NO 9
<211> LENGTH: 5857
<212> TYPE: DNA
<213> ORGANISM: Helicobacter pylori

<400> SEQUENCE: 9

```
cacctgacgc gccctgtagc ggcgcattaa gcgcggcggg tgtggtggtt acgcgcagcg     60
tgaccgctac acttgccagc gccctagcgc ccgctccttt cgctttcttc ccttcctttc    120
tcgccacgtt cgccggcttt ccccgtcaag ctctaaatcg gggctccct ttagggttcc    180 gatttagtgc tttacggcac ctcgaccca aaaaacttga ttagggtgat ggttcacgta      240
gtgggccatc gccctgatag acggttttc gccctttgac gttggagtcc acgttcttta    300
atagtggact cttgttccaa actggaacaa cactcaaccc tatctcggtc tattcttttg    360
atttataagg gattttgccg atttcggcct attggttaaa aaatgagctg atttaacaaa    420
aatttaacgc gaattttaac aaaatattaa cgcttacaat ttccattcgc cattcaggct    480
gcgcaactgt tgggaagggc gatcggtgcg ggcctcttcg ctattacgcc agctggcgaa    540
```

```
aggggatgt gctgcaaggc gattaagttg ggtaacgcca gggttttccc agtcacgacg      600
ttgtaaaacg acggccagtg aattgtaata cgactcacta tagggcgaat tgggtaccgg      660
gccccccctc gatcgacggt atcgatgcgt tttcatcgcc aaaatgctcc acaaattcgc      720
ccgcatcaaa atgccctctc ctttcgcaca aatcatggat cctgttccca taagcccaag      780
aggggcggtt atacgcatcc aatttaggga gagccccaaa catcaagtaa taaagcacat      840
tacccacgat attttttca ctaggcgggc aaccaggaac attgatcacg ggtttatcaa      900
tgattttatg caagggttgc gcgttagagg ggttagggta agccgcttga acgcccccaa      960
aacttgagca tgtgcctatg gcaaaaatag cggctgcgta ttgagcggct ttcctacact     1020
cttcagctcc cgtttcagcg tttgggcctt gagtgaggaa gtattccgtg ccttggggga     1080
tacccccttc taccattaaa atgtaattgt ttttatgctt ttctatggcg tcatgcaagc     1140
ttttttcagc ttgaaaaccg ctcgctacca tgatggtctc atggtattct aggttgatgt     1200
aatcaaagat aatgctatca atggtggggt ctgcgctcct taacaaactt tcgctacaac     1260
cggtgcattc tgccatgtgc aaccaaatca cgggcaatct gttagccact tccaccgcct     1320
tcaaagtcaa gggagcaaaa ctagccggca aggctaacgc tgtgctcatc atgcccgccc     1380
acttcaataa atcgcgccta gaaatgcccg ccccttttaaa ctcgtcttgc aagtttttat     1440
gctcgttgtg agcgttaaac gaacggacta tatcaaggcg ttcttcaatc ttttgatagg     1500 tcttttttttc atcgtagaac atgaccactc cttaattaga gatcttctag agaattcgta     1560
ccctcgagtc tagagcatgc gtcgacaatg aacgcttctg ttaatcttag taaatcaaaa     1620
cattgctaca attcatccca accttgattt cgttatgtct tcaaggaaaa acactttaag     1680
aataggagaa taagatgtct agattagata aaagtaaagt gattaacagc gcattagcgc     1740
tggggaatga ggtcggaatc gaaggtgtaa caacccgtaa actcgcccag aagcttggtg     1800
tagagcagcc tacattgtat tggcatgtaa aaaataagcg ggccctactg gatgcgctgg     1860
cggtggagat cttggcgcgt catcatgatt attcactgcc tgcggcgggg aatcctggc     1920 agtcatttct gcgcaataat gcaatgagtt tccgccgcgc gctgctgcgt taccgtgacg     1980
gggcaaaagt gcacctcggc acgcgtcctg atgaaaaaca gtatgatacg gtggaaaccc     2040
agttacgctt tatgacagaa aacggctttt cactgcgcga cgggctatat gcgatttcag     2100
cggtcagtca ttttaccttta ggtgccgtac tggagcagca ggagcatact gccgccctga     2160
ccgaccgccc tgcagcaccg gacgaaaacc tgccgccgct attgcgggaa gcgctgcaga     2220
ttatggacag tgatgatggt gagcaggcct ttctgcatgg cctggagagc ctgatccggg     2280
ggtttgaggt gcagcttacg gcactgttgc aaatagtctg ataaggcctg cagggatccg     2340
tcgacaaatt ttcattatct aacataata aaaataatac agctgcaatt gattgttttt     2400 tagttttttat tgagattgag ggaatttctt taatattaag tttcatttgg atagaatgcc     2460
accctatttt attagaaaag gaacaaaatg aaaaagtac tcatcattaa cggggccaaa     2520
gcgttcggga gctctggagg gaaactcaat gaaaccttga ctgaccatgc aaaaaagact     2580
ctagagtctt tggggctaga agtggatact acgatcgtgg ataaaggcta tgaacatgct     2640
caagaagtgg agaaagtctt tagcgctgat gcgacgattt ggcaaatgcc tggctggtgg     2700
atgggagagc cttggattgt gaaaaaatac attgatgaag tctttagcgt agggcatgga     2760 aagcttatg ctagcgatgg cagaagctcg caaaaccccca ctaaaaacta cgggaaaggg     2820
ggcttgatgc aaggcaaaaa atacatgttg agcttgactt ggaacgctcc cattgaagcc     2880
```

```
tttaatgatc ctagtgaatt tttttgaaggg gtgggtgtgg atgttgtgta tttgcatttg    2940
cataaagcgt tccaattttt agggctttca gcgttgccca cttttatttg caacgatgtg    3000
gtgaaaaacc cccaagtgga gcagtatctt aactctctca ccacgcattt gcgccaagct    3060
tttggcaagt gattttaaaa ttttttaac cccccattt ctttgggggg cttgtttat       3120 tccacaataa agtctctggg attgagatcg cagcctaaga taagatccct aagattactg    3180
cccaccgttt gataactcgc attgctcaca agtagaatc cgtattttc aaaaggcaca      3240 acaagagtgc cgtctctatc ccttaattgc gcttttgctt tatcccaaca aatatatctt    3300
ggctcttcat ctgtgtagct ttcaaaggct tctctggcgt tttctagcaa gtagtctatg    3360
acagcgctag ccaattcctt agcgtttctt gctattttcc tttgatgatt ggggagctta    3420
acgctttgaa gattatggga agttaagtca tcatcaaggg ttttactaat ctctctggtg    3480
cggtattctt taggcaaatc tttaaacaat cccacttgac agaattgatc cgctaaatat    3540
tcgctcctat tcttcacttc ctctatcccc caagaatggg tgttattgat gaaatagtcg    3600
tttaaatgca aggagctgta ttcttccata agctcgcggc cgccaccgcg gtggagctcc    3660 agctttgtt ccctttagtg agggttaatt tcgagcttgg cgtaatcatg gtcatagctg     3720
tttcctgtgt gaaattgtta ccgctcaca attccacaca acatacgagc cggaagcata     3780
aagtgtaaag cctggggtgc ctaatgagtg agctaactca cattaattgc gttgcgctca    3840
ctgcccgctt tccagtcggg aaacctgtcg tgccagctgc attaatgaat cggccaacgc    3900
gcggggagag cggtttgcg tattgggcgc tcttccgctt cctcgctcac tgactcgctg     3960
cgctcggtcg ttcggctgcg gcgagcggta tcagctcact caaaggcggt aatacggtta    4020
tccacagaat caggggataa cgcaggaaag aacatgtgag caaaaggcca gcaaaaggcc    4080
aggaaccgta aaaaggccgc gttgctggcg ttttccata ggctccgccc ccctgacgag     4140
catcacaaaa atcgacgctc aagtcagagg tggcgaaacc cgacaggact ataaagatac    4200
caggcgtttc cccctggaag ctccctcgtg cgctctcctg ttccgaccct gccgcttacc    4260
ggatacctgt ccgcctttct cccttcggga agcgtggcgc tttctcatag ctcacgctgt    4320
aggtatctca gttcggtgta ggtcgttcgc tccaagctgg gctgtgtgca cgaaccccc    4380 gttcagcccg accgctgcgc cttatccggt aactatcgtc ttgagtccaa cccggtaaga    4440
cacgacttat cgccactggc agcagccact ggtaacagga ttagcagagc gaggtatgta    4500
ggcggtgcta cagagttctt gaagtggtgg cctaactacg gctacactag aaggacagta    4560
tttggtatct gcgctctgct gaagccagtt accttcggaa aaagagttgg tagctcttga    4620
tccggcaaac aaaccaccgc tggtagcggt ggtttttttg tttgcaagca gcagattacg    4680
cgcagaaaaa aaggatctca agaagatcct ttgatctttt ctacggggtc tgacgctcag    4740
tggaacgaaa actcacgtta agggatttg gtcatgagat tatcaaaaag gatcttcacc     4800
tagatccttt taaattaaaa atgaagtttt aaatcaatct aaagtatata tgagtaaact    4860
tggtctgaca gttaccaatg cttaatcagt gaggcaccta tctcagcgat ctgtctattt    4920
cgttcatcca tagttgcctg actccccgtc gtgtagataa ctacgatacg ggagggctta    4980
ccatctggcc ccagtgctgc aatgataccg cgagacccac gctcaccggc tccagattta    5040
tcagcaataa accagccagc cggaagggcc gagcgcagaa gtggtcctgc aactttatcc    5100
gcctccatcc agtctattaa ttgttgccgg gaagctagag taagtagttc gccagttaat    5160
agtttgcgca acgttgttgc cattgctaca ggcatcgtgg tgtcacgctc gtcgtttggt    5220
atggcttcat tcagctccgg ttcccaacga tcaaggcgag ttacatgatc ccccatgttg    5280
```

```
tgcaaaaaag cggttagctc cttcggtcct ccgatcgttg tcagaagtaa gttggccgca    5340
gtgttatcac tcatggttat ggcagcactg cataattctc ttactgtcat gccatccgta    5400
agatgctttt ctgtgactgg tgagtactca accaagtcat tctgagaata gtgtatgcgg    5460
cgaccgagtt gctcttgccc ggcgtcaata cgggataata ccgcgccaca tagcagaact    5520
ttaaaagtgc tcatcattgg aaaacgttct tcggggcgaa aactctcaag gatcttaccg    5580
ctgttgagat ccagttcgat gtaacccact cgtgcaccca actgatcttc agcatctttt    5640
actttcacca gcgtttctgg gtgagcaaaa acaggaaggc aaaatgccgc aaaaaaggga    5700
ataagggcga cacggaaatg ttgaatactc atactcttcc tttttcaata ttattgaagc    5760
atttatcagg gttattgtct catgagcgga tacatatttg aatgtattta gaaaaataaa    5820
caaatagggg ttccgcgcac atttccccga aaagtgc                             5857

<210> SEQ ID NO 10
<211> LENGTH: 4412
<212> TYPE: DNA
<213> ORGANISM: Helicobacter pylori

<400> SEQUENCE: 10
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg ggggctccct ttagggttcc     180
gatttagtgc tttacggcac ctcgacccca aaaaacttga ttagggtgat ggttcacgta     240
gtgggccatc gccctgatag acggtttttc gccctttgac gttggagtcc acgttcttta     300
atagtggact cttgttccaa actgaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat tccattcgc cattcaggct     480 gcgcaactgt tgggaagggc gatcggtgcg ggcctcttcg ctattacgcc agctggcgaa     540
agggggatgt gctgcaaggc gattaagttg ggtaacgcca gggttttccc agtcacgacg     600
ttgtaaaacg acggccagtg aattgtaata cgactcacta tagggcgaat tgggtaccgg     660
gccccccctc gatcgacggt atcgataagc ttcatgcgtt agatgttgca gacaaatacg     720
atgtgcaagt cgctatccac acagacactt tgaatgaagc cggttgcgtg aagacacta     780 tggcagctat tgccggacgc actatgcaca cttttccacac tgaaggtgct ggcggcggac     840
acgctcctga tattattaaa gtagctggtg aacacaacat tcttcccgct tccactaacc     900
ccactatccc tttcactgtg aatacagaag cagaacacat ggacatgctt atggtgtgcc     960
accacttgga taaaagcatt aaagaagatg ttcagttcgc tgattcaagg atccagaatt    1020
cctcgagtct agagattagt taatgaacgc ttctgttaat cttagtaaat caaaacattg    1080
ctataattac atccctatca gtgatagaga tgtcttcaag gaaaaacact ttaagaatag    1140
gagaataaca tatgagtaaa ggagaagaac ttttcactgg agttgtccca attcttgttg    1200
aattagatgg tgatgttaat gggcacaaat tttctgtcag tggagagggt gaaggtgatg    1260
caacatacgg aaaacttacc cttaaattta tttgcactac tggaaaacta cctgttccat    1320
ggccaacact tgtcactact ttcgcgtatg gtcttcaatg ctttgcgaga tacccagatc    1380
atatgaaaca gcatgacttt ttcaagagtg ccatgcccga aggttatgta caggaaagaa    1440
ctatattttt caaagatgac gggaactaca agacacgtgc tgaagtcaag tttgaaggtg    1500
```

```
ataccettgt taatagaatc gagttaaaag gtattgattt taaagaagat ggaaacattc    1560
ttggacacaa attggaatac aactataact cacacaatgt atacatcatg gcagacaaac    1620
aaaagaatgg aatcaaagtt aacttcaaaa ttagacacaa cattgaagat ggaagcgttc    1680
aactagcaga ccattatcaa caaaatactc caattggcga tggccctgtc cttttaccag    1740
acaaccatta cctgtccaca caatctgccc tttcgaaaga tcccaacgaa aagagagacc    1800
acatggtcct tcttgagttt gtaacagctg ctgggattac acatggcatg gatgaactat    1860
acaaataagc ggccgcgtcg acatcgatcc cgggatccct gcttggttgc tctttatcca    1920
acactgggtg tgagatgatc atagagcgtt tagttggcaa tctaagggat ttaaaccccct    1980 tggatttcag cgtggatcat gtggatttgg aatggtttga aacgaggaaa aaaatcgctc    2040
gttttaaaac caggcaaggc aaagacatag ccatacgcct taaagacgct cccaagttgg    2100
ggctctctca agggatatt ttatttaaag aagagaagga aattatcgcc gttaatatct    2160
tggattctga agtcattcac atcctctaga gcggccgcca ccgcggtgga gctccagctt    2220
ttgttccctt tagtgagggt taatttcgag cttggcgtaa tcatggtcat agctgtttcc    2280
tgtgtgaaat tgttatccgc tcacaattcc acacaacata cgagccggaa gcataaagtg    2340
taaagcctgg ggtgcctaat gagtgagcta actcacatta attgcgttgc gctcactgcc    2400 cgcttttccag tcgggaaacc tgtcgtgcca gctgcattaa tgaatcggcc aacgcgcggg    2460
gagaggcggt ttgcgtattg ggcgctcttc cgcttcctcg ctcactgact cgctgcgctc    2520
ggtcgttcgg ctgcggcgag cggtatcagc tcactcaaag gcggtaatac ggttatccac    2580 agaatcagg gataacgcag gaaagaacat gtgagcaaaa ggccagcaaa aggccaggaa    2640
ccgtaaaaag gccgcgttgc tggcgttttt ccataggctc cgccccctg acgagcatca    2700 caaaaatcga cgctcaagtc agaggtggcg aaacccgaca ggactataaa gataccaggc    2760
gtttccccct ggaagctccc tcgtgcgctc tcctgttccg accctgccgc ttaccggata    2820
cctgtccgcc tttctccctt cgggaagcgt ggcgctttct catagctcac gctgtaggta    2880
tctcagttcg gtgtaggtcg ttcgctccaa gctgggctgt gtgcacgaac cccccgttca    2940
gcccgaccgc tgcgccttat ccggtaacta tcgtcttgag tccaacccgg taagacacga    3000
cttatcgcca ctggcagcag ccactggtaa caggattagc agagcgaggt atgtaggcgg    3060
tgctacagag ttcttgaagt ggtggcctaa ctacggctac actagaagga cagtatttgg    3120
tatctgcgct ctgctgaagc cagttacctt cggaaaaaga gttggtagct cttgatccgg    3180
caaacaaacc accgctggta gcggtggttt ttttgtttgc aagcagcaga ttacgcgcag    3240
aaaaaaagga tctcaagaag atcctttgat cttttctacg gggtctgacg ctcagtggaa    3300
cgaaaactca cgttaaggga ttttggtcat gagattatca aaaaggatct tcacctagat    3360
ccttttaaat taaaaatgaa gttttaaatc aatctaaagt atatatgagt aaacttggtc    3420
tgacagttac caatgcttaa tcagtgaggc acctatctca gcgatctgtc tatttcgttc    3480
atccatagtt gcctgactcc ccgtcgtgta gataactacg atacgggagg gcttaccatc    3540
tggccccagt gctgcaatga taccgcgaga cccacgctca ccggctccag atttatcagc    3600
aataaaccag ccagccggaa gggccgagcg cagaagtggt cctgcaactt tatccgcctc    3660
catccagtct attaattgtt gccgggaagc tagagtaagt agttcgccag ttaatagttt    3720
gcgcaacgtt gttgccattg ctacaggcat cgtggtgtca cgctcgtcgt ttggtatggc    3780
ttcattcagc tccggttccc aacgatcaag gcgagttaca tgatccccca tgttgtgcaa    3840
aaaagcggtt agctccttcg gtcctccgat cgttgtcaga agtaagttgg ccgcagtgtt    3900
```

| | |
|---|---|
| atcactcatg gttatggcag cactgcataa ttctcttact gtcatgccat ccgtaagatg | 3960 |
| cttttctgtg actggtgagt actcaaccaa gtcattctga gaatagtgta tgcggcgacc | 4020 |
| gagttgctct tgcccggcgt caatacggga taataccgcg ccacatagca gaactttaaa | 4080 |
| agtgctcatc attggaaaac gttcttcggg gcgaaaactc tcaaggatct taccgctgtt | 4140 |
| gagatccagt tcgatgtaac ccactcgtgc acccaactga tcttcagcat cttttacttt | 4200 |
| caccagcgtt tctgggtgag caaaaacagg aaggcaaaat gccgcaaaaa agggaataag | 4260 |
| ggcgacacgg aaatgttgaa tactcatact cttccttttt caatattatt gaagcattta | 4320 |
| tcagggttat tgtctcatga gcggatacat atttgaatgt atttagaaaa ataaacaaat | 4380 |
| aggggttccg cgcacatttc cccgaaaagt gc | 4412 |

<210> SEQ ID NO 11
<211> LENGTH: 4412
<212> TYPE: DNA
<213> ORGANISM: Helicobacter pylori

<400> SEQUENCE: 11

| | |
|---|---|
| cacctgacgc gccctgtagc ggcgcattaa gcgcggcggg tgtggtggtt acgcgcagcg | 60 |
| tgaccgctac acttgccagc gccctagcgc ccgctccttt cgctttcttc ccttcctttc | 120 |
| tcgccacgtt cgccggcttt ccccgtcaag ctctaaatcg ggggctccct ttagggttcc | 180 |
| gatttagtgc tttacggcac ctcgacccca aaaaacttga ttagggtgat ggttcacgta | 240 |
| gtgggccatc gccctgatag acggtttttc gccctttgac gttggagtcc acgttcttta | 300 |
| atagtggact cttgttccaa actggaacaa cactcaaccc tatctcggtc tattcttttg | 360 |
| atttataagg gattttgccg atttcggcct attggttaaa aaatgagctg atttaacaaa | 420 |
| aatttaacgc gaattttaac aaaatattaa cgcttacaat ttccattcgc cattcaggct | 480 |
| gcgcaactgt tgggaagggc gatcggtgcg ggcctcttcg ctattacgcc agctggcgaa | 540 |
| agggggatgt gctgcaaggc gattaagttg ggtaacgcca gggttttccc agtcacgacg | 600 |
| ttgtaaaacg acggccagtg aattgtaata cgactcacta tagggcgaat tgggtaccgg | 660 |
| gccccccctc gatcgacggt atcgataagc ttcatgcgtt agatgttgca gacaaatacg | 720 |
| atgtgcaagt cgctatccac acagacactt tgaatgaagc cggttgcgtg aagacacta | 780 |
| tggcagctat tgccggacgc actatgcaca ctttccacac tgaaggtgct ggcggcggac | 840 |
| acgctcctga tattattaaa gtagctggtg aacacaacat tcttcccgct tccactaacc | 900 |
| ccactatccc tttcactgtg aatacagaag cagaacacat ggacatgctt atggtgtgcc | 960 |
| accacttgga taaaagcatt aagaagatg ttcagttcgc tgattcaagg atccagaatt | 1020 |
| cctcgagtct agagattagt taatgaacgc ttctgttaat ccctatcagt gatagagatg | 1080 |
| ctataattac atccctatca gtgatagaga tgtcttcaag gaaaaacact ttaagaatag | 1140 |
| gagaataaca tatgagtaaa ggagaagaac ttttcactgg agttgtccca attcttgttg | 1200 |
| aattagatgg tgatgttaat gggcacaaat tttctgtcag tggagagggt gaaggtgatg | 1260 |
| caacatacgg aaaacttacc cttaaattta tttgcactac tggaaaacta cctgttccat | 1320 |
| ggccaacact tgtcactact ttcgcgtatg gtcttcaatg ctttgcgaga tacccagatc | 1380 |
| atatgaaaca gcatgacttt ttcaagagtg ccatgcccga aggttatgta caggaaagaa | 1440 |
| ctatattttt caaagatgac gggaactaca agacacgtgc tgaagtcaag tttgaaggtg | 1500 |
| ataccctttgt taatagaatc gagttaaaag gtattgattt taaagaagat ggaaacattc | 1560 |

```
ttggacacaa attggaatac aactataact cacacaatgt atacatcatg gcagacaaac    1620
aaaagaatgg aatcaaagtt aacttcaaaa ttagacacaa cattgaagat ggaagcgttc    1680
aactagcaga ccattatcaa caaaatactc caattggcga tggccctgtc cttttaccag    1740
acaaccatta cctgtccaca caatctgccc tttcgaaaga tcccaacgaa aagagagacc    1800
acatggtcct tcttgagttt gtaacagctg ctgggattac acatggcatg gatgaactat    1860
acaaataagc ggccgcgtcg acatcgatcc cgggatccct gcttggttgc tctttatcca    1920
acactgggtg tgagatgatc atagagcgtt tagttggcaa tctaagggat ttaaacccct    1980
tggatttcag cgtggatcat gtggatttgg aatggtttga aacgaggaaa aaaatcgctc    2040
gttttaaaac caggcaaggc aaagacatag ccatacgcct taaagacgct cccaagttgg    2100
ggctctctca aggggatatt ttatttaaag aagagaagga aattatcgcc gttaatatct    2160
tggattctga agtcattcac atcctctaga gcggccgcca ccgcggtgga gctccagctt    2220
ttgttccctt tagtgagggt taatttcgag cttggcgtaa tcatggtcat agctgtttcc    2280
tgtgtgaaat tgttatccgc tcacaattcc acacaacata cgagccggaa gcataaagtg    2340
taaagcctgg ggtgcctaat gagtgagcta actcacatta attgcgttgc gctcactgcc    2400
cgcttttcca gtcgggaaacc tgtcgtgcca gctgcattaa tgaatcggcc aacgcgcggg    2460
gagaggcggt ttgcgtattg ggcgctcttc cgcttcctcg ctcactgact cgctgcgctc    2520
ggtcgttcgg ctgcggcgag cggtatcagc tcactcaaag gcggtaatac ggttatccac    2580
agaatcaggg gataacgcag gaaagaacat gtgagcaaaa ggccagcaaa aggccaggaa    2640
ccgtaaaaag gccgcgttgc tggcgttttt ccataggctc cgcccccctg acgagcatca    2700
caaaaatcga cgctcaagtc agaggtggcg aaacccgaca ggactataaa gataccaggc    2760
gtttccccct ggaagctccc tcgtgcgctc tcctgttccg accctgccgc ttaccggata    2820
cctgtccgcc tttctccctt cgggaagcgt ggcgctttct catagctcac gctgtaggta    2880
tctcagttcg gtgtaggtcg ttcgctccaa gctgggctgt gtgcacgaac cccccgttca    2940
gcccgaccgc tgcgccttat ccggtaacta tcgtcttgag tccaacccgg taagacacga    3000
cttatcgcca ctggcagcag ccactggtaa caggattagc agagcgaggt atgtaggcgg    3060
tgctacagag ttcttgaagt ggtggcctaa ctacggctac actagaagga cagtatttgg    3120
tatctgcgct ctgctgaagc cagttacctt cggaaaaaga gttggtagct cttgatccgg    3180
caaacaaacc accgctggta gcggtggttt ttttgtttgc aagcagcaga ttacgcgcag    3240
aaaaaaagga tctcaagaag atcctttgat cttttctacg gggtctgacg ctcagtggaa    3300
cgaaaactca cgttaaggga ttttggtcat gagattatca aaaaggatct tcacctagat    3360
ccttttaaat taaaaatgaa gttttaaatc aatctaaagt atatatgagt aaacttggtc    3420
tgacagttac caatgcttaa tcagtgaggc acctatctca gcgatctgtc tatttcgttc    3480
atccatagtt gcctgactcc ccgtcgtgta gataactacg atacgggagg cttaccatc    3540 tggccccagt gctgcaatga taccgcgaga cccacgctca ccggctccag atttatcagc    3600
aataaaccag ccagccggaa gggccgagcg cagaagtggt cctgcaactt tatccgcctc    3660
catccagtct attaattgtt gccgggaagc tagagtaagt agttcgccag ttaatagttt    3720
gcgcaacgtt gttgccattg ctacaggcat cgtggtgtca cgctcgtcgt ttggtatggc    3780
ttcattcagc tccggttccc aacgatcaag gcgagttaca tgatccccca tgttgtgcaa    3840
aaaagcggtt agctccttcg gtcctccgat cgttgtcaga agtaagttgg ccgcagtgtt    3900
atcactcatg gttatggcag cactgcataa ttctcttact gtcatgccat ccgtaagatg    3960
```

-continued

| | |
|---|---|
| cttttctgtg actggtgagt actcaaccaa gtcattctga gaatagtgta tgcggcgacc | 4020 |
| gagttgctct tgcccggcgt caatacggga taataccgcg ccacatagca gaactttaaa | 4080 |
| agtgctcatc attggaaaac gttcttcggg gcgaaaactc tcaaggatct taccgctgtt | 4140 |
| gagatccagt tcgatgtaac ccactcgtgc acccaactga tcttcagcat cttttacttt | 4200 |
| caccagcgtt tctgggtgag caaaaacagg aaggcaaaat gccgcaaaaa agggaataag | 4260 |
| ggcgacacgg aaatgttgaa tactcatact cttccttttt caatattatt gaagcattta | 4320 |
| tcagggttat tgtctcatga gcggatacat atttgaatgt atttagaaaa ataaacaaat | 4380 |
| aggggttccg cgcacatttc cccgaaaagt gc | 4412 |

<210> SEQ ID NO 12
<211> LENGTH: 4412
<212> TYPE: DNA
<213> ORGANISM: Helicobacter pylori

<400> SEQUENCE: 12

| | |
|---|---|
| cacctgacgc gccctgtagc ggcgcattaa gcgcggcggg tgtggtggtt acgcgcagcg | 60 |
| tgaccgctac acttgccagc gccctagcgc ccgctccttt cgctttcttc ccttcctttc | 120 |
| tcgccacgtt cgccggcttt ccccgtcaag ctctaaatcg ggggctccct ttagggttcc | 180 |
| gatttagtgc tttacggcac ctcgacccca aaaaacttga ttagggtgat ggttcacgta | 240 |
| gtgggccatc gccctgatag acggtttttc gccctttgac gttggagtcc acgttcttta | 300 |
| atagtggact cttgttccaa actgaacaa cactcaaccc tatctcggtc tattcttttg | 360 |
| atttataagg gattttgccg atttcggcct attggttaaa aaatgagctg atttaacaaa | 420 |
| aatttaacgc gaattttaac aaaatattaa cgcttacaat ttccattcgc cattcaggct | 480 |
| gcgcaactgt tgggaagggc gatcggtgcg ggcctcttcg ctattacgcc agctggcgaa | 540 |
| agggggatgt gctgcaaggc gattaagttg ggtaacgcca gggttttccc agtcacgacg | 600 |
| ttgtaaaacg acggccagtg aattgtaata cgactcacta tagggcgaat tgggtaccgg | 660 |
| gccccccctc gatcgacggt atcgataagc ttcatgcgtt agatgttgca gacaaatacg | 720 |
| atgtgcaagt cgctatccac acagacactt tgaatgaagc cggttgcgtg gaagacacta | 780 |
| tggcagctat tgccggacgc actatgcaca cttccacac tgaaggtgct ggcggcggac | 840 |
| acgctcctga tattattaaa gtagctggtg aacacacaat tcttcccgct tccactaacc | 900 |
| ccactatccc tttcactgtg aatacagaag cagaacacat ggacatgctt atggtgtgcc | 960 |
| accacttgga taaaagcatt aaagaagatg ttcagttcgc tgattcaagg atccagaatt | 1020 |
| cctcgagtct agagtcccta tcagtgatag agatgttaat ccctatcagt gatagagatg | 1080 |
| ctataattac atccctatca gtgatagaga tgtcttcaag gaaaaacact ttaagaatag | 1140 |
| gagaataaca tatgagtaaa ggagaagaac ttttcactgg agttgtccca attcttgttg | 1200 |
| aattagatgg tgatgttaat gggcacaaat tttctgtcag tggagagggt gaaggtgatg | 1260 |
| caacatacgg aaaacttacc cttaaattta tttgcactac tggaaaacta cctgttccat | 1320 |
| ggccaacact tgtcactact ttcgcgtatg gtcttcaatg ctttgcgaga tacccagatc | 1380 |
| atatgaaaca gcatgacttt ttcaagagtg ccatgcccga aggttatgta caggaaagaa | 1440 |
| ctatattttt caaagatgac gggaactaca agacacgtgc tgaagtcaag tttgaaggtg | 1500 |
| atacccttgt taatagaatc gagttaaaag gtattgattt taaagaagat ggaaacattc | 1560 |
| ttggacacaa attggaatac aactataact cacacaatgt atacatcatg gcagacaaac | 1620 |

-continued

```
aaaagaatgg aatcaaagtt aacttcaaaa ttagacacaa cattgaagat ggaagcgttc    1680
aactagcaga ccattatcaa caaaatactc caattggcga tggccctgtc cttttaccag    1740
acaaccatta cctgtccaca caatctgccc tttcgaaaga tcccaacgaa aagagagacc    1800
acatggtcct tcttgagttt gtaacagctg ctgggattac acatggcatg gatgaactat    1860
acaaataagc ggccgcgtcg acatcgatcc cgggatccct gcttggttgc tctttatcca    1920
acactgggtg tgagatgatc atagagcgtt tagttggcaa tctaagggat ttaaacccct    1980
tggatttcag cgtggatcat gtggatttgg aatggtttga acgaggaaa aaaatcgctc    2040 gttttaaaac caggcaaggc aaagacatag ccatacgcct taaagacgct cccaagttgg    2100
ggctctctca agggatatt ttatttaaag aagagaagga aattatcgcc gttaatatct    2160
tggattctga agtcattcac atcctctaga gcggccgcca ccgcggtgga gctccagctt    2220
ttgttccctt tagtgagggt taatttcgag cttggcgtaa tcatggtcat agctgtttcc    2280
tgtgtgaaat tgttatccgc tcacaattcc acacaacata cgagccggaa gcataaagtg    2340
taaagcctgg ggtgcctaat gagtgagcta actcacatta attgcgttgc gctcactgcc    2400
cgctttccag tcgggaaacc tgtcgtgcca gctgcattaa tgaatcggcc aacgcgcggg    2460
gagaggcggt ttgcgtattg ggcgctcttc cgcttcctcg ctcactgact cgctgcgctc    2520
ggtcgttcgg ctgcggcgag cggtatcagc tcactcaaag gcggtaatac ggttatccac    2580
agaatcaggg gataacgcag gaaagaacat gtgagcaaaa ggccagcaaa aggccaggaa    2640
ccgtaaaaag gccgcgttgc tggcgttttt ccataggctc cgcccccctg acgagcatca    2700
caaaaatcga cgctcaagtc agaggtggcg aaacccgaca ggactataaa gataccaggc    2760
gtttccccct ggaagctccc tcgtgcgctc tcctgttccg accctgccgc ttaccggata    2820
cctgtccgcc tttctccctt cgggaagcgt ggcgctttct catagctcac gctgtaggta    2880
tctcagttcg gtgtaggtcg ttcgctccaa gctgggctgt gtgcacgaac cccccgttca    2940
gcccgaccgc tgcgccttat ccggtaacta tcgtcttgag tccaacccgg taagacacga    3000
cttatcgcca ctggcagcag ccactggtaa caggattagc agagcgaggt atgtaggcgg    3060
tgctacagag ttcttgaagt ggtggcctaa ctacggctac actagaagga cagtatttgg    3120
tatctgcgct ctgctgaagc cagttacctt cggaaaaaga gttggtagct cttgatccgg    3180
caaacaaacc accgctggta gcggtggttt ttttgtttgc aagcagcaga ttacgcgcag    3240
aaaaaaagga tctcaagaag atcctttgat cttttctacg gggtctgacg ctcagtggaa    3300
cgaaaactca cgttaaggga ttttggtcat gagattatca aaaaggatct tcacctagat    3360
ccttttaaat taaaaatgaa gttttaaatc aatctaaagt atatatgagt aaacttggtc    3420
tgacagttac caatgcttaa tcagtgaggc acctatctca gcgatctgtc tatttcgttc    3480
atccatagtt gcctgactcc ccgtcgtgta gataactacg atacgggagg gcttaccatc    3540
tggccccagt gctgcaatga taccgcgaga cccacgctca ccggctccag atttatcagc    3600
aataaaccag ccagccggaa gggccgagcg cagaagtggt cctgcaactt tatccgcctc    3660
catccagtct attaattgtt gccgggaagc tagagtaagt agttcgccag ttaatagttt    3720
gcgcaacgtt gttgccattg ctacaggcat cgtggtgtca cgctcgtcgt ttggtatggc    3780
ttcattcagc tccggttccc aacgatcaag gcgagttaca tgatccccca tgttgtgcaa    3840
aaaagcggtt agctccttcg gtcctccgat cgttgtcaga agtaagttgg ccgcagtgtt    3900
atcactcatg gttatggcag cactgcataa ttctcttact gtcatgccat ccgtaagatg    3960
cttttctgtg actggtgagt actcaaccaa gtcattctga gaatagtgta tgcggcgacc    4020
```

```
gagttgctct tgcccggcgt caatacggga taataccgcg ccacatagca gaactttaaa    4080
agtgctcatc attggaaaac gttcttcggg gcgaaaactc tcaaggatct taccgctgtt    4140
gagatccagt tcgatgtaac ccactcgtgc acccaactga tcttcagcat cttttacttt    4200
caccagcgtt tctgggtgag caaaaacagg aaggcaaaat gccgcaaaaa agggaataag    4260
ggcgacacgg aaatgttgaa tactcatact cttcctttt caatattatt gaagcattta    4320
tcagggttat tgtctcatga gcggatacat atttgaatgt atttagaaaa ataaacaaat    4380
aggggttccg cgcacatttc cccgaaaagt gc                                 4412
```

<210> SEQ ID NO 13
<211> LENGTH: 4798
<212> TYPE: DNA
<213> ORGANISM: Helicobacter pylori

<400> SEQUENCE: 13

```
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg ggggctccct ttagggttcc     180
gatttagtgc tttacggcac ctcgacccca aaaaacttga ttagggtgat ggttcacgta     240
gtgggccatc gccctgatag acggtttttc gcccttttgac gttggagtcc acgttcttta    300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat ttccattcgc cattcaggct     480
gcgcaactgt tgggaagggc gatcggtgcg ggcctcttcg ctattacgcc agctggcgaa     540
agggggatgt gctgcaaggc gattaagttg gtaacgcca gggttttccc agtcacgacg     600
ttgtaaaacg acggccagtg aattgtaata cgactcacta tagggcgaat tgggtaccgg     660
gccccccctc gatcgacggt atcgatttgc ctgattatgt gatcgcatgc gttggagggg     720
ggtctaacgc tatagggata ttcagcgcat ttttaaacga caaagaagtt aaactcatag     780
gcgtagagcc ggcgggttta gggctagaaa ccaataagca tggggcgact ttgaataagg     840
ggcgtgtggg gattttgcat gggaataaaa cctatctttt acaagatgat gaaggccaga     900
ttgcagaaag ccatagcatt agcgccgggc ttgattatcc aggagtgggg ccagaacaca     960
gctatttaaa agaaagtggg cgtgcggttt atgaaagcgc aagcgatgct gaagcgctag    1020
aagccttcaa gttgttgtgc caaaagaag gcattatccc agcgctagaa agctcacacg    1080
ccttagcgta tgccttaaag ctcgctcaaa aatgcgaaga agaaagcatc atcgtagtga    1140
atttaagcgg cagaggggat aaggatttaa gcaccgttta taacgcttta aaaggaggtt    1200
taaaatgagg tatcaaaaca tgtttgaaac cttaaaaaa cacgaaaaaa tggcgtttat    1260
cccgtttgta accttgggcg atcctaatta tgaattgagt tttgaaatca ttaaaaccct    1320
aattattagc ggggtgagcg ctttagaatt gggtcttgct ttttctgatc ctgtggcgga    1380
tggcattacc atacaagcga gccatttaag ggcgttaaaa cacgctagca tggctaaaaa    1440
tttccagctt ttaaaaaaga ttagagatta caaccacaat attcccatag gcttttagc     1500 gtatgcgaat ttaatttttt cttatggcgt tgatggcttt tacgctcaag ctaaagaatg    1560
cggtatagat agcgttttaa tagcggacat gagatcttct agagaattcc tgcagggatc    1620
cgtcgacatc cgctcaaaaa caccaaatca agcaaatctt tatcgccagc cccaatgcga    1680
```

```
gcagtaaaga tttagaacaa gtcgctacgc attcgcaagg ctatatctac gctttagcca    1740
ggagtggggt tacaggggcg agccgtattt tagagaatga ttcgagtgct attattaaaa    1800
ccttaaaagc ttttagccct accccagcct tactgggctt tggcatttcc aaaaaagaac    1860
acatcacaaa cgctaaaggc atgggtgctg atggcgtgat ttgcggatca gcgttagtca    1920
aaatcataga agaaaattta aacaatgaaa acgccatgct ggaaaaaatt aaagggttta    1980
taggaggaat gatttttttaa ggcttttagg ctttgttgcg ttaaaaatta aagatcacag    2040
attaacaatc atcatcaggt tttattgcat gcgcgttatt attgggtgta tttttataaa    2100
tctgtgaaag gcactgttct tgttgtattg ggctttccga ttctaggcat accattcacc    2160
aaatgtgtag catagtcagg cgttagcgta gaaaataccg ccataagcct aacaacaata    2220
taaaggcagc cttttagtgt ggttgatagt ggcttaaaat tgcgagtatt ttgataataa    2280
aaaagctaat tttcatatac caagccataa gctctttata cacttttaa aaagagctat    2340
tggttgttta gtccttttcg tcttcgggtt ctatgtctat tgtgttattg tcatggttga    2400
ttgctttcaa agtatttacg attttatcca tcttttcttt tgcttcaagc gccttttat    2460
atccttcagc cgcttgttta tatccttctt tttcttcttg agctataccc cataatgctt    2520
taaagattgg ttgcatttca gcttttttgc ttgcttctaa aagacctccg tgttcctttt    2580
tcatttccgc ggtggagctc cagcttttgt tccctttagt gagggttaat ttcgagcttg    2640
gcgtaatcat ggtcatagct gtttcctgtg tgaaattgtt atccgctcac aattccacac    2700
aacatacgag ccggaagcat aaagtgtaaa gcctggggtg cctaatgagt gagctaactc    2760
acattaattg cgttgcgctc actgcccgct ttccagtcgg gaaacctgtc gtgccagctg    2820
cattaatgaa tcggccaacg cgcggggaga ggcggtttgc gtattgggcg ctcttccgct    2880
tcctcgctca ctgactcgct gcgctcggtc gttcggctgc ggcgagcggt atcagctcac    2940
tcaaaggcgg taatacggtt atccacagaa tcaggggata acgcaggaaa gaacatgtga    3000
gcaaaaggcc agcaaaaggc caggaaccgt aaaaaggccg cgttgctggc gtttttccat    3060
aggctccgcc cccctgacga gcatcacaaa aatcgacgct caagtcagag gtggcgaaac    3120
ccgacaggac tataaagata ccaggcgttt ccccctggaa gctccctcgt gcgctctcct    3180
gttccgaccc tgccgcttac cggatacctg tccgcctttc tcccttcggg aagcgtggcg    3240
ctttctcata gctcacgctg taggtatctc agttcggtgt aggtcgttcg ctccaagctg    3300
ggctgtgtgc acgaaccccc cgttcagccc gaccgctgcg ccttatccgg taactatcgt    3360
cttgagtcca acccggtaag acacgactta tcgccactgg cagcagccac tggtaacagg    3420
attagcagag cgaggtatgt aggcggtgct acagagttct tgaagtggtg gcctaactac    3480
ggctacacta aaggacagt atttggtatc tgcgctctgc tgaagccagt taccttcgga    3540
aaaagagttg gtagctcttg atccggcaaa caaaccaccg ctggtagcgg tggttttttt    3600
gtttgcaagc agcagattac gcgcagaaaa aaaggatctc aagaagatcc tttgatcttt    3660
tctacggggt ctgacgctca gtggaacgaa aactcacgtt aagggatttt ggtcatgaga    3720
ttatcaaaaa ggatcttcac ctagatcctt ttaaattaaa aatgaagttt taaatcaatc    3780
taaagtatat atgagtaaac ttggtctgac agttaccaat gcttaatcag tgaggcacct    3840
atctcagcga tctgtctatt tcgttcatcc atagttgcct gactccccgt cgtgtagata    3900
actacgatac gggagggctt accatctggc cccagtgctg caatgatacc gcgagaccca    3960
cgctcaccgg ctccagattt atcagcaata aaccagccag ccggaagggc cgagcgcaga    4020
agtggtcctg caactttatc cgcctccatc cagtctatta attgttgccg ggaagctaga    4080
```

-continued

```
gtaagtagtt cgccagttaa tagtttgcgc aacgttgttg ccattgctac aggcatcgtg   4140
gtgtcacgct cgtcgtttgg tatggcttca ttcagctccg gttcccaacg atcaaggcga   4200
gttacatgat cccccatgtt gtgcaaaaaa gcggttagct ccttcggtcc tccgatcgtt   4260
gtcagaagta agttggccgc agtgttatca ctcatggtta tggcagcact gcataattct   4320
cttactgtca tgccatccgt aagatgcttt tctgtgactg gtgagtactc aaccaagtca   4380
ttctgagaat agtgtatgcg gcgaccgagt tgctcttgcc cggcgtcaat acgggataat   4440
accgcgccac atagcagaac tttaaaagtg ctcatcattg gaaaacgttc ttcggggcga   4500
aaactctcaa ggatcttacc gctgttgaga tccagttcga tgtaacccac tcgtgcaccc   4560
aactgatctt cagcatcttt tactttcacc agcgtttctg ggtgagcaaa acaggaagg   4620 caaaatgccg caaaaaggg aataagggcg cacggaaat gttgaatact catactcttc    4680 cttttcaat attattgaag catttatcag ggttattgtc tcatgagcgg atacatattt    4740
gaatgtattt agaaaaataa acaaataggg gttccgcgca catttccccg aaaagtgc    4798
```

<210> SEQ ID NO 14
<211> LENGTH: 6232
<212> TYPE: DNA
<213> ORGANISM: Helicobacter pylori

<400> SEQUENCE: 14

```
cacctgacgc gccctgtagc ggcgcattaa gcgcggcggg tgtggtggtt acgcgcagcg     60
tgaccgctac acttgccagc gccctagcgc ccgctccttt cgctttcttc ccttcctttc    120
tcgccacgtt cgccggcttt ccccgtcaag ctctaaatcg ggggctccct ttagggttcc    180
gatttagtgc tttacggcac ctcgacccca aaaaacttga ttagggtgat ggttcacgta    240
gtgggccatc gccctgatag acggtttttc gccctttgac gttggagtcc acgttcttta    300
atagtggact cttgttccaa actgaacaa cactcaaccc tatctcggtc tattcttttg     360
atttataagg gattttgccg atttcggcct attggttaaa aaatgagctg atttaacaaa    420
aatttaacgc gaattttaac aaaatattaa cgcttacaat ttccattcgc cattcaggct    480
gcgcaactgt tgggaagggc gatcggtgcg ggcctcttcg ctattacgcc agctggcgaa    540 aggggatgt gctgcaaggc gattaagttg ggtaacgcca gggttttccc agtcacgacg      600
ttgtaaaacg acggccagtg aattgtaata cgactcacta tagggcgaat tgggtaccgg     660
gccccccctc gatcgacggt atcgatttgc ctgattatgt gatcgcatgc gttggagggg    720
ggtctaacgc tatagggata ttcagcgcat ttttaaacga caagaagtt aaactcatag     780 gcgtagagcc ggcgggttta gggctagaaa ccaataagca tggggcgact ttgaataagg    840
ggcgtgtggg gattttgcat gggaataaaa cctatctttt acaagatgat gaaggccaga    900
ttgcagaaag ccatagcatt agcgccgggc ttgattatcc aggagtgggg ccagaacaca    960
gctatttaaa agaaagtggg cgtgcggttt atgaaagcgc aagcgatgct gaagcgctag   1020
aagccttcaa gttgttgtgc aaaaagaag gcattatccc agcgctagaa agctcacacg    1080
ccttagcgta tgccttaaag ctcgctcaaa aatgcgaaga agaaagcatc atcgtagtga    1140
atttaagcgg cagaggggat aaggatttaa gcaccgttta taacgcttta aaaggaggtt    1200
taaaatgagg tatcaaaaca tgtttgaaac cttaaaaaaa cacgaaaaaa tggcgtttat    1260
cccgtttgta accttgggcg atcctaatta tgaattgagt tttgaaatca ttaaaaccct    1320
aattattagc ggggtgagcg ctttagaatt gggtcttgct ttttctgatc ctgtggcgga    1380
```

```
tggcattacc atacaagcga gccatttaag ggcgttaaaa cacgctagca tggctaaaaa   1440
tttccagctt ttaaaaaaga ttagagatta caaccacaat attcccatag ggcttttagc   1500
gtatgcgaat ttaattttt cttatggcgt tgatggcttt tacgctcaag ctaaagaatg    1560
cggtatagat agcgttttaa tagcggacat gagatcttct agagaattcc tgcagggatc   1620
cgatgcttta taactatgga ttaaacactt ttttagtaat ttcttaaaat caattttgga   1680 attttcatt ttgtctaaaa tgagtaagat tattttata agtaaaacaa taattaaaaa    1740
ttagtttatg ttttataaat attaatgtaa attatgtagg gtttatttta taaaaatttt   1800
taaaagcatt taaattattt ctagtttata ttttgtaag taaattttag atatcatcca    1860
aagtttatta cattttaaa gaaaggaatt attgtgccta ccataaatca attggttaga    1920
aaagagcgca aaaagtttt agaaaaatct aaatctccag cgcttaaaaa ttgtccacaa    1980 agaagggag tttgcactag ggtttatact acaacaccta aaaaccaaa ctcagcgtta     2040 agaaagttg ccaaagtaag acttactagt ggctttgaag tgatcagcta tatcggcgt    2100 gaaggtcata acttgcaaga acacagcatt gttttagtgc gtggtggtag ggtaaaagac   2160
ttaccagggg ttaaatatca catcgttcgt ggtgctcttg atacagcagg tgttgcaaaa   2220
agaacagttt ctcgttctaa atatggtgct aaacgtccta agcaggcgc tgcaaaataa    2280 tcattcatac agacaaatcc gttagatgat atagattgaa aagtggatag atttatgata   2340
tagtggatag atttatgata taatgagtta tcaacaaatc ggaatttacg gaggataaat   2400
gatgcaattc acaagattg atataaataa ttggacacga aaagagtatt tcgaccacta    2460
ttttggcaat acgccctgca catatagtat gacggtaaaa ctcgatattt ctaagttgaa   2520
aaaggatgga aaaagttat acccaactct tttatatgga gttacaacga tcatcaatcg    2580
acatgaagag ttcaggaccg cattagatga aaacggacag gtaggcgttt tttcagaaat   2640
gctgccttgc tacacagttt ttcataagga aactgaaacc ttttcgagta tttggactga   2700
gtttacagca gactatactg agtttcttca gaactatcaa aaggatatag acgcttttgg   2760
tgaacgaatg ggaatgtccg caaagcctaa tcctccggaa aacactttcc ctgtttctat    2820
gataccgtgg acaagctttg aaggctttaa cttaaatcta aaaaaggat atgactatct    2880 actgccgata tttacgtttg ggaagtatta tgaggagggc ggaaaatact atattccctt    2940
atcgattcaa gtgcatcatg ccgtttgtga cggctttcat gtttgccgtt ttttggatga   3000
attacaagac ttgctgaata aataaaatcc cagtttgtcg cactgataag gatccgtcga   3060
catccgctca aaaacaccaa atcaagcaaa tctttatcgc cagccccaat gcgagcagta   3120
aagatttaga acaagtcgct acgcattcgc aaggctatat ctacgcttta gccaggagtg   3180
gggttacagg ggcgagccgt attttagaga atgattcgag tgctattatt aaaaccttaa   3240
aagcttttag ccctacccca gccttactgg gctttggcat ttccaaaaaa gaacacatca   3300
caaacgctaa aggcatgggt gctgatggcg tgatttgcgg atcagcgtta gtcaaaatca   3360
tagaagaaaa tttaaacaat gaaaacgcca tgctggaaaa aattaaaggg tttataggag   3420
gaatgatttt ttaaggcttt taggctttgt tgcgttaaaa attaaagatc acagattaac   3480
aatcatcatc aggttttatt gcatgcgcgt tattattggg tgtattttta taaatctgtg   3540
aaaggcactg ttcttgttgt attgggcttt ccgattctag gcataccatt caccaaatgt   3600
gtagcatagt caggcgttag cgtagaaaat accgccataa gcctaacaac aatataaagg   3660 cagccttta gtgtggttga tagtggctta aaattgcgag tattttgata ataaaaaagc    3720
taattttcat ataccaagcc ataagctctt tataacactt ttaaaaagag ctattggttg   3780
```

```
tttagtcctt ttcgtcttcg ggttctatgt ctattgtgtt attgtcatgg ttgattgctt    3840
tcaaagtatt tacgattttta tccatctttt cttttgcttc aagcgccttt ttatatcctt    3900
cagccgcttg tttatatcct tctttttctt cttgagctat accccataat gctttaaaga    3960
ttggttgcat ttcagctttt ttgcttgctt ctaaaagacc tccgtgttcc tttttcattt    4020
ccgcggtgga gctccagctt ttgttcccctt tagtgagggt taatttcgag cttggcgtaa    4080
tcatggtcat agctgtttcc tgtgtgaaat tgttatccgc tcacaattcc acacaacata    4140
cgagccggaa gcataaagtg taaagcctgg ggtgcctaat gagtgagcta actcacatta    4200
attgcgttgc gctcactgcc cgcttttccag tcgggaaacc tgtcgtgcca gctgcattaa    4260
tgaatcggcc aacgcgcggg gagaggcggt ttgcgtattg ggcgctcttc cgcttcctcg    4320
ctcactgact cgctgcgctc ggtcgttcgg ctgcggcgag cggtatcagc tcactcaaag    4380
gcggtaatac ggttatccac agaatcaggg gataacgcag gaaagaacat gtgagcaaaa    4440
ggccagcaaa aggccaggaa ccgtaaaaag gccgcgttgc tggcgttttt ccataggctc    4500 cgccccctg acgagcatca caaaaatcga cgctcaagtc agaggtggcg aaacccgaca    4560
ggactataaa gataccaggc gtttccccct ggaagctccc tcgtgcgctc tcctgttccg    4620
accctgccgc ttaccggata cctgtccgcc tttctccctt cgggaagcgt ggcgctttct    4680
catagctcac gctgtaggta tctcagttcg gtgtaggtcg ttcgctccaa gctgggctgt    4740
gtgcacgaac cccccgttca gcccgaccgc tgcgccttat ccggtaacta tcgtcttgag    4800
tccaacccgg taagacacga cttatcgcca ctggcagcag ccactggtaa caggattagc    4860
agagcgaggt atgtaggcgg tgctacagag ttcttgaagt ggtggcctaa ctacggctac    4920
actagaagga cagtatttgg tatctgcgct ctgctgaagc cagttacctt cggaaaaaga    4980
gttggtagct cttgatccgg caaacaaacc accgctggta gcggtggttt ttttgtttgc    5040
aagcagcaga ttacgcgcag aaaaaaagga tctcaagaag atcctttgat cttttctacg    5100
gggtctgacg ctcagtggaa cgaaaactca cgttaaggga ttttggtcat gagattatca    5160
aaaaggatct tcacctagat ccttttaaat taaaaatgaa gttttaaatc aatctaaagt    5220
atatatgagt aaacttggtc tgacagttac caatgcttaa tcagtgaggc acctatctca    5280
gcgatctgtc tatttcgttc atccatagtt gcctgactcc ccgtcgtgta gataactacg    5340
atacgggagg gcttaccatc tggccccagt gctgcaatga taccgcgaga cccacgctca    5400
ccggctccag atttatcagc aataaaccag ccagccggaa gggccgagcg cagaagtggt    5460
cctgcaactt tatccgcctc catccagtct attaattgtt gccgggaagc tagagtaagt    5520
agttcgccag ttaatagttt gcgcaacgtt gttgccattg ctacaggcat cgtggtgtca    5580
cgctcgtcgt ttggtatggc ttcattcagc tccggttccc aacgatcaag gcgagttaca    5640
tgatccccca tgttgtgcaa aaaagcggtt agctccttcg gtcctccgat cgttgtcaga    5700
agtaagttgg ccgcagtgtt atcactcatg gttatggcag cactgcataa ttctcttact    5760
gtcatgccat ccgtaagatg cttttctgtg actggtgagt actcaaccaa gtcattctga    5820
gaatagtgta tgcggcgacc gagttgctct tgcccggcgt caatacggga taataccgcg    5880
ccacatagca gaactttaaa agtgctcatc attggaaaac gttcttcggg gcgaaaactc    5940
tcaaggatct taccgctgtt gagatccagt tcgatgtaac ccactcgtgc acccaactga    6000
tcttcagcat cttttacttt caccagcgtt tctgggtgag caaaaacagg aaggcaaaat    6060
gccgcaaaaa agggaataag ggcgacacgg aaatgttgaa tactcatact cttcctttt     6120
```

| | | |
|---|---|---|
| caatattatt gaagcattta tcagggttat tgtctcatga gcggatacat atttgaatgt | 6180 | |
| atttagaaaa ataaacaaat aggggttccg cgcacatttc cccgaaaagt gc | 6232 | |

<210> SEQ ID NO 15
<211> LENGTH: 5003
<212> TYPE: DNA
<213> ORGANISM: Helicobacter pylori

<400> SEQUENCE: 15

| | | |
|---|---|---|
| cacctgacgc gccctgtagc ggcgcattaa gcgcggcggg tgtggtggtt acgcgcagcg | 60 | |
| tgaccgctac acttgccagc gccctagcgc ccgctccttt cgctttcttc ccttcctttc | 120 | |
| tcgccacgtt cgccggcttt ccccgtcaag ctctaaatcg ggggctccct ttagggttcc | 180 | |
| gatttagtgc tttacggcac ctcgacccca aaaacttga ttaggtgat ggttcacgta | 240 | |
| gtgggccatc gccctgatag acggttttc gcccttgac gttggagtcc acgttcttta | 300 | |
| atagtggact cttgttccaa actgaacaa cactcaaccc tatctcggtc tattcttttg | 360 | |
| atttataagg gattttgccg atttcggcct attggttaaa aaatgagctg atttaacaaa | 420 | |
| aatttaacgc gaattttaac aaaatattaa cgcttacaat ttccattcgc cattcaggct | 480 | |
| gcgcaactgt tgggaagggc gatcggtgcg ggcctcttcg ctattacgcc agctggcgaa | 540 | |
| aggggggatgt gctgcaaggc gattaagttg ggtaacgcca gggttttccc agtcacgacg | 600 | |
| ttgtaaaacg acggccagtg aattgtaata cgactcacta tagggcgaat tgggtaccgg | 660 | |
| gccccccctc gatcgacggt atcgatattc caccctagcg tgaatgaaag cgtgatcaag | 720 | |
| tttttaggct ttgagcaagt gttgaaaaat tcgctcacca ctttggctat gggggcgct | 780 | |
| aagggggga gcgatttga ccctaagggg aagagcgagc atgagatcat gcgttttgc | 840 | |
| caagcgttca tgaatgaatt ataccgccat attggagcca cgactgatgt gccagctggg | 900 | |
| gatattggag tgggcgaaag agagattggc tatctgtttg ggcaatacaa aaaattagtc | 960 | |
| aatcgttttg agggcgtatt gaccggtaaa ggactcactt atggagggag cttgtgcaga | 1020 | |
| aaagaagcta ccggttatgg gtgcgtgtat tttgctgaag aaatgttgca agaaaggaac | 1080 | |
| agctctttag agggtaaggt ttgcagcgtt tctgggagcg ggaatgtcgc aatttatacc | 1140 | |
| attgaaaaat tgcttcaaat aggagctaaa ccggtaacgg cgagcgattc taatggcatg | 1200 | |
| atttatgaca aagacggcat tgatttagag cttttgaaag aaattaaaga agtgcgtcgt | 1260 | |
| gggaggatca aagaatacgc tttagaaaaa aagagcgcgg aatacacccc aacagaaaat | 1320 | |
| taccccaaag gggggaatgc ggtgtggcat gtgccttgtt ttgcggcttt tcctagtgcg | 1380 | |
| accgagaatg aattgagcgt tttagacgcc aaaaccctcc tttctaatgg gtgtaaatgc | 1440 | |
| gtggctgaag gggcgaacat gccctcaagc aatgaagcga ttggattgtt tttgcaggct | 1500 | |
| aagatttctt atggtatagg caaggcggct aatgctgggg gggtgagcgt gagcggcttg | 1560 | |
| gaaatggcac aaaacgcaag catgcaccct tggagttttg aagtggtgga tgcgaaattg | 1620 | |
| caccatatta tgaaagagat ttataagaat gtctctcaaa ccgctaaaga gtttaaagac | 1680 | |
| cctactaatt ttgtattagg ggccaatatc gctggtttta gaaaagtagc gtctgcgatg | 1740 | |
| atagcgcaag gggtttgatt acagatcttc tagagaattc ctgcagggat ccgtcgacca | 1800 | |
| attttacaaa cccaattttt taaccaactt tctcaccgcg cgcaacaaag gcaaggattt | 1860 | |
| ttgataagct ttgcgataga ttttaaaagt ggtgttttga gagagttcta ataaaggcga | 1920 | |
| agcgttttgt aaaagccggt cataattaac cctcaaatca tcataattaa ccctcaaatc | 1980 | |
| atcaatggat actaacggct tatgcagatc gtactccac atgaaagatg ttgagaattt | 2040 | |

```
gtgataaatc gtatcgtttt ctaaaatcgt tttaaaaaaa tctaggattt ttttaaaact    2100
caaatcttgg taaaagtaag ctttcccatc aagggtgttt aaagggtttt catagagcat    2160
gtctaaataa gcgtttgggt gcgtgtgcag gtatttgata taatcaatcg cttcatcaaa    2220
gttgttgaaa tcatgcacat tcacaaaact tttagggtta aaatctttcg ccacgctggg    2280
actcccccaa taaataggaa tggtatggct aaaatacgca tcaaggattt tttcggttac    2340
atagccataa ccttgcgagt tttcaaaaca gagattgaac ttgtattggc ttaaaaactc    2400
gcttttgttt ccaaccttat agcctaaagt gtttctcaca cttcctcccc cagtaactgg    2460
ctctatggaa tttagagcgt cataaaaagc gttcctcata ggagcgttag cgttgctcgc    2520
tacaaaactg gcaaaccctc ttttttaaaag atcgctctca tcattcacta ctgcgcacaa    2580
attagggtgg ttttctttaa aatgatgaga gggttttttt aaagcataaa ggctgttgtc    2640
tttgagtttg tagggcgcag tggtgtcatt aacaagctcg gctttatagt gcaaatgggc    2700
ataatacaaa ggcattctca ataacgatc attaaaatcc aattcatcaa agcctatggc    2760
gtaatcaaag aggttgaaat taggtgattc gccgcggtgg agctccagct tttgttccct    2820
ttagtgaggg ttaatttcga gcttggcgta atcatggtca tagctgtttc ctgtgtgaaa    2880
ttgttatccg ctcacaattc cacacaacat acgagccgga agcataaagt gtaaagcctg    2940
gggtgcctaa tgagtgagct aactcacatt aattgcgttg cgctcactgc ccgctttcca    3000
gtcgggaaac ctgtcgtgcc agctgcatta atgaatcggc caacgcgcgg ggagaggcgg    3060
tttgcgtatt gggcgctctt ccgcttcctc gctcactgac tcgctgcgct cggtcgttcg    3120
gctgcggcga gcggtatcag ctcactcaaa ggcggtaata cggttatcca cagaatcagg    3180
ggataacgca ggaaagaaca tgtgagcaaa aggccagcaa aaggccagga accgtaaaaa    3240
ggccgcgttg ctggcgtttt tccataggct ccgcccccct gacgagcatc acaaaaatcg    3300
acgctcaagt cagaggtggc gaaacccgac aggactataa agataccagg cgtttccccc    3360
tggaagctcc ctcgtgcgct ctcctgttcc gaccctgccg cttaccggat acctgtccgc    3420
ctttctccct tcgggaagcg tggcgctttc tcatagctca cgctgtaggt atctcagttc    3480
ggtgtaggtc gttcgctcca agctgggctg tgtgcacgaa ccccccgttc agcccgaccg    3540
ctgcgcctta tccggtaact atcgtcttga gtccaacccg gtaagacacg acttatcgcc    3600
actggcagca gccactggta acaggattag cagagcgagg tatgtaggcg gtgctacaga    3660
gttcttgaag tggtggccta actacggcta cactagaagg acagtatttg gtatctgcgc    3720
tctgctgaag ccagttacct tcggaaaaag agttggtagc tcttgatccg gcaaacaaac    3780
caccgctggt agcggtggtt tttttgtttg caagcagcag attacgcgca gaaaaaaagg    3840
atctcaagaa gatcctttga tcttttctac ggggtctgac gctcagtgga acgaaaactc    3900
acgttaaggg attttggtca tgagattatc aaaaaggatc ttcacctaga tccttttaaa    3960
ttaaaaatga agttttaaat caatctaaag tatatatgag taaacttggt ctgacagtta    4020
ccaatgctta atcagtgagg cacctatctc agcgatctgt ctatttcgtt catccatagt    4080
tgcctgactc cccgtcgtgt agataactac gatacgggag ggcttaccat ctggccccag    4140
tgctgcaatg ataccgcgag acccacgctc accggctcca gatttatcag caataaacca    4200
gccagccgga agggccgagc gcagaagtgg tcctgcaact ttatccgcct ccatccagtc    4260
tattaattgt tgccgggaag ctagagtaag tagttcgcca gttaatagtt tgcgcaacgt    4320
tgttgccatt gctacaggca tcgtggtgtc acgctcgtcg tttggtatgg cttcattcag    4380
```

```
ctccggttcc caacgatcaa ggcgagttac atgatccccc atgttgtgca aaaaagcggt    4440
tagctccttc ggtcctccga tcgttgtcag aagtaagttg gccgcagtgt tatcactcat    4500
ggttatggca gcactgcata attctcttac tgtcatgcca tccgtaagat gcttttctgt    4560
gactggtgag tactcaacca agtcattctg agaatagtgt atgcggcgac cgagttgctc    4620
ttgcccggcg tcaatacggg ataataccgc gccacatagc agaactttaa aagtgctcat    4680
cattggaaaa cgttcttcgg ggcgaaaact ctcaaggatc ttaccgctgt tgagatccag    4740
ttcgatgtaa cccactcgtg cacccaactg atcttcagca tcttttactt tcaccagcgt    4800
ttctgggtga gcaaaaacag gaaggcaaaa tgccgcaaaa aagggaataa gggcgacacg    4860
gaaatgttga atactcatac tcttcctttt tcaatattat tgaagcattt atcagggtta    4920
ttgtctcatg agcggataca tatttgaatg tatttagaaa aataaacaaa tagggggttcc    4980 gcgcacattt ccccgaaaag tgc                                             5003

<210> SEQ ID NO 16
<211> LENGTH: 6437
<212> TYPE: DNA
<213> ORGANISM: Helicobacter pylori

<400> SEQUENCE: 16
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg ggggctccct ttagggttcc     180
gatttagtgc tttacggcac ctcgacccca aaaaacttga ttagggtgat ggttcacgta     240
gtgggccatc gccctgatag acggtttttc gccctttgac gttggagtcc acgttcttta     300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat ttccattcgc cattcaggct     480
gcgcaactgt tgggaagggc gatcggtgcg ggcctcttcg ctattacgcc agctggcgaa     540
agggggatgt gctgcaaggc gattaagttg gtaacgcca gggttttccc agtcacgacg     600
ttgtaaaacg acggccagtg aattgtaata cgactcacta tagggcgaat tgggtaccgg     660
gccccccctc gatcgacggt atcgatattc caccctagcg tgaatgaaag cgtgatcaag     720

tttttaggct ttgagcaagt gttgaaaaat tcgctcacca ctttggctat ggggggcgct     780
aaggggggga gcgattttga ccctaaaggg aagagcgagc atgagatcat gcgtttttgc     840
caagcgttca tgaatgaatt taccgccat attggagcca cgactgatgt gccagctggg     900
gatattggag tgggcgaaag agagattggc tatctgtttg gcaatacaa aaaattagtc     960 aatcgttttg agggcgtatt gaccggtaaa ggactcactt atgagggag cttgtgcaga    1020 aaagaagcta ccggttatgg gtgcgtgtat tttgctgaag aaatgттгса agaaaggaac    1080 agctctttag agggtaaggt ttgcagcgtt tctgggagcg ggaatgtcgc aatttatacc    1140

атгgaaaaат tgcttcaaat aggagctaaa ccggtaacgg cgagcgattc taatggcatg    1200

atttatgaca aagacggcat tgatttagag cтттттgaaag aaattaaaga agtgcgtcgt    1260
gggaggatca aagaatacgc tttagaaaaa aagagcgcgg aatacacccc aacagaaaat    1320

таcсссcаааg gggggaatgc ggtgtggcat gtgccttgtt ттgcggcтттт tcctagtgcg    1380 accgagaatg aattgagcgt tttagacgcc aaaaccctcc tttctaatgg gtgtaaatgc    1440
gtggctgaag gggcgaacat gccctcaagc aatgaagcga ттggатггтг tttgcaggct    1500
```

-continued

```
aagatttctt atggtatagg caaggcggct aatgctgggg gggtgagcgt gagcggcttg    1560
gaaatggcac aaaacgcaag catgcaccct tggagttttg aagtggtgga tgcgaaattg    1620
caccatatta tgaaagagat ttataagaat gtctctcaaa ccgctaaaga gtttaaagac    1680
cctactaatt ttgtattagg ggccaatatc gctggtttta gaaaagtagc gtctgcgatg    1740
atagcgcaag gggtttgatt acagatcttc tagagaattc ctgcagggat ccgatgcttt    1800
ataactatgg attaaacact tttttagtaa tttcttaaaa tcaattttgg aattttcat    1860 tttgtctaaa atgagtaaga ttatttttat aagtaaaaca ataattaaaa attagtttat    1920
gttttataaa tattaatgta aattatgtag ggtttatttt ataaaaattt ttaaaagcat    1980
ttaaattatt tctagtttat attttttgtaa gtaaatttta gatatcatcc aaagtttatt    2040
acatttttaa agaaaggaat tattgtgcct accataaatc aattggttag aaaagagcgc    2100
aaaaaagttt tagaaaaatc taaatctcca gcgcttaaaa attgtccaca agaagggga    2160 gtttgcacta gggtttatac tacaacacct aaaaaaccaa actcagcgtt aagaaaagtt    2220
gccaaagtaa gacttactag tggctttgaa gtgatcagct atatcggcgg tgaaggtcat    2280
aacttgcaag aacacagcat tgttttagtg cgtggtggta gggtaaaaga cttaccaggg    2340
gttaaatatc acatcgttcg tggtgctctt gatacagcag gtgttgcaaa agaacagtt    2400 tctcgttcta aatatggtgc taaacgtcct aaagcaggcg ctgcaaaata atcattcata    2460
cagacaaatc cgttagatga tatagattga aaagtggata gatttatgat atagtggata    2520
gatttatgat ataatgagtt atcaacaaat cggaatttac ggaggataaa tgatgcaatt    2580
cacaaagatt gatataaata attggacacg aaaagagtat ttcgaccact attttggcaa    2640
tacgccctgc acatatagta tgacggtaaa actcgatatt tctaagttga aaaggatgg    2700 aaaaaagtta tacccaactc ttttatatgg agttacaacg atcatcaatc gacatgaaga    2760
gttcaggacc gcattagatg aaaacggaca ggtaggcgtt ttttcagaaa tgctgccttg    2820
ctacacagtt tttcataagg aaactgaaac cttttcgagt atttggactg agtttacagc    2880
agactatact gagtttcttc agaactatca aaaggatata gacgcttttg gtgaacgaat    2940
gggaatgtcc gcaaagccta atcctccgga aaacactttc cctgtttcta tgataccgtg    3000
gacaagcttt gaaggcttta acttaaatct aaaaaaagga tatgactatc tactgccgat    3060
atttacgttt gggaagtatt atgaggaggg cggaaaatac tatattccct tatcgattca    3120
agtgcatcat gccgtttgtg acggctttca tgtttgccgt ttttggatg aattacaaga    3180 cttgctgaat aaataaaatc ccagtttgtc gcactgataa ggatccgtcg accaattta    3240 caaacccaat tttttaacca actttctcac cgcgcgcaac aaaggcaagg attttgata    3300 agctttgcga tagattttaa aagtggtgtt ttgagagagt tctaataaag gcgaagcgtt    3360
ttgtaaaagc cggtcataat taaccctcaa atcatcataa ttaaccctca aatcatcaat    3420
ggatactaac ggcttatgca gatcgtactc ccacatgaaa gatgttgaga atttgtgata    3480
aatcgtatcg ttttctaaaa tcgttttaaa aaaatctagg atttttttaa aactcaaatc    3540
ttggtaaaag taagctttcc catcaagggt gtttaagggg ttttcataga gcatgtctaa    3600
ataagcgttt gggtgcgtgt gcaggtattt gatataatca atcgcttcat caaagttgtt    3660
gaaatcatgc acattcacaa aacttttagg gttaaaatct ttcgccacgc tgggactccc    3720
ccaataaata ggaatggtat ggctaaaata cgcatcaagg attttttcgg ttacatagcc    3780
ataaccttgc gagttttcaa aacagagatt gaacttgtat tggcttaaaa actcgctttt    3840
```

```
gtttccaacc ttatagccta aagtgtttct cacacttcct cccccagtaa ctggctctat  3900
ggaatttaga gcgtcataaa aagcgttcct cataggagcg ttagcgttgc tcgctacaaa  3960
actggcaaac cctcttttta aaagatcgct ctcatcattc actactgcgc acaaattagg  4020
gtggttttct ttaaaatgat gagagggttt ttttaaagca taaaggctgt tgtctttgag  4080
tttgtagggc gcagtggtgt cattaacaag ctcggcttta tagtgcaaat gggcataata  4140
caaaggcatt ctcaaataac gatcattaaa atccaattca tcaaagccta tggcgtaatc  4200
aaagaggttg aaattaggtg attcgccgcg gtggagctcc agcttttgtt ccctttagtg  4260
agggttaatt tcgagcttgg cgtaatcatg gtcatagctg tttcctgtgt gaaattgtta  4320
tccgctcaca attccacaca acatacgagc cggaagcata agtgtaaag cctggggtgc   4380
ctaatgagtg agctaactca cattaattgc gttgcgctca ctgcccgctt ccagtcggg   4440
aaacctgtcg tgccagctgc attaatgaat cggccaacgc gcggggagag gcggtttgcg  4500
tattgggcgc tcttccgctt cctcgctcac tgactcgctg cgctcggtcg ttcggctgcg  4560
gcgagcggta tcagctcact caaaggcggt aatacggtta tccacagaat caggggataa  4620
cgcaggaaag aacatgtgag caaaaggcca gcaaaaggcc aggaaccgta aaaaggccgc  4680
gttgctggcg tttttccata ggctccgccc cctgacgag catcacaaaa atcgacgctc    4740
aagtcagagg tggcgaaacc cgacaggact ataaagatac caggcgtttc ccctggaag    4800
ctccctcgtg cgctctcctg ttccgaccct gccgcttacc ggatacctgt ccgcctttct  4860
cccttcggga agcgtggcgc tttctcatag ctcacgctgt aggtatctca gttcggtgta  4920
ggtcgttcgc tccaagctgg gctgtgtgca cgaaccccc gttcagcccg accgctgcgc   4980
cttatccggt aactatcgtc ttgagtccaa cccggtaaga cacgacttat cgccactggc  5040
agcagccact ggtaacagga ttagcagagc gaggtatgta ggcggtgcta cagagttctt  5100
gaagtggtgg cctaactacg gctacactag aaggacagta tttggtatct gcgctctgct  5160
gaagccagtt accttcggaa aaagagttgg tagctcttga tccggcaaac aaaccaccgc  5220
tggtagcggt ggtttttttg tttgcaagca gcagattacg cgcagaaaaa aaggatctca  5280
agaagatcct ttgatctttt ctacgggtc tgacgctcag tggaacgaaa actcacgtta   5340
agggattttg gtcatgagat tatcaaaaag gatcttcacc tagatccttt taaattaaaa  5400
atgaagtttt aaatcaatct aaagtatata tgagtaaact tggtctgaca gttaccaatg  5460
cttaatcagt gaggcaccta tctcagcgat ctgtctattt cgttcatcca tagttgcctg  5520
actccccgtc gtgtagataa ctacgatacg ggagggctta ccatctggcc ccagtgctgc  5580
aatgataccg cgagacccac gctcaccggc tccagattta tcagcaataa accagccagc  5640
cggaagggcc gagcgcagaa gtggtcctgc aactttatcc gcctccatcc agtctattaa  5700
ttgttgccgg gaagctagag taagtagttc gccagttaat agtttgcgca acgttgttgc  5760
cattgctaca ggcatcgtgg tgtcacgctc gtcgtttggt atggcttcat tcagctccgg  5820
ttcccaacga tcaaggcgag ttacatgatc ccccatgttg tgcaaaaaag cggttagctc  5880
cttcggtcct ccgatcgttg tcagaagtaa gttggccgca gtgttatcac tcatggttat  5940
ggcagcactg cataattctc ttactgtcat gccatccgta agatgctttt ctgtgactgg  6000
tgagtactca accaagtcat tctgagaata gtgtatgcgg cgaccgagtt gctcttgccc  6060
ggcgtcaata cgggataata ccgcgccaca tagcagaact ttaaaagtgc tcatcattgg  6120
aaaacgttct cggggcgaaa actctcaag gatcttaccg ctgttgagat ccagttcgat   6180
gtaacccact cgtgcaccca actgatcttc agcatctttt actttcacca gcgtttctgg  6240
```

| | |
|---|---|
| gtgagcaaaa acaggaaggc aaaatgccgc aaaaaaggga ataagggcga cacggaaatg | 6300 |
| ttgaatactc atactcttcc tttttcaata ttattgaagc atttatcagg gttattgtct | 6360 |
| catgagcgga tacatatttg aatgtattta gaaaaataaa caaataggggg ttccgcgcac | 6420 |
| atttccccga aaagtgc | 6437 |

<210> SEQ ID NO 17
<211> LENGTH: 4676
<212> TYPE: DNA
<213> ORGANISM: Helicobacter pylori

<400> SEQUENCE: 17

| | |
|---|---|
| atgaccatga ttacgccaag cttgatactc atcactcaag tggatggcgt ggtaaaagag | 60 |
| cagatcgcat ggcaactcaa tgagatagaa aagcatttca aagccaattg ttgcgtggat | 120 |
| tttaagatcg ctcaaaacga acaagaagag caggatctgt ggttttcaag gcgtaacgct | 180 |
| tctcaaagta ttagcgttta tggtaaaaag aaattgaatg aagatgtaac cgttcctagg | 240 |
| gcgagtttgc cgagtttgtt gcaagaagtc gccaaaataa gccaaaaata cggctttaaa | 300 |
| atcccttgct ttgggcatac gggcgatggc aatgtgcatg tgaatatcat gctagaagat | 360 |
| cctaaaaggg atttagaaaa agggcatgag gctatggaag attttttca ggccgctatc | 420 |
| agtttggagg ggactttaag cggggagcat ggcataggct tgtctaaagc caaattcatg | 480 |
| cctttagcgt tcaatcatag tgaaatggag cttttaggaa atattaaaaa agctcttgat | 540 |
| cctaataata ttttaaaccc ttttaaaatg gggttgtaag atttaaagca aggaaagcgc | 600 |
| ctcgagtcta gagcggccgc gtcgacatcg atcccgggat cctgaatgtt ttaattcttt | 660 |
| ttgtataaat aattcacgct tttacgatga aatatttccc cttttagcc ttactaaaag | 720 |
| gtttttacta tactataagg gatattgcta acgattaagc tgtattggaa gagtttattt | 780 |
| tgcaagaatt aatcttgcct tgtgtgatta gtaacacaag gcaagtgtga taaaccctac | 840 |
| tacaatttca attcaaggag cctaactaaa ataaaatgaa caatttcagt tagggcttta | 900 |
| ttatagcaaa aattatctaa gattacaaag ggtagcgttt ctgttttttgg atttagagcg | 960 |
| ttattttgat tgttttgagt ttaatttact ttttgtttaa taataaatct taactatcat | 1020 |
| aaatgtacaa ttaaagtatt taaaaaaatt ttaaaacaaa aggatataaa atgaaaacca | 1080 |
| ttagaaatag cgtgtttatt ggagcgtctt tactcggcgg ttgcgctagc gttgaggctt | 1140 |
| attttgacgc tttgcatgtt gctcgcgtta aagacgcttg tttatagaaa aagaagcaca | 1200 |
| ccacacgccc aaagactttg atagccctta ccacactgac taaaccagga attcactggc | 1260 |
| cgtcgtttta caacgtcgtg actgggaaaa ccctggcgtt acccaactta atcgccttgc | 1320 |
| agcacatccc cctttcgcca gctggcgtaa tagcgaagag gcccgcaccg atcgcccttc | 1380 |
| ccaacagttg cgcagcctga atggcgaatg cgctaaccg tttttatcag gctctgggag | 1440 |
| gcagaataaa tgatcatatc gtcaattatt acctccacgg ggagagcctg agcaaactgg | 1500 |
| cctcaggcat ttgagaagca cacggtcaca ctgcttccgg tagtcaataa accggtaaac | 1560 |
| cagcaataga cataagcggc tatttaacga ccctgccctg aaccgacgac cgggtcgaat | 1620 |
| ttgctttcga atttctgcca ttcatccgct tattatcact tattcaggcg tagcaccagg | 1680 |
| cgtttaaggg caccaataac tgccttaaaa aaattacgcc ccgccctgcc actcatcgca | 1740 |
| gtactgttgt aattcattaa gcattctgcc gacatggaag ccatcacaga cggcatgatg | 1800 |
| aacctgaatc gccagcggca tcagcacctt gtcgccttgc gtataatatt tgcccatggt | 1860 |

-continued

```
gaaaacgggg gcgaagaagt tgtccatatt ggccacgttt aaatcaaaac tggtgaaact    1920
cacccaggga ttggctgaga cgaaaaacat attctcaata aacccctttag ggaaataggc   1980 caggttttca ccgtaacacg ccacatcttg cgaatatatg tgtagaaact gccggaaatc    2040
gtcgtggtat tcactccaga gcgatgaaaa cgtttcagtt tgctcatgga aaacggtgta    2100
acaagggtga acactatccc atatcaccag ctcaccgtct ttcattgcca tacgaaattc    2160
cggatgagca ttcatcaggc gggcaagaat gtgaataaag gccggataaa acttgtgctt    2220 attttttcttt acggtcttta aaaaggccgt aatatccagc tgaacggtct ggttataggt    2280
acattgagca actgactgaa atgcctcaaa atgttcttta cgatgccatt gggatatatc    2340
aacggtggta tatccagtga tttttttctc cattttagct tccttagctc ctgaaaatct    2400
cgataactca aaaatacgc ccggtagtga tcttatttca ttatggtgaa agttggaacc     2460
tcttacgtgc cgatcaacgt ctcatttttcg ccaaaagttg gcccagggct tcccggtatc   2520
aacagggaca ccaggattta tttattctgc gaagtgatct tccgtcacag gtatttattc   2580
ggcgcctgta gtgccattta cccccattca ctgccagagc cgtgagcgca gcgaactgaa    2640
tgtcacgaaa aagacagcga ctcaggtgcc tgatggtcgg agacaaaagg aatattcagc    2700
gatttgcccg agcttgcgag ggtgctactt aagcctttag ggttttaagg tctgttttgt    2760
agaggagcaa acagcgtttg cgacatcctt ttgtaatact gcggaactga ctaaagtagt    2820
gagttataca cagggctggg atctattctt tttatctttt tttattcttt ctttattcta    2880
taaattataa ccacttgaat ataaacaaaa aaaacacaca aaggtctagc ggaatttaca    2940
gagggtctag cagaatttac aagttttcca gcaaaggtct agcagaattt acagataccc    3000
acaactcaaa ggaaaaggac tagtaattat cattgactag cccatctcaa ttggtatagt    3060
gattaaaatc acctagacca attgagatgt atgtctgaat tagttgtttt caaagcaaat    3120
gaactagcga ttagtcgcta tgacttaacg gagcatgaaa ccaagctaat tttatgctgt    3180
gtggcactac tcaaccccac gattgaaaac cctacaagga aagaacggac ggtatcgttc    3240
acttataacc aatacgctca gatgatgaac atcagtaggg aaaatgctta tggtgtatta    3300
gctaaagcaa ccagagagct gatgacgaga actgtggaaa tcaggaatcc tttggttaaa    3360
ggctttgaga ttttccagtg gacaaactat gccaagttct caagcgaaaa attagaatta    3420 gttttagtg aagagatatt gccttatctt ttccagttaa aaaaattcat aaaatataat     3480
ctggaacatg ttaagtcttt tgaaaacaaa tactctatga ggatttatga gtggttatta    3540
aaagaactaa cacaaaagaa aactcacaag gcaaatatag agattagcct tgatgaattt    3600
aagttcatgt taatgcttga aaataactac catgagttta aaaggcttaa ccaatgggtt    3660
ttgaaaccaa taagtaaaga tttaaacact tacagcaata tgaaattggt ggttgataag    3720
cgaggccgcc cgactgatac gttgattttc caagttgaac tagatagaca aatggatctc    3780
gtaaccgaac ttgagaacaa ccagataaaa atgaatggtg acaaaatacc aacaaccatt    3840
acatcagatt cctacctaca taacggacta agaaaaacac tacacgatgc tttaactgca    3900
aaaattcagc tcaccagttt tgaggcaaaa ttttttgagtg acatgcaaag taagtatgat    3960
ctcaatggtt cgttctcatg gctcacgcaa aaacaacgaa ccacactaga gaacatactg    4020
gctaaatacg gaaggatctg aggttcttat ggctcttgta tctatcagtg aagcatcaag    4080
actaacaaac aaaagtagaa caactgttca ccgttacata tcaagggaa actgtccat      4140 atgcacagat gaaaacggtg taaaaaagat agatacatca gagcttttac gagttttgg    4200 tgcattcaaa gctgttcacc atgaacagat cgacaatgta acagatgaac agcatgtaac    4260
```

| | | |
|---|---|---|
| acctaataga acaggtgaaa ccagtaaaac aaagcaacta gaacatgaaa ttgaacacct | 4320 |
| gagacaactt gttacagctc aacagtcaca catagacagc ctgaaacagg cgatgctgct | 4380 |
| tatcgaatca aagctgccga caacacggga gccagtgacg cctcccgtgg ggaaaaaatc | 4440 |
| atggcaattc tggaagaaat agcgcccaat acgcaaaccg cctctccccg cgcgttggcc | 4500 |
| gattcattaa tgcagctggc acgacaggtt tcccgactgg aaagcgggca gtgagcgcaa | 4560 |
| cgcaattaat gtgagttagc tcactcatta ggcaccccag gctttacact ttatgcttcc | 4620 |
| ggctcgtatg ttgtgtggaa ttgtgagcgg ataacaattt cacacaggaa acagct | 4676 |

<210> SEQ ID NO 18
<211> LENGTH: 6110
<212> TYPE: DNA
<213> ORGANISM: Helicobacter pylori

<400> SEQUENCE: 18

| | | |
|---|---|---|
| atgaccatga ttacgccaag cttgatactc atcactcaag tggatggcgt ggtaaaagag | 60 |
| cagatcgcat ggcaactcaa tgagatagaa aagcatttca agccaattg ttgcgtggat | 120 |
| tttaagatcg ctcaaaacga acaagaagag caggatctgt ggttttcaag cgtaacgct | 180 |
| tctcaaagta ttagcgttta tggtaaaaag aaattgaatg aagatgtaac cgttcctagg | 240 |
| gcgagtttgc cgagtttgtt gcaagaagtc gccaaaataa gccaaaaata cggctttaaa | 300 |
| atcccttgct ttgggcatac gggcgatggc aatgtgcatg tgaatatcat gctagaagat | 360 |
| cctaaaaggg atttagaaaa agggcatgag gctatggaag agattttca ggccgctatc | 420 |
| agtttggagg ggactttaag cggggagcat ggcataggct tgtctaaagc caaattcatg | 480 |
| cctttagcgt tcaatcatag tgaaatggag cttttaggga atattaaaaa agctcttgat | 540 |
| cctaataata ttttaaaccc ttttaaaatg gggttgtaag atttaaagca aggaaagcgc | 600 |
| ctcgagtcta gagcggccgc gtcgacatcg atcccgggat ccgatgcttt ataactatgg | 660 |
| attaaacact tttttagtaa tttcttaaaa tcaattttgg aatttttcat tttgtctaaa | 720 |
| atgagtaaga ttattttat aagtaaaaca ataattaaaa attagtttat gttttataaa | 780 |
| tattaatgta aattatgtag ggtttatttt ataaaaattt ttaaaagcat ttaaattatt | 840 |
| tctagtttat attttgtaa gtaaatttta gatatcatcc aaagtttatt acatttttaa | 900 |
| agaaaggaat tattgtgcct accataaatc aattggttag aaaagagcgc aaaaaagttt | 960 |
| tagaaaaatc taaatctcca gcgcttaaaa attgtccaca agaaggggga gtttgcacta | 1020 |
| gggtttatac tacaacacct aaaaaaccaa actcagcgtt aagaaaagtt gccaaagtaa | 1080 |
| gacttactag tggctttgaa gtgatcagct atatcggcgg tgaaggtcat aacttgcaag | 1140 |
| aacacagcat tgttttagtg cgtggtggta gggtaaaaga cttaccaggg gttaaatatc | 1200 |
| acatcgttcg tggtgctctt gatacagcag gtgttgcaaa agaacagtt tctcgttcta | 1260 |
| aatatggtgc taaacgtcct aaagcaggcg ctgcaaaata atcattcata cagacaaatc | 1320 |
| cgttagatga tatagattga aaagtggata gatttatgat atagtggata gatttatgat | 1380 |
| ataatgagtt atcaacaaat cggaatttac ggaggataaa tgatgcaatt cacaaagatt | 1440 |
| gatataaata attggacacg aaaagagtat ttcgaccact attttggcaa tacgccctgc | 1500 |
| acatatagta tgacggtaaa actcgatatt tctaagttga aaaggatgg aaaaaagtta | 1560 |
| tacccaactc ttttatatgg agttacaacg atcatcaatc gacatgaaga gttcaggacc | 1620 |
| gcattagatg aaaacggaca ggtaggcgtt ttttcagaaa tgctgccttg ctacacagtt | 1680 |

```
tttcataagg aaactgaaac cttttcgagt atttggactg agtttacagc agactatact   1740
gagtttcttc agaactatca aaaggatata gacgcttttg gtgaacgaat gggaatgtcc   1800
gcaaagccta atcctccgga aaacactttc cctgtttcta tgataccgtg gacaagcttt   1860
gaaggcttta acttaaatct aaaaaaagga tatgactatc tactgccgat atttacgttt   1920
gggaagtatt atgaggaggg cggaaaatac tatattccct tatcgattca agtgcatcat   1980
gccgtttgtg acggctttca tgtttgccgt tttttggatg aattacaaga cttgctgaat   2040
aaataaaatc ccagtttgtc gcactgataa ggatcctgaa tgttttaatt cttttttgtat  2100 aaataattca cgcttttacg atgaaatatt tccccttttt agccttacta aaaggttttt   2160
actatactat aagggatatt gctaacgatt aagctgtatt ggaagagttt attttgcaag   2220
aattaatctt gccttgtgtg attagtaaca caaggcaagt gtgataaacc ctactacaat   2280
ttcaattcaa ggagcctaac taaaataaaa tgaacaattt cagttagggc tttattatag   2340
caaaaattat ctaagattac aaagggtagc gtttctgttt ttggatttag agcgttattt   2400
tgattgtttt gagtttaatt acttttttgt ttaataataa atcttaacta tcataaatgt   2460
acaattaaag tatttaaaaa aattttaaaa caaaaggata taaatgaaaa accattagaa   2520
atagcgtgtt tattggagcg tctttactcg gcggttgcgc tagcgttgag gcttattttg   2580
acgctttgca tgttgctcgc gttaaagacg cttgtttata gaaaagaag cacaccacac    2640 gcccaaagac tttgatagcc cttaccacac tgactaaacc aggaattcac tggccgtcgt   2700
tttacaacgt cgtgactggg aaaaccctgg cgttacccaa cttaatcgcc ttgcagcaca   2760
tccccctttc gccagctggc gtaatagcga agaggcccgc accgatcgcc cttcccaaca   2820
gttgcgcagc ctgaatggcg aatggcgcta accgttttta tcaggctctg ggaggcagaa   2880
taaatgatca tatcgtcaat tattacctcc acggggagag cctgagcaaa ctggcctcag   2940
gcatttgaga agcacacggt cacactgctt ccggtagtca ataaaccggt aaaccagcaa   3000
tagacataag cggctattta acgacccgc cctgaaccga cgaccgggtc gaatttgctt    3060
tcgaatttct gccattcatc cgcttattat cacttattca ggcgtagcac caggcgttta   3120
agggcaccaa taactgcctt aaaaaaatta cgccccgccc tgccactcat cgcagtactg   3180
ttgtaattca ttaagcattc tgccgacatg gaagccatca cagacggcat gatgaacctg   3240
aatcgccagc ggcatcagca ccttgtcgcc ttgcgtataa tatttgccca tggtgaaaac   3300
gggggcgaag aagttgtcca tattggccac gtttaaatca aaactggtga aactcaccca   3360
gggattggct gagacgaaaa acatattctc aataaaccct ttagggaaat aggccaggtt   3420
ttcaccgtaa cacgccacat cttgcgaata tatgtgtaga aactgccgga aatcgtcgtg   3480
gtattcactc cagagcgatg aaaacgtttc agtttgctca tggaaaacgg tgtaacaagg   3540
gtgaacacta tcccatatca ccagctcacc gtctttcatt gccatacgaa attccggatg   3600
agcattcatc aggcgggcaa gaatgtgaat aaaggccgga taaaacttgt gcttattttt   3660
ctttacggtc tttaaaaagg ccgtaatatc cagctgaacg gtctggttat aggtacattg   3720
agcaactgac tgaaatgcct caaaatgttc tttacgatgc cattgggata tatcaacggt   3780
ggtatatcca gtgatttttt tctccatttt agcttcctta gctcctgaaa atctcgataa   3840
ctcaaaaaat acgcccggta gtgatcttat ttcattatgg tgaaagttgg aacctcttac   3900
gtgccgatca acgtctcatt ttcgccaaaa gttggcccag gcttccggg tatcaacagg    3960 gacaccagga tttattattt ctgcgaagtg atcttccgtc acaggtattt attcggcgcc   4020
tgtagtgcca tttaccccca ttcactgcca gagccgtgag cgcagcgaac tgaatgtcac   4080
```

```
gaaaaagaca gcgactcagg tgcctgatgg tcggagacaa aaggaatatt cagcgatttg    4140
cccgagcttg cgagggtgct acttaagcct ttagggtttt aaggtctgtt ttgtagagga    4200
gcaaacagcg tttgcgacat ccttttgtaa tactgcggaa ctgactaaag tagtgagtta    4260
tacacagggc tgggatctat tcttttttatc ttttttttatt ctttctttat tctataaatt    4320
ataaccactt gaatataaac aaaaaaaaca cacaaaggtc tagcggaatt tacagagggt    4380
ctagcagaat ttacaagttt tccagcaaag gtctagcaga atttacagat acccacaact    4440
caaaggaaaa ggactagtaa ttatcattga ctagcccatc tcaattggta tagtgattaa    4500
aatcacctag accaattgag atgtatgtct gaattagttg ttttcaaagc aaatgaacta    4560
gcgattagtc gctatgactt aacggagcat gaaaccaagc taattttatg ctgtgtggca    4620
ctactcaacc ccacgattga aaaccctaca aggaaagaac ggacggtatc gttcacttat    4680
aaccaatacg ctcagatgat gaacatcagt agggaaaatg cttatggtgt attagctaaa    4740
gcaaccagag agctgatgac gagaactgtg gaaatcagga atcctttggt taaaggcttt    4800
gagattttcc agtggacaaa ctatgccaag ttctcaagcg aaaaattaga attagttttt    4860
agtgaagaga tattgcctta tcttttccag ttaaaaaaat tcataaaata taatctggaa    4920
catgttaagt cttttgaaaa caaatactct atgaggattt atgagtggtt attaaaagaa    4980
ctaacacaaa agaaaactca caaggcaaat atagagatta gccttgatga atttaagttc    5040
atgttaatgc ttgaaaataa ctaccatgag tttaaaaggc ttaaccaatg ggttttgaaa    5100
ccaataagta aagatttaaa cacttacagc aatatgaaat tggtggttga taagcgaggc    5160
cgcccgactg atacgttgat tttccaagtt gaactagata gacaaatgga tctcgtaacc    5220
gaacttgaga caaccagat aaaaatgaat ggtgacaaaa taccaacaac cattacatca    5280
gattcctacc tacataacgg actaagaaaa acactcacg atgctttaac tgcaaaaatt    5340
cagctcacca gttttgaggc aaaattttg agtgacatgc aaagtaagta tgatctcaat    5400
ggttcgttct catggctcac gcaaaaacaa cgaaccacac tagagaacat actggctaaa    5460
tacggaagga tctgaggttc ttatggctct tgtatctatc agtgaagcat caagactaac    5520
aaacaaaagt agaacaactg ttcaccgtta catatcaaag ggaaaactgt ccatatgcac    5580
agatgaaaac ggtgtaaaaa agatagatac atcagagctt ttacgagttt ttggtgcatt    5640
caaagctgtt caccatgaac agatcgcaa tgtaacagat gaacagcatg taacacctaa    5700
tagaacaggt gaaaccagta aaacaaagca actagaacat gaaattgaac acctgagaca    5760
acttgttaca gctcaacagt cacacataga cagcctgaaa caggcgatgc tgcttatcga    5820
atcaaagctg ccgacaacac gggagccagt gacgcctccc gtggggaaaa aatcatggca    5880
attctggaag aaatagcgcc caatacgcaa accgcctctc cccgcgcgtt ggccgattca    5940
ttaatgcagc tggcacgaca ggtttcccga ctggaaagcg ggcagtgagc gcaacgcaat    6000
taatgtgagt tagctcactc attaggcacc ccaggcttta cactttatgc ttccggctcg    6060
tatgttgtgt ggaattgtga gcggataaca atttcacaca ggaaacagct              6110
```

<210> SEQ ID NO 19
<211> LENGTH: 120
<212> TYPE: DNA
<213> ORGANISM: Artificial Sequence
<220> FEATURE:
<223> OTHER INFORMATION: Primer

<400> SEQUENCE: 19

```
taatatccct atcagtgata gagatgttaa tccctatcag tgatagagat gctacaatta        60
catccaacct tgatttcgtt atgtcttcaa ggaaaaacac tttaagaata ggagaataag       120
```

<210> SEQ ID NO 20
<211> LENGTH: 120
<212> TYPE: DNA
<213> ORGANISM: Artificial
<220> FEATURE:
<223> OTHER INFORMATION: Primer

<400> SEQUENCE: 20

```
taataattag ttaatgaacg cttctgttaa tccctatcag tgatagagat gctacaatta        60
catccaacct tgatttcgtt atgtcttcaa ggaaaaacac tttaagaata ggagaataag       120
```

<210> SEQ ID NO 21
<211> LENGTH: 120
<212> TYPE: DNA
<213> ORGANISM: Artificial Sequence
<220> FEATURE:
<223> OTHER INFORMATION: Primer

<400> SEQUENCE: 21

```
taatatccct atcagtgata gagatgttaa tccctatcag tgatagagat gctacaatta        60
catccctatc agtgatagag atgtcttcaa ggaaaaacac tttaagaata ggagaataag       120
```

<210> SEQ ID NO 22
<211> LENGTH: 120
<212> TYPE: DNA
<213> ORGANISM: Artificial Sequence
<220> FEATURE:
<223> OTHER INFORMATION: Primer

<400> SEQUENCE: 22

```
taataattag ttaatgaacg cttctgttaa tccctatcag tgatagagat gctacaatta        60
catccctatc agtgatagag atgtcttcaa ggaaaaacac tttaagaata ggagaataag       120
```

<210> SEQ ID NO 23
<211> LENGTH: 120
<212> TYPE: DNA
<213> ORGANISM: Artificial Sequence
<220> FEATURE:
<223> OTHER INFORMATION: Primer

<400> SEQUENCE: 23

```
taataattag ttaatgaacg cttctgttaa tcttagtaaa tcaaaacatt gctacaatta        60
catccctatc agtgatagag atgtcttcaa ggaaaaacac tttaagaata ggagaataag       120
```

<210> SEQ ID NO 24
<211> LENGTH: 42
<212> TYPE: DNA
<213> ORGANISM: Artificial Sequence
<220> FEATURE:
<223> OTHER INFORMATION: Primer

<400> SEQUENCE: 24

```
ccgtcgactt gcaaaaagcg tctaaaatct attgtattaa cg                           42
```

<210> SEQ ID NO 25
<211> LENGTH: 35
<212> TYPE: DNA
<213> ORGANISM: Artificial Sequence
<220> FEATURE:
<223> OTHER INFORMATION: Primer

<400> SEQUENCE: 25
gacatattat gttccttgtt ttttgatgag agttc         35

<210> SEQ ID NO 26
<211> LENGTH: 58
<212> TYPE: DNA
<213> ORGANISM: Artificial Sequence
<220> FEATURE:
<223> OTHER INFORMATION: Primer

<400> SEQUENCE: 26
catcaaaaaa caaggaacat aatatgtcta gattagataa aagtaaagtg attaacag         58

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
gctaccgtcg acttgcaaaa agcgtc         26

<210> SEQ ID NO 28
<211> LENGTH: 44
<212> TYPE: DNA
<213> ORGANISM: Artificial Sequence
<220> FEATURE:
<223> OTHER INFORMATION: Primer

<400> SEQUENCE: 28
accgtcgacc aataagattt ggtataaatt ttctttatta tagc         44

<210> SEQ ID NO 29
<211> LENGTH: 45
<212> TYPE: DNA
<213> ORGANISM: Artificial Sequence
<220> FEATURE:
<223> OTHER INFORMATION: Primer

<400> SEQUENCE: 29
ctaatctaga cattgttgta actccttgtt ataaaaaacc caaag         45

<210> SEQ ID NO 30
<211> LENGTH: 50
<212> TYPE: DNA
<213> ORGANISM: Artificial Sequence
<220> FEATURE:
<223> OTHER INFORMATION: Primer

<400> SEQUENCE: 30
caaggagtta caacaatgtc tagattagat aaaagtaaag tgattaacag         50

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
gctaccgtcg accaataaga tttgg         25

<210> SEQ ID NO 32

```
<211> LENGTH: 38
<212> TYPE: DNA
<213> ORGANISM: Artificial Sequence
<220> FEATURE:
<223> OTHER INFORMATION: Primer

<400> SEQUENCE: 32
tcggatcctt atcagactat ttgcaacagt gccgtaag                              38

<210> SEQ ID NO 33
<211> LENGTH: 28
<212> TYPE: DNA
<213> ORGANISM: Artificial Sequence
<220> FEATURE:
<223> OTHER INFORMATION: Primer

<400> SEQUENCE: 33
ctcatcggat ccttatcaga ctatttgc                                         28

<210> SEQ ID NO 34
<211> LENGTH: 91
<212> TYPE: DNA
<213> ORGANISM: Artificial Sequence
<220> FEATURE:
<223> OTHER INFORMATION: Primer

<400> SEQUENCE: 34
caaccttgat tcgttatgt cttcaaggaa aaacacttta agaataggag aataagatgt       60
ctagattaga taaaagtaaa gtgattaaca g                                     91

<210> SEQ ID NO 35
<211> LENGTH: 88
<212> TYPE: DNA
<213> ORGANISM: Artificial Sequence
<220> FEATURE:
<223> OTHER INFORMATION: Primer

<400> SEQUENCE: 35
accgtcgaca atgaacgctt ctgttaatct tagtaaatca aaacattgct ataattacat      60
ccaaccttga tttcgttatg tcttcaag                                         88

<210> SEQ ID NO 36
<211> LENGTH: 88
<212> TYPE: DNA
<213> ORGANISM: Artificial Sequence
<220> FEATURE:
<223> OTHER INFORMATION: Primer

<400> SEQUENCE: 36
accgtcgaca atgaacgctt ctgttaatct tagtaaatca aaacattgct acaattacat      60
ccaaccttga tttcgttatg tcttcaag                                         88

<210> SEQ ID NO 37
<211> LENGTH: 26
<212> TYPE: DNA
<213> ORGANISM: Artificial Sequence
<220> FEATURE:
<223> OTHER INFORMATION: Primer

<400> SEQUENCE: 37
gctaccgtcg acaatgaacg cttctg                                           26

<210> SEQ ID NO 38
<211> LENGTH: 34
```

```
<212> TYPE: DNA
<213> ORGANISM: Artificial Sequence
<220> FEATURE:
<223> OTHER INFORMATION: Primer

<400> SEQUENCE: 38
tctagagaat tcgtaccctc gagtctagag catg                              34

<210> SEQ ID NO 39
<211> LENGTH: 39
<212> TYPE: DNA
<213> ORGANISM: Artificial Sequence
<220> FEATURE:
<223> OTHER INFORMATION: Primer

<400> SEQUENCE: 39
cggatccctg caggccttat cagactattt gcaacagtg                         39

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
cgttagtgtt agaaagcaag cag                                          23

<210> SEQ ID NO 41
<211> LENGTH: 48
<212> TYPE: DNA
<213> ORGANISM: Artificial Sequence
<220> FEATURE:
<223> OTHER INFORMATION: Primer

<400> SEQUENCE: 41
catagttata aagcatcttt aaaatgaatt agtgttatat ctttgaag               48

<210> SEQ ID NO 42
<211> LENGTH: 43
<212> TYPE: DNA
<213> ORGANISM: Artificial Sequence
<220> FEATURE:
<223> OTHER INFORMATION: Primer

<400> SEQUENCE: 42
ctgaataaat aaaatcctaa aaatgttggc gacagaccgg ttc                    43

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
acgcatgatt gattgcagaa ggag                                         24

<210> SEQ ID NO 44
<211> LENGTH: 44
<212> TYPE: DNA
<213> ORGANISM: Artificial Sequence
<220> FEATURE:
<223> OTHER INFORMATION: Primer

<400> SEQUENCE: 44
```
cactaattca ttttaaagat gctttataac tatggattaa acac    44

<210> SEQ ID NO 45
<211> LENGTH: 38
<212> TYPE: DNA
<213> ORGANISM: Artificial Sequence
<220> FEATURE:
<223> OTHER INFORMATION: Primer

<400> SEQUENCE: 45
ccaacatttt taggatttta tttattcagc aagtcttg    38

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
ccaaagccta gtgaatttga atgtc    25

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
atcgcaccag cttcaatttg atc    23

<210> SEQ ID NO 48
<211> LENGTH: 95
<212> TYPE: DNA
<213> ORGANISM: Artificial Sequence
<220> FEATURE:
<223> OTHER INFORMATION: Primer

<400> SEQUENCE: 48
gatgtaattg tagcatctct atcactgata gggattaaca tctctatcac tgatagggat    60
attatttaaa atgaattagt gttatatctt tgaag    95

<210> SEQ ID NO 49
<211> LENGTH: 35
<212> TYPE: DNA
<213> ORGANISM: Artificial Sequence
<220> FEATURE:
<223> OTHER INFORMATION: Primer

<400> SEQUENCE: 49
cagtgataga gatgctacaa ttacatccaa ccttg    35

<210> SEQ ID NO 50
<211> LENGTH: 55
<212> TYPE: DNA
<213> ORGANISM: Artificial Sequence
<220> FEATURE:
<223> OTHER INFORMATION: Primer

<400> SEQUENCE: 50
gatgtaattg tagcatctct atcactgata gggattaaca gaagcgttca ttaac    55

<210> SEQ ID NO 51
<211> LENGTH: 101

```
<212> TYPE: DNA
<213> ORGANISM: Artificial Sequence
<220> FEATURE:
<223> OTHER INFORMATION: Primer

<400> SEQUENCE: 51
gatagggatg taattgtagc atctctatca ctgatagggg ttaacatctc tatcactgat    60
agggatatta tttaaaatga attagtgtta tatctttgaa g                       101

<210> SEQ ID NO 52
<211> LENGTH: 67
<212> TYPE: DNA
<213> ORGANISM: Artificial Sequence
<220> FEATURE:
<223> OTHER INFORMATION: Primer

<400> SEQUENCE: 52
gagatgctac aattacatcc ctatcagtga tagagatgtc ttcaaggaaa aacactttaa    60
gaatagg                                                              67

<210> SEQ ID NO 53
<211> LENGTH: 76
<212> TYPE: DNA
<213> ORGANISM: Artificial Sequence
<220> FEATURE:
<223> OTHER INFORMATION: Primer

<400> SEQUENCE: 53
gacatctcta tcactgatag ggatgtaatt gtagcatctc tatcactgat agggattaac    60
agaagcgttc attaac                                                    76

<210> SEQ ID NO 54
<211> LENGTH: 52
<212> TYPE: DNA
<213> ORGANISM: Artificial Sequence
<220> FEATURE:
<223> OTHER INFORMATION: Primer

<400> SEQUENCE: 54
catccctatc agtgatagag atgtcttcaa ggaaaaacac tttaagaata gg             52

<210> SEQ ID NO 55
<211> LENGTH: 54
<212> TYPE: DNA
<213> ORGANISM: Artificial Sequence
<220> FEATURE:
<223> OTHER INFORMATION: Primer

<400> SEQUENCE: 55
gacatctcta tcactgatag ggatgtaatt gtagcaatgt tttgatttac taag           54

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56 gtcttttac cagctctcgc ttc                                             23

<210> SEQ ID NO 57
<211> LENGTH: 99
<212> TYPE: DNA
```

```
<213> ORGANISM: Artificial Sequence
<220> FEATURE:
<223> OTHER INFORMATION: Primer

<400> SEQUENCE: 57
tgctataatt acatccctat cagtgataga gatgtcttca aggaaaaaca ctttaagaat    60
aggagaataa catatgagta aaggagaaga acttttcac                          99

<210> SEQ ID NO 58
<211> LENGTH: 91
<212> TYPE: DNA
<213> ORGANISM: Artificial Sequence
<220> FEATURE:
<223> OTHER INFORMATION: Primer

<400> SEQUENCE: 58
tccagaattc ctcgagtcta gagattagtt aatgaacgct tctgttaatc ttagtaaatc    60
aaaacattgc tataattaca tccctatcag t                                   91

<210> SEQ ID NO 59
<211> LENGTH: 92
<212> TYPE: DNA
<213> ORGANISM: Artificial Sequence
<220> FEATURE:
<223> OTHER INFORMATION: Primer

<400> SEQUENCE: 59
tccagaattc ctcgagtcta gagattagtt aatgaacgct tctgttaatc cctatcagtg    60
atagagatgc tataattaca tccctatcag tg                                  92

<210> SEQ ID NO 60
<211> LENGTH: 92
<212> TYPE: DNA
<213> ORGANISM: Artificial Sequence
<220> FEATURE:
<223> OTHER INFORMATION: Primer

<400> SEQUENCE: 60
tccagaattc ctcgagtcta gagtccctat cagtgataga gatgttaatc cctatcagtg    60
atagagatgc tataattaca tccctatcag tg                                  92

<210> SEQ ID NO 61
<211> LENGTH: 63
<212> TYPE: DNA
<213> ORGANISM: Artificial Sequence
<220> FEATURE:
<223> OTHER INFORMATION: Primer

<400> SEQUENCE: 61
cgctatggat cccgggatcg atgtcgacgc ggccgcttat ttgtatagtt catccatgcc    60
atg                                                                 63

<210> SEQ ID NO 62
<211> LENGTH: 32
<212> TYPE: DNA
<213> ORGANISM: Artificial Sequence
<220> FEATURE:
<223> OTHER INFORMATION: Primer

<400> SEQUENCE: 62
gcttcaggat ccagaattcc tcgagtctag ag                                  32
```

```
<210> SEQ ID NO 63
<211> LENGTH: 35
<212> TYPE: DNA
<213> ORGANISM: Artificial Sequence
<220> FEATURE:
<223> OTHER INFORMATION: Primer

<400> SEQUENCE: 63
gacggtatcg atgcgttttc atcgccaaaa tgctc                                35

<210> SEQ ID NO 64
<211> LENGTH: 54
<212> TYPE: DNA
<213> ORGANISM: Artificial Sequence
<220> FEATURE:
<223> OTHER INFORMATION: Primer

<400> SEQUENCE: 64
cggatccctg caggaattct ctagaagatc tctaattaag gagtggtcat gttc           54

<210> SEQ ID NO 65
<211> LENGTH: 69
<212> TYPE: DNA
<213> ORGANISM: Artificial Sequence
<220> FEATURE:
<223> OTHER INFORMATION: Primer

<400> SEQUENCE: 65
cttctagaga attcctgcag ggatccgtcg acaaattttc attatcttaa cataataaaa    60
ataatacag                                                             69

<210> SEQ ID NO 66
<211> LENGTH: 38
<212> TYPE: DNA
<213> ORGANISM: Artificial Sequence
<220> FEATURE:
<223> OTHER INFORMATION: Primer

<400> SEQUENCE: 66
cgcggtggcg gccgcgagct tatggaagaa tacagctc                             38

<210> SEQ ID NO 67
<211> LENGTH: 36
<212> TYPE: DNA
<213> ORGANISM: Artificial Sequence
<220> FEATURE:
<223> OTHER INFORMATION: Primer

<400> SEQUENCE: 67
gacggtatcg atattccacc ctagcgtgaa tgaaag                               36

<210> SEQ ID NO 68
<211> LENGTH: 47
<212> TYPE: DNA
<213> ORGANISM: Artificial Sequence
<220> FEATURE:
<223> OTHER INFORMATION: Primer

<400> SEQUENCE: 68
ctgcaggaat tctctagaag atctgtaatc aaacccttg cgctatc                    47

<210> SEQ ID NO 69
<211> LENGTH: 67
<212> TYPE: DNA
<213> ORGANISM: Artificial Sequence
<220> FEATURE:
```

<223> OTHER INFORMATION: Primer

<400> SEQUENCE: 69
cagatcttct agagaattcc tgcagggatc cgtcgaccaa ttttacaaac ccaatttttt        60
aaccaac        67

<210> SEQ ID NO 70
<211> LENGTH: 38
<212> TYPE: DNA
<213> ORGANISM: Artificial Sequence
<220> FEATURE:
<223> OTHER INFORMATION: Primer

<400> SEQUENCE: 70
gctccaccgc ggcgaatcac ctaatttcaa cctctttg        38

<210> SEQ ID NO 71
<211> LENGTH: 35
<212> TYPE: DNA
<213> ORGANISM: Artificial Sequence
<220> FEATURE:
<223> OTHER INFORMATION: Primer

<400> SEQUENCE: 71
gacggtatcg atttgcctga ttatgtgatc gcatg        35

<210> SEQ ID NO 72
<211> LENGTH: 62
<212> TYPE: DNA
<213> ORGANISM: Artificial Sequence
<220> FEATURE:
<223> OTHER INFORMATION: Primer

<400> SEQUENCE: 72
gagatcttct agagaattcc tgcagggatc cgtcgacatc cgctcaaaaa caccaaatca        60
ag        62

<210> SEQ ID NO 73
<211> LENGTH: 48
<212> TYPE: DNA
<213> ORGANISM: Artificial Sequence
<220> FEATURE:
<223> OTHER INFORMATION: Primer

<400> SEQUENCE: 73
ctgcaggaat tctctagaag atctcatgtc cgctattaaa acgctatc        48

<210> SEQ ID NO 74
<211> LENGTH: 36
<212> TYPE: DNA
<213> ORGANISM: Artificial Sequence
<220> FEATURE:
<223> OTHER INFORMATION: Primer

<400> SEQUENCE: 74
gctccaccgc ggaaatgaaa aaggaacacg gaggtc        36

<210> SEQ ID NO 75
<211> LENGTH: 31
<212> TYPE: DNA
<213> ORGANISM: Artificial Sequence
<220> FEATURE:
<223> OTHER INFORMATION: Primer

<400> SEQUENCE: 75

```
ccaagcttga tactcatcac tcaagtggat g                                      31
```

<210> SEQ ID NO 76
<211> LENGTH: 38
<212> TYPE: DNA
<213> ORGANISM: Artificial Sequence
<220> FEATURE:
<223> OTHER INFORMATION: Primer

<400> SEQUENCE: 76

```
ctctagactc gaggcgcttt ccttgcttta aatcttac                               38
```

<210> SEQ ID NO 77
<211> LENGTH: 86
<212> TYPE: DNA
<213> ORGANISM: Artificial Sequence
<220> FEATURE:
<223> OTHER INFORMATION: Primer

<400> SEQUENCE: 77

```
gaaagcgcct cgagtctaga gcggccgcgt cgacatcgat cccgggatcc tgaatgtttt       60
aattcttttt gtataaataa ttcacg                                            86
```

<210> SEQ ID NO 78
<211> LENGTH: 30
<212> TYPE: DNA
<213> ORGANISM: Artificial Sequence
<220> FEATURE:
<223> OTHER INFORMATION: Primer

<400> SEQUENCE: 78

```
gcgaattctg gtttagtcag tgtggtaagg                                        30
```

<210> SEQ ID NO 79
<211> LENGTH: 26
<212> TYPE: DNA
<213> ORGANISM: Artificial Sequence
<220> FEATURE:
<223> OTHER INFORMATION: Primer

<400> SEQUENCE: 79

```
gctaccaagc ttgatactca tcactc                                            26
```

<210> SEQ ID NO 80
<211> LENGTH: 26
<212> TYPE: DNA
<213> ORGANISM: Artificial Sequence
<220> FEATURE:
<223> OTHER INFORMATION: Primer

<400> SEQUENCE: 80

```
ggtagcgaat tctggtttag tcagtg                                            26
```

<210> SEQ ID NO 81
<211> LENGTH: 28
<212> TYPE: DNA
<213> ORGANISM: Artificial Sequence
<220> FEATURE:
<223> OTHER INFORMATION: Primer

<400> SEQUENCE: 81

```
gctaacatat gtccaattta ctgaccgt                                          28
```

<210> SEQ ID NO 82

```
<211> LENGTH: 39
<212> TYPE: DNA
<213> ORGANISM: Artificial Sequence
<220> FEATURE:
<223> OTHER INFORMATION: Primer

<400> SEQUENCE: 82
gctaagtcga cgcggccgct taatcgccat cttccagca                          39

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
cgacactacc gctcacattg                                               20

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
ccacaaaaaa gttcatcacc gcag                                          24

<210> SEQ ID NO 85
<211> LENGTH: 36
<212> TYPE: DNA
<213> ORGANISM: Artificial Sequence
<220> FEATURE:
<223> OTHER INFORMATION: Primer

<400> SEQUENCE: 85
gctaacatat ggctcaagtg attaatacca atagct                             36

<210> SEQ ID NO 86
<211> LENGTH: 42
<212> TYPE: DNA
<213> ORGANISM: Artificial Sequence
<220> FEATURE:
<223> OTHER INFORMATION: Primer

<400> SEQUENCE: 86
gctaagtcga ccagggatcc ttattcttta ggaaaaattt ca                      42

<210> SEQ ID NO 87
<211> LENGTH: 1032
<212> TYPE: DNA
<213> ORGANISM: Helicobacter pylori

<400> SEQUENCE: 87
atgtccaatt tactgaccgt acaccaaaat ttgcctgcat taccggtcga tgcaacgagt   60
gatgaggttc gcaagaacct gatggacatg ttcagggatc gccaggcgtt ttctgagcat  120
acctggaaaa tgcttctgtc cgtttgccgg tcgtgggcgg catggtgcaa gttgaataac  180
cggaaatggt ttcccgcaga acctgaagat gttcgcgatt atcttctata tcttcaggcg  240
cgcggtctgg cagtaaaaac tatccagcaa catttgggcc agctaaacat gcttcatcgt  300
cggtccgggc tgccacgacc aagtgacagc aatgctgttt cactggttat gcggcggatc  360
cgaaaagaaa acgttgatgc cggtgaacgt gcaaaacagg ctctagcgtt cgaacgcact  420
```

```
gatttcgacc aggttcgttc actcatggaa aatagcgatc gctgccagga tatacgtaat      480
ctggcatttc tggggattgc ttataacacc ctgttacgta tagccgaaat tgccaggatc      540
agggttaaag atatctcacg tactgacggt gggagaatgt taatccatat tggcagaacg      600
aaaacgctgg ttagcaccgc aggtgtagag aaggcactta gcctggggt aactaaactg       660 gtcgagcgat ggatttccgt ctctggtgta gctgatgatc cgaataacta cctgttttgc      720
cgggtcagaa aaaatggtgt tgccgcgcca tctgccacca gccagctatc aactcgcgcc      780
ctggaaggga tttttgaagc aactcatcga ttgatttacg gcgctaagga tgactctggt      840
cagagatacc tggcctggtc tggacacagt gcccgtgtcg gagccgcgcg agatatggcc      900
cgcgctggag tttcaatacc ggagatcatg caagctggtg gctggaccaa tgtaaatatt      960
gtcatgaact atatccgtaa cctggatagt gaaacagggg caatggtgcg cctgctggaa     1020
gatggcgatt aa                                                         1032

<210> SEQ ID NO 88
<211> LENGTH: 1231
<212> TYPE: DNA
<213> ORGANISM: Helicobacter pylori

<400> SEQUENCE: 88
gaattcataa cttcgtatag catacattat acgaacggta gtcgactttt ttgcgagttt       60
ttgatcttta taaattctaa aggggtatta aacgcacttc taataacgat tttatagcgc      120
ttcaaagata taacactaat tcattttaaa taataattag ttaatgaacg cttctgttaa      180
tcttagtaaa tcaaaacatt gctacaatta catccaacct tgatttcgtt atgtcttcaa      240
ggaaaaacac tttgtcgaca ggagaatcat atgcaatttc attcatctag cgcgttgatt      300
acgcctttta aaaagatttt gagcgttgat gaggccgctt atgaaacctt gatcaagcgc      360 caaattttc agggcatgga cgcatgcgtg cctgttggca cgacaggaga atccgccacg       420
ctcacccaca aagagcacat gcgttgcatt gaaatcgcca tagaaacttg caaaaacact      480
aaaacgccct caaattcgcg catgaaagtg ttagccggcg tgggcagtaa cgccacgagc      540
gagtcccttt ctttagcaaa gttcgctcaa aaaatcggcg cggatgcgat tttatgcgta      600
agcccttatt ataaccgccc cacccaacaa ggcttgtttg aacattataa aaccatcgct      660
caatcggtgg aaatccctgt catgctttat gatgtgccaa gtagaacagg cgtgtctatt      720
gaagttccaa ccgccctcaa actctttaga gaagtcccta acattaaagc cattaaagaa      780
gcgtctggct ctttgaaaag ggtaacagaa ttgcattatt atgaaaaaga ttttaaaatt      840
tttagtgggg aagattcgct caaccactcc atcatgtttt caggggggtg cggcgtgatt      900
tcagtgaccg gtaatttaat gcccaatctg atttcacaaa tggtcaattg cgcgctcaaa      960
caaaaatacc aacaagccct agaaatccaa aataagcttt tttgtttgca ccaagccctt     1020
tttgtagaaa caaatcccat ccctattaaa atggctatgc atttagccgg cttgattgaa     1080
aacccaagct acagactgcc tttagtggcc ccaagcaaag aaacgattca acttttagaa     1140 aaactttac aacaatatga ggtaattgca tgactgcagc tcgaggatat ctaccgttcg      1200
tatagcatac attatacgaa gttatagatc t                                    1231

<210> SEQ ID NO 89
<211> LENGTH: 627
<212> TYPE: DNA
<213> ORGANISM: Helicobacter pylori
```

<400> SEQUENCE: 89

```
atgagcagat tagataaaag caaagtgatt aatagcgctt tagaattatt aaatgaagtg    60
gggattgaag ggttaaccac cagaaaatta gctcaaaaat taggggtgga caacctacc    120
ttatattggc atgtgaaaaa taaaagagct ttattagatg ctttagctgt ggaaatttta   180
gctagacatc atgattatag cttacctgct gctggggaaa gctggcaaag cttttttaaga  240
aataatgcta tgagctttag aagagcttta ttaagatata gagatggggc taaagtgcat   300
ttagggacca gacctgatga aaacaatat gataccgtgg aaacccaatt aagatttatg    360
accgaaaatg ggtttagctt aagagatggg ttatatgcta ttagcgctgt gagccatttt   420
accttagggg ctgtgttaga acaacaagaa cataccgctg ctttaaccga tagacctgct   480
gctcctgatg aaaatttacc tcctttatta agagaagctt tacaaattat ggatagcgat   540
gatggggaac aagcttttt acatgggtta gaaagcttaa ttagagggtt tgaagtgcaa    600
ttaaccgctt tattacaaat tgtgtaa                                       627
```

<210> SEQ ID NO 90
<211> LENGTH: 126
<212> TYPE: DNA
<213> ORGANISM: Artificial Sequence
<220> FEATURE:
<223> OTHER INFORMATION: Primer

<400> SEQUENCE: 90

```
gtaatatccc tatcagtgat agagatgtta atccctatca gtgatagaga tgctataatt    60
acatccaacc ttgatttcgt tatgtcttca aggaaaaaca ctttaagaat agcagaataa   120
catatg                                                              126
```

<210> SEQ ID NO 91
<211> LENGTH: 126
<212> TYPE: DNA
<213> ORGANISM: Artificial Sequence
<220> FEATURE:
<223> OTHER INFORMATION: Primer

<400> SEQUENCE: 91

```
gtaatatccc tatcagtgat agagatgtta atccctatca gtgatagaga tgctataatt    60
acatccaacc ttgatttcgt tatgtcttca aggaaaaaca ctttaagaat agcagaataa   120
catctg                                                              126
```

<210> SEQ ID NO 92
<211> LENGTH: 126
<212> TYPE: DNA
<213> ORGANISM: Artificial Sequence
<220> FEATURE:
<223> OTHER INFORMATION: Primer

<400> SEQUENCE: 92

```
gtaatatccc tatcagtgat agagatgtta atccctatca gtgatagaga tgctataatt    60
acatccaacc ttgatttcgt tatgtcttca aggaaaaaca ctttaagaat agcagaataa   120
catttg                                                              126
```

<210> SEQ ID NO 93
<211> LENGTH: 126
<212> TYPE: DNA
<213> ORGANISM: Artificial Sequence
<220> FEATURE:
<223> OTHER INFORMATION: Primer

<400> SEQUENCE: 93

```
gtaatatccc tatcagtgat agagatgtta atccctatca gtgatagaga tgctataatt    60
acatccaacc ttgatttcgt tatgtcttca aggaaaaaca ctttaagaat aggagaataa   120
catatg                                                              126
```

<210> SEQ ID NO 94
<211> LENGTH: 126
<212> TYPE: DNA
<213> ORGANISM: Artificial Sequence
<220> FEATURE:
<223> OTHER INFORMATION: Primer

<400> SEQUENCE: 94

```
gtaatatccc tatcagtgat agagatgtta atccctatca gtgatagaga tgctataatt    60
acatccaacc ttgatttcgt tatgtcttca aggaaaaaca ctttaagaat aggagaataa   120
catctg                                                              126
```

<210> SEQ ID NO 95
<211> LENGTH: 126
<212> TYPE: DNA
<213> ORGANISM: Artificial Sequence
<220> FEATURE:
<223> OTHER INFORMATION: Primer

<400> SEQUENCE: 95

```
gtaatatccc tatcagtgat agagatgtta atccctatca gtgatagaga tgctataatt    60
acatccaacc ttgatttcgt tatgtcttca aggaaaaaca ctttaagaat aggagaataa   120
catttg                                                              126
```

<210> SEQ ID NO 96
<211> LENGTH: 6279
<212> TYPE: DNA
<213> ORGANISM: Artificial Sequence
<220> FEATURE:
<223> OTHER INFORMATION: Cassette designed to inducibly transcribe mRNA
      of a gene of interest

<400> SEQUENCE: 96

```
cacctgacgc gccctgtagc ggcgcattaa gcgcggcggg tgtggtggtt acgcgcagcg    60
tgaccgctac acttgccagc gccctagcgc ccgctccttt cgctttcttc ccttcctttc   120
tcgccacgtt cgccggcttt ccccgtcaag ctctaaatcg gggctccct ttagggttcc    180
gatttagtgc tttacggcac ctcgacccca aaaaacttga ttagggtgat ggttcacgta   240
gtgggccatc gccctgatag acggtttttc gccctttgac gttggagtcc acgttcttta   300
atagtggact cttgttccaa actggaacaa cactcaaccc tatctcggtc tattcttttg   360
atttataagg gattttgccg atttcggcct attggttaaa aaatgagctg atttaacaaa   420
aatttaacgc gaattttaac aaaatattaa cgcttacaat tccattcgc cattcaggct    480
gcgcaactgt tgggaagggc gatcggtgcg ggcctcttcg ctattacgcc agctggcgaa   540
agggggatgt gctgcaaggc gattaagttg ggtaacgcca gggttttccc agtcacgacg   600
ttgtaaaacg acggccagtg aattgtaata cgactcacta gggcgaat tgggtaccgg    660
gccccccctc gatcgacggt atcgatttgc ctgattatgt gatcgcatgc gttggagggg   720
ggtctaacgc tatagggata ttcagcgcat ttttaaacga caaagaagtt aaactcatag   780
gcgtagagcc ggcggggttta gggctagaaa ccaataagca tggggcgact ttgaataagg   840
```

```
ggcgtgtggg gattttgcat gggaataaaa cctatctttt acaagatgat gaaggccaga    900
ttgcagaaag ccatagcatt agcgccgggc ttgattatcc aggagtgggg ccagaacaca    960
gctatttaaa agaaagtggg cgtgcggttt atgaaagcgc aagcgatgct gaagcgctag   1020
aagccttcaa gttgttgtgc caaaaagaag gcattatccc agcgctagaa agctcacacg   1080
ccttagcgta tgccttaaag ctcgctcaaa aatgcgaaga agaaagcatc atcgtagtga   1140
atttaagcgg cagaggggat aaggatttaa gcaccgttta taacgcttta aaaggaggtt   1200
taaaatgagg tatcaaaaca tgtttgaaac cttaaaaaaa cacgaaaaaa tggcgtttat   1260
cccgtttgta accttgggcg atcctaatta tgaattgagt tttgaaatca ttaaaaccct   1320
aattattagc ggggtgagcg ctttagaatt gggtcttgct ttttctgatc ctgtggcgga   1380
tggcattacc atacaagcga gccatttaag ggcgttaaaa cacgctagca tggctaaaaa   1440
tttccagctt ttaaaaaaga ttagagatta caaccacaat attcccatag gcttttagc    1500
gtatgcgaat ttaatttttt cttatggcgt tgatggcttt tacgctcaag ctaaagaatg   1560
cggtatagat agcgttttaa tagcggacat gctcgagata agaaaatgg gattaacgat    1620
attgatgagt tcaattacca gtggatctta gtttttaaa ccccctttca aaactaatgc    1680
gagcaagcat gcgtttagat ctagagtaat atccctatca gtgatagaga tgttaatccc   1740
tatcagtgat agagatgcta taattacatc caaccttgat ttcgttatgt cttcaaggaa   1800
aaacacttta agaataggag aataacatat gtccaattta ctgaccgtac accaaaattt   1860
gcctgcatta ccggtcgatg caacgagtga tgaggttcgc aagaacctga tggacatgtt   1920
cagggatcgc caggcgtttt ctgagcatac ctggaaaatg cttctgtccg tttgccggtc   1980
gtgggcggca tggtgcaagt tgaataaccg gaaatggttt cccgcagaac ctgaagatgt   2040
tcgcgattat cttctatatc ttcaggcgcg cggtctggca gtaaaaacta ccagcaaca    2100
tttgggccag ctaaacatgc ttcatcgtcg gtccgggctg ccacgaccaa gtgacagcaa   2160
tgctgtttca ctggttatgc ggcggatccg aaaagaaaac gttgatgccg gtgaacgtgc   2220
aaaacaggct ctagcgttcg aacgcactga tttcgaccag gttcgttcac tcatggaaaa   2280
tagcgatcgc tgccaggata tacgtaatct ggcatttctg gggattgctt ataacaccct   2340
gttacgtata gccgaaattg ccaggatcag ggttaaagat atctcacgta ctgacggtgg   2400
gagaatgtta atccatattg gcagaacgaa aacgctggtt agcaccgcag gtgtagagaa   2460
ggcacttagc ctgggggtaa ctaaactggt cgagcgatgg attccgtcct ctggtgtagc   2520
tgatgatccg aataactacc tgttttgccg ggtcagaaaa aatggtgttg ccgcgccatc   2580
tgccaccagc cagctatcaa ctcgcgccct ggaagggatt tttgaagcaa ctcatcgatt   2640
gatttacggc gctaaggatg actctggtca gagatacctg gcctggtctg acacagtgc    2700
ccgtgtcgga gccgcgcgag atatggcccg cgctggagtt tcaataccgg agatcatgca   2760
agctggtggc tggaccaatg taaatattgt catgaactat atccgtaacc tggatagtga   2820
aacagggca atggtgcgcc tgctggaaga tggcgattaa gcggccgctt cctacaaacc    2880
ctctacttga atttataaaa taattgtgta aacggattta taatgaatat gaaaacttta   2940
atcattatga ttattgtggg cgagttttaa ctttttgct ccattgggta acctatttct    3000
aaaaatgagg ttttagccgc tctgttttta tagttatttt attttcactt ccactaagcc   3060
atatagcgcg ttaatacaat agattttaga cgcttttgc aagtcgacat ccgctcaaaa    3120
acaccaaatc aagcaaatct ttatcgccag ccccaatgcg agcagtaaag atttagaaca   3180
```

```
agtcgctacg cattcgcaag gctatatcta cgctttagcc aggagtgggg ttacaggggc   3240
gagccgtatt ttagagaatg attcgagtgc tattattaaa accttaaaag cttttagccc   3300
taccccagcc ttactgggct tggcatttc caaaaaagaa cacatcacaa acgctaaagg    3360
catgggtgct gatggcgtga tttgcggatc agcgttagtc aaaatcatag aagaaaattt   3420
aaacaatgaa aacgccatgc tggaaaaaat taaagggttt ataggaggaa tgattttttta  3480
aggcttttag gctttgttgc gttaaaaatt aaagatcaca gattaacaat catcatcagg   3540
ttttattgca tgcgcgttat tattgggtgt attttttataa atctgtgaaa ggcactgttc  3600
ttgttgtatt gggctttccg attctaggca taccattcac caaatgtgta gcatagtcag   3660
gcgttagcgt agaaaatacc gccataagcc taacaacaat ataaaggcag ccttttagtg   3720
tggttgatag tggcttaaaa ttgcgagtat tttgataata aaaaagctaa ttttcatata   3780
ccaagccata agctctttat aacactttta aaaagagcta ttggttgttt agtccttttc   3840
gtcttcgggt tctatgtcta ttgtgttatt gtcatggttg attgctttca aagtatttac   3900
gattttatcc atcttttctt ttgcttcaag cgccttttta tatccttcag ccgcttgttt   3960
atatccttct ttttcttctt gagctatacc ccataatgct ttaaagattg gttgcatttc   4020
agcttttttg cttgcttcta aaagacctcc gtgttccttt tcatttccg cggtggagct    4080
ccagcttttg ttccctttag tgagggttaa tttcgagctt ggcgtaatca tggtcatagc   4140
tgtttcctgt gtgaaattgt tatccgctca caattccaca caacatacga gccggaagca   4200
taaagtgtaa agcctggggt gcctaatgag tgagctaact cacattaatt gcgttgcgct   4260
cactgcccgc tttccagtcg ggaaacctgt cgtgccagct gcattaatga atcggccaac   4320
gcgcggggag aggcggtttg cgtattgggc gctcttccgc ttcctcgctc actgactcgc   4380
tgcgctcggt cgttcggctg cggcgagcgg tatcagctca ctcaaaggcg gtaatacggt   4440
tatccacaga atcaggggat aacgcaggaa agaacatgtg agcaaaaggc cagcaaaagg   4500
ccaggaaccg taaaaaggcc gcgttgctgg cgtttttcca taggctccgc ccccctgacg   4560
agcatcacaa aaatcgacgc tcaagtcaga ggtggcgaaa cccgacagga ctataaagat   4620
accaggcgtt tccccctgga agctccctcg tgcgctctcc tgttccgacc ctgccgctta   4680
ccggatacct gtccgccttt ctcccttcgg gaagcgtggc gctttctcat agctcacgct   4740
gtaggtatct cagttcggtg taggtcgttc gctccaagct gggctgtgtg cacgaacccc   4800
ccgttcagcc cgaccgctgc gccttatccg gtaactatcg tcttgagtcc aacccggtaa   4860
gacacgactt atcgccactg gcagcagcca ctggtaacag gattagcaga gcgaggtatg   4920
taggcggtgc tacagagttc ttgaagtggt ggcctaacta cggctacact agaaggacag   4980
tatttggtat ctgcgctctg ctgaagccag ttaccttcgg aaaaagagtt ggtagctctt   5040
gatccggcaa acaaaccacc gctggtagcg gtggtttttt tgtttgcaag cagcagatta   5100
cgcgcagaaa aaaaggatct caagaagatc ctttgatctt ttctacgggg tctgacgctc   5160
agtggaacga aaactcacgt taagggattt tggtcatgag attatcaaaa aggatcttca   5220
cctagatcct tttaaattaa aaatgaagtt ttaaatcaat ctaaagtata tatgagtaaa   5280
cttggtctga cagttaccaa tgcttaatca gtgaggcacc tatctcagcg atctgtctat   5340
ttcgttcatc catagttgcc tgactccccg tcgtgtagat aactacgata cgggagggct   5400
taccatctgg ccccagtgct gcaatgatac cgcgagaccc acgctcaccg gctccagatt   5460
tatcagcaat aaaccagcca gccggaaggg ccgagcgcag aagtggtcct gcaacttat    5520
ccgcctccat ccagtctatt aattgttgcc gggaagctag agtaagtagt tcgccagtta   5580
```

```
atagtttgcg caacgttgtt gccattgcta caggcatcgt ggtgtcacgc tcgtcgtttg   5640
gtatggcttc attcagctcc ggttcccaac gatcaaggcg agttacatga tccccatgt    5700 tgtgcaaaaa agcggttagc tccttcggtc ctccgatcgt tgtcagaagt aagttggccg   5760
cagtgttatc actcatggtt atggcagcac tgcataattc tcttactgtc atgccatccg   5820
taagatgctt ttctgtgact ggtgagtact caaccaagtc attctgagaa tagtgtatgc   5880
ggcgaccgag ttgctcttgc ccggcgtcaa tacgggataa taccgcgcca catagcagaa   5940
ctttaaaagt gctcatcatt ggaaaacgtt cttcggggcg aaaactctca aggatcttac   6000
cgctgttgag atccagttcg atgtaaccca ctcgtgcacc caactgatct tcagcatctt   6060
ttactttcac cagcgtttct gggtgagcaa aacaggaag gcaaatgcc gcaaaaagg      6120 gaataagggc gacacggaaa tgttaatac tcatactctt cctttttcaa tattattgaa    6180
gcatttatca gggttattgt ctcatgagcg gatacatatt tgaatgtatt tagaaaaata   6240
aacaaatagg ggttccgcgc acatttcccc gaaaagtgc                          6279
```

<210> SEQ ID NO 97
<211> LENGTH: 2356
<212> TYPE: DNA
<213> ORGANISM: Artificial Sequence
<220> FEATURE:
<223> OTHER INFORMATION: Cassette synthesized with optimized H. pylori
      codon usage and listeriosylin gene as target gene and without the
      tetRsyn gene (pMA-IEC-LLO)

<400> SEQUENCE: 97

```
cctcgagata aagaaaatgg gattaacgat attgatgagt tcaattacca gtggatctta     60
gttttttaaa ccccctttca aaactaatgc gagcaagcat gcgtttagat ctactagtga    120
attctactcc ttaggatccc atcaattgta ctccttgtta taaaaaccc aaaggcatcc     180 ttgcttttgg ttggaactat aatcggttaa agtttgaaat tttaaagggc tttgttttaa    240
aagcaaaatt taaggagca tgaaaatggg ctataataaa gaaaatttat accaaatctt     300
attgctgcag atgattagaa ttgctatgag cgaacataat gctttatcta gagtaataat    360
tagttaatga acgcttctgt taatcccat cagtgataga gatgctataa ttacatccaa     420
ccttgatttc gttatgtctt caaggaaaaa cactttaaga ataggagaat aacatatgat    480
tttaagagct agcgtgttaa gcgctttatt attagtgggg ttaggggctg ctcctaaaca    540
tagcgtgagc gctaaagatg ctagcgcttt tcataaagaa gatttaatta gcagcatggc    600
tcctcctacc agccctcctg ctagccctaa accccctatt gaaaaaaaac atgctgatga    660
aattgataaa tatattcaag ggttagatta taataaaaat aatgtgttag tgtatcatgg    720
ggatgctgtg accaatgtgc ctcctagaaa agggtataaa gatgggaatg aatatatttgt   780 ggtggaaaaa aaaaaaaaa gcattaatca aataatgct gatattcaag tggtgaatgc      840
tattagcagc ttaacctatc ctgggctttt agtgaaagct aatagcgaat tagtggaaaa    900
tcaacctgat gtgttacctg tgaaaagaga tagcttaacc ttaagcattg atttacctgg    960
gatgaccaat caagataata aaattgtggt gaaaaatgct accaaaagca atgtgaataa   1020
tgctgtgaat accttagtgg aaagatggaa tgaaaatat gctcaagctt atcctaatgt    1080
gagcgctaaa attgattatg atgatgaaat ggcttatagc gaaagccaat taattgctaa   1140
atttgggacc gcttttaaag ctgtgaataa tagcttaaat gtgaatttgt gggctattag    1200 cgaagggaa atgcaagaag aagtgattag ctttaaacaa atttattata atgtgaatgt    1260
```

```
gaatgaacct accagaccta gcagattttt tgggaaagct gtgaccaaag aacaattaca    1320
agctttaggg gtgaatgctg aaaatcctcc tgcttatatt agcagcgtgg cttatgggag    1380
acaagtgtat ttaaaattaa gcaccaatag ccatagcacc aaagtgaaag ctgcttttga    1440
tgctgctgtg agcgggaaaa gcgtgagcgg ggatgtggaa ttaaccaata ttattaaaaa    1500
tagcagcttt aaagctgtga tttatggggg gagcgctaaa gatgaagtgc aaattattga    1560
tgggaattta ggggatttaa gagatatttt aaaaaaaggg gctaccttta atagagaaac    1620
ccctggggtg cctattgctt ataccaccaa ttttttaaaa gataatgaat tagctgtgat    1680
taaaaataat agcgaatata ttgaaaccac cagcaaagct tataccgatg gaaaaattaa    1740
tattgatcat agcggggggt atgtggctca atttaatatt agctgggatg aaattaatta    1800
tgatcctgaa gggaatgaaa ttgtgcaaca taaaaattgg agcgaaaata ataaaagcaa    1860
attagctcat tttaccagca gcatttattt acctgggaat gctagaaata ttaatgtgta    1920
tgctaaagaa tgcaccgggt tagcttggga atggtggaga accgtgattg atgatagaaa    1980 tttacccttta gtgaaaaata gaaatattag catttggggg accaccttat atcctaaata    2040
tagcaatagc gtggataatc ctattgaata agtcgactaa ggtagtgtgg ggtctcccca    2100
tgcgagagta gggaactgcc aggcatcaaa taaaacgaaa ggctcagtcg aaagactggg    2160
cctttcgttt tatctgttgt ttgtcggtga acgctctcct gagtaggaca aatccgccgg    2220
gagcggattt gaacgttgcg aagcaacggc ccggagggtg gcgggcagga cgcccgccat    2280
aaactgccag gcatcaaatt aagcagaagg ccatcctgac ggatggcctt tttgcgtttc    2340
tacaaactct ctcgag                                                    2356
```

<210> SEQ ID NO 98
<211> LENGTH: 1566
<212> TYPE: DNA
<213> ORGANISM: Artificial Sequence
<220> FEATURE:
<223> OTHER INFORMATION: Second fliCsyn

<400> SEQUENCE: 98

```
atggctcaag tgattaatac caatagctta agcttattaa cccaaaataa tttaaataaa      60
agccaaagcg ctttagggac cgctattgaa agattaagca gcgggttaag aattaatagc     120
gctaaagatg atgctgctgg gcaagctatt gctaatagat ttaccgctaa tattaaaggg     180
ttaacccaag ctagcagaaa tgctaatgat gggattagca ttgctcaaac caccgaaggg     240
gctttaaatg aaattaataa taatttacaa agagtgagag aattagctgt gcaaagcgct     300
aatgggacca atagccaaag cgatttagat agcattcaag ctgaaattac ccaaagatta     360
aatgaaattg atagagtgag cgggcaaacc caatttaatg gggtgaaagt gttagctcaa     420
gataatacct taaccattca gtgggggct aatgatgggg aaaccattga tattgattta     480
aaagaaatta gcagcaaaac cttagggtta gataaattaa atgtgcaaga tgcttatacc     540
cctaaagaaa ccgctgtgac cgtggataaa accaccccata aaaatgggac cgataccatt     600
accgctcaaa gcaataccga tattcaaacc gctattgggg ggggggctac cggggtgacc     660 gggctgata ttaaatttaa agatgggcaa tattatttag atgtgaaagg ggggctagc     720 gctggggtgt ataaagctac ctatgatgaa accaccaaaa aagtgaatat tgataccacc     780
gataaaaccc ctttagctac cgctgaagct accgctatta gagggaccgc taccattacc     840
cataatcaaa ttgctgaagt gaccaaagaa ggggtggata ccaccaccgt ggctgctcaa     900
ttagctgctg ctgggggtgac cggggctgat aaagataata ccagcttagt gaaattaagc     960
```

-continued

```
tttgaagata aaaatgggaa agtgattgat gggggtatg ctgtgaaaat gggggatgat    1020
ttttatgctg ctacctatga tgaaaaaacc gggaccatta ccgctaaaac caccacctat    1080
accgatgggg ctgggtggc tcaaaccggg gctgtgaaat ttgggggggc taatgggaaa    1140
agcgaagtgg tgaccgctac cgatgggaaa acctatttag ctagcgattt agataaacat    1200
aattttagaa ccggggggga attaaagaa gtgaataccg ataaaaccga aaatcccttta    1260 caaaaaattg atgctgcttt agctcaagtg gataccttaa gaagcgattt aggggctgtg    1320
caaaatagat ttaatagcgc tattaccaat ttagggaata ccgtgaataa tttaagcagc    1380
gctagaagca gaattgaaga tagcgattat gctaccgaag tgagcaatat gagcagagct    1440
caaattttac aacaagctgg gaccagcgtg ttagctcaag ctaatcaagt gcctcaaaat    1500
gtgttaagct tattaagagg gcctagctta agctttgaaa gatttgaaat ttttcctaaa    1560
gaataa                                                               1566
```

<210> SEQ ID NO 99
<211> LENGTH: 2970
<212> TYPE: DNA
<213> ORGANISM: Artificial Sequence
<220> FEATURE:
<223> OTHER INFORMATION: Resulting PCR fragment and pMA-IEC-Ts-LLO were
      digested with NdeI and SalI to clone fliCsyn in the vector
      replacing the LLO gene (pMA-IEC-Ts-FliCsyn)

<400> SEQUENCE: 99

```
gatatcctcg agataaagaa atgggatta acgatattga tgagttcaat taccagtgga      60 tcttagttt ttaaaccccc tttcaaaact aatgcgagca agcatgcgtt tagatctact     120
agtgaattct actccttagg atcattacac aatttgtaat aaagcggtta attgcacttc    180
aaaccctcta attaagcttt ctaacccatg taaaaaagct tgttccccat catcgctatc    240
cataatttgt aaagcttctc ttaataaagg aggtaaattt tcatcaggag cagcaggtct    300
atcggttaaa gcagcggtat gttcttgttg ttctaacaca gccctaagg taaaatggct    360 cacagcgcta atagcatata acccatctct taagctaaac ccattttcgg tcataaatct    420
taattgggtt tccacggtat catattgttt ttcatcaggt ctggtcccta atgcactttt    480
agccccatct ctatatctta ataaagctct tctaaagctc atagcattat ttcttaaaaa    540
gctttgccag ctttccccag cagcaggtaa gctataatca tgatgtctag ctaaaatttc    600
cacagctaaa gcatctaata aagctctttt attttcaca tgccaatata aggtaggttg    660 ttccaccct aattttgag ctaatttct ggtggtaac ccttcaatcc ccacttcatt      720
taataattct aaagcgctat taatcacttt gctttatct aatctgctca tgaattgtac    780
tccttgttat aaaaaaccca aaggcatcct tgcttttggt tggaactata atcggttaaa    840
gtttgaaatt ttaaagggct ttgttttaaa agcaaaattt aaaggagcat gaaaatgggc    900
tataataaag aaaatttata ccaaatctta ttgctgcaga tgattagaat tgctatgagc    960
gaacataatg ctttatctag agtaataatt agttaatgaa cgcttctgtt aatccctatc    1020
agtgatagag atgctataat tacatccaac cttgatttcg ttatgtcttc aaggaaaaac    1080
actttaagaa taggagaata acatatggct caagtgatta taccaatag cttaagctta    1140 ttaacccaaa ataatttaaa taaaagccaa agcgctttag ggaccgctat tgaaagatta    1200
agcagcgggt taagaattaa tagcgctaaa gatgatgctg ctgggcaagc tattgctaat    1260
agatttaccg ctaatattaa agggttaacc caagctagca gaaatgctaa tgatggggatt    1320
```

```
agcattgctc aaaccaccga aggggcttta aatgaaatta ataataattt acaaagagtg     1380
agagaattag ctgtgcaaag cgctaatggg accaatagcc aaagcgattt agatagcatt     1440
caagctgaaa ttacccaaag attaaatgaa attgatagag tgagcgggca acccaattt      1500
aatggggtga aagtgttagc tcaagataat accttaacca ttcaagtggg gctaatgat      1560
ggggaaacca ttgatattga tttaaagaa attagcagca aaaccttagg gttagataaa      1620
ttaaatgtgc aagatgctta taccctaaa gaaaccgctg tgaccgtgga taaaaccacc      1680
tataaaaatg ggaccgatac cattaccgct caaagcaata ccgatattca aaccgctatt     1740
gggggggggg ctaccggggt gaccggggct gatattaaat ttaaagatgg gcaatattat     1800
ttagatgtga aggggggggc tagcgctggg gtgtataaag ctacctatga tgaaaccacc     1860
aaaaagtga atattgatac caccgataaa acccctttag ctaccgctga agctaccgct     1920
attagaggga ccgctaccat tacccataat caaattgctg aagtgaccaa agaagggtg     1980
gataccacca ccgtggctgc tcaattagct gctgctgggg tgaccggggc tgataaagat     2040
aataccagct tagtgaaatt aagctttgaa gataaaaatg ggaaagtgat tgatgggggg     2100
tatgctgtga aaatggggga tgatttttat gctgctacct atgatgaaaa aaccgggacc     2160
attaccgcta aaaccaccac ctataccgat ggggctgggg tggctcaaac cggggctgtg     2220
aaatttgggg gggctaatgg gaaaagcgaa gtggtgaccg ctaccgatgg gaaaacctat     2280
ttagctagcg atttagataa acataatttt agaaccgggg gggaattaaa agaagtgaat     2340
accgataaaa ccgaaaatcc tttacaaaaa attgatgctg ctttagctca agtggatacc     2400
ttaagaagcg atttaggggc tgtgcaaaat agatttaata gcgctattac caatttaggg     2460
aataccgtga ataatttaag cagcgctaga agcagaattg aagatagcga ttatgctacc     2520
gaagtgagca atatgagcag agctcaaatt ttacaacaag ctgggaccag cgtgttagct     2580
caagctaatc aagtgcctca aaatgtgtta agcttattaa gagggcctag cttaagcttt     2640
gaaagatttg aaattttttcc taagaataa ggatccctgg tcgactaagg tagtgtgggg     2700
tctccccatg cgagagtagg gaactgccag gcatcaaata aaacgaaagg ctcagtcgaa     2760
agactgggcc tttcgtttta tctgttgttt gtcggtgaac gctctcctga gtaggacaaa     2820
tccgccggga gcggatttga acgttgcgaa gcaacggccc ggagggtggc gggcaggacg     2880
cccgccataa actgccaggc atcaaattaa gcagaaggcc atcctgacgg atggccttt     2940
tgcgtttcta caaactctct cgaggatatc                                    2970

<210> SEQ ID NO 100
<211> LENGTH: 8053
<212> TYPE: DNA
<213> ORGANISM: Artificial Sequence
<220> FEATURE:
<223> OTHER INFORMATION: cassette was cloned in the similar digested
      vector pHel2 to yield the shuttle vector pHel2-IEC-Ts-FliCsyn
<220> FEATURE:
<221> NAME/KEY: misc_feature
<222> LOCATION: (4307)..(4307)
<223> OTHER INFORMATION: n is a, c, g, or t

<400> SEQUENCE: 100
tcgagataaa gaaaatggga ttaacgatat tgatgagttc aattaccagt ggatcttagt       60
tttttaaacc ccctttcaaa actaatgcga gcaagcatgc gtttagatct actagtgaat      120
tctactcctt aggatcttta cacaatttgt aataaagcgg ttaattgcac ttcaaaccct      180
ctaattaagc tttctaaccc atgtaaaaaa gcttgttccc catcatcgct atccataatt      240
```

```
tgtaaagctt ctcttaataa aggaggtaaa ttttcatcag gagcagcagg tctatcggtt      300
aaagcagcgg tatgttcttg ttgttctaac acagcccta aggtaaaatg gctcacagcg       360
ctaatagcat ataacccatc tcttaagcta aacccatttt cggtcataaa tcttaattgg     420
gtttccacgg tatcatattg tttttcatca ggtctggtcc ctaaatgcac tttagcccca     480
tctctatatc ttaataaagc tcttctaaag ctcatagcat tatttcttaa aaagctttgc     540
cagctttccc cagcagcagg taagctataa tcatgatgtc tagctaaaat ttccacagct     600
aaagcatcta ataaagctct tttatttttc acatgccaat ataaggtagg ttgttccacc     660
cctaattttt gagctaattt tctggtggtt aaccctttcaa tccccacttc atttaataat     720
tctaaagcgc tattaatcac tttgcttta tctaatctgc tcatgaattg tactccttgt     780
tataaaaaac ccaaaggcat ccttgctttt ggttggaact ataatcggtt aaagtttgaa     840
attttaaagg gctttgtttt aaaagcaaaa tttaaggag catgaaaatg gctataata       900 aagaaaattt ataccaaatc ttattgctgc agatgattag aattgctatg agcgaacata     960
atgctttatc tagagtaata attagttaat gaacgcttct gttaatccct atcagtgata    1020
gagatgctat aattacatcc aaccttgatt tcgttatgtc ttcaaggaaa aacactttaa    1080
gaataggaga ataacatatg gctcaagtga ttaataccaa tagcttaagc ttattaaccc    1140
aaaataattt aaataaaagc caaagcgctt tagggaccgc tattgaaaga ttaagcagcg    1200
ggttaagaat aatagcgct aaagatgatg ctgctgggca agctattgct aatagattta    1260
ccgctaatat taaagggtta acccaagcta gcagaaatgc taatgatggg attagcattg    1320
ctcaaaccac cgaaggggct ttaaatgaaa ttaataataa tttacaaaga gtgagagaat    1380
tagctgtgca aagcgctaat gggaccaata gccaaagcga tttagatagc attcaagctg    1440
aaattaccca aagattaaat gaaattgata gagtgagcgg gcaaacccaa tttaatgggg    1500
tgaaagtgtt agctcaagat aataccttaa ccattcaagt gggggctaat gatggggaaa    1560
ccattgatat tgatttaaaa gaaattagca gcaaaacctt agggttagat aaattaaatg    1620
tgcaagatgc ttataccct aaagaaaccg ctgtgaccgt ggataaaacc acctataaaa    1680
atgggaccga taccattacc gctcaaagca ataccgatat tcaaaccgct attgggggg    1740 gggctaccgg ggtgaccggg gctgatatta aatttaaaga tgggcaatat tatttagatg    1800
tgaaaggggg ggctagcgct ggggtgtata agctaccta tgatgaaacc accaaaaaag    1860
tgaatattga taccaccgat aaaaccccctt tagctaccgc tgaagctacc gctattagag    1920
ggaccgctac cattacccat aatcaaattg ctgaagtgac caaagaaggg gtggatacca    1980
ccaccgtggc tgctcaatta gctgctgctg gggtgaccgg ggctgataaa gataatacca    2040
gcttagtgaa attaagcttt gaagataaaa atgggaaagt gattgatggg gggtatgctg    2100
tgaaaatggg ggatgatttt tatgctgcta ccctatgatga aaaaaccggg accattaccg    2160
ctaaaaccac cacctatacc gatggggctg ggtggctca aaccggggct gtgaaatttg    2220 gggggggctaa tgggaaaagc gaagtggtga ccgctaccga tgggaaaacc tatttagcta    2280
gcgatttaga taaacataat tttagaaccg ggggggaatt aaaagaagtg aataccgata    2340
aaaccgaaaa tccttacaa aaaattgatg ctgctttagc tcaagtggat accttaagaa    2400
gcgatttagg ggctgtgcaa aatagattta atagcgctat taccaattta gggaataccg    2460
tgaataattt aagcagcgct agaagcagaa ttgaagatag cgattatgct accgaagtga    2520
gcaatatgag cagagctcaa attttacaac aagctgggac cagcgtgtta gctcaagcta    2580
atcaagtgcc tcaaaatgtg ttaagcttat taagagggcc tagcttaagc tttgaaagat    2640
```

```
ttgaaatttt tcctaaagaa taaggatccc tggtcgacta aggtagtgtg gggtctcccc   2700
atgcgagagt agggaactgc caggcatcaa ataaaacgaa aggctcagtc gaaagactgg   2760
gcctttcgtt ttatctgttg tttgtcggtg aacgctctcc tgagtaggac aaatccgccg   2820
ggagcggatt tgaacgttgc gaagcaacgg cccggagggt ggcgggcagg acgcccgcca   2880
taaactgcca ggcatcaaat taagcagaag gccatcctga cggatggcct ttttgcgttt   2940
ctacaaactc tctcgagatc tagatatcga tgaattcaaa aaaaaaggc tccaaaagga   3000 gcctttaatg atctaattcg tatcagctca ctcaaaggcg gtaatacggt tatccacaga   3060 atcagggggat aacgcaggaa agaacatgtg agcaaaaggc cagcaaaagg ccaggaaccg   3120
taaaaaggcc gcgttgctgg cgttttccca taggctccgc cccctgacg agcatcacaa   3180 aaatcgacgc tcaagtcaga ggtggcgaaa cccgacagga ctataaagat accaggcgtt   3240
tccccctgga agctccctcg tgcgctctcc tgttccgacc ctgccgctta ccggatacct   3300
gtccgccttt ctcccttcgg gaagcgtggc gctttctcat agctcacgct gtaggtatct   3360
cagttcggtg taggtcgttc gctccaagct gggctgtgtg cacgaacccc ccgttcagcc   3420
cgaccgctgc gccttatccg gtaactatcg tcttgagtcc aacccggtaa gacacgactt   3480
atcgccaccg gcagcagcca ctggtaacag gattagcaga gcgaggtatg taggcggtgc   3540
tacagagttc ttgaagtggt ggcctaacta cggctacact agaaggacag tatttggtat   3600
ctgcgctctg ctgaagccag ttaccttcgg aaaaagagtt ggtagctctt gatccggcaa   3660
acaaaccacc gctggtagcg gtggtttttt tgtttgcaag cagcagatta cgcgcagaaa   3720
aaaaggatct caagaagatc ctttgatctc tgcagttcag taatttcctg catttgcctg   3780
tttccagtcg gtagatattc cacaaaacag cagggaagca gcgcttttcc gctgcataac   3840
cctgcttcgg ggtcattata gcgattttt cggtatatcc atcctttttc gcacgatata   3900
caggattttg ccaaagggtt cgtgtagact ttccttggtg tatccaacgg cgtcagccgg   3960
gcaggatagg tgaagtaggc ccacccgcga gcgggtgttc cttcttcact gtcccttatt   4020
cgcacctggc ggtgctcaac gggaatcctg ctctgcgagg ctggccggct accgccggcg   4080
taacagatga gggcaagcgg atggctgatg aaaccaagct gcagagaagc ttgtccgtta   4140
gcaaatataa tgtgtttagc acctaaaagc gcatctatct tgtgttagcc atctaaccta   4200
aacaaaaccg cctagcgagc gttagcgagc atggacaaaa gcgcatcgca gtttgaaatc   4260
gtaggcgtta gcaggatggg gttttgcgtt agcaaaatca acaagntag cggaaaaccg   4320 gggggggtcac caaaaaaaac cctaaaacta aaatccccaa aatatgtagc gcgtcatgcg   4380
cgttgttttt attacatgtt ttaataacta tgttgttttt acatgttttt acaacgcgcg   4440
cgcgtgtgag ggattggggg ttgcaacccc ctaaataacg aagctgtagg gtttctcatt   4500
tttgggttaa aatgaataaa acagaacttc ttacgagtga taacagaact tcttacgagt   4560
gataacagaa cttcttacga gtgataacag aacttcttac gagtgataac agaacttctt   4620
tattgtgaag ttatgattat taacaatttt tagctaaaat aacaacctaa ggcggtgtaa   4680
catggttgct aatcctagtg ttaacaaatt tggagcaatt agctttaaaa gctagtgggt   4740
tgggagtttg tagcgggtat gcactccgtt aggaggcaca ccatgaaagc attttttgata   4800 gtagtgattt tagtggtaat cttgacacag ccactatatt aaaaccttag cgtttttaata   4860 acccttataa gtccgccaag acttcttaag ggtttcactc ctgttattat atcgtctttt   4920
gaaaaataag cattaaaagg cgcttaaatg cccatgaata cgaattttga acagcttaga   4980
```

```
aaacaagaat tggaattacg aaaattatta gaagaattag aaacgctccc acaaacccca    5040
caaattaaac tgcaaaaaca aaaaatacaa acttacatag acaagataac accaagtatt    5100
ttgagcggtt ttgatcaaaa attcaaagaa attatagaaa atctatcaaa tgaatttgaa    5160
aaagaaaaat ccacaccact caaagagcca caaccaccc ccacaccatg caaagattta     5220
gtggttagca cccctaaaga taacacctat accacctacc acaataacgc taataaggtc    5280
aatctaggga aattgagcga aagggaagcc aatcttttat tcgctatttt tcaaaaactc    5340
aaagatcaag ggaatacect cattcgtttt gaaccgcaag atttgaaacg catgatcatg    5400
gtcaaatcca acctaaccaa cagacaatta ttgcaaatcc tcaaaaactt acttgacaac    5460
ataggcggtg ctaattttg gatcattaga gagcatgttg aaaatggcga aatctatgaa     5520
gatcacacta gctacatgct tttcaaacaa tttgacattc gtatccataa gccaacccaa    5580
actatagaat acttagaagt ccaactcaac gatagctacc actacctgct caacaatcta    5640
ggcatgggcg tcaatacac ttcctttaaa cttttagaat tccaaagggt gaggggcaaa     5700
tacgccaaga cgctctatcg cttactcaag caatacaaaa gcacagggat tttgagcgtg    5760
gaatgggatc aattcaggga gcttttagac attccaaaag attacaaaat ggaaaacatc    5820
gatcaaaaag tcttaactcc aagcctcaag gaactcagaa aaatctatcc ctttgaacac    5880
ttgagctaca aaaagaacg caaaagccac gacaaacgca aggtaacgca tattgatttt     5940
tattttgagc aattgccaca gggcgaaacc aagaaacaaa acaagccga caagcaacgc     6000
gctcaaaggg acatcaagct catagcgtgg gatattcaca accaaatcgc taaaagaaac    6060
gctaaagcca ctatagaagc taggtttctt gagctaaaaa ccttgattgg ttatcagttc    6120
aggcacaaca atgggactat tttacagatt gacaacgcca cttttgaaaa gaatcaaatg    6180
tttttgcatg tttcaaccag caaaaattct caaaaattcc ttgtgtccaa caaacattc    6240
gctttagaac ttctgtttgt caatggatac agcctaaaaa aagacatgtt ggaaattgat    6300
cccccaagta tccacccat caccaacgaa cctatcaagg aatttgcaga atacatcgga    6360
aaaacgatcc acatcaccaa tttcaatgtg gatcaatgcc ctgagggat caataactac     6420
ctgaaaatca ctaggattgt gaaactgaat gacaatcgga tctgtgtttc agtccaagat    6480
gtggataagc ctgagaaact tctaaaacct ttcattgcta aagatgaaaa acatttgaaa    6540
aattggttta agaaacacta tcggtgaaaa ataagtggtg ggattaacaa tcgtccccca    6600
caccttgcaa tgtagttagt tttgcattat tttttctata atctctatca attctgagag    6660
aacatagatt aattcaatga aattttcat tatctatttc ctttctgtaa attttgttaa     6720
atatttatta aaaaaaatt taaagatcac tctttaagtg aacatacaa aggctgtaga     6780
gagtgccaca ttaagcctga tgttttgctt gtgtatagag tgaaaggcaa tatttaact    6840
ttagttaggc ttggcagtca tagtgaattg ttttagacaa atttctttct aaaatcgccc    6900
agaatgaatt tttaattcta atttaatata attcatcggt tttcactcaa acgatgaaa    6960
tagggctatt tttagctcat tattggggta ttttgttttt agttgaaagc taacttcaaa    7020
attcaaaaaa acttcatttc cctttctccg ccatattgtg ttgaaacacc gcccggaacc    7080
cgatataatc cgcccttcaa cagatccgag attttcagga gctaaggaag ctaaaatgga    7140
gaaaaaaatc actggatata ccaccgttga tatatcccaa tggcatcgta aagaacattt    7200
tgaggcattt cagtcagttg ctcaatgtac ctataaccag accgttcagc tggatattac    7260
ggccttttta aagaccgtaa agaaaaataa gcacaagttt tatccggcct ttattcacat    7320
tcttgcccgc ctgatgaatg ctcatccgga attccgtatg gcaatgaaag acggtgagct    7380
```

-continued

```
ggtgatatgg gatagtgttc acccttgtta caccgttttc catgagcaaa ctgaaacgtt    7440
ttcatcgctc tggagtgaat accacgacga tttccggcag tttctacaca tatattcgca    7500
agatgtggcg tgttacggtg aaaacctggc ctatttccct aaagggttta ttgagaatat    7560 gttttcgtc tcagccaatc cctgggtgag tttcaccagt tttgatttaa acgtggccaa    7620
tatggacaac ttcttcgccc ccgttttcac catgggcaaa tattatacgc aaggcgacaa    7680
ggtgctgatg ccgctggcga ttcaggttca tcatgccgtt tgtgatggct tccatgtcgg    7740
cagaatgctt aatgaattac aacagtactg cgatgagtgg cagggcgggg cgtaattttt    7800
ttaaggcagt tattggtgcc cttaaacgcc tggttgctac gcctgaataa gtgataataa    7860
gcggatgaat ggcagaaatt cggatcttcc atacctacca gttctgcgcc tgcaggtcga    7920
taaaccgata caattaaagg ctccttttgg agcttttttt tttggagatt ttcaacgtgg    7980
atctgaattc gagctcggta cccggggatc ctctagagtc gacctgcagg catgcaagct    8040
agctttcgcg agc    8053

<210> SEQ ID NO 101
<211> LENGTH: 77
<212> TYPE: DNA
<213> ORGANISM: Artificial Sequence
<220> FEATURE:
<223> OTHER INFORMATION: urePtetO (III)

<400> SEQUENCE: 101
tccctatcag tgatagagat gttaatccct atcagtgata gagatgctac aattacatcc    60
ctatcagtga tagagat                                                  77

<210> SEQ ID NO 102
<211> LENGTH: 77
<212> TYPE: DNA
<213> ORGANISM: Artificial Sequence
<220> FEATURE:
<223> OTHER INFORMATION: uPtetO (3)

<400> SEQUENCE: 102
tccctatcag tgatagagat gttaatccct atcagtgata gagatgctat aattacatcc    60
ctatcagtga tagagat                                                  77

<210> SEQ ID NO 103
<211> LENGTH: 17
<212> TYPE: DNA
<213> ORGANISM: Artificial Sequence
<220> FEATURE:
<223> OTHER INFORMATION: 4uPtetO5

<400> SEQUENCE: 103
taggagaata acatatg                                                  17

<210> SEQ ID NO 104
<211> LENGTH: 17
<212> TYPE: DNA
<213> ORGANISM: Artificial Sequence
<220> FEATURE:
<223> OTHER INFORMATION: 5uPtetO5

<400> SEQUENCE: 104
taggagaata acatctg                                                  17

<210> SEQ ID NO 105
```

```
<211> LENGTH: 17
<212> TYPE: DNA
<213> ORGANISM: Artificial Sequence
<220> FEATURE:
<223> OTHER INFORMATION: 6uPtetO5

<400> SEQUENCE: 105
taggagaata acatttg                                                         17

<210> SEQ ID NO 106
<211> LENGTH: 17
<212> TYPE: DNA
<213> ORGANISM: Artificial Sequence
<220> FEATURE:
<223> OTHER INFORMATION: 1uPtetO5

<400> SEQUENCE: 106
tagcagaata acatatg                                                         17

<210> SEQ ID NO 107
<211> LENGTH: 17
<212> TYPE: DNA
<213> ORGANISM: Artificial Sequence
<220> FEATURE:
<223> OTHER INFORMATION: 2uPtetO5

<400> SEQUENCE: 107
tagcagaata acatctg                                                         17

<210> SEQ ID NO 108
<211> LENGTH: 17
<212> TYPE: DNA
<213> ORGANISM: Artificial Sequence
<220> FEATURE:
<223> OTHER INFORMATION: 3uPtetO5

<400> SEQUENCE: 108
tagcagaata acatttg                                                         17

<210> SEQ ID NO 109
<211> LENGTH: 77
<212> TYPE: DNA
<213> ORGANISM: Helicobacter pylori

<400> SEQUENCE: 109
attagttaat gaacgcttct gttaatctta gtaaatcaaa acattgctac aattacatcc          60
aaccttgatt tcgttat                                                         77
```

The invention claimed is:

1. A genetic construct comprising, in the 5'-3' direction: (a) a promoter sequence and (b) a urease operon, wherein the promoter sequence comprises a polynucleotide sequence capable of regulating expression of the urease operon in *Helicobacter pylori* and wherein said promoter sequence is modified to comprise a tetracycline (tet) operator sequence.

2. A genetic construct according to claim 1 further comprising a DNA sequence of interest that encodes at least one heterologous antigen, or a functional fragment thereof.

3. A genetic construct according to claim 2, wherein the heterologous antigen or a functional fragment thereof is from a pathogenic microorganism.

4. A genetic construct according to claim 3, wherein the pathogenic microorganism is selected from the group consisting of a virus, a bacterium, a protozoan and a fungus.

5. The genetic construct of claim 1 further comprising (c) a gene termination sequence.

6. The genetic construct of claim 1, wherein the genetic construct is a plasmid vector.

7. The genetic construct claim 1, wherein the promoter is exogenous to *H. pylori* before modification to include the tet operator sequence.

8. The genetic construct according to claim 1, wherein the promoter is a urease gene promoter.

9. A genetic construct according to claim 8, wherein the urease promoter is urease subunit A of *H. pylori*.

10. The genetic construct of claim 1, wherein the promoter is selected from the group consisting of amiE promoter, core urease promoter, revtetR promoter and flaA promoter.

11. An isolated, genetically modified *H. pylori* comprising a genetic construct of claim 1.

12. An immunogenic composition comprising an isolated, genetically modified *Helicobacter pylori* according to claim 11 and a pharmaceutically acceptable carrier.

13. A method for immunizing a mammal against infection with a pathogenic microorganism comprising the step of administering an immunologically effective amount of an immunogenic composition according to claim 12.

* * * * *